United States Patent
Miller et al.

(10) Patent No.: US 10,975,393 B2
(45) Date of Patent: Apr. 13, 2021

(54) ENGINEERED TARGET SPECIFIC NUCLEASES

(71) Applicant: Sangamo Therapeutics, Inc., Richmond, CA (US)

(72) Inventors: Jeffrey C. Miller, Richmond, CA (US); Edward J. Rebar, Richmond, CA (US)

(73) Assignee: Sangamo Therapeutics, Inc., Richmond, CA (US)

(*) Notice: Subject to any disclaimer, the term of this patent is extended or adjusted under 35 U.S.C. 154(b) by 81 days.

(21) Appl. No.: 15/685,580

(22) Filed: Aug. 24, 2017

(65) Prior Publication Data

US 2018/0087072 A1 Mar. 29, 2018

Related U.S. Application Data

(60) Provisional application No. 62/378,978, filed on Aug. 24, 2016, provisional application No. 62/443,981, filed on Jan. 9, 2017.

(51) Int. Cl.
| | |
|---|---|
| *C12N 15/90* | (2006.01) |
| *C12N 9/22* | (2006.01) |
| *C12N 9/14* | (2006.01) |
| *A61K 38/00* | (2006.01) |

(52) U.S. Cl.
CPC ............ *C12N 15/907* (2013.01); *C12N 9/14* (2013.01); *C12N 9/22* (2013.01); *A61K 38/00* (2013.01); *C07K 2319/81* (2013.01)

(58) Field of Classification Search
None
See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas, III et al. | |
| 6,200,759 B1 | 3/2001 | Dove et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,794,136 B1 | 9/2004 | Eisenberg et al. | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,074,596 B2 | 7/2006 | Darzynkiewicz et al. | |
| 7,153,949 B2 | 12/2006 | Kim et al. | |
| 7,163,824 B2 | 1/2007 | Cox, III et al. | |
| 7,217,509 B2 | 5/2007 | Wolffe et al. | |
| 7,253,273 B2 | 8/2007 | Collingwood | |
| 7,262,054 B2 | 8/2007 | Jamieson et al. | |
| 7,361,635 B2 | 4/2008 | Miller et al. | |
| 7,785,792 B2 | 8/2010 | Wolffe et al. | |
| 7,888,121 B2 | 2/2011 | Urnov et al. | |
| 7,914,796 B2 | 3/2011 | Miller et al. | |
| 7,923,542 B2 | 4/2011 | Wolffe et al. | |
| 7,951,925 B2 | 5/2011 | Ando et al. | |
| 7,972,854 B2 | 7/2011 | Miller et al. | |
| 8,034,598 B2 | 10/2011 | Miller | |
| 8,071,370 B2 | 12/2011 | Wolffe et al. | |
| 8,110,379 B2 | 2/2012 | DeKelver et al. | |
| 8,153,773 B2 | 4/2012 | Jemielity et al. | |
| 8,409,861 B2 | 4/2013 | Guschin et al. | |
| 8,563,314 B2 | 10/2013 | Gregory et al. | |
| 8,586,526 B2 | 11/2013 | Gregory et al. | |
| 8,597,912 B2 | 12/2013 | Collingwood et al. | |
| 8,623,618 B2 | 1/2014 | Doyon et al. | |
| 8,697,359 B1 | 4/2014 | Zhang | |
| 8,703,489 B2 | 4/2014 | Wang | |
| 8,771,985 B2 | 7/2014 | Cui et al. | |
| 8,772,453 B2 | 7/2014 | Paschon et al. | |
| 8,945,868 B2 | 2/2015 | Collingwood et al. | |
| 8,956,828 B2 | 2/2015 | Bonini et al. | |
| 8,962,281 B2 | 2/2015 | Doyon et al. | |

(Continued)

FOREIGN PATENT DOCUMENTS

| | | |
|---|---|---|
| WO | WO 95/19431 A1 | 7/1995 |
| WO | WO 96/06166 A1 | 2/1996 |

(Continued)

OTHER PUBLICATIONS

UniProt Accession No. A0A0F2J3F6, Type II restriction endonuclease, created Jun. 24, 2015.*
Ogawa et al. A novel insertional mutation at the third zinc finger coding region of the WT1 gene in Denys-Drash syndrome. Hum. Mol. Genet. 2, 203-204, 1993.*
Beerli, et al., "Engineering Polydactyl Zinc-Finger Transcription Factors," *Nature Biotechnology* 20:135-141 (2002).
Belfort, et al., "Homing Endonucleases; Keeping the House in Order," *Nucleic Acids Res.* 25(17):3379-3388 (1997).
Beurdeley, et al., "Compact Designer Talens for Efficient Genome Engineering," *Nat Comm*:1-8, doi: 10.1038/ncomms2782 (2013).
Boch, et al., "Breaking the Code of DNA Binding Specificity of Tal-Type III Effectors," *Science* 326:1509-1512 (2009).

(Continued)

*Primary Examiner* — Iqbal H Chowdhury
(74) *Attorney, Agent, or Firm* — Dahna S. Pasternak; Pasternak Patent Law

(57) ABSTRACT

Described herein are engineered nucleases comprising mutations in the cleavage domain (e.g., FokI or homologue thereof) and/or DNA binding domain (zinc finger protein, TALE, single guide RNA) such that on-target specificity is increased.

16 Claims, 21 Drawing Sheets

Specification includes a Sequence Listing.

(56) References Cited

U.S. PATENT DOCUMENTS

| | | | |
|---|---|---|---|
| 9,005,973 | B2 | 4/2015 | Cost et al. |
| 9,045,763 | B2 | 6/2015 | DeKelver et al. |
| 9,150,847 | B2 | 10/2015 | Rebar |
| 9,200,266 | B2 | 12/2015 | Wang |
| 9,234,187 | B2 | 1/2016 | Rebar et al. |
| 9,255,250 | B2 | 2/2016 | Gregory et al. |
| 9,394,531 | B2 | 7/2016 | Miller |
| 9,631,186 | B2 | 4/2017 | Wang |
| 2002/0115215 | A1 | 8/2002 | Wolffe et al. |
| 2003/0082552 | A1 | 5/2003 | Wolffe et al. |
| 2003/0232410 | A1 | 12/2003 | Liljedahl et al. |
| 2004/0002092 | A1 | 1/2004 | Arnould et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2005/0267061 | A1 | 12/2005 | Martin |
| 2006/0063231 | A1 | 3/2006 | Li et al. |
| 2006/0188987 | A1 | 8/2006 | Guschin et al. |
| 2007/0218528 | A1 | 9/2007 | Miller |
| 2008/0131962 | A1 | 6/2008 | Miller |
| 2008/0159996 | A1 | 7/2008 | Ando et al. |
| 2009/0305346 | A1 | 12/2009 | Miller |
| 2010/0218264 | A1 | 8/2010 | Cui et al. |
| 2011/0145940 | A1 | 6/2011 | Voytas et al. |
| 2011/0201055 | A1 | 8/2011 | Doyon et al. |
| 2011/0265198 | A1 | 10/2011 | Gregory et al. |
| 2011/0301073 | A1 | 12/2011 | Gregory et al. |
| 2012/0017290 | A1 | 1/2012 | Cui et al. |
| 2012/0040398 | A1 | 2/2012 | Miller |
| 2012/0060230 | A1 | 3/2012 | Collingwood et al. |
| 2013/0122591 | A1 | 5/2013 | Cost et al. |
| 2013/0137104 | A1 | 5/2013 | Cost et al. |
| 2013/0177960 | A1 | 7/2013 | Regar |
| 2013/0177983 | A1 | 7/2013 | Rebar |
| 2013/0196373 | A1 | 8/2013 | Gregory et al. |
| 2014/0120622 | A1 | 5/2014 | Gregory et al. |
| 2014/0301990 | A1 | 10/2014 | Gregory et al. |
| 2015/0056705 | A1 | 2/2015 | Conway et al. |
| 2015/0110762 | A1 | 4/2015 | Holmes et al. |
| 2015/0159172 | A1 | 6/2015 | Miller et al. |
| 2015/0164954 | A1 | 6/2015 | Bonini et al. |
| 2015/0335708 | A1 | 11/2015 | Froelich et al. |
| 2016/0024474 | A1 | 1/2016 | Conway et al. |
| 2016/0030477 | A1 | 2/2016 | Conway et al. |
| 2017/0211075 | A1 | 7/2017 | Lee et al. |

FOREIGN PATENT DOCUMENTS

| | | |
|---|---|---|
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/044376 A2 | 6/2002 |
| WO | WO 02/099084 A2 | 12/2002 |
| WO | WO 03/016496 A2 | 2/2003 |
| WO | WO 2007/014275 A2 | 2/2007 |
| WO | WO 2010/079430 A1 | 7/2010 |
| WO | 2011/097036 A1 | 8/2011 |
| WO | 2012/015938 A2 | 2/2012 |
| WO | WO 2016/183298 A1 | 11/2016 |
| WO | WO 2017/106528 A2 | 6/2017 |
| WO | WO 2017/136049 A1 | 8/2017 |

OTHER PUBLICATIONS

Boissel, et al., "Megatals: A Rare-Cleaving Nuclease Architecture for Therapeutic Genome Engineering," *Nucl Acid Res* 42(4):2591-2601; 1-13, doi: 10.1093/nar/gkt1224 (2013).

Bonas, et al., "Genetic and Structural Characeterization of the Avirulence Gene AVRBS3 From Xanthomonas Campestris pv. Vesicatoria,"*Mol Gen Genet* 218:127-136 (1989).

Chen, et al., "Dynamic Equilibria of Short-Range Electrostatic Interactions At Molecular Interfaces of Protein-DNA Complexes," *J Phys Chem Lett* 6:2733-2737 (2015).

Choo, et al., "Advances in Zinc Finger Engineering," *Current Opinion in Structural Biology* 10:411-416 (2000).

Elrod-Erickson, et al., "High-Resolution Structures of Variant ZIF268-DNA Complexes: Implications for Understanding Zinc Finger-DNA Recognition," *Structure* 6(4): 451-464 (1998).

Fagerlund, et al., "The CPF1 CRISPR-CAS Protein Expands Genome-Editing Tools," *Genom Bio* 16:251 (2015).

Guillinger, et al., "Fusion of Catalytically Inactive CAS9 to FOKL Nuclease Improves the Specificity of Genome Modification," *Nature Biotech.* 32(6):577-582 (2014).

Guilinger et al., "Broad Specificity Profiling of Talens Results in Engineered Nucleases With Improved DNA-Cleavage Specificity," *Nat. Methods* 11(4):429-435 (2014).

Guo, et al., "Directed Evolution of an Enhanced and Highly Efficient FOKI Cleavage Domain for Zinc Finger Nucleases," *J. Mol. Biol.* 400(1):96-107 (2010).

Gupta, et al., "Zinc-Finger Protein-Dependent and Independent Contributions to the to the In Vivo Off-Target Activity of Zinc Finger Nucleases," *Nucl Acids Res* 39(1): 381-392 (2011).

Haft, et al., "A Guild of 45 CRISPR-Associated (CAS) Protein Families and Multiple CRISPR/CAS Subtypes Exist in Prokaryotic Genomes," *PLoS Computational Biology* 1(6):e60 (2005).

Heuer, et al., "Repeat Domain Diversity of AVRBS3-Like Genes in Ralstonia Solanacearum Strains and Association With Host Preferences in the Field," *Applied and Environmental Microbiology* 73(13):4379-4384 (2007).

Isalan, et al., "A Rapid, Generally Applicable Method to Engineer Zinc Fingers Illustrated by Targeting the HIV-1 Promoter," *Nat Biotechnol.* 19(7):656-660 (2001).

Jansen, et al., "Identification of Genes That Are Associated With DNA Repeats in Prokaryotes," *Molecular Microbiology* 43(6):1565-1575 (2002).

Jasin, "Genetic Manipulation of Genomes With Rare-Cutting Endonucleases," *Trends Genet.* 12(6): 224-228 (1996).

Joyce, et al. "Structure-Based Modeling of Protein: DNA Specificity," *Brief Func Genomics* 14(1): 39-49 (2014).

Kay, et al., "A Bacterial Effector Acts as a Plant Transcription Factor and Induces a Cell Size Regulator," *Science* 318:648-651 (2007).

Kim, et al., "Hybrid Restriction Enzymes: Zinc Finger Fusions to FOK I Cleavage Domain," *Proc Nat'l Acad Sci USA* 93(3):1156-1160 (1996).

Kim, et al., "Highly Efficient RNA-Guided Genome Editing in Human Cells Via Delivery of Purified CAS9 Ribonucleoproteins," *Genome Research* 24:1012-1019 (2014).

Kleinstiver, et al. "High-Fidelity CRISPR-CAS9 Nucleases With No Detectable Genome-Wide Off-Target Effects," *Nature* 529(7587): 490-495 (2016).

Makarova, et al., "A DNA Repair System Specific for Thermophilic Archaea and Bacteria Predicted by Genomic Context Analysis," *Nucleic Acids Research* 30(2):482-496 (2002).

Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biology Direct* 1:7 (2006).

McCaffrey, et al., "CRISPR-CAS9 D10A Nickase Target-Specific Fluorescent Labeling of Double Strand DNA for Whole Genome Mapping and Structural Variation Analysis," *Nucleic Acids Res.* 44(2):e11.doi: 10.1093/nar/gkv878 (2015).

Miller, Jeffrey C. thesis entitled "A Two-Color Bacterialtwo-Hybrid System FPR Selecting Sequence-Specific DNA-Binding Protens Via Fluorescence Activated Cell Sorting." 227 pages (2002).

Miller, et al., "An Improved Zinc-Finger Nuclease Architecture for Highly Specific Genome Editing," *Nat Biotechnology* 25:778-785 (2007).

Moscou, et al., "A Simple Cipher Governs DNA Recognition by Tal Effectors," *Science* 326:1501 (2009).

(56) References Cited

OTHER PUBLICATIONS

Olovnikov, et al., "Bacterial Argonaute Samples the Transcriptome to Identify Foreign DNA," *Molecular Cell* 51(5):594-605 (2013).
Pabo, et al., "Design and Selection of Novel CYS2-HIS2 Zinc Finger Proteins," *Ann. Rev. Biochem.* 70:313-340 (2001).
Perez, et al., "Establishment of HIV-1 Resistance in CD4+ T Cells by Genome Editing Using Zinc-Finger Nucleases," *Nature Biotechnology* 26(7):808-816 (2008).
Ran., et al., "In Vivo Genome Editing Using *Staphylococcus aureus* CAS9," *Nature* 520:186-203 (2015).
Schornack, et al., "Gene-For-Gene-Mediated Recognition of Nuclear-Targeted AVRBS3-Like Bacterial Effector Proteins," *Journal of Plant Physiology* 163(3):256-272 (2006).
Segal, et al., "Custom DNA-Binding Proteins Come of Age: Polydactyl Zinc-Finger Proteins," *Current Opinion Biotechnology* 12:632-637 (2001).
Sheng, et al., "Structure-Based Cleavage Mechanism of Thermus Thermophilus Argonaute DNA Guide Strand-Mediated DNA Target Cleavage," *Proc. Natl. Aca. Sci. U.S.A.* 111(2):652-657 (2014).
Sternberg, et al., "Conformational Control of DNA Target Cleavage by CRISPR-CAS9," *Nature* 527(7576):110-113 (2015).
Swarts, et al., "DNA-Guided DNA Interference by a Prokaryotic Argonaute," *Nature* 507(7491):258-261 doi:10.1038/nature12971 (2014).
Takasu, et al., "Efficient Talen Construction for Bombyx Mori Gene Targeting," *PloS One* 8(9): 1-11 (2013).
Urnov, et al., "Highly Efficient Endogenous Human Gene Correction Using Designed Zinc-Finger Nucleases," *Nature* 435(7042):646-651 (2005).
Vogel, "A Bacterial Seek-And-Destroy System for Foreign DNA," *Science* 344(6187):972-973 (2014).
Wah, et al., "Structure of the Multimodular Endonuclease FOKI Bound to DNA," *Nature* 388:97-100 (1997).
Wah, et al., "Structure of FOK1 Has Implications for DNA Cleavage," *Proc. Natl. Acad. Sci. USA* 95(18): 10564-10569 (1998).
Yin, et al., "Therapeutic Genome Editing by Combined Viral and Non-Viral Delivery of CRISPR System Components In Vivo," *Nat Biotech* 34(3):328 (2016).
Yuan, et al., "Crystal Structure of A. Aeolicus Argonaute, A Site-Specific DNA-Guided Endoribonuclease, Provides Insights Into RISC-Mediated mRNA Cleavage," *Molecular Cell* 19:405-419 (2005).
Miller, et al., "Enhancing gene editing specificity by attenuating DNA cleavage kinetics," Nature Biotechnology 37:945-952 (2014).
Waugh, et al., "A Novel Class of FokI Restriction Endonuclease Mutants That Cleave Hemi-methylated Substrates," Journal of Biological Chemistry 269(16): 12298-12303 (1994).
GenBank Accession No. CDC04928.1 (May 31, 2013).
GenBank Accession No. KEI99890.1 (Jun. 24, 2014).
GenBank Accession No. WP_049180434.1 (Jul. 20, 2015).
Provasi, et al., "Editing T Cell Specificity Towards Leukemia by Zinc Finger Nucleases and Lentiviral Gene Transfer," Nat Med 18(5):807-815 (2012).

\* cited by examiner

Figure 1

```
Q L V K S E L E E K K S E L R H K L K Y V P H E Y I E L I E I A R N S
CAGCTGGTGAAGAGCGAGCTGGAGGAGAAGAAGTCCGAGCTGCGGCACAAGCTGAAGTACGTGCCCCACGAGTACATCGAGCTGATCGAGATCGCCAGGAACAGC
                                                                                               416 418

422                                                             448      450
T Q D R I L E M K V M E F F M K V Y G Y R G K H L G S R K P D G A I
ACCCAGGACCGCATCCTGGAGATGAAGGTGATGGAGTTCTTCATGAAGGTGTACGGCTACAGGGGAAAGCACCTGGGCAGCAGAAAGCCTGACGGCGCCATC 467 469                  476   479,480,481                486
Y T V G S F I D Y G V I V D T K A Y S G G Y N L P I G Q A D E M Q R Y
TATACAGTGGGCAGCTTCATCGATTACGGCGTGATCGTGGACACAAAGGCCTACAGCGGCTACAATCTGCCTATCGGCCAGGCCGACGAGATGCAGAGATAC 490             496    499
V E E N Q T R N K H I N P N E M W K V Y P S S V T E F K F L F V S G H
GTGGAGGAGAACCAGACCCGGAATAAGCACATCAACCCCGAGATGTGGAAGGTGTACCCTAGCAGCGTGACCGAGTTCAAGTTCCTGTTCGTGAGCGGCCAC 525 527       531                537,538
F K G N Y K A Q L T R L N H I T N C N G A V L S V E E L L I G G E M I
TTCAAGGGCAACTACAAGGCCCAGCTGACCAGGCTGAACCATCACCAACTGCAATGCCGCCGTGCTGAGCGTGGAGGAGCTGCTGATCGGCGGCGAGATGATC

K A G T L T L E E V R R K F N N G E I N F    (196 residue)
AAAGCCGGCACCCTGACACTGGAGGAGGTGCGGCGCAAGTTCAACAACGGCGAGATCAACTTC    (588 bases)
```

☐ Positions mutated and characterized for improvements in activity and/or specificity ○ Active site residue Residue mutated in ELD/KKR variants Residue numbers are indicated for active site residues, ELD/KKR variants, and heavily mutated positions

Figure 3A

| ZFN1 | ZFN2 | PRJIYLFN | NIFMAEVG | PEVYOHIU |
|---|---|---|---|---|
| 51857_ELD | 51949_KKR | 80.59 | 9.04 | 0.65 |
| 51857_ELD | 51949_KKR_R416S | 80.63 | 0.75 | 0.08 |
| 51857_ELD | 51949_KKR_R422S | 53.31 | 0.36 | 0.02 |
| 51857_ELD | 51949_KKR_R447S | 11.60 | 0.05 | 0.03 |
| 51857_ELD | 51949_KKR_K448S | 80.95 | 1.63 | 0.67 |
| 51857_ELD | 51949_KKR_K525S | 73.55 | 0.34 | 0.03 |
| 51857_ELD_R416S | 51949_KKR | 49.29 | 1.38 | 0.09 |
| 51857_ELD_R422S | 51949_KKR | 55.46 | 1.15 | 0.22 |
| 51857_ELD_R447S | 51949_KKR | 0.09 | 0.07 | 0.05 |
| 51857_ELD_K448S | 51949_KKR | 78.35 | 9.00 | 0.51 |
| 51857_ELD_K525S | 51949_KKR | 22.39 | 0.37 | 0.11 |
| 51857_ELD_R416S | 51949_KKR_R416S | 48.70 | 0.26 | 0.05 |
| 51857_ELD_R422S | 51949_KKR_R422S | 19.78 | 0.14 | 0.04 |
| 51857_ELD_R447S | 51949_KKR_R447S | 0.47 | 0.11 | 0.06 |
| 51857_ELD_K448S | 51949_KKR_K448S | 69.45 | 2.59 | 0.34 |
| 51857_ELD_K525S | 51949_KKR_K525S | 6.53 | 0.07 | 0.05 |

Figure 3B

| ZFN1 | ZFN2 | PRJIYLFN | NIFMAEVG | PEVYOHIU |
|---|---|---|---|---|
| 51857_KKR | 51949_ELD | 88.28 | 9.26 | 0.87 |
| 51857_KKR | 51949_ELD_R416S | 81.35 | 1.68 | 0.38 |
| 51857_KKR | 51949_ELD_R422S | 67.78 | 0.12 | 0.12 |
| 51857_KKR | 51949_ELD_R447S | 70.79 | 0.09 | 0.08 |
| 51857_KKR | 51949_ELD_K448S | 83.02 | 1.00 | 0.33 |
| 51857_KKR | 51949_ELD_K525S | 76.60 | 0.06 | 0.09 |
| 51857_KKR_R416S | 51949_ELD | 59.43 | 0.76 | 0.12 |
| 51857_KKR_R422S | 51949_ELD | 71.64 | 3.27 | 0.26 |
| 51857_KKR_R447S | 51949_ELD | 25.01 | 0.07 | 0.06 |
| 51857_KKR_K448S | 51949_ELD | 83.71 | 15.88 | 0.34 |
| 51857_KKR_K525S | 51949_ELD | 33.14 | 0.21 | 0.11 |
| 51857_KKR_R416S | 51949_ELD_R416S | 68.35 | 0.04 | 0.11 |
| 51857_KKR_R422S | 51949_ELD_R422S | 26.25 | 0.07 | 0.11 |
| 51857_KKR_R447S | 51949_ELD_R447S | 1.42 | 0.06 | 0.11 |
| 51857_KKR_K448S | 51949_ELD_K448S | 84.31 | 3.06 | 0.71 |
| 51857_KKR_K525S | 51949_ELD_K525S | 6.99 | 0.06 | 0.09 |

Each ZFN delivered at 2 μg mRNA

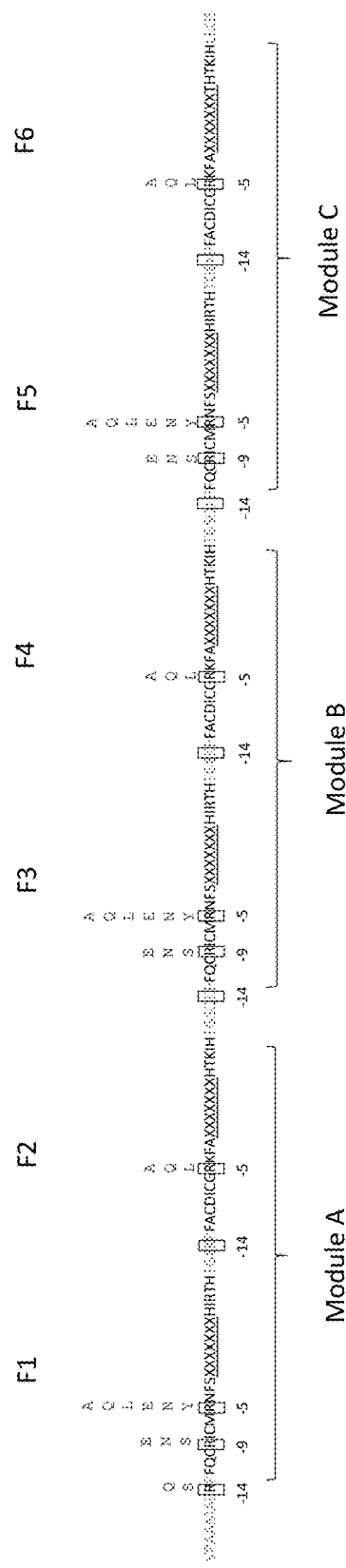
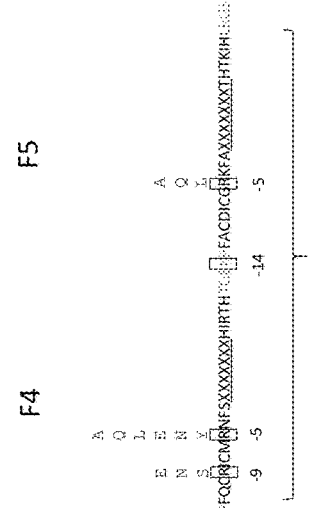
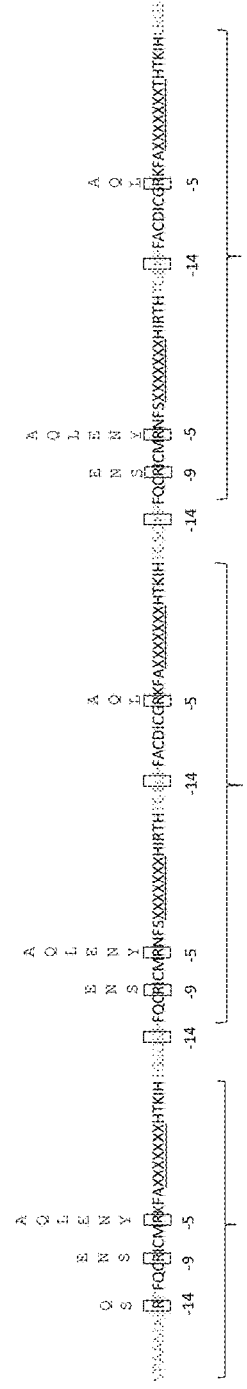
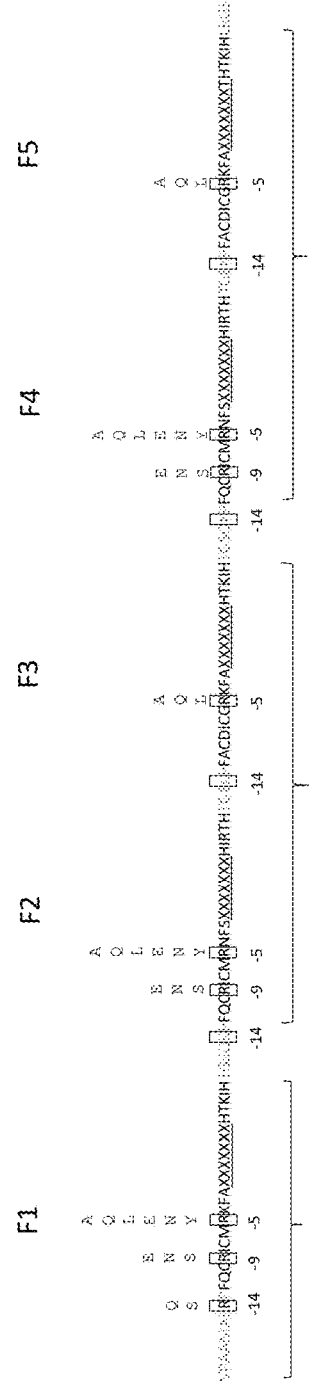
Figure 7A
Figure 7B

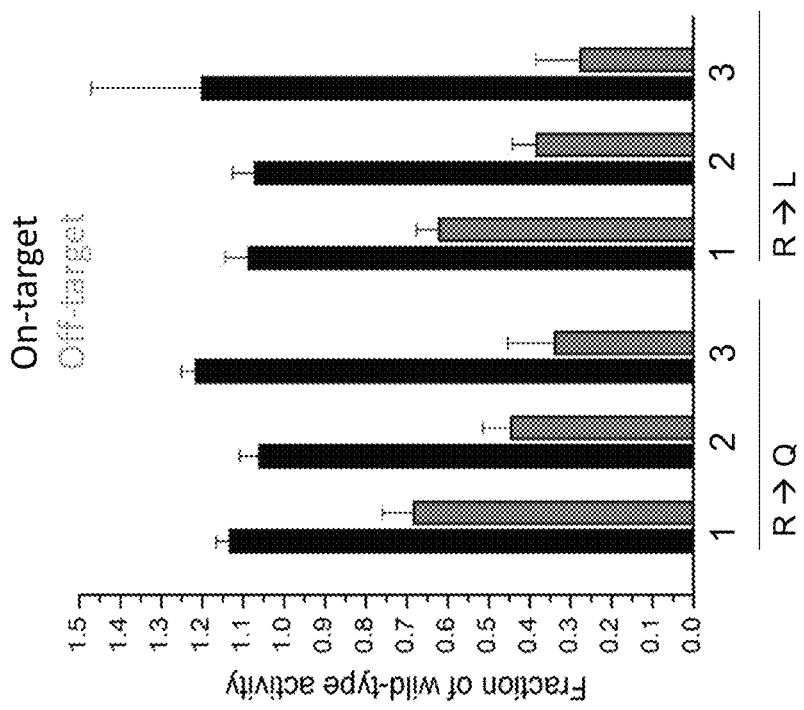

Figure 12

51857/51949 2a: 120 μg mRNA
51857/51949 R416S:
60 μg 51949-R416S,
6.6 μg 51857

| Name | SEQ ID NO: | PRJYLFN | 51857/51949 2a ZFN | 51857/51949 2a control | 51857/51949 R416S ZFN | 51857/51949 R416S control | ratio |
|---|---|---|---|---|---|---|---|
| PRJYLFN | 13 | PRJYLFN | 53.24 | 0.17 | | 0.22 | 0.87 |
| NIFMAEVG | 14 | NIFMAEVG | 18.20 | 0.06 | 0.59 | 0.04 | 5.44 |
| GJZEIYTO | 15 | PEVYOHIU | 1.87 | 0.06 | 0.15 | 0.07 | 12.76 |
| QYYPVRQWMN | 50 | GJZEIYTO | 1.46 | 0.07 | 0.10 | 0.10 | 14.69 |
| ZJCRPAXW | 22 | QYYPVRQW | 1.08 | 0.10 | 0.09 | 0.08 | 12.51 |
| RFGIYSHZ | 16 | ZJCRPAXW | 0.95 | 0.06 | 0.20 | 0.05 | 4.53 |
| XCVJFHQB | 18 | RFGIYSHZ | 0.90 | 0.10 | 0.03 | 0.13 | 20.65 |
| ZMIYSTJN | 19 | XCVJFHQB | 0.83 | 0.10 | 0.13 | 0.08 | 6.58 |
| WOEIMTLA | 35 | ZMIYSTJN | 0.81 | 0.08 | 0.04 | 0.04 | 7.27 |
| QRMXFJNY | 21 | WOEIMTLA | 0.65 | 0.05 | 0.11 | 0.09 | 8.88 |
| EMQNZDWX | 24 | QRMXFJNY | 0.60 | 0.09 | 0.07 | 0.09 | 7.76 |
| DYNFTSJP | 45 | EMQNZDWX | 0.59 | 0.08 | 0.08 | 0.09 | 4.54 |
| IRSUAEVF | 39 | DYNFTSJP | 0.57 | 0.32 | 0.13 | 0.27 | 9.41 |
| RFTBCWPJ | 17 | IRSUAEVF | 0.55 | 0.03 | 0.06 | 0.05 | 5.24 |
| TXHJLGPN | 44 | RFTBCWPJ | 0.52 | 0.11 | 0.10 | 0.11 | 6.02 |
| ZTIFQRKB | 47 | TXHJLGPN | 0.47 | 0.07 | 0.09 | 0.09 | 5.96 |
| XFDECBQY | 46 | ZTIFQRKB | 0.46 | 0.06 | 0.08 | 0.06 | 4.02 |
| WBEAFQRU | 42 | XFDECBQY | 0.37 | 0.11 | 0.08 | 0.10 | 4.86 |
| EKYIXRAH | 51 | WBEAFQRU | 0.28 | 0.09 | 0.08 | 0.08 | 6.39 |
| TBUYHVX | 36 | EKYIXRAH | 0.24 | 0.07 | 0.04 | 0.06 | 5.52 |
| SIJYTMVG | 30 | TBUYHVX | 0.19 | 0.09 | 0.04 | 0.10 | 5.12 |
| AKRHSGPT | 38 | SIJYTMVG | 0.19 | 0.07 | 0.04 | 0.12 | 2.77 |
| RSYQNPLG | 29 | AKRHSGPT | 0.15 | 0.11 | 0.07 | 0.06 | 4.90 |
| HBXGRVYT | 26 | RSYQNPLG | 0.14 | 0.27 | 0.03 | 0.25 | 0.99 |
| ATWDXHSC | 40 | HBXGRVYT | 0.12 | 0.06 | 0.14 | 0.07 | 2.60 |
| ZLRCYHDF | 27 | ATWDXHSC | 0.11 | 0.06 | 0.05 | 0.07 | 1.46 |
| RXDOKCGI | 43 | ZLRCYHDF | 0.11 | 0.05 | 0.08 | 0.13 | 3.01 |
| OTHMRBJL | 28 | RXDOKCGI | 0.11 | 0.08 | 0.04 | 0.07 | 2.46 |
| RDEWOSIT | 32 | OTHMRBJL | 0.10 | 0.05 | 0.04 | 0.05 | 2.46 |
| BCGJKHUV | 31 | QDMBZRWH | 0.09 | 0.07 | 0.03 | 0.08 | 3.47 |
| LXAFJWRI | 23 | RDEWOSIT | 0.09 | 0.06 | 0.03 | 0.06 | 3.15 |
| YPLXMQCB | 33 | BCGJKHUV | 0.09 | 0.06 | 0.06 | 0.08 | 1.37 |
| ZFUQTLMT | 48 | LXAFJWRI | 0.09 | 0.09 | 0.10 | 0.09 | 0.89 |
| QBFUYVGW | 57 | YPLXMQCB | 0.09 | 0.06 | 0.06 | 0.03 | 1.44 |
| LPRCNGHU | 37 | ZFUQTLMT | 0.07 | 0.03 | 0.03 | 0.04 | 2.45 |
| YJRBCUNZ | 25 | QBFUYVGW | 0.07 | 0.10 | 0.04 | 0.11 | 1.80 |
| TPHSLVEM | 34 | LPRCNGHU | 0.06 | 0.08 | 0.03 | 0.06 | 1.99 |
| ZCNLWTPH | 49 | YJRBCUNZ | 0.05 | 0.05 | 0.02 | 0.06 | 1.38 |
| ADWZQXZI | 52 | TPHSLVEM | 0.04 | 0.04 | 0.03 | 0.03 | 2.69 |
| | | ZCNLWTPH | 0.04 | 0.08 | 0.04 | 0.07 | 1.31 |
| | | ADWZQXZI | 0.02 | 0.04 | ND | ND | ND |

Parental ZFN pair (SBS51857/SBS51949)

| Locus | | # capture events | % indels, CD34 cells | | |
|---|---|---|---|---|---|
| chromo-some | base | | ug left ZFN / ug right ZFN | 60 / 60 | 6.6 / 60 |
| 2 | 60495268 | 2516 | | | |
| 8 | 119856442 | 2202 | | | |
| 4 | 7829724 | 214 | | .41 | |
| 12 | 132241502 | 207 | | | nd |
| 12 | 62164812 | 179 | | 2.17 | .31 |
| 1 | 54506812 | 162 | | .83 | .19 |
| 2 | 23702832 | 133 | | .58 | .08 |
| 10 | 132654830 | 124 | | 1.04 | .25 |
| 14 | 67422056 | 116 | | .86 | .06 |
| 17 | 69624230 | 101 | | .48 | .05 |
| 10 | 68571178 | 72 | | 1.54 | .31 |
| 13 | 75549350 | 72 | | .72 | .13 |
| 16 | 15141542 | 69 | | nd | nd |
| 16 | 67184174 | 69 | | | |
| 14 | 21223340 | 68 | | .18 | |
| 14 | 73749924 | 66 | | .39 | .06 |
| X | 134914730 | 65 | | 4.04 | .49 |
| 6 | 53805954 | 65 | | | |
| 1 | 29182166 | 59 | | .20 | .07 |
| 20 | 37707466 | 53 | | 1.05 | .07 |
| 10 | 101133378 | 50 | | | |
| 7 | 131503656 | 49 | | .08 | |
| 7 | 124995298 | 46 | | .13 | |
| 8 | 29495582 | 44 | | .05 | |
| 21 | 33308802 | 41 | | .19 | .04 |
| 8 | 94988046 | 40 | | .25 | |
| 19 | 45406684 | 39 | | nd | nd |

Variant ZFN pair (SBS63014/SBS65721)

| Locus | | # capture events | % indels, CD34 cells | | |
|---|---|---|---|---|---|
| chromo-some | base | | ug left ZFN / ug right ZFN | 60 / 60 | 20 / 60 |
| 2 | 60495270 | 7372 | | | |
| 8 | 119856444 | 157 | | .05 | nd |
| 16 | 67184174 | 71 | | nd | nd |
| 2 | 23702834 | 65 | | .04 | 0.03 |
| 17 | 29624236 | 60 | | | |
| 10 | 69789196 | 38 | | | |
| 2 | 60494824 | 36 | | | |
| X | 66004392 | 34 | | | |
| 10 | 132654830 | 33 | | .08 | |
| 8 | 29495582 | 33 | | .07 | 0.05 |
| 4 | 7829724 | 29 | | | |
| 21 | 36901830 | 27 | | | |
| 21 | 46423666 | 20 | | nd | nd |
| 16 | 88559110 | 19 | | | |
| 19 | 51327818 | 19 | | | |
| 16 | 169090708 | 18 | | | |
| 6 | 54506812 | 17 | | | |
| 5 | 132776212 | 17 | | | |
| 9 | 91430050 | 17 | | | |
| 1 | 612400 | 17 | | | |
| 1 | 612500 | 16 | | | |
| 11 | 107771554 | 15 | | nd | nd |
| 11 | 70518296 | 15 | | | |
| 20 | 48636010 | 15 | | | |
| 8 | 94988046 | 15 | | nd | nd |
| 1 | 26938300 | 15 | | | |
| 8 | 66165666 | 15 | | | |

| | | |
|---|---|---|
| Off Target loci w/significant indels: | 21 | 13 |
| Aggregate % Off Target indels: | 28.0% | 3.4% |

| | | |
|---|---|---|
| | 4 | 2 |
| | 0.26% | 0.08% |

Figure 13

| Chromo-some | Base # | Integrant count | % indels ZFN | % indels control | pval if < 0.05 |
|---|---|---|---|---|---|
| 2 | 60495266 | 1893 | 79.54 | .11 | <0.00001 |
| 8 | 119856440 | 85 | .15 | .1 | NS |
| 3 | 184689238 | 33 | .07 | .07 | NS |
| 10 | 132654832 | 16 | .07 | .06 | NS |
| 11 | 108224088 | 13 | .03 | .02 | NS |
| 16 | 671184174 | 12 | nd1 | nd1 | NS |
| 1 | 223123858 | 12 | .02 | .05 | NS |
| 2 | 23702834 | 12 | .07 | .05 | NS |
| 1 | 29182168 | 10 | nd2 | nd2 | NS |
| 20 | 48636010 | 9 | .04 | .05 | NS |
| 1 | 204975770 | 9 | .02 | .05 | NS |
| 2 | 62164816 | 9 | .0 | .04 | NS |
| 1 | 116494398 | 9 | .06 | .01 | NS |
| 16 | 34590356 | 8 | nd2 | nd2 | NS |
| 8 | 94988044 | 8 | .11 | .03 | NS |
| 1 | 21635648 | 7 | .06 | .02 | NS |
| 19 | 51327822 | 7 | nd2 | nd2 | NS |
| 4 | 7829724 | 7 | .04 | .06 | NS |
| X | 66004390 | 7 | .12 | .04 | NS |
| 10 | 91591624 | 7 | .07 | .02 | NS |
| 16 | 15220090 | 7 | .13 | .11 | NS |
| 6 | 28540486 | 7 | .02 | .05 | NS |
| 9 | 98755464 | 7 | .06 | .05 | NS |
| 14 | 73740924 | 6 | .0 | .2 | NS |
| 10 | 69789200 | 6 | .02 | nd1 | NS |
| 16 | 18131716 | 6 | .09 | .06 | NS |
| 18 | 45431502 | 6 | .05 | .21 | NS |
| 4 | 59602300 | 6 | .24 | .07 | NS |
| 18 | 2920000 | 6 | .09 | .06 | NS |
| 2 | 96873180 | 5 | .04 | .04 | NS |

| Chromo-some | Base # | Integrant count | % indels ZFN | % indels control | pval if < 0.05 |
|---|---|---|---|---|---|
| 17 | 721818 | 5 | .04 | .04 | NS |
| 2 | 112583538 | 5 | .03 | .07 | NS |
| 2 | 169268666 | 5 | nd1 | nd1 | NS |
| 8 | 26449836 | 5 | .03 | .12 | NS |
| 8 | 29495584 | 5 | .04 | .04 | NS |
| 11 | 10961236 | 5 | .22 | .24 | NS |
| 16 | 46386624 | 5 | .08 | .05 | NS |
| 16 | 88559110 | 5 | .03 | .01 | NS |
| 2 | 164741410 | 5 | .08 | .06 | NS |
| 5 | 176402584 | 5 | .03 | .03 | NS |
| 5 | 95714316 | 5 | .0 | .13 | NS |
| 6 | 84224380 | 5 | .03 | .06 | NS |
| 7 | 106878380 | 5 | .19 | .18 | NS |
| 9 | 37906562 | 4 | .02 | .07 | NS |
| 1 | 211655464 | 4 | .04 | .05 | NS |
| 13 | 755549352 | 4 | .02 | .06 | NS |
| 14 | 49586826 | 4 | .09 | .08 | NS |
| 16 | 46399565 | 4 | .1 | .09 | NS |
| 1 | 154649476 | 4 | .08 | .18 | NS |
| 10 | 21001996 | 4 | nd2 | nd2 | NS |
| 13 | 79775980 | 4 | .0 | .05 | NS |
| 15 | 82322852 | 4 | .02 | .28 | NS |
| 15 | 82322918 | 4 | .09 | .12 | NS |
| 15 | 85267112 | 4 | .05 | .03 | NS |
| 15 | 85267176 | 4 | nd2 | nd2 | NS |
| 16 | 34586904 | 4 | .03 | .04 | NS |
| 17 | 210164474 | 4 | nd1 | nd1 | NS |
| 19 | 14243018 | 4 | .04 | .1 | NS |
| 2 | 173593302 | 4 | | | |

Figure 14

NS: pvalue > 0.05
nd1: no data – locus did not amplify or did not sequence
nd2: no data – background high (>1%) or sequencing depth insufficient (<1000 reads)

Figure 15A

ELD

| | | full dose | | | half dose | | | parentals |
|---|---|---|---|---|---|---|---|---|
| on | | 29.64 | 30.09 | 29.29 | 20.23 | 19.34 | 21.01 | |
| ratio | | 4.49 | 3.88 | 4.23 | 7.96 | 9.25 | 9.62 | |

| | R416E | S418E | N476D | I479T | Q481A | Q481E | K525S |
|---|---|---|---|---|---|---|---|
| on | 46.99 | ND | 44.56 | 30.54 | 41.21 | 40.57 | 39.15 |
| ratio | 15.03 | ND | 137.79 | 88.36 | 133.38 | 139.98 | 44.95 |

| | R416E | S418E | N476D | I479T | Q481A | Q481E | K525S |
|---|---|---|---|---|---|---|---|
| R416E | NA | 20.74 | 40.36 | 21.55 | 2.83 | 41.39 | 34.38 |
| S418E | 20.74 | NA | 31.37 | 11.14 | 3.20 | 38.73 | 24.79 |
| N476D | 40.36 | 31.37 | NA | 20.03 | 12.76 | 50.65 | 42.41 |
| I479T | 21.55 | 11.14 | 20.03 | NA | 8.92 | 35.78 | 25.90 |
| Q481A | 2.83 | 3.20 | 12.76 | 8.92 | NA | ND | 15.18 |
| Q481E | 41.39 | 38.73 | 50.65 | 35.78 | ND | NA | 48.15 |
| K525S | 34.38 | 24.79 | 42.41 | 25.90 | 15.18 | 48.15 | NA |

| | R416E | S418E | N476D | I479T | Q481A | Q481E | K525S |
|---|---|---|---|---|---|---|---|
| R416E | NA | 94.13 | 213.54 | 61.74 | 19.59 | 225.41 | 166.24 |
| S418E | 94.13 | NA | 221.16 | 62.37 | 16.08 | 400.31 | 160.35 |
| N476D | 213.54 | 221.16 | NA | 180.94 | 88.57 | 242.53 | 270.45 |
| I479T | 61.74 | 62.37 | 180.94 | NA | 72.43 | 196.60 | 139.72 |
| Q481A | 19.59 | 16.08 | 88.57 | 72.43 | NA | ND | 67.80 |
| Q481E | 225.41 | 400.31 | 242.53 | 196.60 | ND | NA | 274.23 |
| K525S | 166.24 | 160.35 | 270.45 | 139.72 | 67.80 | 274.23 | NA |

Figure 15B single mutants

KKR

| | R416E | S418E | N476D | I479T | Q481A | Q481E | K525S |
|---|---|---|---|---|---|---|---|
| on | 41.76 | ND | 20.04 | 36.62 | 36.52 | 37.26 | 35.00 |
| ratio | 35.99 | ND | 78.85 | 45.83 | 113.98 | 137.34 | 22.10 |

| | R416E | S418E | N476D | I479T | Q481A | Q481E | K525S |
|---|---|---|---|---|---|---|---|
| R416E | NA | 20.09 | 20.88 | 42.32 | 0.05 | 31.75 | 30.56 |
| S418E | 20.09 | NA | 2.68 | 35.49 | 1.55 | 17.90 | 10.28 |
| N476D | 20.88 | 2.68 | NA | 5.09 | 4.44 | 3.08 | 8.06 |
| I479T | 42.32 | 35.49 | 5.09 | NA | 25.89 | 35.07 | 37.19 |
| Q481A | 0.05 | 1.55 | 4.44 | 25.89 | NA | ND | 4.99 |
| Q481E | 31.75 | 17.90 | 3.08 | 35.07 | ND | NA | 24.26 |
| K525S | 30.56 | 10.28 | 8.06 | 37.19 | 4.99 | 24.26 | NA |

| | R416E | S418E | N476D | I479T | Q481A | Q481E | K525S |
|---|---|---|---|---|---|---|---|
| R416E | NA | 151.13 | 121.14 | 220.35 | 0.28 | 163.74 | 146.79 |
| S418E | 151.13 | NA | 15.27 | 234.26 | 9.60 | 135.16 | 55.61 |
| N476D | 121.14 | 15.27 | NA | 26.81 | 22.35 | 17.28 | 52.10 |
| I479T | 220.35 | 234.26 | 26.81 | NA | 204.61 | 218.88 | 151.36 |
| Q481A | 0.28 | 9.60 | 22.35 | 204.61 | NA | ND | 36.01 |
| Q481E | 163.74 | 135.16 | 17.28 | 218.88 | ND | NA | 142.63 |
| K525S | 146.79 | 55.61 | 52.10 | 151.36 | 36.01 | 142.63 | NA |

Figure 15C double mutant grid on-target

ELD_KKR

| | R416E | S418E | N476D | I479T | Q481A | Q481E | K525S |
|---|---|---|---|---|---|---|---|
| on | 61.25 | ND | 4.22 | 26.01 | 70.60 | 38.76 | 42.82 |
| ratio | 138.11 | ND | 36.30 | 153.83 | 383.30 | 221.20 | 299.99 |

| | R416E | S418E | N476D | I479T | Q481A | Q481E | K525S |
|---|---|---|---|---|---|---|---|
| R416E | NA | 1.12 | 0.08 | 9.58 | 0.04 | 15.79 | 18.64 |
| S418E | 1.12 | NA | 0.03 | 0.07 | 0.06 | 0.25 | 0.04 |
| N476D | 0.08 | 0.03 | NA | 0.01 | NA | 0.04 | 0.03 |
| I479T | 9.58 | 0.07 | 0.01 | NA | 1.92 | 1.71 | 0.87 |
| Q481A | 0.04 | 0.06 | 0.04 | 1.92 | NA | ND | 2.27 |
| Q481E | 15.79 | 0.25 | 0.04 | 1.71 | ND | NA | 1.58 |
| K525S | 18.64 | 0.04 | 0.03 | 0.87 | 2.27 | 1.58 | NA |

| | R416E | S418E | N476D | I479T | Q481A | Q481E | K525S |
|---|---|---|---|---|---|---|---|
| R416E | NA | 5.75 | 0.90 | 93.64 | 0.34 | 146.87 | 110.61 |
| S418E | 5.75 | NA | 0.19 | 0.39 | 0.39 | 1.60 | 0.28 |
| N476D | 0.90 | 0.19 | NA | 0.06 | 0.60 | 0.22 | 0.19 |
| I479T | 93.64 | 0.39 | 0.06 | NA | 14.25 | 11.29 | 6.00 |
| Q481A | 0.34 | 0.39 | 0.60 | 14.25 | NA | ND | 12.73 |
| Q481E | 146.87 | 1.60 | 0.22 | 11.29 | ND | NA | 10.24 |
| K525S | 110.61 | 0.28 | 0.19 | 6.00 | 12.73 | 10.24 | NA |

Figure 15D double mutant grid on-off ratio

Figure 16A

ELD

| | R416D | K448A | R422H | I479Q | K525A | N527D |
|---|---|---|---|---|---|---|
| | ND | 46.84 | 36.93 | 16.28 | 25.31 | 29.19 |
| | ND | 45.64 | ND | 11.10 | 18.22 | ND |
| | ND | ND | ND | ND | ND | ND |
| | ND | ND | ND | ND | ND | ND |
| | 0.98 | 35.37 | 15.51 | 4.15 | 8.65 | 15.47 |
| | ND | ND | ND | ND | ND | ND |
| | ND | ND | ND | 4.00 | 5.58 | ND |
| | NA | 33.83 | ND | ND | ND | ND |
| | 33.83 | NA | ND | 51.54 | 43.95 | 32.41 |
| | ND | ND | NA | 31.90 | 31.01 | ND |
| | 4.00 | 51.54 | 31.90 | NA | 27.87 | ND |
| | 5.58 | 43.95 | 31.01 | 27.87 | NA | 23.46 |
| | ND | 32.41 | ND | ND | 23.46 | NA |

| | R416D | K448A | R422H | I479Q | K525A | N527D |
|---|---|---|---|---|---|---|
| | ND | 22.04 | 56.30 | 129.05 | 171.87 | 103.79 |
| | ND | 125.00 | ND | 60.83 | 132.51 | ND |
| | ND | ND | ND | ND | ND | ND |
| | ND | ND | ND | ND | ND | ND |
| | 6.23 | 173.76 | 84.46 | 28.92 | 65.76 | 72.82 |
| | ND | ND | ND | ND | ND | ND |
| | ND | ND | ND | ND | ND | ND |
| | NA | 54.89 | ND | 24.24 | 26.88 | ND |
| | 54.89 | NA | ND | 421.61 | 65.65 | 32.34 |
| | ND | ND | NA | 232.64 | 152.49 | ND |
| | 24.24 | 421.61 | 232.64 | NA | 252.87 | ND |
| | 26.88 | 65.65 | 152.49 | 252.87 | NA | 116.95 |
| | ND | 32.34 | ND | ND | 116.95 | NA |

KKR

| | R416D | K448A | R422H | I479Q | K525A | N527D |
|---|---|---|---|---|---|---|
| | ND | 46.84 | 36.93 | 16.28 | 25.31 | 29.19 |
| | ND | 45.64 | ND | 11.10 | 18.22 | ND |
| | ND | ND | ND | ND | ND | ND |
| | ND | ND | ND | ND | ND | ND |
| | 0.98 | 35.37 | 15.51 | 4.15 | 8.65 | 15.47 |
| | ND | ND | ND | ND | ND | ND |
| | ND | ND | ND | 4.00 | 5.58 | ND |
| | NA | 33.83 | ND | ND | ND | ND |
| | 33.83 | NA | ND | 51.54 | 43.95 | 32.41 |
| | ND | ND | NA | 31.90 | 31.01 | ND |
| | 4.00 | 51.54 | 31.90 | NA | 27.87 | ND |
| | 5.58 | 43.95 | 31.01 | 27.87 | NA | 23.46 |
| | ND | 32.41 | ND | ND | 23.46 | NA |

| | R416D | K448A | R422H | I479Q | K525A | N527D |
|---|---|---|---|---|---|---|
| | ND | 22.04 | 56.30 | 129.05 | 171.87 | 103.79 |
| | ND | 125.00 | ND | 60.83 | 132.51 | ND |
| | ND | ND | ND | ND | ND | ND |
| | ND | ND | ND | ND | ND | ND |
| | 6.23 | 173.76 | 84.46 | 28.92 | 65.76 | 72.82 |
| | ND | ND | ND | ND | ND | ND |
| | ND | ND | ND | ND | ND | ND |
| | NA | 54.89 | ND | 24.24 | 26.88 | ND |
| | 54.89 | NA | ND | 421.61 | 65.65 | 32.34 |
| | ND | ND | NA | 232.64 | 152.49 | ND |
| | 24.24 | 421.61 | 232.64 | NA | 252.87 | ND |
| | 26.88 | 65.65 | 152.49 | 252.87 | NA | 116.95 |
| | ND | 32.34 | ND | ND | 116.95 | NA |

| position | mutation |
|---|---|
| 393 | K393S |
| 394 | K394S |
| 398 | R398S |
| 416 | R416A |
| 416 | R416C |
| 416 | R416D |
| 416 | R416E |
| 416 | R416F |
| 416 | R416G |
| 416 | R416H |
| 416 | R416M |
| 416 | R416N |
| 416 | R416Q |
| 416 | R416S |
| 416 | R416T |
| 416 | R416W |
| 417 | N417D |
| 418 | S418A |
| 418 | S418D |
| 418 | S418E |
| 418 | S418I |
| 418 | S418Q |
| 418 | S418T |
| 418 | S418V |
| 419 | T419D |
| 419 | T419S |
| 421 | D421S |

| position | mutation |
|---|---|
| 422 | R422A |
| 422 | R422D |
| 422 | R422E |
| 422 | R422G |
| 422 | R422H |
| 422 | R422L |
| 422 | R422N |
| 422 | R422P |
| 422 | R422Q |
| 422 | R422S |
| 422 | R422T |
| 422 | R422V |
| 423 | I423L |
| 425 | E425Q |
| 426 | M426I |
| 442 | H442R |
| 446 | S446D |
| 446 | S446G |
| 446 | S446R |
| 447 | R447A |
| 447 | R447Q |
| 447 | R447S |
| 448 | K448A |
| 448 | K448C |
| 448 | K448E |
| 448 | K448Q |
| 448 | K448R |
| 448 | K448S |
| 471 | Y471F |

| position | mutation |
|---|---|
| 472 | S472D |
| 472 | S472K |
| 473 | G473K |
| 476 | N476A |
| 476 | N476C |
| 476 | N476D |
| 476 | N476E |
| 476 | N476G |
| 476 | N476I |
| 476 | N476K |
| 476 | N476Q |
| 476 | N476S |
| 476 | N476T |
| 476 | N476V |
| 478 | P478D |
| 478 | P478S |
| 479 | I479A |
| 479 | I479C |
| 479 | I479F |
| 479 | I479G |
| 479 | I479H |
| 479 | I479L |
| 479 | I479M |
| 479 | I479N |
| 479 | I479Q |
| 479 | I479S |
| 479 | I479T |
| 479 | I479V |
| 479 | I479Y |

| position | mutation |
|---|---|
| 480 | G480A |
| 480 | G480C |
| 480 | G480D |
| 480 | G480E |
| 480 | G480F |
| 480 | G480K |
| 480 | G480L |
| 480 | G480P |
| 480 | G480Q |
| 480 | G480S |
| 480 | G480W |
| 481 | Q481A |
| 481 | Q481C |
| 481 | Q481D |
| 481 | Q481E |
| 481 | Q481H |
| 481 | Q481M |
| 481 | Q481N |
| 481 | Q481S |
| 481 | Q481T |
| 522 | G522S |
| 523 | H523E |
| 523 | H523F |
| 523 | H523K |

| position | mutation |
|---|---|
| 525 | K525A |
| 525 | K525C |
| 525 | K525D |
| 525 | K525E |
| 525 | K525G |
| 525 | K525H |
| 525 | K525I |
| 525 | K525M |
| 525 | K525N |
| 525 | K525Q |
| 525 | K525S |
| 525 | K525T |
| 525 | K525V |
| 527 | N527T |
| 528 | Y528F |
| 530 | A530E |
| 530 | A530K |
| 531 | Q531E |
| 531 | Q531I |
| 531 | Q531L |
| 531 | Q531M |
| 531 | Q531T |
| 531 | Q531V |
| 531 | Q531Y |

| mutation1 | mutation2 |
|---|---|
| R416D | K448A |
| R416D | I479Q |
| R416E | S418E |
| R416E | R422H |
| R416E | K448A |
| R416E | N476D |
| R416E | I479Q |
| R416E | I479T |
| R416E | Q481E |
| R416E | K525A |
| R416E | K525S |
| R416S | K525S |
| S418E | K448A |
| S418E | N476D |
| S418E | I479Q |
| S418E | I479T |
| S418E | Q481E |
| S418E | K525A |
| S418E | K525S |
| R422H | I479Q |
| R422H | Q481A |
| R422H | K525A |
| R422S | K525S |
| K448A | I479Q |
| K448A | Q481A |
| K448A | K525A |
| K448S | K525S |
| N476D | I479Q |
| N476D | Q481A |
| N476D | Q481E |
| N476D | K525S |
| I479Q | Q481A |
| I479Q | K525A |
| I479T | Q481A |
| I479T | Q481E |
| I479T | K525S |
| Q481A | K525A |
| Q481E | K525S |

SEQUENCE LISTING

<160> NUMBER OF SEQ ID NOS: 72

<210> SEQ ID NO 1
<211> LENGTH: 579
<212> TYPE: PRT
<213> ORGANISM: Unknown
<220> FEATURE:
<223> OTHER INFORMATION: Description of Unknown:
      Wild type FokI cleavage half domain

<400> SEQUENCE: 1

```
Met Val Ser Lys Ile Arg Thr Phe Gly Trp Val Gln Asn Pro Gly Lys
1               5                   10                  15

Phe Glu Asn Leu Lys Arg Val Val Gln Val Phe Asp Arg Asn Ser Lys
            20                  25                  30

Val His Asn Glu Val Lys Asn Ile Lys Ile Pro Thr Leu Val Lys Glu
        35                  40                  45

Ser Lys Ile Gln Lys Glu Leu Val Ala Ile Met Asn Gln His Asp Leu
    50                  55                  60

Ile Tyr Thr Tyr Lys Glu Leu Val Gly Thr Gly Thr Ser Ile Arg Ser
65                  70                  75                  80

Glu Ala Pro Cys Asp Ala Ile Ile Gln Ala Thr Ile Ala Asp Gln Gly
                85                  90                  95

Asn Lys Lys Gly Tyr Ile Asp Asn Trp Ser Ser Asp Gly Phe Leu Arg
            100                 105                 110

Trp Ala His Ala Leu Gly Phe Ile Glu Tyr Ile Asn Lys Ser Asp Ser
        115                 120                 125

Phe Val Ile Thr Asp Val Gly Leu Ala Tyr Ser Lys Ser Ala Asp Gly
    130                 135                 140

Ser Ala Ile Glu Lys Glu Ile Leu Ile Glu Ala Ile Ser Ser Tyr Pro
145                 150                 155                 160

Pro Ala Ile Arg Ile Leu Thr Leu Leu Glu Asp Gly Gln His Leu Thr
                165                 170                 175

Lys Phe Asp Leu Gly Lys Asn Leu Gly Phe Ser Gly Glu Ser Gly Phe
            180                 185                 190

Thr Ser Leu Pro Glu Gly Ile Leu Leu Asp Thr Leu Ala Asn Ala Met
        195                 200                 205

Pro Lys Asp Lys Gly Glu Ile Arg Asn Asn Trp Glu Gly Ser Ser Asp
    210                 215                 220

Lys Tyr Ala Arg Met Ile Gly Gly Trp Leu Asp Lys Leu Gly Leu Val
225                 230                 235                 240

Lys Gln Gly Lys Lys Glu Phe Ile Ile Pro Thr Leu Gly Lys Pro Asp
                245                 250                 255

Asn Lys Glu Phe Ile Ser His Ala Phe Lys Ile Thr Gly Glu Gly Leu
            260                 265                 270

Lys Val Leu Arg Arg Ala Lys Gly Ser Thr Lys Phe Thr Arg Val Pro
        275                 280                 285

Lys Arg Val Tyr Trp Glu Met Leu Ala Thr Asn Leu Thr Asp Lys Glu
    290                 295                 300

Tyr Val Arg Thr Arg Arg Ala Leu Ile Leu Glu Ile Leu Ile Lys Ala
305                 310                 315                 320

Gly Ser Leu Lys Ile Glu Gln Ile Gln Asp Asn Leu Lys Lys Leu Gly
                325                 330                 335

Phe Asp Glu Val Ile Glu Thr Ile Glu Asn Asp Ile Lys Gly Leu Ile
            340                 345                 350
```

```
Asn Thr Gly Ile Phe Ile Glu Ile Lys Gly Arg Phe Tyr Gln Leu Lys
            355                 360                 365

Asp His Ile Leu Gln Phe Val Ile Pro Asn Arg Gly Val Thr Lys Gln
        370                 375                 380

Leu Val Lys Ser Glu Leu Glu Glu Lys Ser Glu Leu Arg His Lys
385                 390                 395                 400

Leu Lys Tyr Val Pro His Glu Tyr Ile Glu Leu Ile Glu Ile Ala Arg
                405                 410                 415

Asn Ser Thr Gln Asp Arg Ile Leu Glu Met Lys Val Met Glu Phe Phe
            420                 425                 430

Met Lys Val Tyr Gly Tyr Arg Gly Lys His Leu Gly Gly Ser Arg Lys
        435                 440                 445

Pro Asp Gly Ala Ile Tyr Thr Val Gly Ser Pro Ile Asp Tyr Gly Val
    450                 455                 460

Ile Val Asp Thr Lys Ala Tyr Ser Gly Gly Tyr Asn Leu Pro Ile Gly
465                 470                 475                 480

Gln Ala Asp Glu Met Gln Arg Tyr Val Glu Glu Asn Gln Thr Arg Asn
                485                 490                 495

Lys His Ile Asn Pro Asn Glu Trp Trp Lys Val Tyr Pro Ser Ser Val
            500                 505                 510

Thr Glu Phe Lys Phe Leu Phe Val Ser Gly His Phe Lys Gly Asn Tyr
        515                 520                 525

Lys Ala Gln Leu Thr Arg Leu Asn His Ile Thr Asn Cys Asn Gly Ala
    530                 535                 540

Val Leu Ser Val Glu Glu Leu Leu Ile Gly Gly Glu Met Ile Lys Ala
545                 550                 555                 560

Gly Thr Leu Thr Leu Glu Glu Val Arg Arg Lys Phe Asn Asn Gly Glu
                565                 570                 575

Ile Asn Phe

<210> SEQ ID NO 2
<211> LENGTH: 588
<212> TYPE: DNA
<213> ORGANISM: Unknown
<220> FEATURE:
<223> OTHER INFORMATION: Description of Unknown:
      Wild type FokI cleavage half domain

<400> SEQUENCE: 2
cagctggtga agagcgagct ggaggagaag aagtccgagc tgcggcacaa gctgaagtac      60
gtgccccacg agtacatcga gctgatcgag atcgccagga acagcaccca ggaccgcatc     120
ctggagatga aggtgatgga gttcttcatg aaggtgtacg gctacagggg aaagcacctg     180
ggcggaagca gaaagcctga cggcgccatc tatacagtgg gcagccccat cgattacggc     240
gtgatcgtgg acacaaaggc ctacagcggc ggctacaatc tgcctatcgg ccaggccgac     300
gagatgcaga gatacgtgga ggagaaccag accggaata agcacatcaa ccccaacgag     360
tggtggaagg tgtaccctag cagcgtgacc gagttcaagt tcctgttcgt gagcggccac     420
ttcaagggca actacaaggc ccagctgacc aggctgaacc acatcaccaa ctgcaatggc     480
gccgtgctga gcgtggagga gctgctgatc ggcggcgaga tgatcaaagc cggcaccctg     540
acactggagg aggtgcggcg caagttcaac aacggcgaga tcaacttc                  588

<210> SEQ ID NO 3
<211> LENGTH: 28
<212> TYPE: PRT
```

```
<213> ORGANISM: Unknown
<220> FEATURE:
<223> OTHER INFORMATION: Description of Unknown:
      Zinc finger protein

<400> SEQUENCE: 3

Lys Pro Phe Gln Cys Arg Ile Cys Met Arg Asn Phe Ser Arg Ser Asp
1               5                   10                  15

His Leu Thr Thr His Ile Arg Thr His Thr Gly Glu
            20                  25

<210> SEQ ID NO 4
<211> LENGTH: 23
<212> TYPE: PRT
<213> ORGANISM: Unknown
<220> FEATURE:
<223> OTHER INFORMATION: Description of Unknown:
      Zinc finger protein

<400> SEQUENCE: 4

Phe Gln Cys Arg Ile Cys Met Arg Asn Phe Ser Arg Ser Asp His Leu
1               5                   10                  15

Thr Thr His Ile Arg Thr His
            20

<210> SEQ ID NO 5
<211> LENGTH: 23
<212> TYPE: PRT
<213> ORGANISM: Unknown
<220> FEATURE:
<223> OTHER INFORMATION: Description of Unknown:
      Zinc finger protein

<400> SEQUENCE: 5

Phe Ala Cys Asp Ile Cys Gly Arg Lys Phe Ala Arg Ser Asp Glu Arg
1               5                   10                  15

Lys Arg His Thr Lys Ile His
            20

<210> SEQ ID NO 6
<211> LENGTH: 23
<212> TYPE: PRT
<213> ORGANISM: Unknown
<220> FEATURE:
<223> OTHER INFORMATION: Description of Unknown:
      Zinc finger protein

<400> SEQUENCE: 6

Phe Ala Cys Pro Glu Cys Pro Lys Arg Phe Met Arg Ser Asp His Leu
1               5                   10                  15

Ser Lys His Ile Lys Thr His
            20

<210> SEQ ID NO 7
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Q, S, or R
<220> FEATURE:
<221> NAME/KEY: MOD_RES
<222> LOCATION: (13)..(13)
```

```
<223> OTHER INFORMATION: E, N, S, or R
<220> FEATURE:
<221> NAME/KEY: MOD_RES
<222> LOCATION: (17)..(17)
<223> OTHER INFORMATION: A, Q, L, E, N, Y, or R
<220> FEATURE:
<221> NAME/KEY: MOD_RES
<222> LOCATION: (21)..(27)
<223> OTHER INFORMATION: Any amino acid
<220> FEATURE:
<221> NAME/KEY: MOD_RES
<222> LOCATION: (45)..(45)
<223> OTHER INFORMATION: A, Q, L, or R
<220> FEATURE:
<221> NAME/KEY: MOD_RES
<222> LOCATION: (49)..(55)
<223> OTHER INFORMATION: Any amino acid
<220> FEATURE:
<221> NAME/KEY: MOD_RES
<222> LOCATION: (70)..(70)
<223> OTHER INFORMATION: E, N, S, or R
<220> FEATURE:
<221> NAME/KEY: MOD_RES
<222> LOCATION: (74)..(74)
<223> OTHER INFORMATION: A, Q, L, E, N, Y, or R
<220> FEATURE:
<221> NAME/KEY: MOD_RES
<222> LOCATION: (78)..(84)
<223> OTHER INFORMATION: Any amino acid
<220> FEATURE:
<221> NAME/KEY: MOD_RES
<222> LOCATION: (102)..(102)
<223> OTHER INFORMATION: A, Q, L, or R
<220> FEATURE:
<221> NAME/KEY: MOD_RES
<222> LOCATION: (106)..(112)
<223> OTHER INFORMATION: Any amino acid
<220> FEATURE:
<221> NAME/KEY: MOD_RES
<222> LOCATION: (127)..(127)
<223> OTHER INFORMATION: E, N, S, or R
<220> FEATURE:
<221> NAME/KEY: MOD_RES
<222> LOCATION: (131)..(131)
<223> OTHER INFORMATION: A, Q, L, E, N, Y, or R
<220> FEATURE:
<221> NAME/KEY: MOD_RES
<222> LOCATION: (135)..(141)
<223> OTHER INFORMATION: Any amino acid
<220> FEATURE:
<221> NAME/KEY: MOD_RES
<222> LOCATION: (159)..(159)
<223> OTHER INFORMATION: A, Q, L, or R
<220> FEATURE:
<221> NAME/KEY: MOD_RES
<222> LOCATION: (163)..(169)
<223> OTHER INFORMATION: Any amino acid

<400> SEQUENCE: 7

Val Pro Ala Ala Met Ala Glu Xaa Pro Phe Gln Cys Xaa Ile Cys Met
1               5                   10                  15

Xaa Asn Phe Ser Xaa Xaa Xaa Xaa Xaa Xaa Xaa His Ile Arg Thr His
            20                  25                  30

Thr Gly Glu Lys Pro Phe Ala Cys Asp Ile Cys Gly Xaa Lys Phe Ala
        35                  40                  45

Xaa Xaa Xaa Xaa Xaa Xaa Xaa His Thr Lys Ile His Thr Gly Ser Gln
    50                  55                  60

Lys Pro Phe Gln Cys Xaa Ile Cys Met Xaa Asn Phe Ser Xaa Xaa Xaa
65                  70                  75                  80

Xaa Xaa Xaa Xaa His Ile Arg Thr His Thr Gly Glu Lys Pro Phe Ala
                85                  90                  95

Cys Asp Ile Cys Gly Xaa Lys Phe Ala Xaa Xaa Xaa Xaa Xaa Xaa Xaa
```

```
                100             105                 110
His Thr Lys Ile His Thr Gly Ser Gln Lys Pro Phe Gln Cys Xaa Ile
            115                 120                 125

Cys Met Xaa Asn Phe Ser Xaa Xaa Xaa Xaa Xaa Xaa His Ile Arg
        130                 135                 140

Thr His Thr Gly Glu Lys Pro Phe Ala Cys Asp Ile Cys Gly Xaa Lys
145                 150                 155                 160

Phe Ala Xaa Xaa Xaa Xaa Xaa Xaa Xaa Thr His Thr Lys Ile His Leu
                165                 170                 175

Arg Gly Ser

<210> SEQ ID NO 8
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Q, S, or R
<220> FEATURE:
<221> NAME/KEY: MOD_RES
<222> LOCATION: (13)..(13)
<223> OTHER INFORMATION: E, N, S, or R
<220> FEATURE:
<221> NAME/KEY: MOD_RES
<222> LOCATION: (17)..(17)
<223> OTHER INFORMATION: A, Q, L, E, N, Y, or R
<220> FEATURE:
<221> NAME/KEY: MOD_RES
<222> LOCATION: (21)..(27)
<223> OTHER INFORMATION: Any amino acid
<220> FEATURE:
<221> NAME/KEY: MOD_RES
<222> LOCATION: (42)..(42)
<223> OTHER INFORMATION: E, N, S, or R
<220> FEATURE:
<221> NAME/KEY: MOD_RES
<222> LOCATION: (46)..(46)
<223> OTHER INFORMATION: A, Q, L, E, N, Y, or R
<220> FEATURE:
<221> NAME/KEY: MOD_RES
<222> LOCATION: (50)..(56)
<223> OTHER INFORMATION: Any amino acid
<220> FEATURE:
<221> NAME/KEY: MOD_RES
<222> LOCATION: (74)..(74)
<223> OTHER INFORMATION: A, Q, L, or R
<220> FEATURE:
<221> NAME/KEY: MOD_RES
<222> LOCATION: (78)..(84)
<223> OTHER INFORMATION: Any amino acid
<220> FEATURE:
<221> NAME/KEY: MOD_RES
<222> LOCATION: (99)..(99)
<223> OTHER INFORMATION: E, N, S, or R
<220> FEATURE:
<221> NAME/KEY: MOD_RES
<222> LOCATION: (103)..(103)
<223> OTHER INFORMATION: A, Q, L, E, N, Y, or R
<220> FEATURE:
<221> NAME/KEY: MOD_RES
<222> LOCATION: (107)..(113)
<223> OTHER INFORMATION: Any amino acid
<220> FEATURE:
<221> NAME/KEY: MOD_RES
<222> LOCATION: (131)..(131)
<223> OTHER INFORMATION: A, Q, L, or R
<220> FEATURE:
<221> NAME/KEY: MOD_RES
<222> LOCATION: (135)..(141)
```

<223> OTHER INFORMATION: Any amino acid

<400> SEQUENCE: 8

Val Pro Ala Ala Met Ala Glu Xaa Pro Phe Gln Cys Xaa Ile Cys Met
1               5                   10                  15

Xaa Lys Phe Ala Xaa Xaa Xaa Xaa Xaa Xaa His Thr Lys Ile His
            20                  25                  30

Thr Gly Ser Gln Lys Pro Phe Gln Cys Xaa Ile Cys Met Xaa Asn Phe
        35                  40                  45

Ser Xaa Xaa Xaa Xaa Xaa Xaa His Ile Arg Thr His Thr Gly Glu
    50                  55                  60

Lys Pro Phe Ala Cys Asp Ile Cys Gly Xaa Lys Phe Ala Xaa Xaa Xaa
65                  70                  75                  80

Xaa Xaa Xaa Xaa His Thr Lys Ile His Thr Gly Ser Gln Lys Pro Phe
                85                  90                  95

Gln Cys Xaa Ile Cys Met Xaa Asn Phe Ser Xaa Xaa Xaa Xaa Xaa
            100                 105                 110

Xaa His Ile Arg Thr His Thr Gly Glu Lys Pro Phe Ala Cys Asp Ile
        115                 120                 125

Cys Gly Xaa Lys Phe Ala Xaa Xaa Xaa Xaa Xaa Xaa Thr His Thr
130                 135                 140

Lys Ile His Leu Arg Gly Ser
145                 150

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Gly Glu Lys Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Gly Gly Gln Arg Pro
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Gly Gln Lys Pro
1               5

<210> SEQ ID NO 12
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Gly Ser Gln Lys Pro
1               5

<210> SEQ ID NO 13
<211> LENGTH: 76
<212> TYPE: DNA
<213> ORGANISM: Homo sapiens

<400> SEQUENCE: 13
ctaatcagag gccaaaccct tcctggagcc tgtgataaaa gcaactgtta gcttgcacta     60
gactagcttc aaagtt                                                    76

<210> SEQ ID NO 14
<211> LENGTH: 76
<212> TYPE: DNA
<213> ORGANISM: Homo sapiens

<400> SEQUENCE: 14
cttcctgcgg ggttttgtgc aaataaccca tgctcgggag cgaggccctg ggaaggagta     60
tctcgcttct ttgggt                                                    76

<210> SEQ ID NO 15
<211> LENGTH: 76
<212> TYPE: DNA
<213> ORGANISM: Homo sapiens

<400> SEQUENCE: 15
cctaccccca ccacctcacc ttccctcagc cttgtgtttc agcccagtt agctgccctt      60 agttgctgat gtattg                                                    76

<210> SEQ ID NO 16
<211> LENGTH: 76
<212> TYPE: DNA
<213> ORGANISM: Homo sapiens

<400> SEQUENCE: 16
agcacgtttc tccagtttcc agcctggggc ctggctataa agcaaatgct cagtccagca     60
ttgcggaatg caaggg                                                    76

<210> SEQ ID NO 17
<211> LENGTH: 76
<212> TYPE: DNA
<213> ORGANISM: Homo sapiens

<400> SEQUENCE: 17
acagcaccgt gctgcacggc gtcctccggc cttgctgcct ggcaatgggt agccacctgg     60
cgtctgtctc agaata                                                    76

<210> SEQ ID NO 18
<211> LENGTH: 76
<212> TYPE: DNA
<213> ORGANISM: Homo sapiens

<400> SEQUENCE: 18
```

```
ttcccagaag gcgattgaac ctgaagctgc gcctggcgcg tgagcctgtg ggggggacgc    60
ggctgagggg cttttga                                                   76

<210> SEQ ID NO 19
<211> LENGTH: 76
<212> TYPE: DNA
<213> ORGANISM: Homo sapiens

<400> SEQUENCE: 19
tatcccttcc ccaagtgcaa ccaacagttg ctctaaagct aggctggtgg agttggggaa    60
agggccagca agtgag                                                    76

<210> SEQ ID NO 20
<211> LENGTH: 76
<212> TYPE: DNA
<213> ORGANISM: Homo sapiens

<400> SEQUENCE: 20
tcctccatgc tcagaaagcc tttcttggag ccaggcacac aggaaatgtt agctagttag    60
cattggctct aatact                                                    76

<210> SEQ ID NO 21
<211> LENGTH: 76
<212> TYPE: DNA
<213> ORGANISM: Homo sapiens

<400> SEQUENCE: 21
tagctgggga gagattgcct ctctcagggc ctagccagtt cctagaaata gcaagggctc    60
agctgagagc atgctt                                                    76

<210> SEQ ID NO 22
<211> LENGTH: 76
<212> TYPE: DNA
<213> ORGANISM: Homo sapiens

<400> SEQUENCE: 22
tcccccggaa gtgtccgcac ctcctagagc ccagcgagcg agcgtttgtg cttttgtcct    60
ttgaaccggg tgtggt                                                    76

<210> SEQ ID NO 23
<211> LENGTH: 76
<212> TYPE: DNA
<213> ORGANISM: Homo sapiens

<400> SEQUENCE: 23
gactcattca tccactcatt ctgagcactt gctgcacact aggccctggg ctggggcttc    60
agcccaggag ttcact                                                    76

<210> SEQ ID NO 24
<211> LENGTH: 76
<212> TYPE: DNA
<213> ORGANISM: Homo sapiens

<400> SEQUENCE: 24
atgtagtctg acggccgcga ctggttcgta gcttttgagt gaggcggcgg gaagggagcg    60
agggaagagc ggcagt                                                    76

<210> SEQ ID NO 25
<211> LENGTH: 76
```

```
<212> TYPE: DNA
<213> ORGANISM: Homo sapiens

<400> SEQUENCE: 25
tcatgttatg gaagtggctt ctttccttaa gccttatgaa taagcctctg ctagcttcaa      60
actttgtgtg cagctt                                                     76

<210> SEQ ID NO 26
<211> LENGTH: 76
<212> TYPE: DNA
<213> ORGANISM: Homo sapiens

<400> SEQUENCE: 26
cataaagcac ttacaacagt gcctggcaaa tgcctagtgc acagcaagtg ttagctattg      60
ttaatgacta tccatt                                                     76

<210> SEQ ID NO 27
<211> LENGTH: 76
<212> TYPE: DNA
<213> ORGANISM: Homo sapiens

<400> SEQUENCE: 27
atttttgccc ctgtcttctc ttttcctcct ttgctgcatc ccaggctcca gcctttcagc      60
cctatttgca gtaccc                                                     76

<210> SEQ ID NO 28
<211> LENGTH: 76
<212> TYPE: DNA
<213> ORGANISM: Homo sapiens

<400> SEQUENCE: 28
acaaggggtt caaggttatg aataacctgt gctaatccca gaggcccag dacagagtaa      60 gtgggaacaa acactg                                                     76

<210> SEQ ID NO 29
<211> LENGTH: 76
<212> TYPE: DNA
<213> ORGANISM: Homo sapiens

<400> SEQUENCE: 29
cggaagttaa tatgatcatt gctaacattt gctgtgtttc aggcactgta agcatgtata      60
tgggtcctta aaggga                                                     76

<210> SEQ ID NO 30
<211> LENGTH: 76
<212> TYPE: DNA
<213> ORGANISM: Homo sapiens

<400> SEQUENCE: 30
tgagcccaga aacccttac ccttcctcct gcctcttgag aggccagtgt taggtgttag      60
ccggggtgca aagctc                                                     76

<210> SEQ ID NO 31
<211> LENGTH: 76
<212> TYPE: DNA
<213> ORGANISM: Homo sapiens

<400> SEQUENCE: 31
aacctggtgc gagcagcccg ggctacaggg ttgcctgagg tgtgggtccc aggatggagg      60
```
agccccaggc cggcgg                                                        76

<210> SEQ ID NO 32
<211> LENGTH: 76
<212> TYPE: DNA
<213> ORGANISM: Homo sapiens

<400> SEQUENCE: 32
acttcggtga aggaagtcat cagtgcagtt gccgacaagc tgggctccgg ggagggcctg       60
atcatagtca agatga                                                        76

<210> SEQ ID NO 33
<211> LENGTH: 76
<212> TYPE: DNA
<213> ORGANISM: Homo sapiens

<400> SEQUENCE: 33
ggggccaggc aggaagaaca gctaactcta gctcacctgc aaggctcagc actgggttca       60
tttgaagtag tgtcct                                                        76

<210> SEQ ID NO 34
<211> LENGTH: 76
<212> TYPE: DNA
<213> ORGANISM: Homo sapiens

<400> SEQUENCE: 34
ctcctttggg tgtggacggg actaacactt gctccatgtc agggctgcag gacctcctgg       60
ctgttgacag caggca                                                        76

<210> SEQ ID NO 35
<211> LENGTH: 76
<212> TYPE: DNA
<213> ORGANISM: Homo sapiens

<400> SEQUENCE: 35
gatgtttgaa aagcgctgag cctggcctgg cacctaaaca gctcagcaag tgttagccag       60
gatcactagc agtaat                                                        76

<210> SEQ ID NO 36
<211> LENGTH: 76
<212> TYPE: DNA
<213> ORGANISM: Homo sapiens

<400> SEQUENCE: 36
accctgccga tttccttcca gttgctcgct ggggcaaccg gctaggctgg aggaagggcg       60
aggacggtgt cacccc                                                        76

<210> SEQ ID NO 37
<211> LENGTH: 76
<212> TYPE: DNA
<213> ORGANISM: Homo sapiens

<400> SEQUENCE: 37
gaacatggtg aggacaaaat gatgtccagg agcctttttct ttggccattg ctagcctgag      60
acgaaaagtc agtggc                                                        76

<210> SEQ ID NO 38
<211> LENGTH: 76
<212> TYPE: DNA
<213> ORGANISM: Homo sapiens

<400> SEQUENCE: 38
agtctgtcag tctatcgtcc ctacctgcag cccaaagcat aagcaacatc ttgcccagct    60
cagaggtgac aacctc    76

<210> SEQ ID NO 39
<211> LENGTH: 76
<212> TYPE: DNA
<213> ORGANISM: Homo sapiens

<400> SEQUENCE: 39
caccgaccca aggaccactc cttccaggaa cctagcctaa agcaaaggtg cagacagccc    60
ggggccaccg ctgacc    76

<210> SEQ ID NO 40
<211> LENGTH: 76
<212> TYPE: DNA
<213> ORGANISM: Homo sapiens

<400> SEQUENCE: 40
ttgcaaaagg aagtttgaag ctagcagagg ctgattcatg aggttcaagg aaagaagtca    60
tctctgtaac ataaaa    76

<210> SEQ ID NO 41
<211> LENGTH: 76
<212> TYPE: DNA
<213> ORGANISM: Homo sapiens

<400> SEQUENCE: 41
cgtcccccag agtcctgttt cctctccttc agcccccaaa tgagcaaagg ttaggcccca    60
cccctgctga gtcagc    76

<210> SEQ ID NO 42
<211> LENGTH: 76
<212> TYPE: DNA
<213> ORGANISM: Homo sapiens

<400> SEQUENCE: 42
gtcaggggac agggtttcct agcatccgcg agccttacag aaaggcaact gtgcagtgct    60
ccagctggct ttctca    76

<210> SEQ ID NO 43
<211> LENGTH: 76
<212> TYPE: DNA
<213> ORGANISM: Homo sapiens

<400> SEQUENCE: 43
accatcagag aagctaacct ttcctgaggc ctaactactt tgcaggtcct gtattatgtc    60
ctctatagac attagg    76

<210> SEQ ID NO 44
<211> LENGTH: 76
<212> TYPE: DNA
<213> ORGANISM: Homo sapiens

<400> SEQUENCE: 44
gatcatttca aagaaaacat tctggaacag ttgcctatgg gcacggcagg gtgacggtgc    60
tgcttctggg tttgac    76

```
<210> SEQ ID NO 45
<211> LENGTH: 76
<212> TYPE: DNA
<213> ORGANISM: Homo sapiens

<400> SEQUENCE: 45
gaagggcaga gaactataat gacacagttg ctttattgct ggacccagga cagtttatac      60
agcagttcgg aaaggc                                                     76

<210> SEQ ID NO 46
<211> LENGTH: 76
<212> TYPE: DNA
<213> ORGANISM: Homo sapiens

<400> SEQUENCE: 46
acttattgta agtgacgcat gtgaccagtt gccaattgtt caggctacag cttggatctg      60
ttagcatcct cattta                                                     76

<210> SEQ ID NO 47
<211> LENGTH: 76
<212> TYPE: DNA
<213> ORGANISM: Homo sapiens

<400> SEQUENCE: 47
cccaggggct gtgggacact cagagagcct atgcctgtgc cctgggctcc gggaggggag      60
aggatctggg ggccag                                                     76

<210> SEQ ID NO 48
<211> LENGTH: 77
<212> TYPE: DNA
<213> ORGANISM: Homo sapiens

<400> SEQUENCE: 48
ccccaggggc tgtgggacac tcagagagcc tatgcctgtg ccctgggctc cggagaggga     60
gaggatctgg gggccag                                                    77

<210> SEQ ID NO 49
<211> LENGTH: 42
<212> TYPE: DNA
<213> ORGANISM: Homo sapiens

<400> SEQUENCE: 49
agcttcctgc agcctccctc aaagcagatg ttagcactat ta                         42

<210> SEQ ID NO 50
<211> LENGTH: 42
<212> TYPE: DNA
<213> ORGANISM: Homo sapiens

<400> SEQUENCE: 50
cctcacctag aacctgggcc cctgcaactg taacctgtgg ca                         42

<210> SEQ ID NO 51
<211> LENGTH: 42
<212> TYPE: DNA
<213> ORGANISM: Homo sapiens

<400> SEQUENCE: 51
ccagaggaag aacagttgct tgggtctagg cctcaggaag gg                         42
```

```
<210> SEQ ID NO 52
<211> LENGTH: 43
<212> TYPE: DNA
<213> ORGANISM: Homo sapiens

<400> SEQUENCE: 52
cctgtgctgg ggcctgggag gcaggcggct gctagccatc ctg                    43

<210> SEQ ID NO 53
<211> LENGTH: 42
<212> TYPE: DNA
<213> ORGANISM: Homo sapiens

<400> SEQUENCE: 53
tgacttagga agcagttgct acctgccagg ccccaggcta gg                     42

<210> SEQ ID NO 54
<211> LENGTH: 40
<212> TYPE: DNA
<213> ORGANISM: Homo sapiens

<400> SEQUENCE: 54
tcagtgattg ggttccgaat cctcctcctg aaagtggccg                        40

<210> SEQ ID NO 55
<211> LENGTH: 40
<212> TYPE: DNA
<213> ORGANISM: Homo sapiens

<400> SEQUENCE: 55
ccatatgcag aaaacagaaa ctgtacccct tccttacacc                        40

<210> SEQ ID NO 56
<211> LENGTH: 40
<212> TYPE: DNA
<213> ORGANISM: Homo sapiens

<400> SEQUENCE: 56
tggccctttg cagaaaaggt tgttgaaccc taccgtaaac                        40

<210> SEQ ID NO 57
<211> LENGTH: 40
<212> TYPE: DNA
<213> ORGANISM: Homo sapiens

<400> SEQUENCE: 57
ccggagagaa ggctccggtt cagcactgag atcaggacgg                        40

<210> SEQ ID NO 58
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Leu Val Lys Gly Glu Met Glu Lys Lys Lys Ser Asp Leu Arg His Lys
 1               5                  10                  15

Leu Lys His Val Pro His Glu Tyr Ile Glu Leu Ile Glu Ile Ala Gln
                20                  25                  30

Asp Ser Lys Gln Asn Arg Leu Phe Glu Phe Lys Val Val Glu Phe Leu
         35                 40                  45
```

```
Lys Glu Val Tyr Asp Tyr Asn Gly Lys His Leu Gly Gly Ser Arg Lys
 50                  55                  60

Pro Asp Gly Ala Leu Tyr Thr Asn Gly Leu Lys Thr Asp Tyr Gly Ile
 65                  70                  75                  80

Ile Leu Asp Thr Lys Ala Tyr Lys Asp Gly Tyr Ser Leu Pro Ile Ser
                 85                  90                  95

Gln Ala Asp Glu Met Gln Arg Tyr Val Asp Glu Asn Asn Arg Asn
            100                 105                 110

Ala Ile Ile Asn Pro Asn Glu Trp Trp Lys Val Tyr Pro Asn Ser Ile
            115                 120                 125

Leu Asp Phe Lys Phe Leu Phe Val Ser Gly Phe Phe Lys Gly Asp Tyr
130                 135                 140

Lys Lys Gln Leu Ala Arg Val Ser Asn Leu Thr Lys Arg Lys Gly Ala
145                 150                 155                 160

Val Leu Ser Val Glu Gln Leu Leu Gly Gly Lys Ile Lys Asp
                165                 170                 175

Gly Ser Leu Thr Leu Glu Asp Val Gly Asp Lys Phe Asn Asn Asp Glu
            180                 185                 190

Ile Ile Phe
        195

<210> SEQ ID NO 59
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Ile Val Lys Ser Ser Ile Glu Met Ser Lys Ala Asn Met Arg Asp
 1               5                  10                  15

Asn Leu Gln Met Leu Pro His Asp Tyr Ile Glu Leu Ile Glu Ile Ser
                 20                  25                  30

Gln Asp Pro Tyr Gln Asn Arg Ile Phe Glu Met Lys Val Met Asp Leu
            35                  40                  45

Phe Ile Asn Glu Tyr Gly Phe Ser Gly Ser His Leu Gly Gly Ser Arg
 50                  55                  60

Lys Pro Asp Gly Ala Met Tyr Ala His Gly Phe Gly Val Ile Val Asp
 65                  70                  75                  80

Thr Lys Ala Tyr Lys Asp Gly Tyr Asn Leu Pro Ile Ser Gln Ala Asp
                 85                  90                  95

Glu Met Glu Arg Tyr Val Arg Glu Asn Ile Asp Arg Asn Glu His Val
            100                 105                 110

Asn Ser Asn Arg Trp Trp Asn Ile Phe Pro Glu Asp Thr Asn Glu Tyr
            115                 120                 125

Lys Phe Leu Phe Val Ser Gly Phe Phe Lys Gly Asn Phe Glu Lys Gln
130                 135                 140

Leu Glu Arg Ile Ser Ile Asp Thr Gly Val Gln Gly Gly Ala Leu Ser
145                 150                 155                 160

Val Glu His Leu Leu Leu Gly Ala Glu Tyr Ile Lys Arg Gly Ile Leu
                165                 170                 175

Thr Leu Tyr Asp Phe Lys Asn Ser Phe Leu Asn Lys Glu Ile Gln Phe
            180                 185                 190

<210> SEQ ID NO 60
```

```
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Lys Ser Ser Thr Glu Glu Leu Lys Ala Gln Leu Arg Thr Gln Leu Thr
1               5                   10                  15

Asn Ile Ser Leu Asp Tyr Leu Gln Leu Val Asp Ile Ser Thr Asp Ser
                20                  25                  30

Lys Gln Asn Arg Leu Phe Glu Met Lys Val Met Asp Leu Phe Ile Asn
            35                  40                  45

Glu Leu Asp Phe Lys Gly Ser His Leu Gly Gly Arg Lys Pro Asp
        50                  55                  60

Gly Ala Val Tyr Thr Thr Asn Tyr Gly Ile Ile Val Asp Thr Lys Ala
65                  70                  75                  80

Tyr Lys Asp Gly Tyr Asn Leu Pro Ile Ser Gln Ala Asp Glu Met Glu
                85                  90                  95

Arg Tyr Val Arg Glu Asn Ile Asp Arg Asn Lys Gly Ile Asn Pro Asn
            100                 105                 110

Glu Trp Trp Thr Ile Phe Pro Ser Ser Ile Asn Asp Phe Thr Phe Leu
        115                 120                 125

Phe Val Ser Gly Tyr Phe Lys Gly Asn Phe Glu Gly Gln Leu Gln Arg
130                 135                 140

Ile Ser Met Ser Thr Gly Ile Lys Gly Gly Ala Ile Gly Val Glu His
145                 150                 155                 160

Leu Leu Leu Cys Ala Glu Tyr Tyr Lys Arg Gly Ile Leu Ser His Gln
                165                 170                 175

Asp Ile Arg Asp Ser Phe Lys Asn Ala Glu Ile Glu Phe
            180                 185

<210> SEQ ID NO 61
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ile Lys Ser Asn Ile Ser Leu Leu Lys Asp Glu Leu Arg Gly Gln Ile
1               5                   10                  15

Ser His Ile Ser His Glu Tyr Leu Ser Leu Ile Asp Leu Ala Phe Asp
                20                  25                  30

Ser Lys Gln Asn Arg Leu Phe Glu Met Lys Val Leu Glu Leu Leu Val
            35                  40                  45

Asn Glu Tyr Gly Phe Lys Gly Arg His Leu Gly Gly Ser Arg Lys Pro
        50                  55                  60

Asp Gly Ile Val Tyr Ser Thr Thr Leu Glu Asp Asn Phe Gly Ile Ile
65                  70                  75                  80

Val Asp Thr Lys Ala Tyr Ser Glu Gly Tyr Ser Leu Pro Ile Ser Gln
                85                  90                  95

Ala Asp Glu Met Glu Arg Tyr Val Arg Glu Asn Ser Asn Arg Asp Glu
            100                 105                 110

Glu Val Asn Pro Asn Lys Trp Trp Glu Asn Phe Ser Glu Glu Val Lys
        115                 120                 125
```

```
Lys Tyr Tyr Phe Val Phe Ile Ser Gly Ser Phe Lys Gly Lys Phe Glu
            130                 135                 140

Glu Gln Leu Arg Arg Leu Ser Met Thr Thr Gly Val Asn Gly Ser Ala
145                 150                 155                 160

Val Asn Val Val Asn Leu Leu Leu Gly Ala Glu Lys Ile Arg Ser Gly
                165                 170                 175

Glu Met Thr Ile Glu Glu Leu Glu Arg Ala Met Phe Asn Asn Ser Glu
            180                 185                 190

<210> SEQ ID NO 62
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Lys Leu Ala Lys Ser Ser Gln Ser Glu Thr Lys Glu Lys Leu Arg Glu
1               5                   10                  15

Lys Leu Arg Asn Leu Pro His Glu Tyr Leu Ser Leu Val Asp Leu Ala
            20                  25                  30

Tyr Asp Ser Lys Gln Asn Arg Leu Phe Glu Met Lys Val Ile Glu Leu
        35                  40                  45

Leu Thr Glu Glu Cys Gly Phe Gln Gly Leu His Leu Gly Gly Ser Arg
    50                  55                  60

Arg Pro Asp Gly Val Leu Tyr Thr Ala Gly Leu Thr Asp Asn Tyr Gly
65                  70                  75                  80

Ile Ile Leu Asp Thr Lys Ala Tyr Ser Ser Gly Tyr Ser Leu Pro Ile
                85                  90                  95

Ala Gln Ala Asp Glu Met Glu Arg Tyr Val Arg Glu Asn Gln Thr Arg
            100                 105                 110

Asp Glu Leu Val Asn Pro Asn Gln Trp Trp Glu Asn Phe Glu Asn Gly
        115                 120                 125

Leu Gly Thr Phe Tyr Phe Leu Phe Val Ala Gly His Phe Asn Gly Asn
    130                 135                 140

Val Gln Ala Gln Leu Glu Arg Ile Ser Arg Asn Thr Gly Val Leu Gly
145                 150                 155                 160

Ala Ala Ala Ser Ile Ser Gln Leu Leu Leu Ala Asp Ala Ile Arg
                165                 170                 175

Gly Gly Arg Met Asp Arg Glu Arg Leu Arg
            180                 185

<210> SEQ ID NO 63
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Lys Ile Ser Lys Thr Asn Ile Leu Glu Leu Asp Lys Val Arg Asp
1               5                   10                  15

Lys Leu Lys Tyr Val Asp His Arg Tyr Leu Ala Leu Ile Asp Leu Ala
            20                  25                  30

Tyr Asp Gly Thr Ala Asn Arg Asp Phe Glu Ile Gln Thr Ile Asp Leu
        35                  40                  45
```

Leu Ile Asn Glu Leu Lys Phe Lys Gly Val Arg Leu Gly Glu Ser Arg
 50                  55                  60

Lys Pro Asp Gly Ile Ile Ser Tyr Asn Ile Asn Gly Val Ile Ile Asp
 65                  70                  75                  80

Asn Lys Ala Tyr Ser Thr Gly Tyr Asn Leu Pro Ile Asn Gln Ala Asp
                 85                  90                  95

Glu Met Ile Arg Tyr Ile Glu Glu Asn Gln Thr Arg Asp Glu Lys Ile
            100                 105                 110

Asn Ser Asn Lys Trp Trp Glu Ser Phe Asp Glu Lys Val Lys Asp Phe
        115                 120                 125

Asn Tyr Leu Phe Val Ser Phe Phe Lys Gly Asn Phe Lys Asn Asn
    130                 135                 140

Leu Lys His Ile Ala Asn Arg Thr Gly Val Asn Gly Gly Ala Ile Asn
145                 150                 155                 160

Val Glu Asn Leu Leu Tyr Phe Ala Glu Glu Leu Lys Ala Gly Arg Ile
                165                 170                 175

Ser Tyr Leu Asp Ser Phe Lys Met Tyr Asn Asn Asp Glu Ile
                180                 185                 190

<210> SEQ ID NO 64
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Val Lys Ser Glu Val Ser Val Phe Lys Asp Tyr Leu Arg Thr His Leu
1               5                   10                  15

Thr His Val Asp His Arg Tyr Leu Ile Leu Val Asp Leu Gly Phe Asp
                20                  25                  30

Gly Ser Ser Asp Arg Asp Tyr Glu Met Lys Thr Ala Glu Leu Phe Thr
            35                  40                  45

Ala Glu Leu Gly Phe Met Gly Ala Arg Leu Gly Asp Thr Arg Lys Pro
 50                  55                  60

Asp Val Cys Val Tyr His Gly Ala Asn Gly Leu Ile Ile Asp Asn Lys
 65                  70                  75                  80

Ala Tyr Gly Lys Gly Tyr Ser Leu Pro Ile Lys Gln Ala Asp Glu Ile
                 85                  90                  95

Tyr Arg Tyr Ile Glu Glu Asn Lys Glu Arg Asp Ala Arg Leu Asn Pro
            100                 105                 110

Asn Gln Trp Trp Lys Val Phe Asp Glu Ser Val Thr His Phe Arg Phe
        115                 120                 125

Ala Phe Ile Ser Gly Ser Phe Thr Gly Gly Phe Lys Asp Arg Ile Glu
    130                 135                 140

Leu Ile Ser Met Arg Ser Gly Ile Cys Gly Ala Ala Val Asn Ser Val
145                 150                 155                 160

Asn Leu Leu Leu Met Ala Glu Glu Leu Lys Ser Gly Arg Leu Asp Tyr
                165                 170                 175

Glu Glu Trp Phe Gln Tyr Phe Asp Asn Asp Glu Ile Ser Phe
            180                 185                 190

<210> SEQ ID NO 65
<211> LENGTH: 192
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 65

```
Gln Glu Leu Lys Asp Glu Gln Ala Glu Lys Arg Lys Ala Lys Phe Leu
1               5                   10                  15

Lys Glu Thr Asn Leu Pro Met Lys Tyr Ile Glu Leu Leu Asp Ile Ala
            20                  25                  30

Tyr Asp Gly Lys Arg Asn Arg Asp Phe Glu Ile Val Thr Met Glu Leu
        35                  40                  45

Phe Arg Asn Val Tyr Arg Leu His Ser Lys Leu Leu Gly Gly Gly Arg
    50                  55                  60

Lys Pro Asp Gly Leu Leu Tyr Gln Asp Arg Phe Gly Val Ile Val Asp
65                  70                  75                  80

Thr Lys Ala Tyr Gly Lys Gly Tyr Ser Lys Ser Ile Asn Gln Ala Asp
                85                  90                  95

Glu Met Ile Arg Tyr Ile Glu Asp Asn Lys Arg Arg Asp Glu Asn Arg
            100                 105                 110

Asn Pro Ile Lys Trp Trp Glu Ala Phe Pro Asp Thr Ile Pro Glu Phe
        115                 120                 125

Tyr Phe Met Trp Val Ser Ser Lys Phe Ile Gly Lys Phe Gln Glu Gln
    130                 135                 140

Leu Asp Tyr Thr Ser Asn Glu Thr Gln Ile Lys Gly Ala Ala Leu Asn
145                 150                 155                 160

Val Glu Gln Leu Leu Leu Gly Ala Asp Leu Val Leu Lys Gly Gln Leu
                165                 170                 175

His Ile Ser Asp Leu Pro Ser Tyr Phe Gln Asn Lys Glu Ile Glu Phe
            180                 185                 190
```

<210> SEQ ID NO 66
<211> LENGTH: 189
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Lys Val Ser Lys Thr Asn Ile Leu Glu Leu Lys Asp Asn Thr Arg Glu
1               5                   10                  15

Lys Leu Val Tyr Leu Asp His Arg Tyr Leu Ser Leu Phe Asp Leu Ala
            20                  25                  30

Tyr Asp Asp Lys Ala Ser Arg Asp Phe Glu Ile Gln Thr Ile Asp Leu
        35                  40                  45

Leu Ile Asn Glu Leu Gln Phe Lys Gly Leu Arg Leu Gly Glu Arg Arg
    50                  55                  60

Lys Pro Asp Gly Ile Ile Tyr Gly Val Asn Gly Val Ile Ile Asp Asn
65                  70                  75                  80

Lys Ala Tyr Ser Lys Gly Tyr Asn Leu Pro Ile Arg Gln Ala Asp Glu
                85                  90                  95

Met Ile Arg Tyr Ile Gln Glu Asn Gln Ser Arg Asp Glu Lys Leu Asn
            100                 105                 110

Pro Asn Lys Trp Trp Glu Asn Phe Glu Glu Thr Ser Lys Phe Asn
        115                 120                 125

Tyr Leu Phe Ile Ser Ser Lys Phe Ile Ser Gly Phe Lys Lys Asn Leu
```

```
                130               135               140
Gln Tyr Ile Ala Asp Arg Thr Gly Val Asn Gly Gly Ala Ile Asn Val
145                 150               155               160

Glu Asn Leu Leu Cys Phe Ala Glu Met Leu Lys Ser Gly Lys Leu Glu
                165               170               175

Tyr Asn Asp Phe Phe Asn Gln Tyr Asn Asn Asp Glu Ile
                180               185
```

<210> SEQ ID NO 67
<211> LENGTH: 185
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Ile Glu Glu Gln Lys Ala Ile Phe Leu Gln Lys Thr Lys Leu Pro Leu
1               5                   10                  15

Ser Tyr Ile Glu Leu Leu Glu Ile Ala Arg Asp Gly Lys Arg Ser Arg
                20                  25                  30

Asp Phe Glu Phe Ile Thr Met Glu Leu Phe Lys Asn Ile Tyr Lys Ile
            35                  40                  45

Asn Ala Arg Ile Leu Gly Gly Ala Arg Lys Pro Asp Gly Val Leu Tyr
50                  55                  60

Met Pro Glu Phe Gly Val Ile Val Asp Thr Lys Ala Tyr Ala Asp Gly
65                  70                  75                  80

Tyr Ser Lys Ser Ile Ala Gln Ala Asp Glu Met Ile Arg Tyr Ile Glu
                85                  90                  95

Asp Asn Lys Arg Arg Asp Pro Ser Arg Asn Ser Thr Lys Trp Trp Glu
            100                 105                 110

His Phe Pro Thr Ser Ile Asn Asn Phe Tyr Phe Leu Trp Val Ser Ser
        115                 120                 125

Val Phe Val Asn Lys Phe His Glu Gln Leu Ser Tyr Thr Ala Gln Glu
130                 135                 140

Thr Gln Thr Val Gly Ala Ala Leu Ser Val Glu Gln Leu Leu Leu Gly
145                 150                 155                 160

Ala Asp Ser Val Leu Lys Gly Asn Leu Thr Thr Glu Lys Phe Ile Asp
                165                 170                 175

Ser Phe Lys Asn Gln Glu Ile Val Phe
            180                 185
```

<210> SEQ ID NO 68
<211> LENGTH: 9
<212> TYPE: PRT
<213> ORGANISM: Unknown
<220> FEATURE:
<223> OTHER INFORMATION: Description of Unknown: "LAGLIDADG" family peptide motif sequence

<400> SEQUENCE: 68

```
Leu Ala Gly Leu Ile Asp Ala Asp Gly
1               5
```

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 69

Asn Glu Leu Asp
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Lys Lys Arg
1

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tgtcaggatt gggttccg                                                    18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ctcctgaaag tggccggg                                                    18
```

ENGINEERED TARGET SPECIFIC NUCLEASES

CROSS-REFERENCE TO RELATED APPLICATIONS

The present application claims the benefit of U.S. Provisional Application No. 62/378,978, filed Aug. 24, 2016 and U.S. Provisional Application No. 62/443,981, filed Jan. 9, 2017, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Oct. 10, 2019, is named 83250156SL10_10_19.txt and is 41,529 bytes in size.

STATEMENT OF RIGHTS TO INVENTIONS MADE UNDER FEDERALLY SPONSORED RESEARCH

Not applicable.

TECHNICAL FIELD

The present disclosure is in the fields of polypeptide and genome engineering and homologous recombination.

BACKGROUND

Artificial nucleases, such as engineered zinc finger nucleases (ZFN), transcription-activator like effector nucleases (TALENs), the CRISPR/Cas system with an engineered crRNA/tracr RNA (single guide RNA'), also referred to as RNA guided nucleases, and/or nucleases based on the Argonaute system (e.g., from *T. thermophilus*, known as 'TtAgo', (Swarts et al (2014) *Nature* 507(7491): 258-261), comprise DNA binding domains (nucleotide or polypeptide) associated with or operably linked to cleavage domains, and have been used for targeted alteration of genomic sequences. For example, nucleases have been used to insert exogenous sequences, inactivate one or more endogenous genes, create organisms (e.g., crops) and cell lines with altered gene expression patterns, and the like. See, e.g., U.S. Pat. Nos. 9,255,250; 9,200,266; 9,045,763; 9,005,973; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983 and 20130177960 and 20150056705. For instance, a pair of nucleases (e.g., zinc finger nucleases, TALENs, dCas-Fok fusions) may be used to cleave genomic sequences. Each member of the pair generally includes an engineered (non-naturally occurring) DNA-binding protein linked to one or more cleavage domains (or half-domains) of a nuclease. When the DNA-binding proteins bind to their target sites, the cleavage domains that are linked to those DNA binding proteins are positioned such that dimerization and subsequent cleavage of the genome can occur.

Generally, intermolecular ion pairs (salt bridges) are essential for many DNA-protein interactions. Often, charged amino acid side chains (i.e. —NH3+, =NH2+) interact with the negatively charged phosphate groups of the DNA backbone to form a salt bridge. These ion pairs can be quite dynamic and can alternate between direct pairing of the two ions and pairing that is a 'solvent-separated ion pair' when a solvent (e.g. a water molecule) is inserted between the two ions (Chen et al (2015) *J Phys Chem Lett* 6:2733-2737).

In regards to zinc finger proteins, the specificity of a ZFP for a target DNA sequence is dependent upon sequence specific contacts between the zinc finger domains and specific DNA bases. In addition, the zinc finger domains also comprise amino acid residues that take part in non-specific ion pair interactions with the phosphates of the DNA backbone. Elrod-Erickson et al ((1996) *Structure* 4:1171) demonstrated through co-crystallization of a zinc finger protein and its cognate DNA target that there are specific amino acids capable of interacting with the phosphates on the DNA backbone through formation of hydrogen bonds. Zinc finger proteins that employ the well-known Zif268 backbone typically have an arginine as the amino terminal residue of their second strand of β-sheet, which is also the second position carboxyl-terminal to the second invariant cysteine (see FIG. 5A). This position can be referred to as (−5) within each zinc finger domain, as it is $5^{th}$ residue preceding the start of the α-helix (FIG. 5A). The arginine at this position can interact with a phosphate on the DNA backbone via formation of a charged hydrogen bond with its side-chain guanidinium group. Zinc finger proteins in the Zif268 backbone also frequently have a lysine at a position that is 4 residues amino-terminal to the first invariant cysteine. This position can be referred to as (−14) within each finger, as it is $14^{th}$ residue preceding the start of the α-helix for zinc fingers with two residues between the zinc coordinating cysteine residues (FIG. 5A). The lysine can interact with a phosphate on the DNA backbone via formation of a water-mediated charged hydrogen bond with its side-chain amino group. Since phosphate groups are found all along the DNA backbone, this type of interaction between the zinc finger and a DNA molecule is generally considered to be non-sequence specific (J. Miller, Massachusetts Institute of Technology Ph.D. Thesis, 2002).

Recent studies have hypothesized that non-specific phosphate contacting side chains in some nucleases may also account for some amount of non-specificity cleavage activity of those nucleases (Kleinstiver et al, (2016) *Nature* 529(7587):490-5; Guilinger et al (2014) *Nat Meth:* 429-435). Researchers have proposed that these nucleases may possess 'excess DNA-binding energy', meaning that the nucleases may have a greater affinity for their DNA target than is required to substantially bind and cleave the target site. Thus, attempts were made to decrease the cationic charges in the TALE DNA binding domain (Guilinger, ibid) or the Cas9 DNA binding domain (Kleinstiver, ibid) to lower the DNA-binding energy of these nucleases, which resulted in increased cleavage specificity in vitro. However, additional studies (Sternberg et al (2015) *Nature* 527(7576):110-113) also suggest a role in proper folding and activation of the Cas9 nuclease domain for some of the cationic amino acids that were mutated in the Kleinstiver study of the Cas9 DNA binding domain. Thus, the exact role of these amino acids in Cas9 activity is not known.

For optimal cleavage specificity by a sequence-selective (artificial) nuclease, it is desirable to arrange conditions so that on-target binding and activity is not saturating. Under saturating conditions—by definition—an excess of nuclease is used over what is necessary to achieve complete on-target activity. This excess provides no on-target benefit but can nonetheless result in increased cleavage at off-target sites. For monomeric nucleases, saturating conditions may be readily avoided by performing a simple dose response study to identify and avoid the saturating plateau on a titration curve. However, for a dimeric nuclease such as ZFN, TALEN or dCas-Fok, identifying and avoiding saturating conditions may be more complicated if the binding affinities of the individual monomers are dissimilar. In such cases, a dose response study using a simple 1:1 nuclease ratio will only reveal the saturation point of the weaker binding monomer. Under such a scenario, if, for example, monomer affinities differ by a factor of 10, then at the saturation point identified in a 1:1 titration study the higher affinity monomer will be present at a concentration that is 10-fold higher than it needs to be. The resulting excess of the higher affinity monomer can in turn lead to increased off-target activity without providing any beneficial increase in cleavage at the intended target, potentially leading to a decreased specificity overall for any given nuclease pair.

To decrease off-target cleavage events, engineered obligate heterodimeric cleavage half-domains have been developed. See, e.g., U.S. Pat. Nos. 7,914,796; 8,034,598; 8,962,281 and 8,623,618; U.S. Patent Publication Nos. 20080131962 and 20120040398. These obligate heterodimers dimerize and cleave their targets only when the differing engineered cleavage domains are positioned at the appropriate target site by the ZFPs, thereby reducing and/or eliminating monomeric off-target cleavage.

However, there remains a need for additional methods and compositions to engineered nuclease cleavage systems to decrease off-target cleavage activity.

SUMMARY

The present disclosure provides methods and compositions to increase the specificity of a nuclease (e.g., nuclease pair) for its intended target relative to other unintended cleavage sites, also known as off-target sites. Thus, described herein are artificial nucleases (e.g., zinc finger nucleases (ZFNs), TALENs, CRISPR/Cas nucleases) comprising mutations in one or more of the DNA binding domain regions (e.g., the backbone of a zinc finger protein or TALE) and/or one or more mutations in a FokI nuclease cleavage domain or cleavage half domain. Further, described herein are methods to increase specificity of cleavage activity by using these novel nucleases (e.g., ZFNs, TALENs, etc.) and/or through independent titration of the engineered cleavage half-domain partners of a nuclease complex. When used individually or in combination, the methods and compositions of the invention provide surprising and unexpected increases in targeting specificity via reductions in off-target cleavage activity. The disclosure also provides methods of using these compositions for targeted cleavage of cellular chromatin in a region of interest and/or integration of a transgene via targeted integration at a predetermined region of interest in cells.

Thus, in one aspect, described herein is an engineered nuclease cleavage half domain comprising one or more mutations as compared to a parental (e.g., wild-type) cleavage domain from which these mutants are derived. In certain embodiments, the one or more mutations are one or more of the mutations shown in any of the appended Tables and Figures, including any combination of these mutants with each other and with other mutants (such as dimerization and/or catalytic domain mutants as well as nickase mutations). Mutations as described herein, include but are not limited to, mutations that change the charge of the cleavage domain, for example mutations of positively charged residues to non-positively charged residues (e.g., mutations of K and R residues (e.g., mutated to S); N residues (e.g., to D), and Q residues (e.g., to E); mutations to residues that are predicted to be close to the DNA backbone based on molecular modeling and that show variation in FokI homologs (FIGS. 1 and 17); and/or mutations at other residues (e.g., U.S. Pat. No. 8,623,618 and Guo et al, (2010) *J. Mol. Biol.* 400(1):96-107).

The most promising mutations were found using the second criteria. The initial promising mutations were positively charged residues predicted to be close to the DNA backbone when FokI is bound to DNA. The cleavage domains described herein may include one, two, three, four, five or more of the mutations described herein and may further include additional known mutations. Therefore, mutations of the invention do not include specific mutations disclosed in U.S. Pat. No. 8,623,618 (e.g., N527D, S418P, K448M, Q531R, etc.) when used alone; however, provided here are novel mutants that can be used in combination with the mutants of U.S. Pat. No. 8,623,618. Nickase mutants wherein one of the catalytic nuclease domains in a dimer pair comprises one or more mutations rendering it catalytically inactive (see U.S. Pat. Nos. 8,703,489; 9,200,266; and 9,631,186) may also be used in combination with any of the mutants described herein. Nickases can be ZFN nickases, TALEN nickases and CRISPR/dCas systems.

In certain embodiments, the engineered cleavage half domains are derived from FokI or FokI homologues and comprise a mutation in one or more of amino acid residues 416, 422, 447, 448, and/or 525, numbered relative to the wild-type full length FokI as shown in SEQ ID NO:1 or corresponding residues in FokI homologues (see, FIG. 17). In other embodiments, the cleavage half domains derived from FokI comprises a mutation in one or more of amino acid residues 414-426, 443-450, 467-488, 501-502, and/or 521-531, including one or more of 387, 393, 394, 398, 400, 416, 418, 422, 427, 434, 439, 441, 442, 444, 446, 448, 472, 473, 476, 478, 479, 480, 481, 487, 495, 497, 506, 516, 523, 525, 527, 529, 534, 559, 569, 570, and/or 571. The mutations may include mutations to residues found in natural restriction enzymes homologous to FokI at the corresponding positions (FIG. 17). In certain embodiments, the mutations are substitutions, for example substitution of the wild-type residue with any different amino acid, for example alanine (A), cysteine (C), aspartic acid (D), glutamic acid (E), histidine (H), phenylalanine (F), glycine (G), asparagine (N), serine (S) or threonine (T). Any combination of mutants is contemplated, including but not limited to those shown in the appended Tables and Figures. In certain embodiments, the FokI nuclease domain comprises a mutation at one or more of 416, 422, 447, 479 and/or 525 (numbered relative to wild-type, SEQ ID NO:1). The nuclease domains may also comprise one or more mutations at positions 418, 432, 441, 448, 476, 481, 483, 486, 487, 490, 496, 499, 523, 527, 537, 538 and 559, including but not limited to ELD, KKR, ELE, KKS. See, e.g., U.S. Pat. No. 8,623,618. In still further embodiments, the cleavage domain includes mutations at one or more of the residues shown in Table 15 (e.g., 419, 420, 425, 446, 447, 470, 471, 472, 475, 478, 480, 492, 500, 502, 521, 523, 526, 530, 536, 540, 545, 573 and/or 574). In certain embodiments, the variant cleavage domains described herein include mutations to the residues involved in nuclease dimerization (dimerization domain mutations), and one or more additional mutations; for example to phosphate contact residues: e.g. dimerization mutants (such as ELD, KKR, ELE, KKS, etc.) in combination with one, two, three, four, five, six or more mutations at amino acid positions outside of the dimerization domain, for example in amino acid residues that may participate in phosphate contact. In a preferred embodiment, the mutation at positions 416, 422, 447, 448 and/or 525 comprise replacement of a positively charged amino acid with an uncharged or a negatively charged amino acid. In other embodiments, mutations at positions 446, 472 and/or 478 (and optionally additional residues for example in the dimerization or catalytic domains) are made.

In other embodiments, the engineered cleavage half domain comprises mutations in the dimerization domain, for example, amino acid residues 490, 537, 538, 499, 496 and 486 in addition to the mutations described herein. In a preferred embodiment, the invention provides fusion proteins wherein the engineered cleavage half-domain comprises a polypeptide in which the wild-type Gln (Q) residue at position 486 is replaced with a Glu (E) residue, the wild-type Ile (I) residue at position 499 is replaced with a Leu (L) residue and the wild-type Asn (N) residue at position 496 is replaced with an Asp (D) or a Glu (E) residue ("ELD" or "ELE") in addition to one or more mutations described herein. In another embodiment, the engineered cleavage half domains are derived from a wild-type FokI or FokI homologue cleavage half domain and comprise mutations in the amino acid residues 490, 538 and 537, numbered relative to wild-type FokI (SEQ ID NO:1) in addition to the one or more mutations at amino acid residues 416, 422, 447, 448, or 525. In a preferred embodiment, the invention provides a fusion protein, wherein the engineered cleavage half-domain comprises a polypeptide in which the wild-type Glu (E) residue at position 490 is replaced with a Lys (K) residue, the wild-type Ile (I) residue at position 538 is replaced with a Lys (K) residue, and the wild-type His (H) residue at position 537 is replaced with a Lys (K) residue or an Arg (R) residue ("KKK" or "KKR") (see U.S. Pat. No. 8,962,281, incorporated by reference herein) in addition to one or more mutations described herein.

In another embodiment, the engineered cleavage half domains are derived from a wild-type FokI cleavage half domain or homologues thereof and comprise mutations in the amino acid residues 490, and 538, numbered relative to wild-type FokI in addition to the one or more mutations at amino acid residues 416, 422, 447, 448, or 525. In a preferred embodiment, the invention provides a fusion protein, wherein the engineered cleavage half-domain comprises a polypeptide in which the wild-type Glu (E) residue at position 490 is replaced with a Lys (K) residue, and the wild-type Ile (I) residue at position 538 is replaced with a Lys (K) residue ("KK") in addition to one or more mutations at positions 416, 422, 447, 448, or 525. In a preferred embodiment, the invention provides a fusion protein, wherein the engineered cleavage half-domain comprises a polypeptide in which the wild-type Gln (Q) residue at position 486 is replaced with an Glu (E) residue, and the wild-type Ile (I) residue at position 499 is replaced with a Leu (L) residue ("EL") (See U.S. Pat. No. 8,034,598, incorporated by reference herein) in addition to one or more mutations at positions 416, 422, 447, 448, or 525.

In one aspect, the invention provides fusion molecules wherein the engineered cleavage half-domain comprises a polypeptide in which the wild-type amino acid residue at one or more of positions 387, 393, 394, 398, 400, 402, 416, 422, 427, 434, 439, 441, 446, 447, 448, 469, 472, 478, 487, 495, 497, 506, 516, 525, 529, 534, 559, 569, 570, 571 in the FokI catalytic domain are mutated. In some embodiments, the one or more mutations alter the wild type amino acid from a positively charged residue to a neutral residue or a negatively charged residue. In any of these embodiments, the mutants described may also be made in a FokI domain comprising one or more additional mutations. In preferred embodiments, these additional mutations are in the dimerization domain, e.g. at positions 499, 496, 486, 490, 538 and 537. Mutations include substitutions, insertions and/or deletions of one or more amino acid residues.

In yet another aspect, any of the engineered cleavage half domains described above may be incorporated into artificial nucleases, for example by associating them with a DNA-binding domain, including but not limited to zinc finger nucleases, TALENs, CRISPR/Cas nucleases, and the like. The zinc finger proteins of the zinc finger nucleases may comprise non-canonical zinc-coordinating residues (e.g. CCHC rather than the canonical C2H2 configuration, see U.S. Pat. No. 9,234,187).

In another aspect, fusion molecules comprising a DNA binding domain and an engineered FokI or homologue thereof cleavage half-domain as described herein that produce an artificial nuclease are provided. In certain embodiments, the DNA-binding domain of the fusion molecule is a zinc finger binding domain (e.g., an engineered zinc finger binding domain). In other embodiments, the DNA-binding domain is a TALE DNA-binding domain. In still further embodiments, the DNA binding domain comprises a DNA binding molecule (e.g. guide RNA) and a catalytically inactive Cas9 or Cfp1 protein (dCas9 or dCfp1). In some embodiments, the engineered fusion molecules form a nuclease complex with a catalytically inactive engineered cleavage half-domain such that the dimeric nuclease is only capable of cleaving only one strand of a double-stranded DNA molecule, forming a nickase (see U.S. Pat. No. 9,200,266).

The methods and compositions of the invention also include mutations to one or more amino acids within the DNA binding domain outside the residues that recognize the nucleotides of the target sequence (e.g., one or more mutations to the 'ZFP backbone' (outside the DNA recognition helix region) or to the 'TALE backbone' (outside of the RVDs)) that can interact non-specifically with phosphates on the DNA backbone. Thus, in certain embodiments, the invention includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), (−9) and/or position (−14) relative to the DNA binding helix. In some embodiments, a zinc finger may comprise one or more mutations at (−5), (−9) and/or (−14). In further embodiments, one or more zinc fingers in a multi-finger zinc finger protein may comprise mutations in (−5), (−9) and/or (−14). In some embodiments, the amino acids at (−5), (−9) and/or (−14) (e.g. an arginine (R) or lysine (K)) are mutated to an alanine (A), leucine (L), Ser (S), Asp (N), Glu (E), Tyr (Y) and/or glutamine (Q).

In another aspect, polynucleotides encoding any of the engineered cleavage half-domains or fusion proteins as described herein are provided.

In yet another aspect, cells comprising any of the nucleases, polypeptides (e.g., fusion molecules or fusion polypeptides) and/or polynucleotides as described herein are also provided. In one embodiment, the cells comprise a pair of fusion polypeptides, one fusion polypeptide comprising, in addition to one or more mutations in amino acid residues 393, 394, 398, 416, 421, 422, 442, 444, 447, 448, 473, 480, 530 and/or 525, an ELD or ELE cleavage half-domain and one fusion polypeptide comprising, in addition to one or more mutations at residues 393, 394, 398, 416, 421, 422, 442, 444, 446, 447, 448, 472, 473, 478, 480, 530 and/or 525, a KKK or KKR cleavage half-domain (see U.S. Pat. No. 8,962,281).

In any of these fusion polypeptides described herein, the ZFP partners may further comprise mutations in the zinc finger DNA binding domain in the (−5), (−9) and/or (−14) positions. In some embodiments, the Arg (R) at position −5 is changed to a Tyr (Y), Asp (N), Glu (E), Leu (L), Gln (Q), or Ala (A). In other embodiments, the Arg (R) at position (−9) is replaced with Ser (S), Asp (N), or Glu (E). In further embodiments, the Arg (R) at position (−14) is replaced with Ser (S) or Gln (Q). In other embodiments, the fusion polypeptides can comprise mutations in the zinc finger DNA binding domain where the amino acids at the (−5), (−9) and/or (−14) positions are changed to any of the above listed amino acids in any combination.

Also provided herein are cells that have been modified by the polypeptides and/or polynucleotides of the invention. In some embodiments, the cells comprise a nuclease-mediated insertion of a transgene, or a nuclease-mediated knock out of a gene. The modified cells, and any cells derived from the modified cells do not necessarily comprise the nucleases of the invention more than transiently, but the genomic modifications mediated by such nucleases remain.

In yet another aspect, methods for targeted cleavage of cellular chromatin in a region of interest; methods of causing homologous recombination to occur in a cell; methods of treating infection; and/or methods of treating disease are provided. These methods maybe practiced in vitro, ex vivo or in vivo or a combination thereof. The methods involve cleaving cellular chromatin at a predetermined region of interest in cells by expressing a pair of fusion polypeptides as described herein (i.e., a pair of fusion polypeptides in which one or both fusion polypeptide(s) comprises the engineered cleavage half-domains as described herein). In certain embodiments, the targeted cleavage of the on-target site is increased by at least 50 to 200% (or any value therebetween) or more, including 50%-60% (or any value therebetween), 60%-70% (or any value therebetween), 70%-80% (or any value therebetween), 80%-90% (or any value therebetween), 90% to 200% (or any value therebetween), as compared to cleavage domains without the mutations as described herein. Similarly, using the methods and compositions as described herein, off-target site cleavage is reduced by 1-100 or more-fold, including but not limited to 1-50-fold (or any value therebetween).

The engineered cleavage half domains described herein can be used in methods for targeted cleavage of cellular chromatin in a region of interest and/or homologous recombination at a predetermined region of interest in cells. Cells include cultured cells, cell lines, cells in an organism, cells that have been removed from an organism for treatment in cases where the cells and/or their descendants will be returned to the organism after treatment, and cells removed from an organism, modified using the fusion molecules of the invention, and then returned to the organism in a method of treatment (cell therapy). A region of interest in cellular chromatin can be, for example, a genomic sequence or portion thereof. Compositions include fusion molecules or polynucleotides encoding fusion molecules that comprise a DNA binding molecule (e.g., an engineered zinc finger or TALE binding domain or an engineered CRISPR guide RNA) and a cleavage half domain as described.

A fusion molecule can be expressed in a cell, e.g., by delivering the fusion molecule to the cell as a polypeptide, or by delivering a polynucleotide encoding the fusion molecule to a cell, wherein the polynucleotide, if DNA, is transcribed and is translated, to generate the fusion molecule. Further, if the polynucleotide is an mRNA encoding the fusion molecule, following delivery of the mRNA to the cell, the mRNA is translated, thus generating the fusion molecule.

In other aspects of the invention are provided methods and compositions for increasing engineered nuclease specificity. In one aspect, methods are provided for increasing overall on-target cleavage specificity by decreasing off-target cleavage activity. In some embodiments, the engineered cleavage half-domain partners of an engineered nuclease complex are used to contact a cell, where each partner of the complex is given in a ratio to the other partner other than one to one. In some embodiments, the ratio of the two partners (half cleavage domains) is given at a 1:2, 1:3, 1:4, 1:5, 1:6, 1:8, 1:9, 1:10 or 1:20 ratio, or any value therebetween. In other embodiments, the ratio of the two partners is greater than 1:30. In other embodiments, the two partners are deployed at a ratio that is chosen to be different from 1:1. In some aspects, each partner is delivered to the cell as an mRNA or is delivered in a viral or non-viral vector where different quantities of mRNA or vector encoding each partner are delivered. In further embodiments, each partner of the nuclease complex may be comprised on a single viral or non-viral vector, but is deliberately expressed such that one partner is expressed at a higher or lower value that the other, ultimately delivering the cell a ratio of cleavage half domains that is other than one to one. In some embodiments, each cleavage half domain is expressed using different promoters with different expression efficiencies. In other embodiments, the two cleavage domains are delivered to the cell using a viral or non-viral vector where both are expressed from the same open reading frame, but the genes encoding the two partners are separated by a sequence (e.g. self-cleaving 2A sequence or IRES) that results in the 3' partner being expressed at a lower rate, such that the ratios of the two partners are 1:2, 1:3, 1:4, 1:5, 1:6, 1:8, 1:9, 1:10 or 1:20 ratio, or any value therebetween. In other embodiments, the two partners are deployed at a ratio that is chosen to be different from 1:1.

Also provided are methods to decrease off-target nuclease activity when two or more nuclease complexes are used. For example, the invention provides methods for varying the ratio of DNA binding molecules when two or more nuclease complexes are used. In some embodiments, the DNA binding molecules are polypeptide DNA binding domains (e.g., ZFNs, TALENs, dCas-Fok, megaTALs, meganucleases), while in others, the DNA binding molecules are guide RNAs for use with RNA-guided nucleases. In preferred embodiments, the ratio of the two or more DNA binding molecules is 1:2, 1:3, 1:4, 1:5, 1:6, 1:8, 1:9, 1:10 or 1:20 ratio, or any value therebetween. In other embodiments, the two DNA binding molecules are deployed at a ratio that is chosen to be different from 1:1. In some aspects, the non-1:1 ratio is achieved by altering the ratio of guide RNAs used to transfect a cell. In other aspects, the ratio is altered by changing the ratio of each Cas9 protein-guide RNA complex used to treat the cells of interest. In a still further aspect, the altered ratio is achieved by using differing ratios of DNAs encoding the guide RNAs (viral or non-viral) for treatment of the cells, or by using promoters with different expression strengths to differentially express the DNA binding molecules inside the cells. Off-target events can be reduced by 2 to 1000-fold (or any amount therebetween) or more, including but not limited to, reduction by at least 10, 50, 60, 70, 80, 100, 150, 200, 250, 300, 350, 400, 450, 500, 600, 700, 800, 900, 1000-fold (of any value therebetween) or more.

Accordingly, in another aspect, a method for cleaving cellular chromatin in a region of interest can comprise (a) selecting a first sequence in the region of interest; (b) engineering a first DNA-binding molecule to specifically bind to the first sequence; (c) expressing a first fusion molecule in the cell, the first fusion molecule comprising the first DNA-binding molecule (e.g., zinc finger, TALE, sgRNA), and a cleavage domain (or half-domain); and (d) expressing a second fusion protein in the cell, the second fusion molecule comprising a second DNA-binding domain, and a second cleavage domain (or half-domain), wherein at least one of the fusion molecules comprises a linker as described herein, and further wherein the first fusion molecule binds to the first sequence, and the second fusion molecule binds to a second sequence located between 2 and 50 nucleotides from the first sequence, such that an active nuclease complex can form and cellular chromatin is cleaved in the region of interest. In certain embodiments, both fusion molecules comprise a linker as described herein between the DNA binding domain and the catalytic nuclease domain.

Also provided are methods of altering a region of cellular chromatin, for example to introduce targeted mutations. In certain embodiments, methods of altering cellular chromatin comprise introducing into the cell one or more targeted nucleases to create a double-stranded break in cellular chromatin at a predetermined site, and a donor polynucleotide, having homology to the nucleotide sequence of the cellular chromatin in the region of the break. Cellular DNA repair processes are activated by the presence of the double-stranded break and the donor polynucleotide is used as a template for repair of the break, resulting in the introduction of all or part of the nucleotide sequence of the donor into the cellular chromatin. Thus, a sequence in cellular chromatin can be altered and, in certain embodiments, can be converted into a sequence present in a donor polynucleotide.

Targeted alterations include, but are not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations. Alterations can also include conversion of base pairs that are part of a coding sequence such that the encoded amino acid is altered.

The donor polynucleotide can be DNA or RNA, can be linear or circular, and can be single-stranded or double-stranded. It can be delivered to the cell as naked nucleic acid, as a complex with one or more delivery agents (e.g., liposomes, nanoparticles, poloxamers) or contained in a viral delivery vehicle, such as, for example, an adenovirus, lentivirus or an Adeno-Associated Virus (AAV). Donor sequences can range in length from 10 to 1,000 nucleotides (or any integral value of nucleotides therebetween) or longer. In some embodiments, the donor comprises a full-length gene flanked by regions of homology with the targeted cleavage site. In some embodiments, the donor lacks homologous regions and is integrated into a target locus through homology independent mechanism (i.e. NHEJ). In other embodiments, the donor comprises a smaller piece of nucleic acid flanked by homologous regions for use in the cell (i.e. for gene correction). In some embodiments, the donor comprises a gene encoding a functional or structural component such as a shRNA, RNAi, miRNA or the like. In other embodiments, the donor comprises sequences encoding a regulatory element that binds to and/or modulates expression of a gene of interest. In other embodiments, the donor is a regulatory protein of interest (e.g. ZFP TFs, TALE TFs or a CRISPR/Cas TF) that binds to and/or modulates expression of a gene of interest.

For any of the aforementioned methods, the cellular chromatin can be in a chromosome, episome or organellar genome. Cellular chromatin can be present in any type of cell including, but not limited to, prokaryotic and eukaryotic cells, fungal cells, plant cells, animal cells, mammalian cells, primate cells and human cells.

In yet another aspect, cells comprising any of the polypeptides (e.g., fusion molecules) and/or polynucleotides as described herein are also provided. In one embodiment, the cells comprise a pair of fusion molecules, each comprising a cleavage domain as disclosed herein. Cells include cultured cells, cells in an organism and cells that have been removed from an organism for treatment in cases where the cells and/or their descendants will be returned to the organism after treatment. A region of interest in cellular chromatin can be, for example, a genomic sequence or portion thereof.

In another aspect, described herein is a kit comprising a fusion protein as described herein or a polynucleotide encoding one or more zinc finger proteins, cleavage domains and/or fusion proteins as described herein; ancillary reagents; and optionally instructions and suitable containers. The kit may also include one or more nucleases or polynucleotides encoding such nucleases.

These and other aspects will be readily apparent to the skilled artisan in light of disclosure as a whole.

BRIEF DESCRIPTION OF THE DRAWINGS

FIG. 1 depicts the amino acid sequence (SEQ ID NO:1) and nucleotide sequence (SEQ ID NO:2) of a portion of a wild-type FokI nuclease. The sequence shows the FokI catalytic nuclease domain, and numbering is with respect to the wild type FokI protein used to generate the crystal structures 1FOK.pdb and 2FOK.pdb (Wah ibid) (amino acid Q of the nuclease domain begins at 384). Boxed positions indicate possible mutation sites.

FIG. 2A indicates the locations of amino acids R422, R416 and K525. FIG. 2B indicates the locations of amino acids R447, K448 and R422. FIG. 2C is an illustration showing a subset of the different types of ZFNs (SEQ ID NOS 71-72, respectively, in order of appearance) that can be made incorporating 1, 2 or 3 (1x, 2x, or 3x, respectively) mutations (either R-> Q or R-> L) in the zinc finger backbone. Black arrows indicate the positions of the mutations.

FIGS. 3A and 3B show activity of BCL11A-specific ZFNs bearing the novel FokI mutations described herein. FIG. 3A shows targeted modification in CD34+ cells for BCL11A-specific ZFNs SBS #51857-ELD/SBS #51949-KKR against the BCL11A cognate target (indicated with the unique 'license plate' identifier PRJIYLFN, SEQ ID NO:13) and two off-target sites also identified by their 'license plate' identifiers NIFMAEVG (SEQ ID NO:14) and PEVYOHIU (SEQ ID NO:20). ZFPs are described in WO 2016/183298. All experiments were done with 2 μg of each ZFN mRNA for nuclease delivery and values represent the percentage of sequence reads that contain insertions and deletions (% indels) consistent with nuclease activity. FIG. 3A shows the results when a serine residue was substituted into positions 416, 422, 447, 448 and 525 of the FokI domain in one or both ZFNs. FIG. 3B shows a similar data set except that the heterodimeric dimerization domain FokI backbones have been switched, i.e. FIG. 3A shows results using mutations in pair SBS #51857-ELD/SBS #51949-KKR, while FIG. 3B shows results using mutations in pair SBS #51857-KKR/SBS #51949-ELD.

FIG. 5A (SEQ ID NO:3) shows the amino acids in the second finger of the Zif268 protein where the beta sheet and alpha helical structures are indicated. Also shown are the location of the amino acids involved in specific DNA base recognition (−1 through 6). Positively charged residues with the potential to interact with the phosphate backbone on the DNA are indicated by squares. Invariant cysteine residues involved in zinc coordination are underlined. FIG. 5B is a close-up drawing of a single finger in its three-dimensional state (the solid sphere represents the coordinated zinc ion), and indicates how the different regions of each zinc finger tend to interact with DNA. The DNA is represented by a diagram where phosphates are indicated by the letter P and DNA bases are shown in boxes with rounded corners. Gray arrows indicate the approximate position of the residue positions indicated in boxes and black arrows indicate interactions between the zinc finger protein and the DNA.

FIGS. 7A and 7B (SEQ ID NO:7 and 8) depict drawings of the ZFP backbones including modules of either a six-finger zinc finger protein (FIG. 7A, SEQ ID NO:7) or a five-finger zinc finger protein (FIG. 7B, SEQ ID NO:8). Letters above some of the boxed positions indicate mutations that were tested at the indicated position. The identity of each finger is given by labels F1 through F6. These proteins are each assembled from three different "modules" indicated as "Module A", Module B", and "Module C". Mutations to positions −14, −9, and −5 of the N-terminal finger in each module can be made by altering the sequence of the PCR primer used during the assembly process.

FIGS. 8A through 8C are graphs depicting on-target and off-target cleavage activity for the TCRA (TRAC)-specific ZFN (PCT Publication WO2017106528) comprising the novel zinc finger backbone mutations of the invention herein. The TCRA (TRAC)-specific ZFNs both contain 6 zinc finger repeats and for experimental ease mutations at position −5 were only introduced to the N-terminal finger of each module (e.g. F1, F3, or F5 in the full-length ZFN). Thus, each individual ZFN could have 0, 1, 2, or 3 mutations and the entire ZFN pair could have up to 6 mutations in total (e.g. 0, 1, 2, 3, 4, 5, or 6 mutations). Plotted values indicate the average of all tested ZFN pairs with the indicated number and types of mutations at position −5. Error bars represent standard error of the mean. For each ZFN pair, the three off-targets indicated in Table 3 were measured; off-target values averaged to generate the plotted values include the fraction of activity of the parent TCRA (TRAC) ZFNs for each of these three off-targets for each construct. FIG. 8A shows the fraction of activity of the parent TCRA (TRAC) ZFNs, where the datasets show the changes in either on-target (black bars) or off-target (grey bars) activity from substitution of the indicated amino acids at position −5 in one or more of the zinc finger repeats of only one of the two ZFNs in the pair. FIG. 8B shows the fraction of activity from making the indicated arginine-alanine substitution in one or both ZFN partners simultaneously. The left half of FIG. 8B represents ZFN pairs where the indicated number of mutations occur in only one ZFN in the pair (and corresponds to the left third of FIG. 8A) while the right half of FIG. 8B represents ZFN pairs where the same number of mutations were made to both ZFNs in the pair (e.g. 2 represents one mutation in each ZFN in the pair, 4 represents two mutations in each ZFN in the pair, and 6 represents three mutations in each ZFN in the pair. The experiments done in FIGS. 8A and 8B were with CD34+ cells at a dose of 6 µg per experiment. FIG. 8C shows similar data to the right two thirds of FIG. 8A where the dosage of RNAs were 2 µg per experiment.

FIG. 12 is a table listing the on- and off-target cleavage activity for the BCL11A-specific ZFNs when CD34+ cells were treated with either a single mRNA encoding both ZFN partners as described above, (51857/51949 2a), or treated with the titrated dose of the ZFN partners where one partner (51949) comprises a FokI R->S mutation at position 416. The 'license plate' identifiers are shown in Table 1 of Example 2 (SEQ ID NO:13-53). The data corresponding to PRJIYLFN represents the fraction of sequence reads at the intended target in BCL11A containing indels consistent with ZFN activity. Data corresponding to all other 'license plate' identifiers listed in the left-most column corresponds to confirmed or suspected off-target loci for the 51857/51949 ZFN pair. The ratio shown in the right column indicates the activity in the sample treated with 51857/51949 2a divided by the activity in the sample treated with titrated 51857/51949 R416S at the indicated locus.

FIG. 13 shows the results of an unbiased capture assay, comparing two ZFN pairs. The left panel ("Parental ZFN pair") shows results using the pair SBS51857 and SBS51949 and the right panel ("Variant ZFN Pair") shows result using SBS63014 and SBS65721), which pair comprises the parental pair and, additionally, the ZFP backbone mutations as described herein as well as a FokI R416S mutation un the SBS65721 construct. In particular, in the variant pair, each ZFN of the pair comprises three R->Q mutations in the fingers and the SBS65721 construct further comprises the FokI R416S mutation. The data demonstrates that the mutations decrease the number of unique capture events from 21 locations for the parental pair to 4 in the variant. Further, when the partners in the ZFN pairs are given in non-equal amounts, the capture events also decrease. For the parental pair, the capture events fall from 21 (equal dosing) to 13 (unequal dosing) locations (28% to 3.4% aggregate off-targets, respectively), and for the variant pair, the capture events fall from 4 to 2 (0.26% to 0.08% aggregate off-target cleavage, respectively). The combination of these two approaches causes an overall decrease in 21 locations in the parent to 2 in the variant dosed in unequal partner concentrations, for a decrease from 28% off target events in aggregate for the parental pair to 0.08% off target events in the aggregate for the variant.

FIG. 14 shows results demonstrating reduced off-target cleavage events using ZFNs as described herein produced in large-scale manufacturing conditions. The ZFN pair used comprised SBS63014 and SBS65722.

FIGS. 15A through 15D show results demonstrating reduced off-target cleavage events using ZFN mutants (targeted to AAVS1) as described herein. FIG. 15A depicts the activity results from the parent ZFNs 30035/30054. FIG. 15B depicts the on-target and ratio of on-target/off-target cleavage activity for three sets of FokI mutants: ELD FokI mutants comprising additional single mutations (left most data set); KKR FokI mutants comprising additional single mutations (middle data set); and both ELD and KKR FokI mutants comprising the same additional single mutations (right most data set). FIG. 15C shows a grid of on-target activity where the ELD or KKR FokI domains comprise two mutations, and FIG. 15D shows the on-target/off-target ratios for the data shown in FIG. 15C.

FIGS. 16A and 16B show results demonstrating reduced off-target cleavage events using exemplary AAVS1-targeted ZFN mutants as described herein. FIG. 16A shows mutants in ELD and KKR context and FIG. 16B shows mutants in ELD-KKR context.

FIG. 18 shows exemplary mutations in which the position corresponds to the FokI or FokI homologues shown in FIG. 17.

DETAILED DESCRIPTION

Figure 2B:
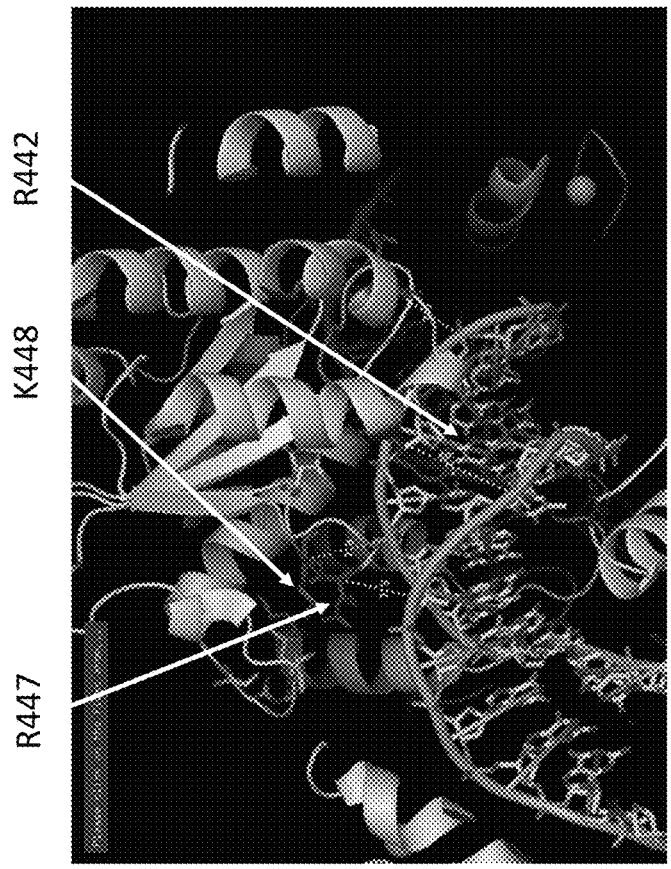
FIGS. 2A through 2C are schematics showing models of the FokI domain interacting with a DNA molecule.

Disclosed herein are methods and compositions for increasing specificity of on-target engineered nuclease cleavage via differentially decreasing off-target cleavage. The methods involve decreasing the non-specific interactions between the FokI cleavage domain and DNA, decreasing non-specific interactions between the zinc finger backbone and DNA, and altering the relative ratios of each half-cleavage domain partner away from the default ratio of 1:1.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$. "Non-specific binding" refers to, non-covalent interactions that occur between any molecule of interest (e.g. an engineered nuclease) and a macromolecule (e.g. DNA) that are not dependent on-target sequence.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity. In the case of an RNA-guided nuclease system, the RNA guide is heterologous to the nuclease component (Cas9 or Cfp1) and both may be engineered.

A "DNA binding molecule" is a molecule that can bind to DNA. Such DNA binding molecule can be a polypeptide, a domain of a protein, a domain within a larger protein or a polynucleotide. In some embodiments, the polynucleotide is DNA, while in other embodiments, the polynucleotide is RNA. In some embodiments, the DNA binding molecule is a protein domain of a nuclease (e.g. the FokI domain), while in other embodiments, the DNA binding molecule is a guide RNA component of an RNA-guided nuclease (e.g. Cas9 or Cfp1).

A "DNA binding protein" (or binding domain) is a protein, or a domain within a larger protein, that binds DNA in a sequence-specific manner, for example through one or more zinc fingers or through interaction with one or more RVDs in a zinc finger protein or TALE, respectively. The term zinc finger DNA binding protein is often abbreviated as zinc finger protein or ZFP.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526, incorporated by reference herein in its entirety.

Zinc finger and TALE DNA-binding domains can be "engineered" to bind to a predetermined nucleotide sequence, for example via engineering (altering one or more amino acids) of the recognition helix region of a naturally occurring zinc finger protein or by engineering of the amino acids involved in DNA binding (the "repeat variable diresidue" or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs and binding data. See, for example, U.S. Pat. Nos. 8,586,526; 6,140,081; 6,453,242; and 6,534,261; see also WO 98/53058; WO 98/53059; WO 98/53060; WO 02/016536 and WO 03/016496.

A "selected" zinc finger protein, TALE protein or CRISPR/Cas system is not found in nature whose production results primarily from an empirical process such as phage display, interaction trap, rational design or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970; WO 01/88197 and WO 02/099084.

"TtAgo" is a prokaryotic Argonaute protein thought to be involved in gene silencing. TtAgo is derived from the bacteria *Thermus thermophilus*. See, e.g. Swarts et al, ibid; G. Sheng et al., (2013) *Proc. Natl. Acad. Sci. U.S.A.* 111, 652). A "TtAgo system" is all the components required including e.g. guide DNAs for cleavage by a TtAgo enzyme.

"Recombination" refers to a process of exchange of genetic information between two polynucleotides, including but not limited to, capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In certain methods of the disclosure, one or more targeted nucleases as described herein create a double-stranded break (DSB) in the target sequence (e.g., cellular chromatin) at a predetermined site (e.g., a gene or locus of interest). The DSB mediates integration of a construct (e.g. donor) as described herein. Optionally, the construct has homology to the nucleotide sequence in the region of the break. An expression construct may be physically integrated or, alternatively, the expression cassette is used as a template for repair of the break via homologous recombination, resulting in the introduction of all or part of the nucleotide sequence as in the expression cassette into the cellular chromatin. Thus, a first sequence in cellular chromatin can be altered and, in certain embodiments, can be converted into a sequence present in an expression cassette. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional engineered nucleases can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence or via cleavage of the target sequence(s) followed by error-prone NHEJ-mediated repair that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize. The term "cleavage domain" is used interchangeably with the term "cleavage half-domain." The term "FokI cleavage domain" includes the FokI sequence as shown in SEQ ID NO:1 as well as any FokI homologues, including but not limited to the sequences shown in FIG. 17.

An "engineered cleavage half-domain" is a cleavage half-domain that has been modified so as to form obligate heterodimers with another cleavage half-domain (e.g., another engineered cleavage half-domain).

The term "sequence" refers to a nucleotide sequence of any length, which can be DNA or RNA; can be linear, circular or branched and can be either single-stranded or double stranded. The term "transgene" refers to a nucleotide sequence that is inserted into a genome. A transgene can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids, minicircles and certain viral genomes. The liver specific constructs described herein may be episomally maintained or, alternatively, may be stably integrated into the cell.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, ligases, deubiquitinases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™) Agrobacterium-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of fusion molecules include, but are not limited to, fusion proteins (for example, a fusion between a protein DNA-binding domain and a cleavage domain), fusions between a polynucleotide DNA-binding domain (e.g., sgRNA) operatively associated with a cleavage domain, and fusion nucleic acids (for example, a nucleic acid encoding the fusion protein).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci that are targeted by nuclease(s) include CCR5, HPRT, AAVS1, Rosa and albumin. See, e.g., U.S. Pat. Nos. 7,951,925; 8,771,985; 8,110,379; 7,951,925; U.S. Publication Nos. 20100218264; 20110265198; 20130137104; 20130122591; 20130177983; 20130177960; 20150056705 and 20150159172.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid or protein (e.g., coding function, ability to hybridize to another nucleic acid, enzymatic activity assays) are well-known in the art.

A polynucleotide "vector" or "construct" is capable of transferring gene sequences to target cells. Typically, "vector construct," "expression vector," "expression construct," "expression cassette," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the expression cassettes of the invention can be administered. Subjects of the present invention include those with a disorder.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Cancer, monogenic diseases and graft versus host disease are non-limiting examples of conditions that may be treated using the compositions and methods described herein.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease. An "intended" or "on-target" sequence is the sequence to which the binding molecule is intended to bind and an "unintended" or "off-target" sequence includes any sequence bound by the binding molecule that is not the intended target.

DNA-Binding Molecules/Domains

Described herein are compositions comprising a DNA-binding molecule/domain that specifically binds to a target site in any gene or locus of interest. Any DNA-binding molecule/domain can be used in the compositions and methods disclosed herein, including but not limited to a zinc finger DNA-binding domain, a TALE DNA binding domain, the DNA-binding portion (guide or sgRNA) of a CRISPR/Cas nuclease, or a DNA-binding domain from a meganuclease.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties. In certain embodiments, the DNA-binding domain comprises a zinc finger protein disclosed in U.S. Patent Publication No. 2012/0060230 (e.g., Table 1), incorporated by reference in its entirety herein.

An engineered zinc finger binding domain can have a novel binding specificity, compared to a naturally-occurring zinc finger protein. Engineering methods include, but are not limited to, rational design and various types of selection.

Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in U.S. Pat. No. 6,794,136.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

In some embodiments, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996)*J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

Figure 5:
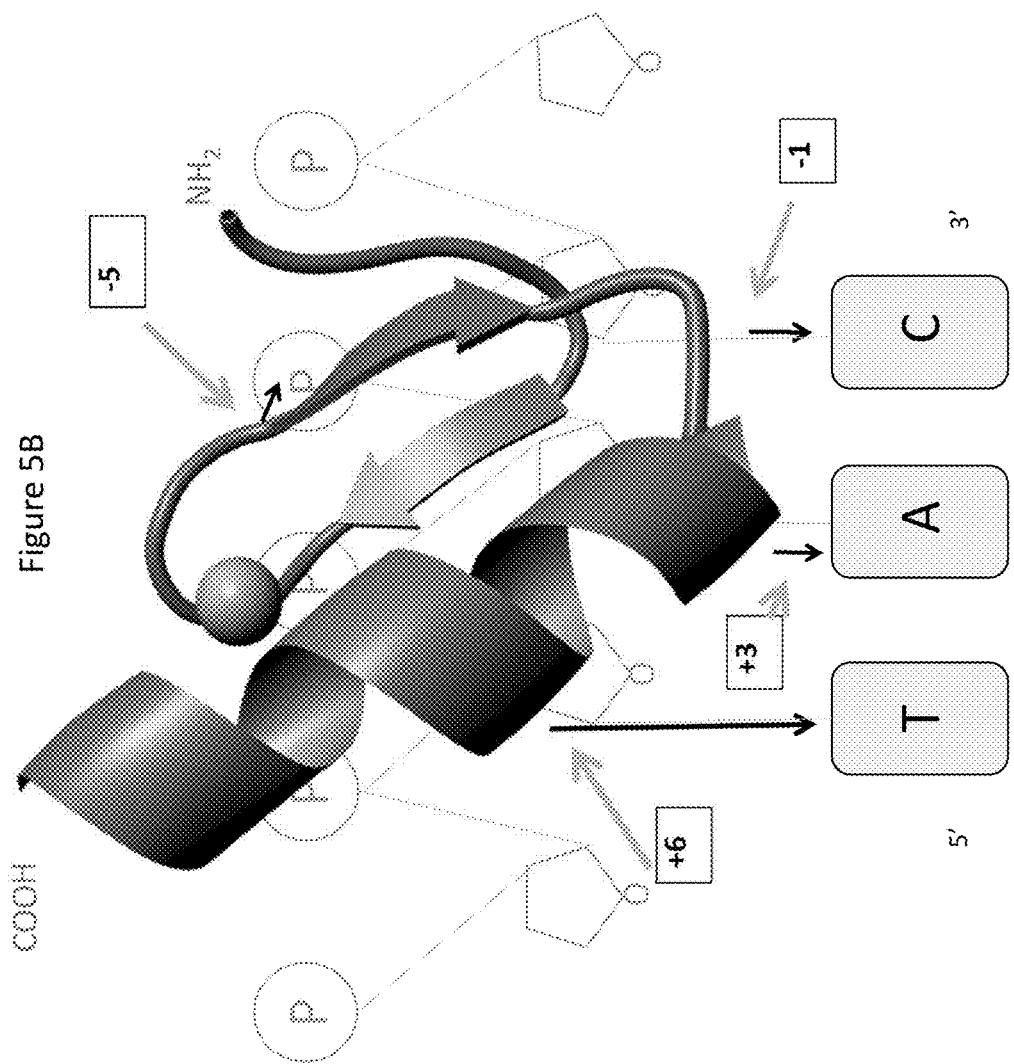
FIGS. 5A and 5B are schematics depicting the backbone region of a zinc finger.

In certain embodiments, the zinc finger protein used with the mutant cleavage domains described herein comprises one or more mutations (substitutions, deletions, and/or insertions) to the backbone regions (e.g., regions outside the 7-amino acid recognition helix region numbered −1 to 6), for example at one or more of positions −14, −9 and/or −5 (see, e.g., FIG. 5A). The wild-type residue at one or more these positions may be deleted, replaced with any amino acid residue and/or include on or more additional residues. In some embodiments, the Arg (R) at position −5 is changed to a Tyr (Y), Asp (N), Glu (E), Leu (L), Gln (Q), or Ala (A). In other embodiments, the Arg (R) at position (−9) is replaced with Ser (S), Asp (N), or Glu (E). In further embodiments, the Arg (R) at position (−14) is replaced with Ser (S) or Gln (Q). In other embodiments, the fusion polypeptides can comprise mutations in the zinc finger DNA binding domain where the amino acids at the (−5), (−9) and/or (−14) positions are changed to any of the above listed amino acids in any combination.

In other embodiments, the DNA binding domain comprises an engineered domain from a Transcriptional Activator-Like (TAL) effector (TALE) similar to those derived from the plant pathogens *Xanthomonas* (see Boch et al, (2009) *Science* 326: 1509-1512 and Moscou and Bogdanove, (2009) *Science* 326: 1501) and Ralstonia (see Heuer et al (2007) *Applied and Environmental Microbiology* 73(13): 4379-4384); U.S. Patent Publication Nos. 20110301073 and 20110145940. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 base pairs in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 base pairs and the repeats are typically 91-100% homologous with each other (Bonas et al, ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN), including TALENs with atypical RVDs. See, e.g., U.S. Pat. No. 8,586,526.

In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) *Nat Comm:* 1-8 DOI: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

In addition, as disclosed in these and other references, zinc finger domains and/or multi-fingered zinc finger proteins or TALEs may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136. In certain embodiments, the DNA-binding domain is part of a CRISPR/Cas nuclease system, including a single guide RNA (sgRNA) DNA binding molecule that binds to DNA. See, e.g., U.S. Pat. No. 8,697,359 and U.S. Patent Publication Nos. 20150056705 and 20150159172. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to affect a panoply of outcomes including gene knock-out, targeted gene addition, gene correction, targeted gene deletion using techniques standard in the art for exploitation of DNA breaks.

Thus, any DNA-binding molecule/domain can be used.

Fusion Molecules

Fusion molecules comprising DNA-binding domains (e.g., ZFPs or TALEs, CRISPR/Cas components such as single guide RNAs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Publication Nos. 20050064474; 20060188987 and 2007/0218528 for details regarding fusions of DNA-binding domains and nuclease cleavage domains, incorporated by reference in their entireties herein.

Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J Virol.* 72:5610-5618 (1998) and Doyle & Hunt, Neuroreport 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5,-6,-7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in U.S. Patent Publications 2002/0115215 and 2003/0082552 and in WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935. Furthermore, single guide RNAs of the CRISPR/Cas system associate with functional domains to form active transcriptional regulators and nucleases.

In certain embodiments, the target site is present in an accessible region of cellular chromatin. Accessible regions can be determined as described, for example, in U.S. Pat. Nos. 7,217,509 and 7,923,542. If the target site is not present in an accessible region of cellular chromatin, one or more accessible regions can be generated as described in U.S. Pat. Nos. 7,785,792 and 8,071,370. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3) (Cordingley et al. (1987) *Cell* 48:261-270; Pina et al. (1990) *Cell* 60:719-731; and Cirillo et al. (1998) *EMBO J.* 17:244-254).

The fusion molecule may be formulated with a pharmaceutically acceptable carrier, as is known to those of skill in the art. See, for example, *Remington's Pharmaceutical Sciences*, 17th ed., 1985; and U.S. Pat. Nos. 6,453,242 and 6,534,261.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in U.S. Pat. Nos. 6,534,261 and 6,933,113.

Functional domains that are regulated by exogenous small molecules or ligands may also be selected. For example, RheoSwitch® technology may be employed wherein a functional domain only assumes its active conformation in the presence of the external RheoChem™ ligand (see for example US 20090136465). Thus, the ZFP may be operably linked to the regulatable functional domain wherein the resultant activity of the ZFP-TF is controlled by the external ligand.

Nucleases

In certain embodiments, the fusion protein comprises a DNA-binding binding domain and cleavage (nuclease) domain. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. Chames et al. (2005) *Nucleic Acids Res* 33(20):e178; Arnould et al. (2006) *J Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs and/or TALEs have been fused to nuclease domains to create ZFNs and TALENs—a functional entity that is able to recognize its intended nucleic acid target through its engineered (ZFP or TALE) DNA binding domain and cause the DNA to be cut near the DNA binding site via the nuclease activity. See, e.g., Kim et al. (1996) *Proc Nat'l Acad Sci USA* 93(3):1156-1160. More recently, such nucleases have been used for genome modification in a variety of organisms. See, for example, United States Patent Publications 20030232410; 20050208489; 20050026157; 20050064474; 20060188987; 20060063231; and International Publication WO 07/014275.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In any of the nucleases described herein, the nuclease can comprise an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) *Nat Comm:* 1-8 DOI: 10.1038/ncomms2782). Any TALENs may be used in combination with additional TALENs (e.g., one or more TALENs (cTAL-ENs or FokI-TALENs) with one or more mega-TALs) or other DNA cleavage enzymes.

In certain embodiments, the nuclease comprises a meganuclease (homing endonuclease) or a portion thereof that exhibits cleavage activity. Naturally-occurring meganucleases recognize 15-40 base-pair cleavage sites and are commonly grouped into four families: the LAGLIDADG family (SEQ ID NO: 68), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TeeI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J Mol. Biol.* 263:163-180; Argast et al. (1998) *J. Mol. Biol.* 280:345-353 and the New England Biolabs catalogue.

DNA-binding domains from naturally-occurring meganucleases, primarily from the LAGLIDADG family (SEQ ID NO: 68), have been used to promote site-specific genome modification in plants, yeast, *Drosophila*, mammalian cells and mice, but this approach has been limited to the modification of either homologous genes that conserve the meganuclease recognition sequence (Monet et al. (1999), Biochem. Biophysics. Res. Common. 255: 88-93) or to pre-engineered genomes into which a recognition sequence has been introduced (Route et al. (1994), Mol. Cell. Biol. 14: 8096-106; Chilton et al. (2003), Plant Physiology. 133: 956-65; Puchta et al. (1996), Proc. Natl. Acad. Sci. USA 93: 5055-60; Rong et al. (2002), Genes Dev. 16: 1568-81; Gouble et al. (2006), 1 Gene Med. 8(5):616-622). Accordingly, attempts have been made to engineer meganucleases to exhibit novel binding specificity at medically or biotechnologically relevant sites (Porteus et al. (2005), Nat. Biotechnol. 23: 967-73; Sussman et al. (2004), J Mol. Biol. 342: 31-41; Epinat et al. (2003), Nucleic Acids Res. 31: 2952-62; Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication Nos. 20070117128; 20060206949; 20060153826; 20060078552; and 20040002092). In addition, naturally-occurring or engineered DNA-binding domains from meganucleases can be operably linked with a cleavage domain from a heterologous nuclease (e.g., FokI) and/or cleavage domains from meganucleases can be operably linked with a heterologous DNA-binding domain (e.g., ZFP or TALE).

In other embodiments, the nuclease is a zinc finger nuclease (ZFN) or TALE DNA binding domain-nuclease fusion (TALEN). ZFNs and TALENs comprise a DNA binding domain (zinc finger protein or TALE DNA binding domain) that has been engineered to bind to a target site in a gene of choice and cleavage domain or a cleavage half-domain (e.g., from a restriction and/or meganuclease as described herein).

As described in detail above, zinc finger binding domains and TALE DNA binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain or TALE protein can have a novel binding specificity, compared to a naturally-occurring protein. Engineering methods include, but are not limited to, rational design and various types of selection. Rational design includes, for example, using databases comprising triplet (or quadruplet) nucleotide sequences and individual zinc finger or TALE amino acid sequences, in which each triplet or quadruplet nucleotide sequence is associated with one or more amino acid sequences of zinc fingers or TALE repeat units which bind the particular triplet or quadruplet sequence. See, for example, U.S. Pat. Nos. 6,453,242 and 6,534,261, incorporated by reference herein in their entireties.

Selection of target sites; and methods for design and construction of fusion proteins (and polynucleotides encoding same) are known to those of skill in the art and described in detail in U.S. Pat. Nos. 7,888,121 and 8,409,861, incorporated by reference in their entireties herein.

In addition, as disclosed in these and other references, zinc finger domains, TALEs and/or multi-fingered zinc finger proteins may be linked together using any suitable linker sequences, including for example, linkers of 5 or more amino acids in length. (e.g., TGEKP (SEQ ID NO:9), TGGQRP (SEQ ID NO:10), TGQKP (SEQ ID NO:11), and/or TGSQKP (SEQ ID NO:12). See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. See, also, U.S. Pat. No. 8,772,453.

Thus, nucleases such as ZFNs, TALENs and/or meganucleases can comprise any DNA-binding domain and any nuclease (cleavage) domain (cleavage domain, cleavage half-domain). As noted above, the cleavage domain may be heterologous to the DNA-binding domain, for example a zinc finger or TAL-effector DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-10 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises a FokI cleavage domain used to generate the crystal structures 1FOK.pdb and 2FOK.pdb (see Wah et al (1997) *Nature* 388:97-100) having the sequence shown below:

```
Wild type FokI cleavage half domain
                                                 (SEQ ID NO: 1)
QLVKSELEEKKSELRHKLKYVPHEYIELIEIARNSTQDRILEMKVMEFFM
KVYGYRGKHLGGSRKPDGAIYTVGSPIDYGVIVDTKAYSGGYNLPIGQAD
EMQRYVEENQTRNKHINPNEWWKVYPSSVTEFKFLFVSGHFKGNYKAQLT
RLNHITNCNGAVLSVEELLIGGEMIKAGTLTLEEVRRKFNNGEINF
```

Cleavage half domains derived from FokI may comprise a mutation in one or more of amino acid residues as shown in SEQ ID NO:1. Mutations include substitutions (of a wild-type amino acid residue for a different residue, insertions (of one or more amino acid residues) and/or deletions (of one or more amino acid residues). In certain embodiments, one or more of residues 414-426, 443-450, 467-488, 501-502, and/or 521-531 (numbered relative to SEQ ID NO:1 and sequences shown FIG. 17) are mutated since these residues are located close to the DNA backbone in a molecular model of a ZFN bound to its target site described in Miller et al. ((2007) Nat Biotechnol 25:778-784). In certain embodiments, one or more residues at positions 416, 422, 447, 448, and/or 525 are mutated. In certain embodiments, the mutation comprises a substitution of a wild-type residue with any different residue, for example an alanine (A) residue, a cysteine (C) residue, an aspartic acid (D) residue, a glutamic acid (E) residue, a histidine (H) residue, a phenylalanine (F) residue, a glycine (G) residue, an asparagine (N) residue, a serine (S) residue or a threonine (T) residue. In other embodiments, the wild-type residue at one or more of positions 416, 418, 422, 446, 448, 476, 479, 480, 481, and/or 525 are replaced with any other residues, including but not limited to, R416D, R416E, S418E, S418D, R422H, S446D, K448A, N476D, I479Q, I479T, G480D, Q481A, Q481E, K525S, K525A, N527D, R416E+R422H, R416D+R422H, R416E+K448A, R416D+R422H, K448A+ I479Q, K448A+Q481A. K448A+K525A.

In certain embodiments, the cleavage domain comprises one or more engineered cleavage half-domain (also referred to as dimerization domain mutants) that minimize or prevent homodimerization, as described, for example, in U.S. Pat. Nos. 7,914,796; 8,034,598 and 8,623,618; and U.S. Patent Publication No. 20110201055, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I (numbered relative to SEQ ID NO:1 and sequences shown FIG. 17) are all targets for influencing dimerization of the Fok I cleavage half-domains. The mutations may include mutations to residues found in natural restriction enzymes homologous to FokI. In a preferred embodiment, the mutation at positions 416, 422, 447, 448 and/or 525 (numbered relative to SEQ ID NO:1 and sequences shown FIG. 17) comprise replacement of a positively charged amino acid with an uncharged or a negatively charged amino acid. In another embodiment, the engineered cleavage half domain comprises mutations in amino acid residues 499, 496 and 486 in addition to the mutations in one or more amino acid residues 416, 422, 447, 448, or 525, all numbered relative to SEQ ID NO:1 or sequences shown FIG. 17.

In certain embodiments, the compositions described herein include engineered cleavage half-domains of Fok I that form obligate heterodimers as described, for example, in U.S. Pat. Nos. 7,914,796; 8,034,598; 8,9624,281 and 8,623, 618; U.S.

Patent Publication Nos. 20080131962 and 20120040398. Thus, in one preferred embodiment, the invention provides fusion proteins wherein the engineered cleavage half-domain comprises a polypeptide in which the wild-type Gln (Q) residue at position 486 is replaced with a Glu (E) residue, the wild-type Ile (I) residue at position 499 is replaced with a Leu (L) residue and the wild-type Asn (N) residue at position 496 is replaced with an Asp (D) or a Glu (E) residue ("ELD" or "ELE") in addition to one or more mutations at positions 416, 422, 447, 448, or 525 (numbered relative to SEQ ID NO:1 and sequences shown FIG. 17). In another embodiment, the engineered cleavage half domains are derived from a wild-type FokI cleavage half domain and comprise mutations in the amino acid residues 490, 538 and 537, numbered relative to wild-type FokI (SEQ ID NO:1 and sequences shown FIG. 17) in addition to the one or more mutations at amino acid residues 416, 422, 447, 448, or 525. In a preferred embodiment, the invention provides a fusion protein, wherein the engineered cleavage half-domain comprises a polypeptide in which the wild-type Glu (E) residue at position 490 is replaced with a Lys (K) residue, the wild-type Ile (I) residue at position 538 is replaced with a Lys (K) residue, and the wild-type His (H) residue at position 537 is replaced with a Lys (K) residue or an Arg (R) residue ("KKK" or "KKR") (see U.S. Pat. No. 8,962,281, incorporated by reference herein) in addition to one or more mutations at positions 416, 422, 447, 448, or 525. See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/ or "Sharkey" mutations (see Guo et al, (2010) J Mol. Biol. 400(1):96-107).

In another embodiment, the engineered cleavage half domains are derived from a wild-type FokI cleavage half domain and comprise mutations in the amino acid residues 490, and 538, numbered relative to wild-type FokI or a FokI homologue in addition to the one or more mutations at amino acid residues 416, 422, 447, 448, or 525. In a preferred embodiment, the invention provides a fusion protein, wherein the engineered cleavage half-domain comprises a polypeptide in which the wild-type Glu (E) residue at position 490 is replaced with a Lys (K) residue, and the wild-type Ile (I) residue at position 538 is replaced with a Lys (K) residue ("KK") in addition to one or more mutations at positions 416, 422, 447, 448, or 525. In a preferred embodiment, the invention provides a fusion protein, wherein the engineered cleavage half-domain comprises a polypeptide in which the wild-type Gln (Q) residue at position 486 is replaced with an Glu (E) residue, and the wild-type Ile (I) residue at position 499 is replaced with a Leu (L) residue ("EL") (See U.S. Pat. No. 8,034,598, incorporated by reference herein) in addition to one or more mutations at positions 416, 422, 447, 448, or 525.

Figure 17:
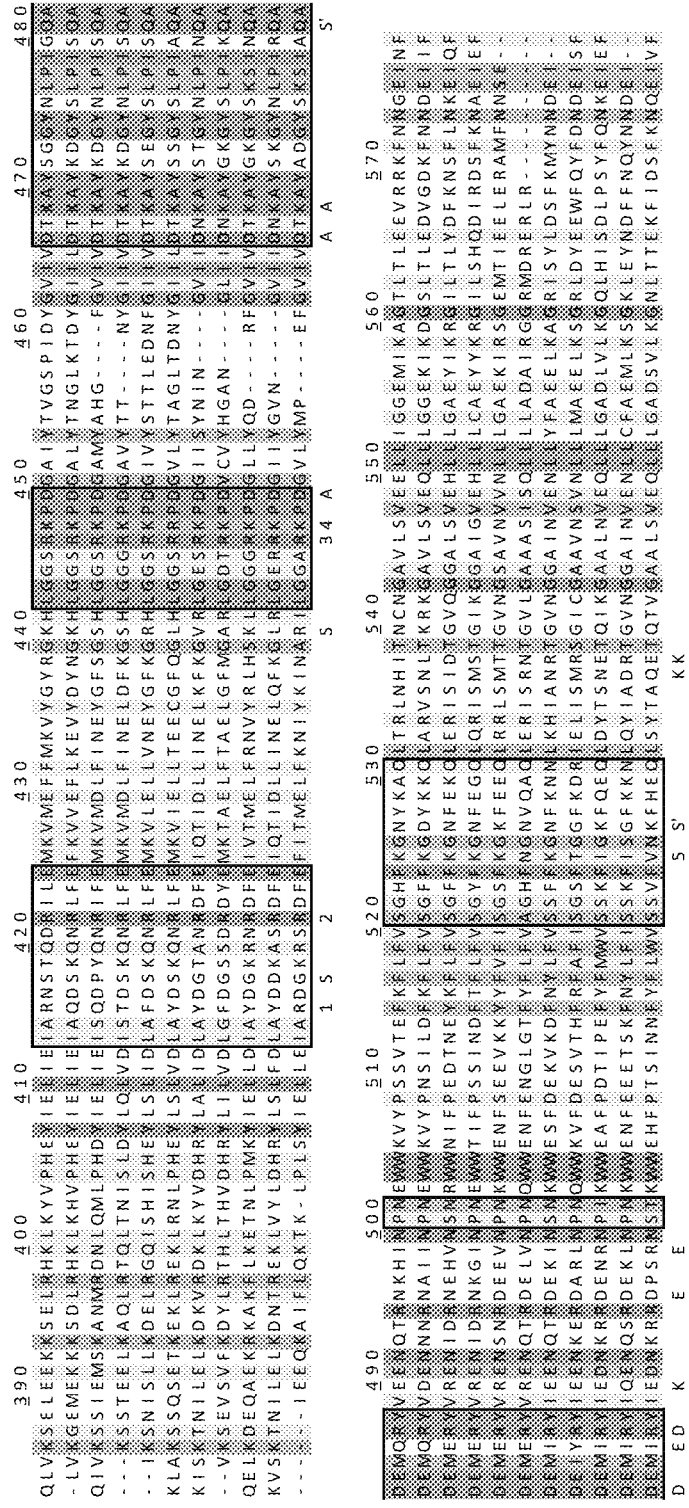
FIG. 17 shows an alignment of FokI and FokI homologues (SEQ ID NOS: 58-67, respectively, in order of appearance). Shading indicates the degree of conservation. Numbering is according to the wild type FokI domain (SEQ ID NO:1).

In one aspect, the invention provides a fusion protein wherein the engineered cleavage half-domain comprises a polypeptide in which the wild-type amino acid residue at one or more of positions 387, 393, 394, 398, 400, 402, 416, 422, 427, 434, 439, 441, 447, 448, 469, 487, 495, 497, 506, 516, 525, 529, 534, 559, 569, 570, 571 in the FokI catalytic domain are mutated. Nuclease domains comprising one or more mutations as shown in any of the appended Tables and Figures are provided. In some embodiments, the one or more mutations alter the wild type amino acid from a positively charged residue to a neutral residue or a negatively charged residue. In any of these embodiments, the mutants described may also be made in a FokI domain comprising one or more additional mutations. In preferred embodiments, these additional mutations are in the dimerization domain, e.g. at positions 418, 432, 441, 481, 483, 486, 487, 490, 496, 499, 523, 527, 537, 538 and/or 559. Non-limiting examples of mutations include mutations (e.g., substitutions) of the wild-type residues of any cleavage domain (e.g., FokI or homologue of FokI) at positions 393, 394, 398, 416, 421, 422, 442, 444, 472, 473, 478, 480, 525 or 530 with any amino acid residue (e.g., K393X, K394X, R398X, R416S, D421X, R422X, K444X, S472X, G473X, S472, P478X, G480X, K525X, and A530X, where the first residue depicts wild-type and X refers to any amino acid that is substituted for the wild-type residue). In some embodiments, X is E, D, H, A, K, S, T, D or N. Other exemplary mutations include S418E, S418D, S446D, K448A, I479Q, I479T, Q481A, Q481N, Q481E, A530E and/or A530K wherein the amino acid residues are numbered relative to full length FokI wild-type cleavage domain and homologues thereof (FIG. 17). In certain embodiments, combinations may include 416 and 422, a mutation at position 416 and K448A, K448A and I479Q, K448A and Q481A and/or K448A and a mutation at position 525. In one embodiment, the wild-residue at position 416 may be replaced with a Glu (E) residue (R416E), the wild-type residue at position 422 is replaced with a His (H) residue (R422H), and the wild-type residue at position 525 is replaced with an Ala (A) residue. The cleavage domains as described herein can further include additional mutations, including but not limited to at positions 432, 441, 483, 486, 487, 490, 496, 499, 527, 537, 538 and/or 559, for example dimerization domain mutants (e.g., ELD, KKR) and or nickase mutants (mutations to the catalytic domain). The cleavage half-domains with the mutations described herein form heterodimers as known in the art.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs and/or TALENs) can be screened for activity prior to use, for example in a yeast-based chromosomal system as described in as described in U.S. Pat. No. 8,563,314.

In certain embodiments, the nuclease comprises a CRISPR/Cas system. The CRISPR (clustered regularly interspaced short palindromic repeats) locus, which encodes RNA components of the system, and the Cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al, (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "'Cas" includes both Cas9 and Cfp1 proteins. Thus, as used herein, a "CRISPR/Cas system" refers both CRISPR/Cas and/or CRISPR/Cfp1 systems, including both nuclease and/or transcription factor systems.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran et al (2015) *Nature* 510, p. 186).

The nuclease(s) may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266; 8,703,489 and Guillinger et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery et al. (2016) *Nucleic Acids Res.* 44(2):e11. doi: 10.1093/nar/gkv878. Epub 2015 Oct. 19.

Delivery

The proteins (e.g., nucleases), polynucleotides and/or compositions comprising the proteins and/or polynucleotides described herein may be delivered to a target cell by any suitable means, including, for example, by injection of the protein and/or mRNA components.

Suitable cells include but not limited to eukaryotic and prokaryotic cells and/or cell lines. Non-limiting examples of such cells or cell lines generated from such cells include T-cells, COS, CHO (e.g., CHO—S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Suitable cells also include stem cells such as, by way of example, embryonic stem cells, induced pluripotent stem cells (iPS cells), hematopoietic stem cells, neuronal stem cells and mesenchymal stem cells.

Methods of delivering proteins comprising DNA-binding domains as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

DNA binding domains and fusion proteins comprising these DNA binding domains as described herein may also be delivered using vectors containing sequences encoding one or more of the DNA-binding protein(s). Additionally, additional nucleic acids (e.g., donors) also may be delivered via these vectors. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences and/or additional nucleic acids as appropriate. Thus, when one or more DNA-binding proteins as described herein are introduced into the cell, and additional DNAs as appropriate, they may be carried on the same vector or on different vectors. When multiple vectors are used, each vector may comprise a sequence encoding one or multiple DNA-binding proteins and additional nucleic acids as desired.

Conventional viral and non-viral based gene transfer methods can be used to introduce nucleic acids encoding engineered DNA-binding proteins in cells (e.g., mammalian cells) and target tissues and to co-introduce additional nucleotide sequences as desired. Such methods can also be used to administer nucleic acids (e.g., encoding DNA-binding proteins and/or donors) to cells in vitro. In certain embodiments, nucleic acids are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™, Lipofectin™, and Lipofectamine™ RNAiMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7) p. 643).

The use of RNA or DNA viral based systems for the delivery of nucleic acids encoding engineered DNA-binding proteins, and/or donors (e.g. CARs or ACTRs) as desired takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* USA 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* USA 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother* 44(1):10-20 (1997); Dranoff et al., *Hum. Gene Ther.* 1:111-2 (1997).

Recombinant adeno-associated virus vectors (rAAV) are a promising alternative gene delivery system based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV8.2, AAV9 and AAVrh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., (*Proc. Natl. Acad. Sci. USA* 92:9747-9751 (1995)), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Delivery methods for CRISPR/Cas systems can comprise those methods described above. For example, in animal models, in vitro transcribed Cas encoding mRNA or recombinant Cas protein can be directly injected into one-cell stage embryos using glass needles to genome-edited animals. To express Cas and guide RNAs in cells in vitro, typically plasmids that encode them are transfected into cells via lipofection or electroporation. Also, recombinant Cas protein can be complexed with in vitro transcribed guide RNA where the Cas-guide RNA ribonucleoprotein is taken up by the cells of interest (Kim et al (2014) *Genome Res* 24(6):1012). For therapeutic purposes, Cas and guide RNAs can be delivered by a combination of viral and non-viral techniques. For example, mRNA encoding Cas may be delivered via nanoparticle delivery while the guide RNAs and any desired transgene or repair template are delivered via AAV (Yin et al (2016) *Nat Biotechnol* 34(3) p. 328).

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have incorporated the vector.

Ex vivo cell transfection for diagnostics, research, transplant or for gene therapy (e.g., via re-infusion of the transfected cells into the host organism) is well known to those of skill in the art. In a preferred embodiment, cells are isolated from the subject organism, transfected with a DNA-binding proteins nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Tad (differentiated antigen presenting cells) (see Inaba et al., *J. Exp. Med.* 176:1693-1702 (1992)).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific ZFNs (see, U.S. Pat. No. 8,597,912) in the stem cells, or those that are disrupted in a caspase, again using caspase-6 specific ZFNs for example.

Vectors (e.g., retroviruses, adenoviruses, liposomes, etc.) containing therapeutic DNA-binding proteins (or nucleic acids encoding these proteins) can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells, including T-cells and stem cells of any type. Suitable cell lines for protein expression are known to those of skill in the art and include, but are not limited to COS, CHO (e.g., CHO—S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera* fugiperda (Sf), and fungal cells such as *Saccharomyces, Pichia* and *Schizosaccharomyces*. Progeny, variants and derivatives of these cell lines can also be used.

Applications

Use of engineered nucleases in treatment and prevention of disease is expected to be one of the most significant developments in medicine in the coming years. The methods and compositions described herein serve to increase the specificity of these novel tools to ensure that the desired target sites will be the primary place of cleavage. Minimizing or eliminating off-target cleavage will be required to realize the full potential of this technology, for all in vitro, in vivo and ex vivo applications.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, phenylketonuria (PKU). *porphyria*, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Such methods also allow for treatment of infections (viral or bacterial) in a host (e.g., by blocking expression of viral or bacterial receptors, thereby preventing infection and/or spread in a host organism) to treat genetic diseases.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. See, U.S. Patent Publication No. 2008/015996. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4.

Thus, heterodimeric cleavage domain variants as described herein provide broad utility for improving ZFN specificity in gene modification applications. These variant cleavage domains may be readily incorporated into any existing ZFN by either site directed mutagenesis or subcloning to improve the in vivo specificity of any ZFN dimers.

As noted above, the compositions and methods described herein can be used for gene modification, gene correction, and gene disruption. Non-limiting examples of gene modification includes homology directed repair (HDR)-based targeted integration; HDR-based gene correction; HDR-based gene modification; HDR-based gene disruption; NHEJ-based gene disruption and/or combinations of HDR, NHEJ, and/or single strand annealing (SSA). Single-Strand Annealing (SSA) refers to the repair of a double strand break between two repeated sequences that occur in the same orientation by resection of the DSB by 5'-3' exonucleases to expose the 2 complementary regions. The single-strands encoding the 2 direct repeats then anneal to each other, and the annealed intermediate can be processed such that the single-stranded tails (the portion of the single-stranded DNA that is not annealed to any sequence) are be digested away, the gaps filled in by DNA Polymerase, and the DNA ends rejoined. This results in the deletion of sequences located between the direct repeats.

Compositions comprising cleavage domains (e.g., ZFNs, TALENs, CRISPR/Cas systems) and methods described herein can also be used in the treatment of various genetic diseases and/or infectious diseases.

The compositions and methods can also be applied to stem cell based therapies, including but not limited to: correction of somatic cell mutations by short patch gene conversion or targeted integration for monogenic gene therapy; disruption of dominant negative alleles; disruption of genes required for the entry or productive infection of pathogens into cells; enhanced tissue engineering, for example, by modifying gene activity to promote the differentiation or formation of functional tissues; and/or disrupting gene activity to promote the differentiation or formation of functional tissues; blocking or inducing differentiation, for example, by disrupting genes that block differentiation to promote stem cells to differentiate down a specific lineage pathway, targeted insertion of a gene or siRNA expression cassette that can stimulate stem cell differentiation, targeted insertion of a gene or siRNA expression cassette that can block stem cell differentiation and allow better expansion and maintenance of pluripotency, and/or targeted insertion of a reporter gene in frame with an endogenous gene that is a marker of pluripotency or differentiation state that would allow an easy marker to score differentiation state of stem cells and how changes in media, cytokines, growth conditions, expression of genes, expression of siRNA, shRNA or miRNA molecules, exposure to antibodies to cell surface markers, or drugs alter this state; somatic cell nuclear transfer, for example, a patient's own somatic cells can be isolated, the intended target gene modified in the appropriate manner, cell clones generated (and quality controlled to ensure genome safety), and the nuclei from these cells isolated and transferred into unfertilized eggs to generate patient-specific hES cells that could be directly injected or differentiated before engrafting into the patient, thereby reducing or eliminating tissue rejection; universal stem cells by knocking out MHC receptors (e.g., to generate cells of diminished or altogether abolished immunological identity). Cell types for this procedure include but are not limited to, T-cells, B cells, hematopoietic stem cells, and embryonic stem cells. Additionally, induced pluripotent stem cells (iPSC) may be used which would also be generated from a patient's own somatic cells. Therefore, these stem cells or their derivatives (differentiated cell types or tissues) could be potentially engrafted into any person regardless of their origin or histocompatibility.

The compositions and methods can also be used for somatic cell therapy, thereby allowing production of stocks of cells that have been modified to enhance their biological properties. Such cells can be infused into a variety of patients, independent of the donor source of the cells and their histocompatibility to the recipient.

In addition to therapeutic applications, the increased specificity provided by the variants described herein when used in engineered nucleases can be used for crop engineering, cell line engineering and the construction of disease models. The obligate heterodimer cleavage half-domains provide a straightforward means for improving nuclease properties.

The engineered cleavage half domains described can also be used in gene modification protocols requiring simultaneous cleavage at multiple targets either to delete the intervening region or to alter two specific loci at once. Cleavage at two targets would require cellular expression of four ZFNs or TALENs, which could yield potentially ten different active ZFN or TALEN combinations. For such applications, substitution of these novel variants for the wild-type nuclease domain would eliminate the activity of the undesired combinations and reduce chances of off-target cleavage. If cleavage at a certain desired DNA target requires the activity of the nuclease pair A+B, and simultaneous cleavage at a second desired DNA target requires the activity of the nuclease pair X+Y, then use of the mutations described herein can prevent the pairings of A with A, A with X, A with Y and so on. Thus, these FokI mutations decrease non-specific cleavage activity as a result of "illegitimate" pair formation and allow the generation of more efficient orthogonal mutant pairs of nucleases (see co-owned patent U.S. Patent Publication Nos. 20080131962 and 20090305346).

EXAMPLES

Example 1: Preparation of ZFNs

ZFNs targeted to sites in the BCL11A and TCRA (targeting the constant region, also known as TRAC) genes were designed and incorporated into plasmids vectors essentially as described in Urnov et al. (2005) *Nature* 435(7042):646-651, Perez et al (2008) *Nature Biotechnology* 26(7): 808-816, and PCT Patent Publication No. WO 2016183298 and PCT Publication No. WO2017106528. Also used were AAVS1 targeted ZFNs as described in U.S. Publication No. 20150110762.

Example 2: Mutants in FokI Residues Targeting Interaction with Phosphates

Using models of the FokI cleavage domain (Miller et al (2007) *Nat Biotech* 25(7):778-85), positively charged arginine or lysine amino acid residues were identified (FIG. 1) that potentially interact with the phosphates on the DNA backbone.

Figure 2A:
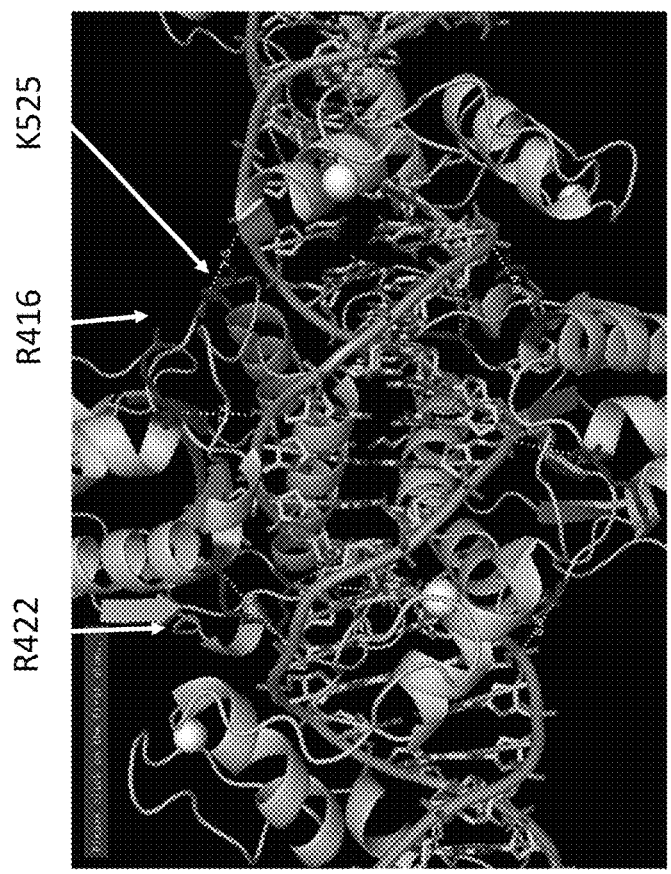
Figure 2C:
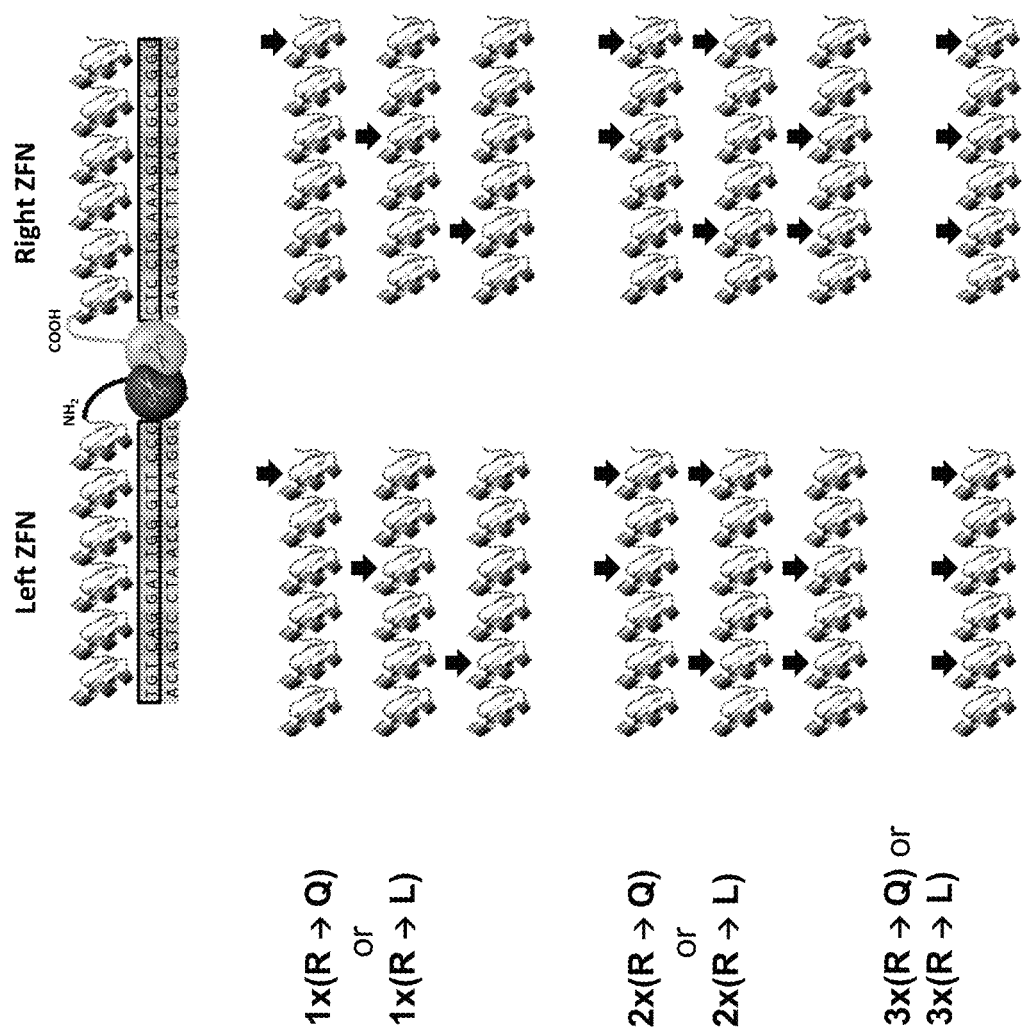

The identified positions in the FokI domain (amino acids 416, 422, 447, 448 and 525) were then specifically changed (mutated) to serine residues to eliminate the interaction between the original positive amino acid and the negatively charged phosphates on the DNA (see FIGS. 2A and 2B). When both ZFN partners comprise these mutations, a number of different combinations can result (see illustration in FIG. 2C). These new FokI mutants were made in the 'KKR' FokI partner of the ELD/KKR heterodimers (see U.S. Pat. No. 8,962,281), and were then linked to a ZFN pair specific for the BCL11A enhancer region, SBS #51857 ELD/SBS #51949 KKR or SBS #51857 KKR/SBS #51949 ELD, the 'parent' proteins highlighted in grey in FIG. 3. The mutations were made in each partner and then tested for cleavage activity against the original BCL11A target in CD34+ T cells in various combinations as shown on FIG. 3. Off-target sites had been previously identified by unbiased capture analysis (PCT Patent Publication No. WO 2016/183298). The off-target sites are listed below in Table 1, where each site is identified with a unique and randomly generated 'license plate' letter identifier, where the license plate PRJIYLFN indicated the intended target BCL11A sequence. In the table below, the locus of each site is indicated as well (coordinates are listed in agreement with the hg38 assembly of the U.C. Santa Cruz Human Genome Browser sequence database, (Kent et al (2002), *Genome Res.*12(6):996-1006).

TABLE 1

SBS#51857/SBS#51949 identified cleavage sites

| License plate | Seq ID | Sequence (5'→3') | Chromosome: hg38 locus | Type |
|---|---|---|---|---|
| PRJIYLFN (intended target) | 13 | CTAATCAGAGGCCAAACCCTTCCTGGAGCCTGTGATAAAAGCAA CTGTTAGCTTGCACTAGACTAGCTTCAAAGTT | Chr2:60495265 | Intron |
| NIFMAEVG | 14 | CTTCCTGCGGGGTTTTGTGCAAATAACCCATGCTCGGGAGCGAG GCCCTGGGAAGGAGTATCTCGCTTCTTTGGGT | Chr8:119856440 | intergenic |
| GJZEIYTO | 15 | CCTACCCCCACCACCTCACCTTCCCTCAGCCTTGTGTTTCAGCCCC AGTTAGCTGCCCTTAGTTGCTGATGTATTG | Chr6:53805960 | intron |

TABLE 1-continued

SBS#51857/SBS#51949 identified cleavage sites

| License plate | Seq ID | Sequence (5'→3') | Chromosome: hg38 locus | Type |
|---|---|---|---|---|
| RFGIYSHZ | 16 | AGCACGTTTCTCCAGTTTCCAGCCTGGGGCCTGGCTATAAAGCAA ATGCTCAGTCCAGCATTGCGGAATGCAAGGG | Chr2:23702834 | intron |
| RFTBCWPJ | 17 | ACAGCACCGTGCTGCACGGCGTCCTCCGGCCTTGCTGCCTGGCA ATGGGTAGCCACCTGGCGTCTGTCTCAGAATA | Chr13:75549354 | 5 UTR |
| XCVJFHOB | 18 | TTCCCAGAAGGCGATTGAACCTGAAGCTGCGCCTGGCGCGTGAG CCTGTGGGGGGGACGCGGCTGAGGGGCTTTGA | Chr10:132654830 | intron |
| ZMIYSTJN | 19 | TATCCCTTCCCCAAGTGCAACCAACAGTTGCTCTAAAGCTAGGCT GGTGGAGTTGGGGAAAGGGCCAGCAAGTGAG | Chr10:69571178 | intergenic |
| PEVYOHIU | 20 | TCCTCCATGCTCAGAAAGCCTTTCTTGGAGCCAGGCACACAGGA AATGTTAGCTAGTTAGCATTGGCTCTAATACT | Chr2:62164811 | intergenic |
| QRMXFJNY | 21 | TAGCTGGGGAGAGATTGCCTCTCTCAGGGCCTAGCCAGTTCCTA GAAATAGCAAGGGCTCAGCTGAGAGCATGCTT | Chr14:67422067 | intergenic |
| QBFUYVGW | 22 | TCCCCCGGAAGTGTCCGCACCTCCTAGAGCCCAGCGAGCGAGCG TTTTGTGCTTTTGTCCTTTGAACCGGGTGTGGT | Chr1:29182166 | intergenic |
| ZJCRPAXW | 23 | GACTCATTCATCCACTCATTCTGAGCACTTGCTGCACACTAGGCC CTGGGCTGGGGCTTCAGCCCAGGAGTTCACT | Chr1:54506813 | intergenic |
| LXAFJWRI | 24 | ATGTAGTCTGACGGCCGCGACTGGTTCGTAGCTTTTGAGTGAGG CGGCGGGAAGGGAGCGAGGGAAGAGCGGCAGT | Chr2:84459584 | intergenic |
| EMQNZDWX | 25 | TCATGTTATGGAAGTGGCTTCTTTCCTTAAGCCTTATGAATAAGC CTCTGCTAGCTTCAAACTTTGTGTGCAGCTT | Chr20:37707468 | intron |
| YJRBCUNZ | 26 | CATAAAGCACTTACAACAGTGCCTGGCAAATGCCTAGTGCACAG CAAGTGTTAGCTATTGTTAATGACTATCCATT | Chr1:19916857 | intergenic |
| HBXGRVYT | 27 | ATTTTTGCCCCTGTCTTCTCTTTTCCTCCTTTGCTGCATCCCAGGCT CCAGCCTTTCAGCCCTATTTGCAGTACCC | Chr1:204975770 | intronic |
| ZLRCYHDF | 28 | ACAAGGGGTTCAAGGTTATGAATAACCTGTGCTAATCCCAGAGG CCCCAGGACAGAGTAAGTGGGAACAAACACTG | Chr7:131503657 | 3 UTR |
| OTHMRBJL | 29 | CGGAAGTTAATATGATCATTGCTAACATTTGCTGTGTTTCAGGCA CTGTAAGCATGTATATGGGTCCTTAAAGGGA | Chr11:108224087 | intron |
| RSYQNPLG | 30 | TGAGCCCAGAAACCCCTTACCCTTCCTCCTGCCTCTTGAGAGGCC AGTGTTAGGTGTTAGCCGGGGTGCAAAGCTC | Chr20:44683649 | intergenic |
| SIJYTMVG | 31 | AACCTGGTGCGAGCAGCCCGGGCTACAGGGTTGCCTGAGGTGT GGGTCCCAGGATGGAGGAGCCCCAGGCCGGCGG | Chr19:45406704 | coding |
| BCGJKHUV | 32 | ACTTCGGTGAAGGAAGTCATCAGTGCAGTTGCCGACAAGCTGGG CTCCGGGGAGGGCCTGATCATAGTCAAGATGA | Chr2:173018748 | coding |
| RDEWOSIT | 33 | GGGGCCAGGCAGGAAGAACAGCTAACTCTAGCTCACCTGCAAG GCTCAGCACTGGGTTCATTTGAAGTAGTGTCCT | Chr3:47439806 | intron |
| YPLXMQCB | 34 | CTCCTTTGGGTGTGGACGGGACTAACACTTGCTCCATGTCAGGG CTGCAGGACCTCCTGGCTGTTGACAGCAGGCA | Chr16:85317248 | intergenic |
| TPHSLVEM | 35 | GATGTTTGAAAAGCGCTGAGCCTGGCCTGGCACCTAAACAGCTC AGCAAGTGTTAGCCAGGATCACTAGCAGTAAT | Chr19:45686044 | intergenic |
| WOEIMTLA | 36 | ACCCTGCCGATTTCCTTCCAGTTGCTCGCTGGGGCAACCGGCTAG GCTGGAGGAAGGGCGAGGACGGTGTCACCCC | ChrX:134914734 | intron |
| TBUYJIVX | 37 | GAACATGGTGAGGACAAAATGATGTCCAGGAGCCTTTTCTTTGG CCATTGCTAGCCTGAGACGAAAAGTCAGTGGC | Chr17:40557500 | intron |
| LPRCNGHU | 38 | AGTCTGTCAGTCTATCGTCCCTACCTGCAGCCCAAAGCATAAGCA ACATCTTGCCCAGCTCAGAGGTGACAACCTC | Chr1:42891189 | intergenic |
| AKRHSGPT | 39 | CACCGACCCAAGGACCACTCCTTCCAGGAACCTAGCCTAAAGCA AAGGTGCAGACAGCCCGGGGCCACCGCTGACC | Chr17:28854518 | intergenic |
| IRSUAEVF | 40 | TTGCAAAAGGAAGTTTGAAGCTAGCAGAGGCTGATTCATGAGGT TCAAGGAAAGAAGTCATCTCTGTAACATAAAA | ChrX:30280457 | intergenic |

TABLE 1-continued

SBS#51857/SBS#51949 identified cleavage sites

| License plate | Seq ID | Sequence (5'→3') | Chromosome: hg38 locus | Type |
|---|---|---|---|---|
| ATWDXHSC | 41 | CGTCCCCCAGAGTCCTGTTTCCTCTCCTTCAGCCCCCAAATGAGCAAAGGTTAGGCCCCACCCCTGCTGAGTCAGC | Chr12:56636086 | intronc |
| QDMBZRWI | 42 | GTCAGGGGACAGGGTTTCCTAGCATCCGCGAGCCTTACAGAAAGGCAACTGTGCAGTGCTCCAGCTGGCTTTCTCA | Chr10:26734303 | intron |
| WBEAFQRU | 43 | ACCATCAGAGAAGCTAACCTTTCCTGAGGCCTAACTACTTTGCAGGTCCTGTATTATGTCCTCTATAGACATTAGG | Chr12:104048818 | intron |
| RXDOKCGI | 44 | GATCATTTCAAAGAAAACATTCTGGAACAGTTGCCTATGGGCACGGCAGGGTGACGGTGCTGCTTCTGGGTTTGAC | Chr11:11842581 | intronic |
| TXHULGPN | 45 | GAAGGGCAGAGAACTATAATGACACAGTTGCTTTATTGCTGGACCCAGGACAGTTTATACAGCAGTTCGGAAAGGC | Chr11:33894467 | intergenic |
| DYNFTSUP | 46 | ACTTATTGTAAGTGACGCATGTGACCAGTTGCCAATTGTTCAGGCTACAGCTTGGATCTGTTAGCATCCTCATTTA | Chr11:102685873 | intergenic |
| XFDECBQY | 47 | CCCAGGGGCTGTGGGACACTCAGAGAGCCTATGCCTGTGCCCTGGGCTCCGGGAGGGAGAGGATCTGGGGGCCAG | Chr16:2122341 | intron |
| ZTIFQRKB | 48 | CCCCAGGGGCTGTGGGACACTCAGAGAGCCTATGCCTGTGCCCTGGGCTCCGGGAGGGGAGAGGATCTGGGGGCCAG | Chr16:15141541 | intergenic |
| ZFUQTLMTFC | 49 | AGCTTCCTGCAGCCTCCCTCAAAGCAGATGTTAGCACTATTA | Chr10:73205435 | intronic |
| ZCNLWTPH | 50 | CCTCACCTAGAACCTGGGCCCCTGCAACTGTAACCTGTGGCA | Chr19:1198151 | intergenic |
| QYYPVRQWMN | 51 | CCAGAGGAAGAACAGTTGCTTGGGTCTAGGCCTCAGGAAGGG | Chr10:101133375 | intron |
| EKYJXRAHKV | 52 | CCTGTGCTGGGGCCTGGGAGGCAGGCGGCTGCTAGCCATCCTG | Chr6:89888014 | intergenic |
| ADWZQXZI | 53 | TGACTTAGGAAGCAGTTGCTACCTGCCAGGCCCCAGGCTAGG | Chr9:128604027 | intronic |

The data presented in FIG. 3 demonstrated that certain mutations decreased the activity of the proteins against the against the cognate BCL11A target site, with a commensurate drop in off-target cleavage activity (e.g. see 51857-ELD/51949-KKR_R447S: on-target activity reduced to 11.60% indels, as compared to the parent of 80.59%; activity at the NIFMAEVG off-target also fell to 0.05% as compared to the value of 9.04% for the parent and activity at the PEVYOHIU off-target fell to 0.03% from value of 0.65% for the parent (FIG. 3A)). However, for other mutations, the on-target cleavage activity remained robust while activity at both measured off-target sites decreased substantially. For example, the pair 51857-ELD/51949-KKR_R416S had an on-target activity for BCL11A that is very similar to the parent proteins (80.63% indels for the mutant pair versus 80.59% for the parent at the 2 μg dose (20 μg/mL)), while the activity at the two off-targets decreased substantially (0.75% for the mutant pair versus 9.04% for the parents at off-target site NIFMAEVG and 0.08% for the mutant pair versus 0.65% for the parents at off-target site PEVYOHIU) (FIG. 3A).

The mutant proteins were also assembled using the heterodimeric FokI domain in the opposite orientation, i.e., whereas FIG. 3A showed the results with 51857-ELD/51949-KKR, FIG. 3B depicts the results with 51857-KKR/51949-ELD. Again, there were some pairs that maintained robust on-target activity (e.g. 51857-KKR/51949-ELD_K448S) similar to the parent pair (83.02% versus 88.28%, respectively), yet displayed decreased activity on the off-target locations (1.00% versus 9.26% for NIFMAEVG; 0.33% versus 0.87% for PEVYOHIU (FIG. 3B).

The experiments were also performed using a pair of TCRA (TRAC)-specific ZFNs: SBS #52742_ELD/SBS #52774_KKR (U.S. Patent Publication No. US-2017-0211075-A1). These experiments were carried out in K562 cells where the cells were treated with either 100 or 400 ng of mRNA encoding each ZFN. The ZFN pairs consisted of one mutated partner as disclosed below in Table 2 and one non-mutated partner. In these experiments, all the positively charged amino acids identified in FIG. 1 were mutated to Serine (S). In brief, 2×10e5 cells were used per transfection where the mRNAs were delivered to the cell via use of the Amaxa 96-well shuttle system. Transfected cells were harvested at day 3 following the transfection and processed for MiSeq (Illumina) analysis per standard methods. The data are shown below in Table 2, and demonstrated that some of the mutations maintained robust on-target activity, while others (e.g. 52742 ELD_K469S, identified as an active site residue in FIG. 1) knocked out cleavage activity.

TABLE 2

On-Target results for TCRA (TRAC) ZFNs with FokI mutations

| | % total indels | | | % total indels | |
|---|---|---|---|---|---|
| 52742 variant | 400 ng | 100 ng | 52774 variant | 400 ng | 100 ng |
| ELD | 90.72 | 71.46 | KKR | 89.08 | 70.58 |
| Fok_ELD_K387S | 92.31 | 66.35 | Fok_KKR_K387S | 89.06 | 62.70 |
| Fok_ELD_K393S | 73.06 | 23.09 | Fok_KKR_K393S | 65.89 | 17.98 |
| Fok_ELD_K394S | 71.15 | 21.86 | Fok_KKR_K394S | 67.44 | 25.09 |
| Fok_ELD_R398S | 86.23 | 41.21 | Fok_KKR_R398S | 84.61 | 42.28 |

TABLE 2-continued

On-Target results for TCRA (TRAC) ZFNs with FokI mutations

| 52742 variant | % total indels 400 ng | % total indels 100 ng | 52774 variant | % total indels 400 ng | % total indels 100 ng |
|---|---|---|---|---|---|
| Fok_ELD_K400S | 88.16 | 63.12 | Fok_KKR_K400S | 83.15 | 0.13 |
| Fok_ELD_K402S | 84.49 | 40.64 | Fok_KKR_K402S | 79.76 | 0.15 |
| Fok_ELD_R416S | 92.91 | 67.06 | Fok_KKR_R416S | 87.11 | 45.48 |
| Fok_ELD_R422S | 88.98 | 47.48 | Fok_KKR_R422S | 69.98 | 20.95 |
| Fok_ELD_K427S | 75.15 | 25.24 | Fok_KKR_K427S | 73.51 | 25.40 |
| Fok_ELD_K434S | 88.65 | 57.40 | Fok_KKR_K434S | 88.50 | 64.84 |
| Fok_ELD_R439S | 85.58 | 56.54 | Fok_KKR_R439S | 88.38 | 70.39 |
| Fok_ELD_K441S | 88.15 | 61.13 | Fok_KKR_K441S | 78.26 | 72.33 |
| Fok_ELD_R447S | 70.26 | 25.74 | Fok_KKR_R447S | 36.08 | 15.06 |
| Fok_ELD_K448S | 90.95 | 68.02 | Fok_KKR_K448S | 91.39 | 79.43 |
| Fok_ELD_K469S | 0.16 | 0.12 | Fok_KKR_K469S | 0.52 | 0.29 |
| Fok_ELD_R487S | 0.45 | 0.21 | Fok_KKR_R487S | 0.30 | 0.18 |
| Fok_ELD_R495S | 2.52 | 0.58 | Fok_KKR_R495S | 5.71 | 1.15 |
| Fok_ELD_K497S | 87.46 | 54.80 | Fok_KKR_K497S | 87.18 | 59.54 |
| Fok_ELD_K506S | 85.54 | 58.14 | Fok_KKR_K506S | 86.05 | 62.42 |
| Fok_ELD_K516S | 42.50 | 12.38 | Fok_KKR_K516S | 0.16 | 25.48 |
| Fok_ELD_K525S | 91.00 | 60.36 | Fok_KKR_K525S | 88.31 | 46.52 |
| Fok_ELD_K529S | 85.01 | 46.71 | Fok_KKR_K529S | 88.34 | 64.13 |
| Fok_ELD_R534S | 2.23 | 0.57 | Fok_KKR_R534S | 87.46 | 60.69 |
| Fok_ELD_K559S | 86.45 | 47.69 | Fok_KKR_K559S | 88.27 | 58.47 |
| Fok_ELD_R569S | 22.45 | 5.20 | Fok_KKR_R569S | 64.99 | 18.87 |
| Fok_ELD_R570S | 84.97 | 46.82 | Fok_KKR_R570S | 89.58 | 62.32 |
| Fok_ELD_K571S | 84.93 | 44.61 | Fok_KKR_K571S | 87.75 | 70.77 |

Off-target analyses were also done to determine the top off-target cleavage sites as determined by unbiased capture analysis (PCT Patent Publication No. WO 2016/183298). Four genomic loci (the intended target in TCRA (TRAC) and three off-targets) identified for this ZFN pair by the unbiased capture assay are presented below in Table 3.

TABLE 3

Cleavage sites for TCRA (TRAC)-specific ZFN

| License plate | Seq ID | Sequence (5'→3') | Chromosome: hg38 locus | Type |
|---|---|---|---|---|
| JBSCKVMP (intended target) | 54 | TCAGTGATTGGGTTCCGAATCCTCCTCCTGAAAGTGGCCG | Chr14:22550603 | coding |
| XSKWTVWD | 55 | CCATATGCAGAAAACAGAAACTGTACCCCTTCCTTACACC | Chr18:30735897 | intergenic |
| XVFENVRX | 56 | TGGCCCTTTGCAGAAAAGGTTGTTGAACCCTACCGTAAAC | Chr16:4780553 | intronic |
| KXWACMTR | 57 | CCGGAGAGAAGGCTCCGGTTCAGCACTGAGATCAGGACGG | Chr1:53220206 | intergenic |

Nuclease activity at two off-target sites (referred to as OT11 or XVFENVRX and OT16 or XSKWTVWD, shown above in Table 3) at the 400 ng of mRNA dose of each ZFN were analyzed, where one partner in the ZFN pair had the indicated mutation and the other retained the unmodified ELD or KKR FokI domain. The data shown (Table 4) indicate the percent indels (activity) observed using 400 ng of each ZFN partner. These data also showed that some of the mutations maintained nearly equivalent on-target activity but showed a decrease in off-target activities. For example, for SBS #52774_KKR_K387S showed an on-target activity of 89.06% indels at 400 ng (compared to 89.08 for the 52774_KKR parent) and a combined off-target activity at OT11 and OT16 of 6.39% indels (compared to 15.07% for the 52774_KKR parent). The results included FokI mutations tested in the BCL11A-specific ZFN where alteration of the positive charges at positions 416, 422, 447, 448 and 525 reduced the off-target activity.

TABLE 4

Off-target cleavage of TRAC ZFN FokI mutants

| | % indels | | | | | % indels | | | |
|---|---|---|---|---|---|---|---|---|---|
| 52742 | On-target | OT16 | OT11 | OT11 + OT16 | 52774 | On-target | OT16 | OT11 | OT11 + OT16 |
| ELD | 90.72 | 7.39 | 5.82 | 13.21 | KKR | 89.08 | 7.80 | 7.27 | 15.07 |
| Fok_ELD_K387S | 92.31 | 13.15 | 4.32 | 17.47 | Fok_KKR_K387S | 89.06 | 3.12 | 3.27 | 6.39 |
| Fok_ELD_K393S | 73.06 | 0.87 | 0.60 | 1.47 | Fok_KKR_K393S | 65.89 | 1.04 | 0.71 | 1.76 |
| Fok_ELD_K394S | 71.15 | 0.79 | 0.61 | 1.40 | Fok_KKR_K394S | 67.44 | 1.02 | 0.77 | 1.79 |
| Fok_ELD_R398S | 86.23 | 2.64 | 1.86 | 4.50 | Fok_KKR_R398S | 84.61 | 3.10 | 2.04 | 5.14 |
| Fok_ELD_K400S | 88.16 | 4.13 | 2.55 | 6.68 | Fok_KKR_K400S | 83.15 | 2.49 | 1.60 | 4.09 |
| Fok_ELD_K402S | 84.49 | 2.10 | 1.64 | 3.74 | Fok_KKR_K402S | 79.76 | 2.93 | 1.21 | 4.13 |
| Fok_ELD_R416S | 92.91 | 6.29 | 3.08 | 9.37 | Fok_KKR_R416S | 87.11 | 0.74 | 0.93 | 1.68 |
| Fok_ELD_R422S | 88.98 | 1.18 | 1.09 | 2.27 | Fok_KKR_R422S | 69.98 | 0.26 | 1.07 | 1.33 |
| Fok_ELD_K427S | 75.15 | 1.18 | 0.89 | 2.07 | Fok_KKR_K427S | 73.51 | 2.16 | 1.30 | 3.46 |
| Fok_ELD_K434S | 88.65 | 5.52 | 3.50 | 9.03 | Fok_KKR_K434S | 88.5 | 6.76 | 5.44 | 12.20 |
| Fok_ELD_R439S | 85.58 | 4.51 | 2.77 | 7.29 | Fok_KKR_R439S | 88.38 | 7.39 | 5.62 | 13.01 |
| Fok_ELD_K441S | 88.15 | 5.96 | 3.44 | 9.40 | Fok_KKR_K441S | 78.26 | 4.93 | 3.38 | 8.30 |
| Fok_ELD_R447S | 70.26 | 0.32 | 0.14 | 0.46 | Fok_KKR_R447S | 36.08 | 0.11 | 0.18 | 0.29 |
| Fok_ELD_K448S | 90.95 | 5.28 | 1.96 | 7.24 | Fok_KKR_K448S | 91.39 | 2.05 | 1.12 | 3.18 |
| Fok_ELD_K469S | 0.16 | 0.18 | 0.15 | 0.33 | Fok_KKR_K469S | 0.52 | 0.18 | 0.14 | 0.32 |
| Fok_ELD_R487S | 0.45 | 0.16 | 0.12 | 0.28 | Fok_KKR_R487S | 0.3 | 0.17 | 0.11 | 0.28 |
| Fok_ELD_R495S | 2.52 | 0.14 | 0.12 | 0.26 | Fok_KKR_R495S | 5.71 | 0.15 | 0.13 | 0.28 |
| Fok_ELD_K497S | 87.46 | 3.56 | 2.66 | 6.23 | Fok_KKR_K497S | 87.18 | 6.13 | 6.44 | 12.57 |
| Fok_ELD_K506S | 85.54 | 4.06 | 3.05 | 7.10 | Fok_KKR_K506S | 86.05 | 4.22 | 2.55 | 6.77 |
| Fok_ELD_K516S | 42.5 | 0.45 | 0.34 | 0.79 | Fok_KKR_K516S | 0.16 | 0.11 | 0.15 | 0.26 |
| Fok_ELD_K525S | 91 | 0.81 | 2.13 | 2.94 | Fok_KKR_K525S | 88.31 | 0.96 | 0.79 | 1.75 |
| Fok_ELD_K529S | 85.01 | 1.99 | 1.46 | 3.45 | Fok_KKR_K529S | 88.34 | 6.45 | 4.83 | 11.27 |
| Fok_ELD_R534S | 2.23 | 0.14 | 0.15 | 0.29 | Fok_KKR_R534S | 87.46 | 4.44 | 3.29 | 7.74 |
| Fok_ELD_K559S | 86.45 | 2.72 | 1.84 | 4.56 | Fok_KKR_K559S | 88.27 | 4.27 | 2.61 | 6.88 |
| Fok_ELD_R569S | 22.45 | 0.25 | 0.22 | 0.47 | Fok_KKR_R569S | 64.99 | 1.39 | 1.05 | 2.45 |
| Fok_ELD_R570S | 84.97 | 2.73 | 1.96 | 4.68 | Fok_KKR_R570S | 89.58 | 7.98 | 6.20 | 14.18 |
| Fok_ELD_K571S | 84.93 | 2.27 | 1.96 | 4.23 | Fok_KKR_K571S | 87.75 | 8.24 | 6.11 | 14.34 |

Figure 4:
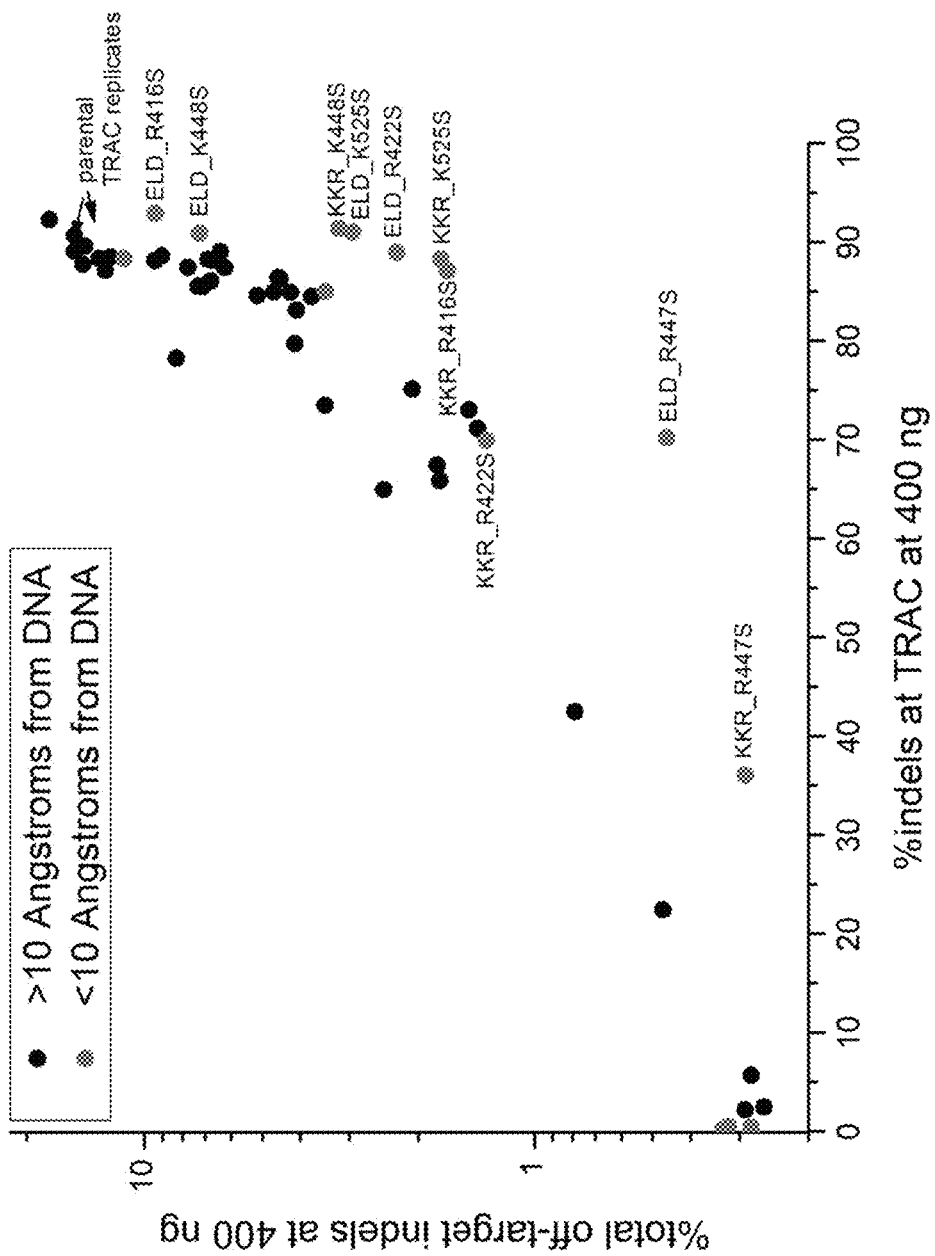
FIG. 4 is a plot depicting on-target and off-target activity for a number of the TCRA (constant region targeted, also known as TRAC)-specific ZFN FokI variants (PCT Publication WO2017106528). Except for the two replicates of the parental ZFN pair, the FokI domain in one of the two ZFNs bears a mutation at a positively charged residue. The distance between the alpha carbon of the mutated residue in FokI and the nearest phosphate oxygen in the DNA backbone of a ZFN-DNA molecular model (Miller et al (2007) *Nat Biotech* 25(7):778-785) was calculated and the data points are color-coded based on this calculated distance (either <10 Angstroms: grey; >10 Angstroms: black). Each data point represents the on-target activity and combined off-target activity for a different ZFN pair bearing FokI mutations on one of the ZFNs in the pair. Data points representing the parental pair are indicated.

The data was then compared to the estimated distance between the mutated amino acid residue and the DNA molecule to examine the effect on both on- and off-target cleavage (FIG. 4). Each ZFN pair's activity is shown as a single point and demonstrated that the proteins with the most desirable profiles (high on-target activity and low off-target activity) were those whose mutations were within 10 Angstroms from the DNA molecule (FIG. 4). Data points corresponding to ZFN pairs where one ZFN bears a FokI mutation at position 416, 422, 447, 448, or 525 are indicated.

These results demonstrated that mutations to one or more of residues 416, 422, 447, 448, or 525 can increase on-target activity while decreasing off-target activity.

Example 3: Design of Novel Engineered Zinc Finger Backbone Mutations

Figure 6:
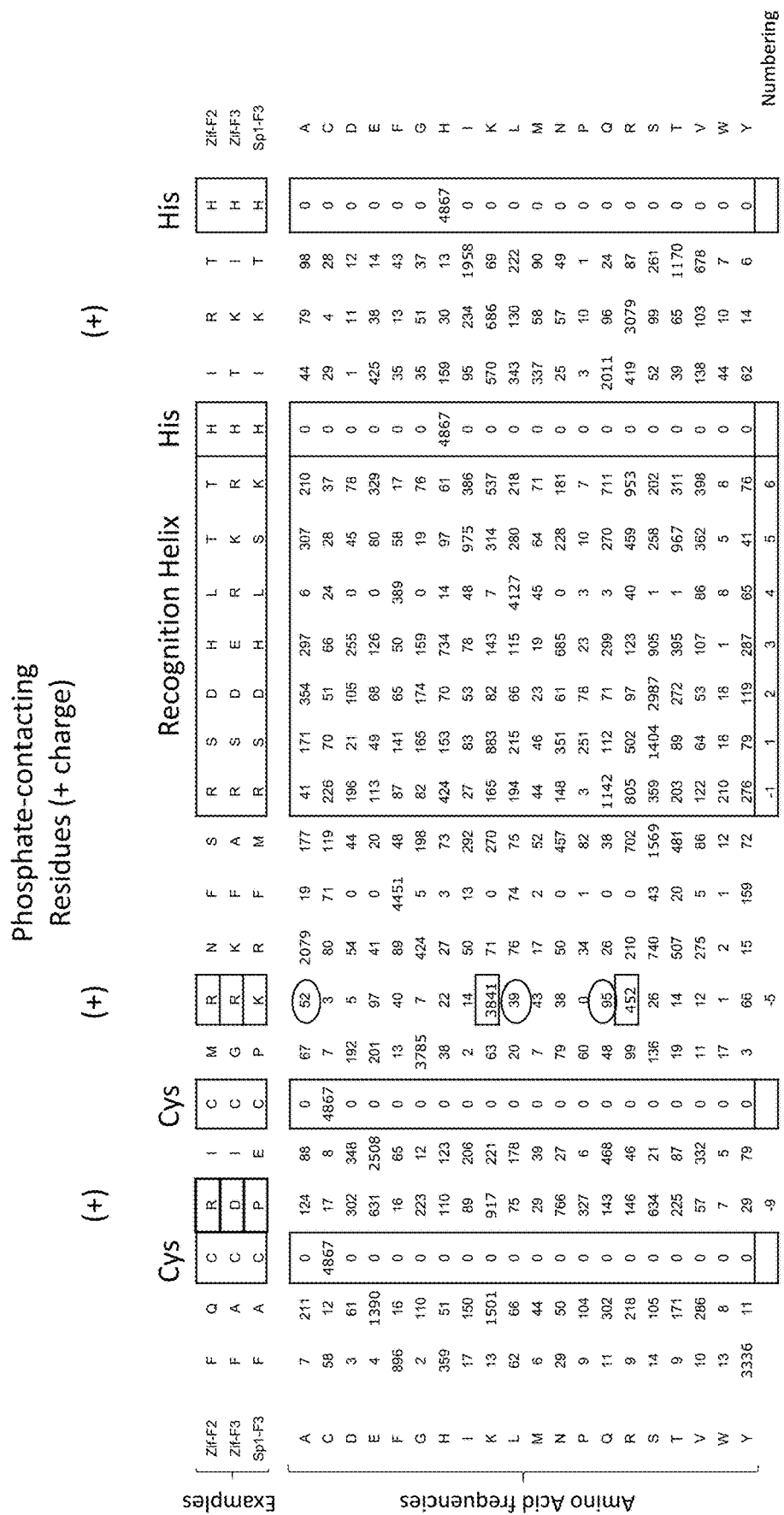
FIG. 6 (SEQ ID NO:4-6) depicting the conservation of amino acids at each position within a zinc finger. The first lines show an alignment of amino acid sequences in the well-known zinc fingers from Zif268 and Sp1 (finger 2 from Zif268 (SEQ ID NO:4), finger 3 from Zif268 (SEQ ID NO:5) and finger 2 of Sp1 (SEQ ID NO:6)). The zinc coordinating cysteine and histidine residues are boxed, as are the recognition helices. The arginine (R) and lysine (K) positively charged residues that contact the DNA backbone phosphates are also indicated in boxes. The numbers under the first three lines are the frequencies of each amino acid at each position, where 4867 different naturally occurring zinc fingers were analyzed. The letters on the left of the diagram are the one-letter codes corresponding to the amino acid residues whose frequencies are given in the table. Three non-charged amino acids, alanine, leucine and glutamine (indicated in ovals) were identified to occur at the phosphate contacting position at a low, but nonzero frequency.

Previous studies had suggested that there may be some interaction between the positively charged amino acid residues in a zinc finger 'backbone' (regions of the structure that are not involved in the site-specific recognition of DNA nucleotides) and the phosphates on the DNA molecule (Elrod-Erickson et al, ibid), see FIG. 5A. The amino acids at positions −14, −9, and −5 (all relative to the conventional numbering of the alpha helix region) are often positively charged and may interact with the negatively charged phosphates in the DNA backbone (see FIG. 5B). Accordingly, 4867 zinc finger sequences were analyzed for the presence of amino acid residues at each position in a finger sequence (see FIG. 6). In position −5, the neutral amino acids alanine, leucine and glutamine were observed at a low, but nonzero frequency, and so these amino acids were used in the modifications of the finger backbone. Positions in 6 and 5 finger ZFPs were also identified along with potential substitutions (FIGS. 7A and 7B).

The mutations were made in the TCRA (TRAC)-specific ZFN pair SBS #52774/SBS #52742 (see PCT Publication WO2017106528). For these proteins, a total of 21 variants were made of each partner ((F1, F3, F5, F1+F3, F1+F5, F3+F5, F1+F3+F5)×(R->A, R->Q, R->L)). A representative selection of the data (Table 5) demonstrated that many of the pairs showed a decreased in off-target activity against three off-targets analyzed. In this table, the 52774 ZFN was combined with variants of the 52742 ZFN bearing the indicated mutations at position −5 finger 1 (F1), finger 3 (F3) and finger 5 (F5). The type of mutation made is also indicated where all mutants in this data set are Arginine (R) to Glutamine (Q) mutants. For example, the protein labeled 52742-F1RQ indicates a mutant where the arginine at position −5 in finger 1 has been altered to be a glutamine. The top portion of the table displays activity as % indels and the bottom half of the table shows activity as a fraction of average of the activity of the two replicates of the parental ZFN pair 52774/52742. These experiments demonstrated that these mutations could have an impact on off-target cleavage. For example, while on-target cleavage was maintained at a robust level for the 52742-F1RQ;F3RQ;F5RQ mutant (69.96% on-target activity compared with 62.59% activity for the parent proteins at the 6 µg dose), off-target cleavage dropped (OT16 showed 19.16% cleavage activity for the parent proteins and 1.43% activity in the triple mutant).

TABLE 5

Exemplary data for zinc finger backbone mutations

| | TCRA (TRAC) | | OT16 | | OT11 | | OT3 | |
| --- | --- | --- | --- | --- | --- | --- | --- | --- |
| | | | \multicolumn{2}{c}{license plate} | | | | |
| | JBSCKVMP | | XSKWTVWD | | XVFENVRX | | KXWACMTR | |
| Samples | 6 ug | 2 ug | 6 ug | 2 ug | 6 ug | 2 ug | 6 ug | 2 ug |
| 52742 | 62.59 | 32.08 | 19.16 | 6.9 | 4.32 | 2.43 | 1.59 | 1.21 |
| 52742 | 62.75 | 25.86 | 15.26 | 5.32 | 4.33 | 2.61 | 1.41 | 1.3 |
| 52742-F1RQ | 68.58 | 35.42 | 14.46 | 8.26 | 4.16 | 2.75 | 0.64 | 0.42 |
| 52742-F1RQ; F3RQ | 65.72 | 30.07 | 5.11 | 1.9 | 1.09 | 1.15 | 0.22 | 0.22 |
| 52742-F1RQ; F3RQ; F5RQ | 69.96 | 36.09 | 1.43 | 1.16 | 0.47 | 0.43 | 0.19 | 0.16 |
| 52742 | 1 | 1.11 | 1.11 | 1.13 | 1 | 0.96 | 1.06 | 0.97 |
| 52742 | 1 | 0.89 | 0.89 | 0.87 | 1 | 1.04 | 0.94 | 1.03 |
| 52742-F1RQ | 1.09 | 1.22 | 0.84 | 1.35 | 0.96 | 1.09 | 0.42 | 0.34 |
| 52742-F1RQ; F3RQ | 1.05 | 1.04 | 0.3 | 0.31 | 0.25 | 0.46 | 0.15 | 0.18 |
| 52742-F1RQ; F3RQ; F5RQ | 1.12 | 1.25 | 0.08 | 0.19 | 0.11 | 0.17 | 0.13 | 0.13 |

Starting with the TCRA (TRAC)-specific parent ZFNs 52742 and 52774, the Arginines (R) in the first finger of each module were replaced with either Alanine (A), Glutamine (Q), or Leucine (L). The constructs were tested in CD34+ cells where the cells were treated with 6 µg of mRNA encoding each ZFN partner (see FIG. 8A). For these data sets, each data bar shown is in the average of the data for all mutations of each type, and the error bars represent the standard error. For example, in FIG. 8A for the left most black bar indicating on-target activity, this value is an average of the on-target for all 6 mutants in the ZFN pair that could have a single mutation. Referring to the diagram in FIG. 7, these thus include a single mutation in the N-terminal finger of module A of 52742 (F1 in the full-length protein), a single mutation in the N-terminal finger of module B of 52742 (F3 in the full-length protein), a single mutation in the N-terminal finger of module C of 52742 (F5 in the full-length protein) and the similar set of mutations in the partner 52774 protein. For the second black bar (indicating on-target activity), the on-target pool is an average of all 2 mutation proteins (a set of 6 possibilities, where the mutations are made in a single partner ZFN), and for the third black bar, the on-target pool is an average of the 2 possibilities with all three modules in either the left or right ZFN mutated. For the off-target data, shown by the grey bars, similar pools were made except that the data from the three off-target sites were combined such that the pool for single or double mutations in the off-target data set each comprised 18 data points, and the pool for the three mutations comprised 6 data points. The mutations resulted in an up to 4.8 fold decrease in off-target activity.

Figure 8A:
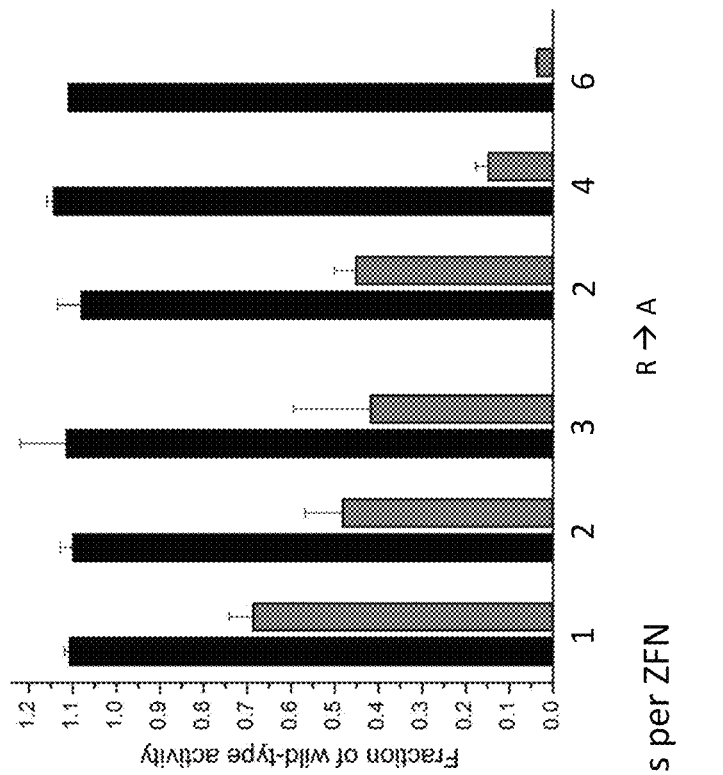
Figure 8B:
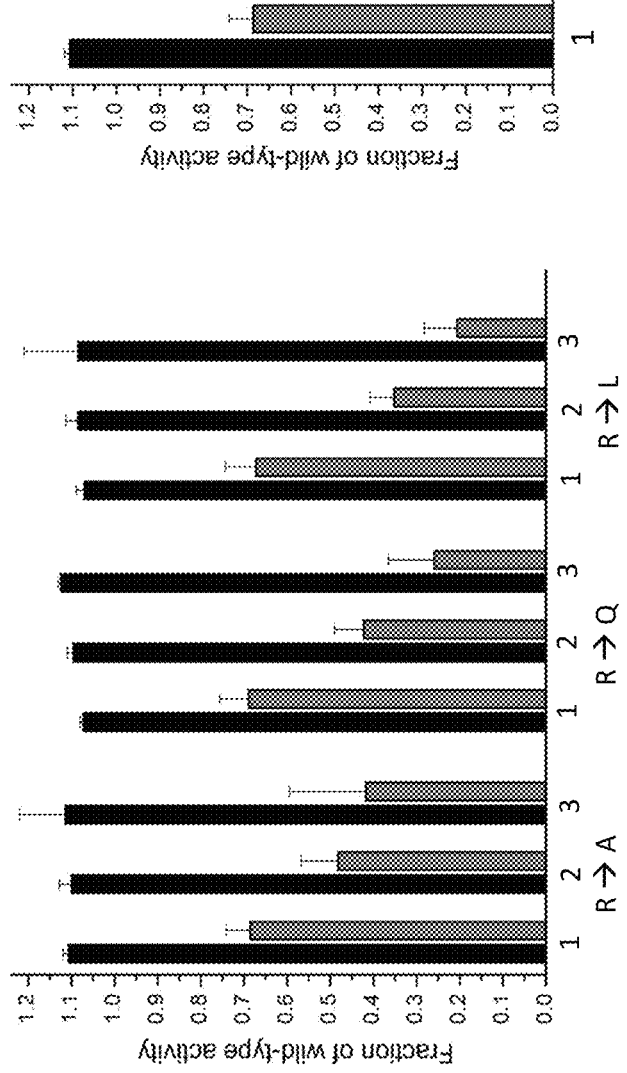

The experiments were also carried out where both partners of a ZFN pair were mutated in a similar fashion (right half of FIG. 8B). For example, if the N-terminal finger in module A was altered to be an alanine, (52742-F1RA), then the partner protein would also be mutated at the N-terminal finger in module A (52774-F1RA) for a total of 2 mutations in the ZFN dimer. Only alanine substitutions were tested simultaneously in both ZFNs in the dimer and this data is shown on the right half of FIG. 8B (indicated with 2, 4, or 6). The R->A mutations made to only one ZFN in the dimer (indicated by 1, 2, or 3) from the left third of FIG. 8A is shown again in the left half of FIG. 8B for comparison purposes. FIG. 8C is similar to the right portion of FIG. 8A except only 2 (20 µg/mL) of RNA was used. These experiments demonstrated that these mutations could generate a 27-fold decrease in off-target activity when a total of six mutations occur in both ZFNs in the dimer.

Figure 9:
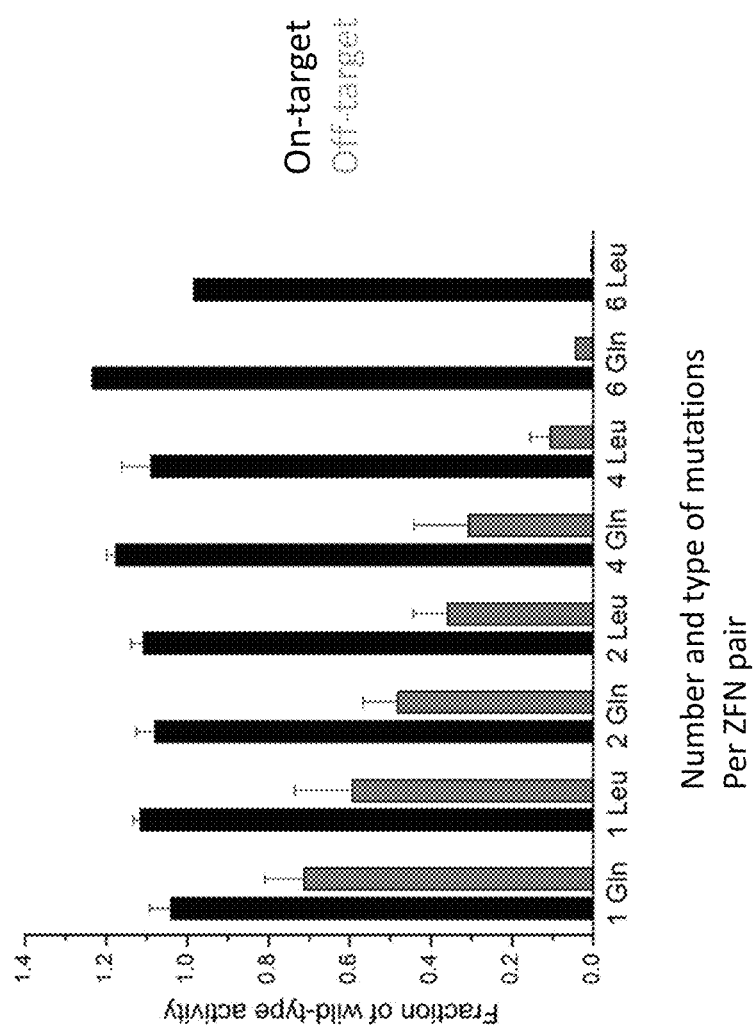
FIG. 9 is a graph depicting on-target (black bars) and off-target (grey bars) cleavage activity at off-target site NIFMAEVG for the BCL11A-specific ZFNs comprising the novel zinc finger backbone mutations of the invention (in this case, the three-letter abbreviation is used and indicates the number of arginine residues at position −5 that were mutated to the indicated residue; e.g. "6 Gln" indicates that 6 arginines (3 per ZFN) were mutated to 6 glutamines in the ZFN pair). Error bars represent standard error. Experiments were done in CD34+ cells at a dose of 2 µg mRNA per ZFN per experiment.

These experiments were also performed with the BCL11A-specific ZFN pair 51857-ELD/51949-KKR described above. The experimental design was similar to what was described for the TCRA (TRAC)-specific ZFN pair, and the results are shown in FIG. 9A. The data presented shows the results for the pairs comprising either R->Q (Gln) or R->L (Leu) mutations dosed at 2 (20 µg/mL) where the off-target results depicted were for only one off-target site (NIFMAEVG, see Table 1).

Additional amino acid variants at the −5 position were made by replacing R with E, N, Y, A, or L. In addition to altering the amino acids at the −5 position, a series of mutations were made in positions −9 and −14 in Finger 1 of the BCL11A-specific ZFN pair 51857/51949. These were tested for on and off-target activity as described above, alone and in combination with −5 alterations in fingers 2-6. The data are shown below in Table 6. Each protein had the same DNA-specificity helix regions as described for the parent proteins above but was given a new SBS identifier number to reflect the ZFP backbone mutations. In brief, the full names of the proteins reflect the variants listed in the finger. Thus, the "cR" portion of the full name refers to changes being made in the C-terminal finger of the two-finger module (refer to FIG. 7), and "nR" refers to the changes being made in the N-terminal finger of the two-finger module. The description "rQa" means alterations were made in the −5 position in the A module, and the finger that it was made in is defined by either cR or nR. Thus, SBS #65461 (full name 51857-NELD-cR-5Qa) is a SBS #51857 derivative where the alterations are made in the C-terminal finger, at the −5 position, where Q is replacing the R in Module A. This can also be seen in the table where there is a Q indicated in the F2, −5 column. When changes were made to the −14 position, as for SBS #65459 (full name 51857-NELD-nR-14Q-5Qabc) it is indicated. Thus, SBS #65459 is a SBS #51857 derivative, where the changes are made to the N-terminal finger in the modules, where −14 of Finger 1 has been changed from R to Q, and the −5 positions in the N-terminal finger of modules A, B, and C have been changed from R to Q. In case of SBS #65460, the −14 of Finger 1 has been changed from R to S. Again, this can also be determined from the table. The denotations "NELD" and "CKKR" indicate the type of FokI nuclease domains (either "ELD" or "KKR" FokI domain variants) and other aspects of the vector (see PCT Publication No. WO 2017/136049).

Table 6A shows the pairings of the mutations made in the SBS #51857 derivative partner with either the SBS #51949 partner, or a SBS #51949 partner comprising alterations that inserted a Q in the N-terminal fingers at positions −5 in modules A, B, and C, where this partner further comprises the R416S mutation in the FokI domain, where the experiments were carried out using 2 μg of mRNA encoding each ZFN. These experiments were also done using mutations in the SBS #51949 protein (see Table 6B) where mutations in the phosphate interacting amino acids of the FokI domain were also tested in combination with the backbone mutations. These data indicated that the additional alterations were capable of having an influence on the specificity of the ZFN pairs.

TABLE 6A

Alterations in backbone positions for ZFN SBS#51857

| | | Finger 1 (F1) | | F2 | F3 | F4 | F5 | F6 | aa | Right partner: 51949-CKKR | | | Right partner: 51949-CKKR-nR-5Qabc-R416S | | |
|---|---|---|---|---|---|---|---|---|---|---|---|---|---|---|---|
| SBS# | Full Name | −14 | −9 | −5 | −5 | −5 | −5 | −5 | −5 | change | Bcl11a | OT1 | TXHULGPN | Bcl11a | OT1 | TXHULGPN |
| 51857 | 51857-NELD (AV-A) | | | | | | | | | 0 | 70.1 | 3.83 | 0.11 | 59.2 | 0.15 | 0.08 |
| 65461 | 51857-NELD_cR-5Qa | | | | Q | | | | | 1 | 68.4 | 2.18 | 0.11 | 55.5 | 0.35 | 0.07 |
| 65462 | 51857-NELD_cR-5Qb | | | | | Q | | | | 1 | 69.2 | 1.18 | 0.14 | 63.4 | 0.09 | 0.04 |
| 65463 | 51857-NELD_cR-5Qc | | | | | | | Q | | 1 | 59.7 | 0.85 | 0.08 | 55.5 | 0.20 | 0.07 |
| 65464 | 51857-NELD_cR-5Qab | | | | Q | Q | | | | 2 | NA | 1.00 | 0.04 | 53.7 | 0.05 | 0.07 |
| 65465 | 51857-NELD_cR-5Qac | | | | Q | | | Q | | 2 | 62.3 | 0.74 | 0.03 | 55.1 | 0.13 | 0.06 |
| 65466 | 51857-NELD_cR-5Qbc | | | | | Q | | Q | | 2 | 62.4 | 0.38 | 0.05 | 57.9 | 0.15 | 0.08 |
| 65467 | 51857-NELD_cR-5Qabc | | | | Q | Q | | Q | | 3 | 59.2 | 0.27 | 0.05 | 53.2 | 0.08 | 0.08 |
| 63014 | 51857-NELD_nR-5Qabc (AV-B) | | | Q | Q | Q | | | | 3 | 55.7 | 0.73 | 0.07 | 55.5 | 0.15 | 0.02 |
| 65453 | 51857-NELD_nR-5Eabc | | | E | E | E | | | | 3 | 41.6 | 0.20 | 0.04 | 44.9 | 0.04 | 0.07 |
| 65454 | 51857-NELD_nR-5Nabc | | | N | N | N | | | | 3 | 7.8 | 0.13 | 0.02 | 48.3 | 0.08 | 0.07 |
| 65455 | 51857-NELD_nR-5Yabc | | | Y | Y | Y | | | | 3 | 42.8 | 0.50 | 0.03 | 42.4 | 0.09 | 0.10 |
| 65459 | 51857-NELD_nR-14Q-5Qabc | Q | | Q | Q | Q | | | | 4 | 55.9 | 0.53 | 0.05 | 52.9 | 0.19 | 0.07 |
| 65460 | 51857-NELD_nR-14S-5Qabc | S | | Q | Q | Q | | | | 4 | 54.3 | 0.66 | 0.06 | 53.3 | 0.07 | 0.07 |
| 65469 | 51857-NELD_nR-5Qabc, cR-5Qa | | | Q | Q | Q | Q | | | 4 | 44.6 | 0.24 | 0.06 | 50.8 | 0.01 | 0.08 |
| 65470 | 51857-NELD_nR-5Qabc, cR-5Qb | | | Q | Q | Q | | Q | | 4 | 44.5 | 0.22 | 0.07 | 49.8 | 0.06 | 0.02 |
| 65471 | 51857-NELD_nR-5Qabc, cR-5Qc | | | Q | Q | Q | | | Q | 4 | NA | 0.09 | 0.05 | 53.9 | 0.05 | 0.06 |
| 65472 | 51857-NELD_nR-5Qabc, cR-5Qab | | | Q | Q | Q | Q | Q | | 5 | 37.3 | 0.15 | 0.04 | 41.2 | 0.06 | 0.08 |

TABLE 6A-continued

Alterations in backbone positions for ZFN SBS#51857

| | | Finger 1 (F1) | | | F2 | F3 | F4 | F5 | F6 | aa change | Right partner: 51949-CKKR | | | Right partner: 51949-CKKR-nR-5Qabc-R416S | | |
|---|---|---|---|---|---|---|---|---|---|---|---|---|---|---|---|---|
| SBS# | Full Name | −14 | −9 | −5 | −5 | −5 | −5 | −5 | −5 | | Bcl11a | OT1 | TXHULGPN | Bcl11a | OT1 | TXHULGPN |
| 65473 | 51857-NELD_nR-5Qabc, cR-5Qac | | | | Q | Q | | Q | Q | 5 | 26.9 | 0.13 | 0.05 | 33.2 | 0.08 | 0.02 |
| 65474 | 51857-NELD_nR-5Qabc, cR-5Qbc | | | | Q | | Q | Q | Q | 5 | 25.2 | 0.11 | 0.04 | 37.4 | 0.08 | 0.09 |
| 65475 | 51857-NELD_nR-5Qabc, cR-5Qabc | | | Q | Q | Q | Q | Q | Q | 6 | 20.1 | 0.15 | 0.06 | 29.1 | 0.13 | 0.09 |
| 65477 | 51857-NELD_nR-5Eabc, cR-5Qabc | | | E | Q | E | Q | E | Q | 6 | 3.3 | 0.07 | 0.05 | 4.5 | 0.09 | 0.08 |
| 65478 | 51857-NELD_nR-5Nabc, cR-5Qabc | | | N | Q | N | Q | N | Q | 6 | 0.1 | 0.09 | 0.05 | 0.2 | 0.09 | 0.05 |
| 65479 | 51857-NELD_nR-5Yabc, cR-5Qabc | | | Y | Q | Y | Q | Y | Q | 6 | 0.2 | 0.09 | 0.05 | 0.1 | 0.06 | 0.03 |
| 65481 | 51857-NELD_nR-9Na-5Qabc, cR-5Qabc | | N | Q | Q | Q | Q | Q | Q | 7 | 15.1 | 0.11 | 0.03 | 27.3 | 0.15 | 0.03 |
| 65482 | 51857-NELD_nR-9Sa-5Qabc, cR-5Qabc | | S | Q | Q | Q | Q | Q | Q | 7 | 18.8 | 0.12 | 0.05 | 23.7 | 0.06 | 0.07 |
| 65483 | 51857-NELD_nR-14Q-5Qabc, cR-5Qabc | Q | | Q | Q | Q | Q | Q | Q | 7 | 12.4 | 0.19 | 0.07 | 21.0 | 0.07 | 0.07 |
| 65484 | 51857-NELD_nR-14S-5Qabc, cR-5Qabc | S | | Q | Q | Q | Q | Q | Q | 7 | 12.5 | 0.06 | 0.06 | 22.5 | 0.05 | 0.04 |
| 65468 | 51857-NELD_nR-14S-5Qabc, cR-5Aabc | Q | | Q | A | Q | A | Q | A | 7 | 24.0 | 0.13 | 0.04 | 30.2 | 0.07 | 0.02 |
| 65476 | 51857-NELD_nR-14S-5Qabc, cR-5Labc | Q | | Q | L | Q | L | Q | L | 7 | 5.4 | 0.11 | 0.04 | 12.9 | 0.10 | 0.04 |

TABLE 6B

Alterations in other backbone positions and FokI for ZFN SBS#51949

| | | Finger 1 (F1) | | F2 | F3 | F4 | F5 | aa change | Right partner: 51949-CKKR | | | Right partner: 51949-CKKR-nR-5Qabc-R416S | | |
|---|---|---|---|---|---|---|---|---|---|---|---|---|---|---|
| SBS# | Full Name | −14 | −9 | −5 | −5 | −5 | −5 | −5 | Bcl11a | OT1 | TXHULGPN | Bcl11a | OT1 | TXHULGPN |
| 51949 | 51949-CKKR (AV-C) | | | | | | | 0 | 64.3 | 3.24 | 0.10 | 33.1 | 0.28 | 0.09 |
| 51949-R416S | 51949-CKKR-R416S (AV-D) | | | | | | | 0 | 68.8 | 0.52 | 0.06 | 38.7 | 0.07 | 0.11 |

TABLE 6B-continued

Alterations in other backbone positions and FokI for ZFN SBS#51949

| | | Finger 1 (F1) | | F2 | F3 | F4 | F5 | aa | Right partner: 51949-CKKR | | | Right partner: 51949-CKKR-nR-5Qabc-R416S | | |
|---|---|---|---|---|---|---|---|---|---|---|---|---|---|---|
| SBS# | Full Name | −14 | −9 | −5 | −5 | −5 | −5 | change | Bcl11a | OT1 | TXHULGPN | Bcl11a | OT1 | TXHULGPN |
| 65529 | 51949-CKKR-R416S_cR-5Qb | | | | Q | | | 1 | 69.2 | 0.17 | 0.08 | 44.9 | 0.13 | 0.10 |
| 65530 | 51949-CKKR-R416S_cR-5Qc | | | | | Q | | 1 | 67.7 | 0.20 | 0.04 | 56.4 | 0.08 | 0.08 |
| 65528 | 51949-CKKR-R416S_cR-5Qbc | | | | Q | Q | | 2 | 73.3 | 0.12 | 0.06 | 53.6 | 0.07 | 0.06 |
| 63022-R416S* | 51949-CKKR-R416S_nR-5Qabc (AV-G) | | | Q | Q | Q | | 3 | 71.9 | 0.18 | 0.04 | 50.1 | 0.15 | 0.06 |
| 65509 | 51949-CKKR-R416S_nR-5Eabc | | | E | E | E | | 3 | 49.8 | 0.07 | 0.04 | 37.3 | 0.08 | 0.04 |
| 65510 | 51949-CKKR-R416S_nR-5Nabc | | | N | N | N | | 3 | 67.6 | 0.19 | 0.06 | 46.7 | 0.05 | 0.05 |
| 65511 | 51949-CKKR-R416S_nR-5Yabc | | | Y | Y | Y | | 3 | 64.5 | 0.17 | 0.14 | 41.8 | 0.10 | 0.08 |
| 65515 | 51949-CKKR-R416S_nR-14Q-5Qabc | Q | | Q | Q | Q | | 4 | 66.4 | 0.15 | 0.06 | 47.2 | 0.15 | 0.14 |
| 65516 | 51949-CKKR-R416S_nR-14S-5Qabc | S | | Q | Q | Q | | 4 | 65.1 | 0.12 | 0.06 | 43.4 | 0.12 | 0.10 |
| 65525 | 51949-CKKR-R416S_nR-5Qabc, cR-5Qb | | | Q | Q | Q | Q | 4 | 71.3 | 0.12 | 0.07 | 45.7 | 0.08 | 0.06 |
| 65526 | 51949-CKKR-R416S_nR-5Qabc, cR-5Qc | | | Q | Q | | Q | 4 | 69.7 | 0.08 | 0.05 | 53.0 | 0.18 | 0.11 |
| 65527 | 51949-CKKR-R416S_nR-5Qabc, cR-5Qbc | | | Q | Q | Q | Q | 5 | 66.7 | 0.09 | 0.06 | 43.2 | 0.10 | 0.07 |
| 65517 | 51949-CKKR-R416S_nR-5Eabc, cR-5Qbc | | | E | E | Q | E | Q | 5 | 12.9 | 0.09 | 0.02 | 10.6 | 0.07 | 0.11 |
| 65518 | 51949-CKKR-R416S_nR-5Nabc, cR-5Qbc | | | N | N | Q | N | Q | 5 | 60.6 | 0.02 | 0.05 | NA | 0.07 | 0.05 |
| 65519 | 51949-CKKR-R416S_nR-5Yabc, cR-5Qbc | | | Y | Y | Q | Y | Q | 5 | 65.5 | 0.12 | 0.04 | 43.8 | 0.08 | 0.03 |
| 65521 | 51949-CKKR-R416S_nR-9N-5Qabc, cR-5Qbc | | N | Q | Q | Q | Q | 6 | 70.8 | 0.09 | 0.05 | 51.8 | 0.12 | 0.07 |

TABLE 6B-continued

Alterations in other backbone positions and FokI for ZFN SBS#51949

| | | Finger 1 (F1) | | F2 | F3 | F4 | F5 | aa | Right partner: 51949-CKKR | | | Right partner: 51949-CKKR-nR-5Qabc-R416S | | |
|---|---|---|---|---|---|---|---|---|---|---|---|---|---|---|
| SBS# | Full Name | −14 | −9 | −5 | −5 | −5 | −5 | change | Bcl11a | OT1 | TXHULGPN | Bcl11a | OT1 | TXHULGPN |
| 65523 | 51949-CKKR-R416S_nR-14Q-5Qabc,cR-5Qbc | Q | | Q | Q | Q | Q | 6 | 61.0 | 0.10 | 0.07 | 42.5 | 0.10 | 0.04 |
| 65524 | 51949-CKKR-R416S_nR-14S-5Qabc,cR-5Qbc | S | | Q | Q | Q | Q | 6 | 51.9 | 0.08 | 0.09 | 38.8 | 0.07 | 0.07 |
| 65531 | 51949-CKKR-R416S_nR-14Q-5Qabc,cR-5Abc | Q | | Q | Q | A | Q | A | 6 | 50.7 | 0.06 | 0.04 | 38.7 | 0.05 | 0.10 |
| 65532 | 51949-CKKR-R416S_nR-14Q-5Qabc,cR-5Lbc | Q | | Q | Q | L | Q | L | 6 | 40.5 | 0.05 | 0.07 | 31.0 | 0.16 | 0.05 |
| 51949-K525S | 51949-CKKR-K525S (AV-E) | | | | | | | 0 | 49.0 | 0.16 | 0.05 | 31.1 | 0.08 | 0.05 |
| 65554 | 51949-CKKR-K525S_cR-5Qc | | | | | | Q | 1 | 35.5 | 0.10 | 0.13 | 37.9 | 0.10 | 0.06 |
| 65552 | 51949-CKKR-K525S_cR-5Qbc | | | | Q | | Q | 2 | 55.9 | 0.10 | 0.05 | 37.4 | 0.58 | 0.02 |
| 63022-K525S** | 51949-CKKR-K525S_nR-5Qabc (AV-H) | | | Q | Q | | Q | 3 | 59.5 | 0.04 | 0.05 | 44.9 | 0.14 | 0.10 |
| 65533 | 51949-CKKR-K525S_nR-5Eabc | | | E | E | | E | 3 | 0.1 | 0.09 | 0.04 | 0.1 | 0.11 | 0.08 |
| 65534 | 51949-CKKR-K525S_nR-5Nabc | | | N | N | | N | 3 | 52.8 | 0.03 | 0.04 | NA | 0.06 | NA |
| 65535 | 51949-CKKR-K525S_nR-5Yabc | | | Y | Y | | Y | 3 | 53.1 | 0.12 | 0.06 | 35.6 | 0.07 | 0.19 |
| 65539 | 51949-CKKR-K525S_nR-14Q-5Qabc | Q | | Q | Q | | Q | 4 | 52.1 | 0.10 | 0.10 | 38.1 | 0.10 | 0.05 |
| 65540 | 51949-CKKR-K525S_nR-14S-5Qabc | S | | Q | Q | | Q | 4 | 54.2 | 0.08 | 0.10 | 34.1 | 0.11 | 0.06 |
| 65549 | 51949-CKKR-K525S_nR-5Qabc,cR-5Qb | | | Q | Q | Q | Q | 4 | 56.7 | 0.03 | 0.12 | 37.3 | 0.10 | 0.05 |
| 65550 | 51949-CKKR-K525S_nR-5Qabc,cR-5Qc | | | Q | Q | | Q | Q | 4 | 57.3 | 0.12 | 0.09 | 36.0 | 0.11 | 0.00 |
| 65551 | 51949-CKKR-K525S_nR-5Qabc,cR-5Qbc | | | Q | Q | Q | Q | 5 | 50.8 | 0.09 | 0.05 | 34.5 | 0.06 | 0.00 |

TABLE 6B-continued

Alterations in other backbone positions and FokI for ZFN SBS#51949

| | | Finger 1 (F1) | | F2 | F3 | F4 | F5 | aa | Right partner: 51949-CKKR | | | Right partner: 51949-CKKR-nR-5Qabc-R416S | | |
|---|---|---|---|---|---|---|---|---|---|---|---|---|---|---|
| SBS# | Full Name | −14 | −9 | −5 | −5 | −5 | −5 | change | Bcl11a | OT1 | TXHULGPN | Bcl11a | OT1 | TXHULGPN |
| 65541 | 51949-CKKR-K525S_nR-5Eabc, cR-5Qbc | | | E | E | Q | E | Q | 5 | 2.5 | 0.09 | 0.08 | 1.9 | 0.18 | 0.05 |
| 65542 | 51949-CKKR-K525S_nR-5Nabc, cR-5Qbc | | | N | N | Q | N | Q | 5 | 36.4 | 0.06 | 0.02 | 22.8 | 0.07 | 0.03 |
| 65543 | 51949-CKKR-K525S_nR-5Yabc, cR-5Qbc | | | Y | Y | Q | Y | Q | 5 | 53.1 | 0.09 | 0.08 | 32.0 | 0.13 | 0.15 |
| 65545 | 51949-CKKR-K525S_nR-9N-5Qabc, cR-5Qbc | | N | Q | Q | Q | Q | 6 | 51.2 | 0.15 | 0.07 | 33.0 | 0.08 | 0.13 |
| 65547 | 51949-CKKR-K525S_nR-14Q-5Qabc, cR-5Qbc | Q | | Q | Q | Q | Q | Q | 6 | 36.1 | 0.09 | 0.05 | 22.5 | 0.08 | 0.02 |
| 65548 | 51949-CKKR-K525S_nR-14S-5Qabc, cR-5Qbc | S | | Q | Q | Q | Q | Q | 6 | 28.7 | 0.06 | 0.05 | 20.1 | 0.09 | 0.10 |
| 65555 | 51949-CKKR-K525S_nR-14Q-5Qabc, cR-5Abc | Q | | Q | Q | A | Q | A | 6 | 36.3 | 0.14 | 0.08 | 21.8 | 0.10 | 0.11 |
| 65556 | 51949-CKKR-K525S_nR-14Q-5Qabc, cR-5Lbc | Q | | Q | Q | L | Q | L | 6 | 25.0 | 0.06 | 0.05 | NA | 0.10 | 0.04 |

*63022-R416S is also known as SBS#65721.
**63022-K525S is also known as SBS#65722.

The experiments were repeated using CD34+ cells where the RNAs were delivered to the cells using a BTX transfection system using conditions optimized according to manufacturer's instructions. Three concentrations of RNA were used: 60, 20 and 5 μg/mL final concentration. The data is shown below in Table 6C and demonstrates that robust on-target cleavage can be detected even at very low levels of ZFN mRNA such that off target cleavage is substantially reduced (>100×). Mutations are indicated in the nomenclature shown in FIG. 2C. The experiment was repeated using just the parental and the 3×(R->Q)/3×(R->Q) pair from Table 6C below to determine the robustness of the results. As seen in Table 6D, the results were highly repeatable.

TABLE 6C

Titration of on and off target effects:

| | | % indels | | | | | | | | |
|---|---|---|---|---|---|---|---|---|---|---|
| ZFN modification | | BCL11A | | | NIFMAEVG (OT1) | | | PEVYOHIU (OT3) | | |
| Left ZFN | Right ZFN | 60 μg | 20 μg | 5 μg | 60 μg | 20 μg | 5 μg | 60 μg | 20 μg | 5 μg |
| SBS51857 | SBS51949 | 82.7 | 87.0 | 76.5 | 28.0 | 5.02 | 0.34 | 4.77 | 0.32 | (0.03) |
| 3x (R->Q) SBS63014 | 3x (R->Q)* SBS65721 | 88.3 | 86.4 | 78.0 | 0.55 | 0.08 | (0.01) | 0.04 | (0.01) | (0.02) |
| 3x (R->Q) SBS63014 | 4x (R->Q)* SBS65526 | 85.4 | 86.3 | 73.4 | 0.17 | (0.03) | (0.03) | (0.02) | (0.00) | (0.01) |

TABLE 6C-continued

Titration of on and off target effects:

| ZFN modification | | % indels | | | | | | | |
|---|---|---|---|---|---|---|---|---|---|
| | | BCL11A | | | NIFMAEVG (OT1) | | | PEVYOHIU (OT3) | |
| Left ZFN | Right ZFN | 60 µg | 20 µg | 5 µg | 60 µg | 20 µg | 5 µg | 60 µg | 20 µg | 5 µg |
| 3x (R->Q) SBS63014 | 5x (R->Q)* SBS65527 | 83.6 | 86.5 | 71.7 | (0.03) | (0.01) | (0.02) | (0.02) | (0.03) | (0.00) |

Numbers in parenthesis indicate values where no evidence of nuclease cleavage was found.
*indicates that the right ZFN further comprised an additional R416S mutation in the FokI nuclease domain.

TABLE 6D

Repeat measurements of on-target activity

| ZFN modification | | % indels | | | | |
|---|---|---|---|---|---|---|
| | | BCL11A % indels, replicate | | | | % indels, |
| Left ZFN | Right ZFN | #1 | #2 | #3 | #4 | average |
| SBS51857 | SBS51949 | 76.8 | 79.0 | 82.8 | 80.1 | 79.7 |
| 3x (R->Q) SBS63014 | 3x (R->Q)* SBS65721 | 80.5 | 81.7 | 81.0 | 83.4 | 81.6 |

*indicates that the right ZFN further comprised an additional R416S mutation in the FokI nuclease domain.

SBS #51857 partner resulted in a decrease in off-target cleavage (approximately 8-fold) while maintaining robust on-target cleavage. For example, when 60 µg/mL of 51949 mRNA was used in combination with 6.6 µg/mL of 51857 mRNA, on-target modification remained approximately the same as when 60 µg/mL of each ZFN was used (76.1% indels when 60 µg/mL of each was used, 78.3% indels when 60 µg/mL of 51949 was used in combination with 6.6 µg/mL of 51857), while the aggregate off-target went from 32.4% indels to 4.0%. Note that reducing the mRNA input for both ZFNs equally lead to a gradual drop in on-target modification while off-target modification was only substantially reduced when the on-target modification was reduced.

TABLE 7

Single ZFN titration

| µg/mL RNA | | | % indels at each locus | | | | | |
|---|---|---|---|---|---|---|---|---|
| | | | NIFMAEVG | GJZEIYTO | PEVYOHIU | ZJCRPAXW | TXHULGPN | Aggregate |
| 51949 | 51857 | BCL11A | OT1 | OT2 | OT3 | OT4 | OT5 | off-target |
| 60.0 | 60.0 | 76.1 | 24.6 | 2.81 | 3.06 | 1.12 | 0.79 | 32.4 |
| 40.0 | 40.0 | 76.5 | 14.6 | 1.69 | 1.77 | 0.80 | 0.43 | 19.3 |
| 20.0 | 20.0 | 71.5 | 4.9 | 0.62 | 0.36 | 0.35 | 0.08 | 6.3 |
| 10.0 | 10.0 | 62.0 | 1.3 | 0.10 | 0.14 | 0.26 | 0.08 | 1.9 |
| 60.0 | 20.0 | 78.3 | 11.8 | 1.38 | 1.32 | 0.58 | 0.40 | 15.5 |
| 60.0 | 6.6 | 78.9 | 2.8 | 0.27 | 0.36 | 0.40 | 0.19 | 4.0 |
| 60.0 | 2.2 | 73.7 | 0.9 | 0.15 | 0.29 | 0.28 | 0.10 | 1.8 |

Example 4: Titration of ZFN Partners for Optimal On-Target Activity

Figure 10:
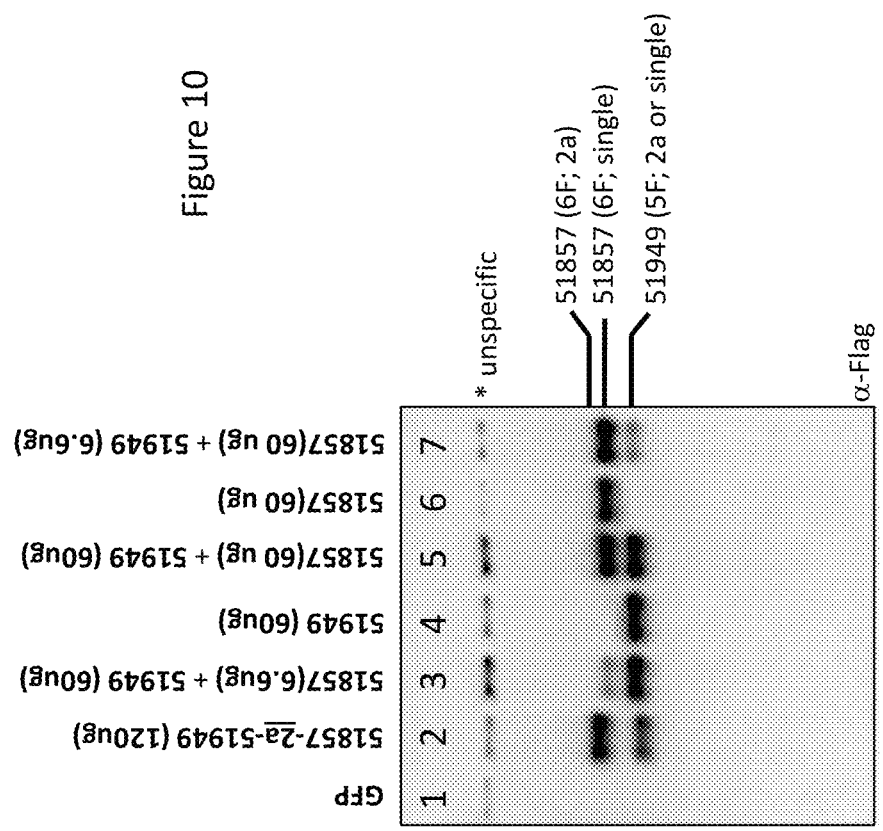
FIG. 10 depicts a Western blot for detection of BCL11A-specific ZFN expression in CD34+ cells following transfection with either mRNA encoding both ZFN partners on a single polynucleotide linked by a 2A sequence (51857-2a-51949), dosing with mRNAs encoding the ZFNs separately; or a mixture of the two mRNAs encoding each partner at the indicated doses. The proteins were detected by an anti-Flag antibody and demonstrate that the amount of protein expressed following mRNA transfection is in line with the amount of mRNA used. As expected, the 2a construct produced a larger amount of the 5' ZFN SBS #51857 as compared to the 3'ZFN, SBS #51949.

Titrating each partner of a ZFN pair individually may allow for determining the optimal concentration of each ZFN partner, and thus have maximum on-target modification by the pair while minimizing off-target modifications. Each individual ZFN half domain may have its own kinetics of binding to its cognate DNA target so through separate titration of each, optimal activity may be achieved. Accordingly, the BCL11A specific pair SBS #51949/SBS #51857 was used for titration studies in CD34+ cells using ZFNs introduced as mRNAs, where high concentrations of the ZFNs were used to allow detection of off-target cleavage. The experiments (Table 7 below) found that titrating the Western analysis was also performed to demonstrate that the expression of each ZFN partner correlated with the amount of ZFN-encoding mRNA being delivered (FIG. 10). In this experiment, CD34+ cells were transfected with the ZFNs indicated and 24 hours later expression of the ZFN proteins was detected using an anti-Flag antibody (the expression constructs comprised an encoded Flag tag). Also analyzed was the expression of the two proteins when the ZFNs were co-introduced as a single RNA separated by a 2a self-cleaving peptide sequence (see lane 2 in FIG. 10).

Figure 11:
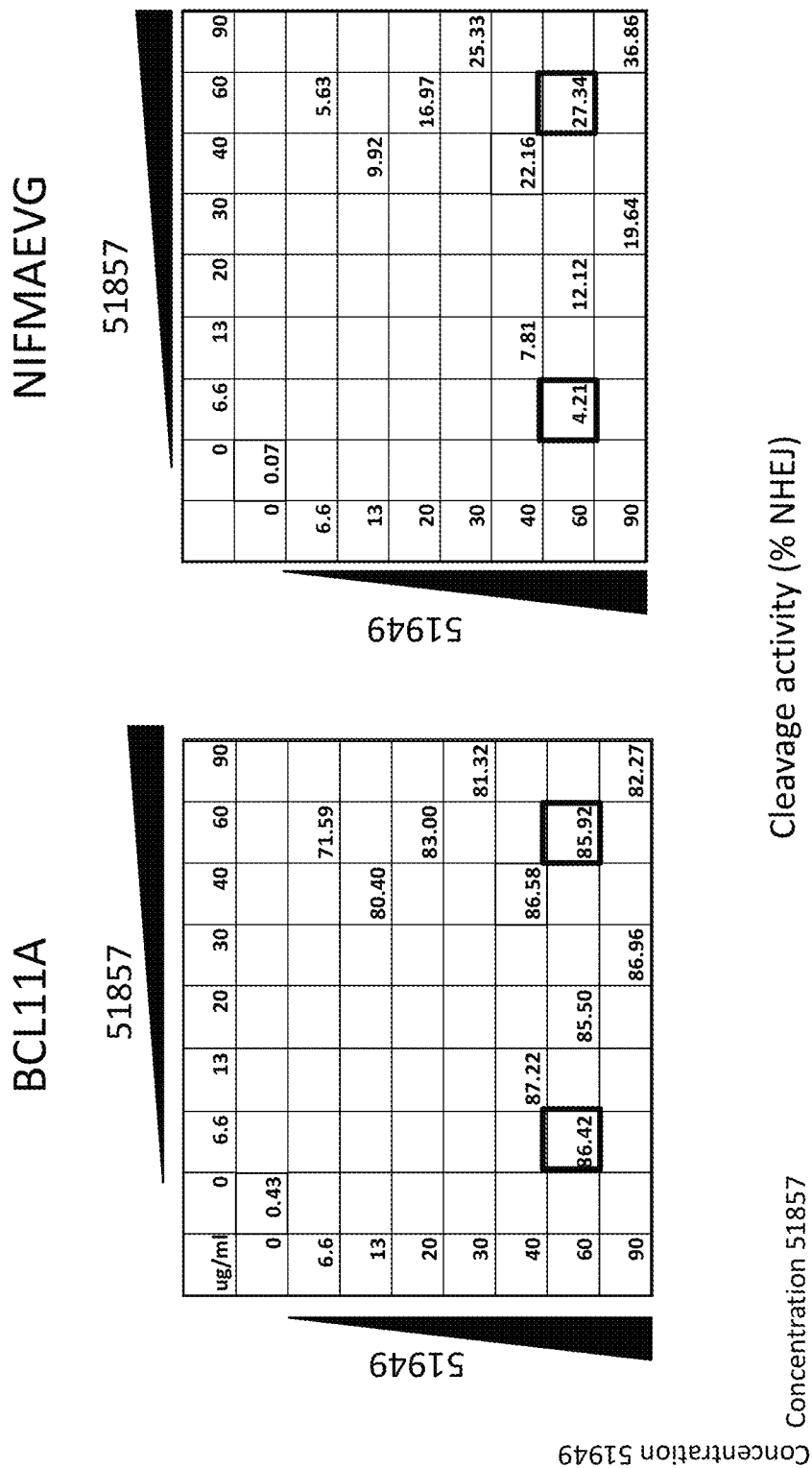
FIG. 11 depicts titration of dosing for the two BCl11A-specific ZFN partners 51949 and 51857 against either the on-target location (BCL11A, left panel) or against the off-target location NIFMAEVG (right panel). The results demonstrate that changing the ratios of the ZFN partners can preserve on-target activity while decreasing off-target activity (compare the BCL11A target at either 60 µg of each mRNA (on-target activity of 85.92% indels, or 60 µg 51949, 6.6 µg 51857 on-target activity of 86.42%) with decreased off-target (27.34% off-target activity with 60 µg of each mRNA are used compared to 4.21% indels when 60 µg 51949 are used with 6.6 µg 51857)).

Titrations were repeated varying both ZFNs independently to see if there was any effect on both on- or off-target cleavage activity. The results (FIG. 11) demonstrated that a down titration of both partners decreased off-target cleavage, but the affect was strongest for SBS #51857. Boxes in the BCL11A on-target chart in FIG. 11 indicate a maintenance of cleavage activity against the intended BCL11A target using 60 µg of SBS #51949 mRNA with either 6.6 or 60 µg of SBS #51857 mRNA, while the off-target activity at site NIFMAEVG dropped from 27 to 4% indels with the decreased dose of SBS #51857.

Example 5: Combining ZFN Partner Titrations and FokI-Phosphate Contact Mutations Next, analyses were carried out to measure the activity of ZFN partner titrations combined with exemplary FokI mutations. The BCL11A-specific ZFNs comprising the Fok mutations were used in the ratios shown above to preserve on-target activity while decreasing off-target cutting. The experiments were carried out in CD34+ cells where the cells were transfected with mRNAs encoding the ZFNs. The data is presented below in Table 8. The "On/off ratio" indicates the ratio of on-target to all off-target activity combined for the indicated sample. The combination of 6.6 µg/mL of SBS #51857 and 60 µg/mL SBS #51949-R416S FokI mutant yielded similar levels of on-target activity (84.85% vs. 78.17% for 60 µg of both parental ZFNs) while dramatically lowering the activity at all five monitored off-target sites and yielding a 32-fold improvement in On-target/off-target ratio (89.52 vs. 2.76 for 60 µg/mL of each parental ZFN).

given in equal quantities to CD34+ cells (60 µg/mL final concentration) or at 6.6 µg and 60 µg final concentrations, for the parent pair, and at 20 µg and 60 µg final concentrations, for the variant.

The results are shown in FIG. 13, and demonstrate that while the parent and variant demonstrated robust cleavage activity at both concentration conditions (>80% indels), off-target capture events were greatly reduced, especially for the variant pair when delivered at the non-equal doses. The combination of the ZFN FokI mutations and the non-equal concentrations of ZFN partners resulted in a 350-fold increase in cleavage specificity.

Example 6: Combining ZFP Backbone Mutations with FokI Phosphate Contact Mutations We also generated ZFNs comprising the zinc finger backbone mutations described in Example 3 with the FokI phosphate contact mutations described in Example 2. This combination was tested with the BCL11A-specific ZFN pair in CD34+ cells at two doses: 6 µg or 2 µg. The results are presented below in Table 9 and demonstrate that combining

TABLE 8

Combining FokI mutants and reduced titration of ZFN partners: % NHEJ activity

| mRNA1 | µg/mL | mRNA2 | µg/mL | BCL11A | NIFMAEVG OT1 | GJZEIYTO OT2 | PEVYOHIU OT3 | ZJCRPAXW OT4 | TXHULGPN OT5 | On/off ratio |
|---|---|---|---|---|---|---|---|---|---|---|
| 51857 | 60 | 51949 | 60 | 78.17 | 21.96 | 2.09 | 2.92 | 0.73 | 0.61 | 2.76 |
| 51857 | 60 | 51949 R416S | 60 | 84.87 | 6.11 | 0.31 | 1.08 | 0.65 | 0.12 | 10.27 |
| 51857 | 60 | 51949 K448S | 60 | 81.03 | 8.90 | 0.72 | 4.40 | 1.29 | 0.64 | 5.08 |
| 51857 | 60 | 51949 K525S | 60 | 80.17 | 0.89 | 0.09 | 0.13 | 0.20 | 0.04 | 59.47 |
| 51857 | 6.6 | 51949 | 60 | 85.21 | 3.39 | 0.38 | 0.49 | 0.14 | 0.10 | 18.98 |
| 51857 | 6.6 | 51949 R416S | 60 | 84.85 | 0.68 | 0.06 | 0.11 | 0.08 | 0.03 | 89.52 |
| 51857 | 6.6 | 51949 K448S | 60 | 83.46 | 1.01 | 0.09 | 0.34 | 0.22 | 0.06 | 48.55 |
| 51857 | 6.6 | 51949 K525S | 60 | 67.92 | 0.14 | 0.01 | 0.02 | 0.04 | 0.01 | 292.27 |

All off-target sites previously listed in Table 1 were examined for the effect on off-target activity by combining the titration and FokI mutant approach (see FIG. 12).

The data showed an aggregate decrease in off-target activity of approximately 30-fold.

The data was also analyzed in terms on the numbers of capture events detected by the unbiased capture assay described above following cleavage. The BCL11A-specific pairs described above in Table 6D, both the parent pair (SBS51857/SBS51949) and the variant pair (SBS63014/SBS65721), were used and the number of off target capture events assayed. In this experiment, the ZFNs were either these two types of approaches can significantly impact the amount of off-target activity. In this table, the backbone mutations are shown as the type of mutation per module (A, B and/or C, referring to FIG. 7). For example, in a sample labeled 51949 LeuABC R416S, the protein comprised R->L backbone substitutions in fingers 1 (module A), 3 (module B), and 5 (module C), and furthermore carried the R416S FokI mutation. In several examples, there were ZFN pairs with no detectable off-target activity while retaining full on-target activity. These examples are boxed in Table 9.

TABLE 9

Activity (% NHEJ) for ZFNs comprising ZFN backbone and FokI phosphate contact mutations.

| mRNA1 | mRNA2 | BCL11A | | NIFMAEVG OT1 | | TXHULGPN OT5 | |
|---|---|---|---|---|---|---|---|
| | | 6 µg | 2 µg | 6 µg | 2 µg | 6 µg | 2 µg |
| 51857 | 51949 | 84.26 | 88.68 | 22.61 | 7.16 | 1.47 | 0.18 |
| 51857 | 51949 R416S | 91.99 | 88.89 | 5.28 | 1.07 | 0.34 | 0.09 |
| 51857 | 51949 LeuABC | 89.95 | 89.01 | 3.04 | 0.56 | 0.24 | ND |
| 51857 | 51949 LeuABC R416S | 92.38 | 88.70 | 0.22 | 0.12 | ND | ND |
| 51857 | 51949 LeuABC K525S | 89.01 | 79.28 | ND | 0.13 | ND | ND |
| 51857 | 51949 GlnABC | 92.04 | 91.85 | 9.46 | 2.01 | 0.24 | ND |
| 51857 | 51949 GlnABC R416S | 94.72 | 92.14 | 1.28 | 0.19 | ND | ND |
| 51857 | 51949 GlnABC K525S | 91.08 | 85.91 | 0.55 | ND | ND | ND |
| 51857 LeuABC | 51949 LeuABC | 87.07 | 66.48 | 0.10 | ND | 0.06 | ND |
| 51857 LeuABC | 51949 LeuABC R416S | 83.69 | 69.00 | ND | ND | ND | ND |

TABLE 9-continued

Activity (% NHEJ) for ZFNs comprising ZFN backbone and FokI phosphate contact mutations.

| mRNA1 | mRNA2 | BCL11A 6 µg | BCL11A 2 µg | NIFMAEVG OT1 6 µg | NIFMAEVG OT1 2 µg | TXHULGPN OT5 6 µg | TXHULGPN OT5 2 µg |
|---|---|---|---|---|---|---|---|
| 51857 LeuABC | 51949 LeuABC K525S | 76.25 | 46.93 | 0.06 | ND | ND | ND |
| 51857 GlnABC | 51949 GlnABC | 92.98 | 88.05 | 0.87 | ND | ND | ND |
| 51857 GlnABC | 51949 GlnABC R416S | 95.01 | 93.44 | 0.16 | ND | ND | ND |
| 51857 GlnABC | 51949 GlnABC K525S | 90.79 | 82.38 | ND | ND | ND | ND |

ND: No activity detected

Example 7: Combining Partner Titration, ZFP Backbone and FokI Phosphate Contact Mutations Activity measurements are also done where the optimal partnering titrations are combined with ZFNs comprising ZFP backbone mutations and ZFN FokI mutations. The ZFNs are tested in CD34+ cells as described above and demonstrate increased specificity of the ZFN pair through a decreased level of off-target activity.

Example 8: Specificity of ZFN in CD34+ Cells at Clinical Scale

The specificity of the BCL11A variant pair SBS63014/SBS65722 was also tested in a large-scale procedure that is suitable for generating cell materials for a clinical trial. In brief, approximately 95-130 million CD34+ cells per lot were transduced using a Maxcyte devise according to manufacturer's specifications. 80 µg/mL of the SBS63014 mRNAs and 20 µg/mL of the SBS #65722 mRNAs were used, and the cells were assayed two days later for off-target cleavage using the unbiased capture assay.

The results showed that when 47 different potential capture loci were analyzed by PCR (see FIG. 14), no significant modification was detectable except at the target location, where 79.54% indels were found. This data demonstrates that these nucleases as described herein are highly specific even when used in a large-scale manufacturing procedure.

Example 9: Further Specificity Studies

Specificity studies were also conducted using AAVS1-targeted ZFNs with various mutations as described above. In particular, ZFNs SBS #30035 and SBS #30054 as described U.S. Publication No. 20150110762 were used for studies of various mutants including dimerization mutants (e.g., ELD, KKR and additional mutants), other mutations (e.g., Sharkey) as well as phosphate contact mutants in activity assays as described above.

For the results in the following Tables, the indicated FokI mutant(s) was/were introduced into either the ELD FokI domain of SBS 30035 (labeled ELD_X where X is the FokI mutation), the KKR FokI domain of SBS 30054 (labeled KKR_X where X is the FokI mutation), or introduced into the FokI domains of both constructs (labeled ELD_KKR_X where X is the same FokI mutation introduced into both ELD and KKR FokI domains). The results for the combination of the unmodified "parental constructs" 30035 and 30054 are labeled as "parental", "parentals", "parental ZFNs", or the like. A lower dose of each parental construct is often labeled "half dose". The negative control with no nucleases is usually labeled "GFP". The ratio of the % indels at the intended locus (often labeled as "AAVS1") divided by the sum of the % indels at all of the off-targets measured in a given experiment is often labeled as "ratio", "on/off ratio", etc.

The location of the AAVS1 target and off-targets is shown below, where 'hg38' denotes the assembled genome data according to the UCSC genome browser database, build hg38:

| locus | hg38 coordinates | |
|---|---|---|
| AAVS1 | chr19 | 55115767 |
| OT1 | chr3 | 184229822 |
| OT2 | chr1 | 198172185 |
| OT3 | chr3 | 50189772 |
| OT4 | chr20 | 35020706 |
| OT5 | chr1 | 181141477 |

Tables 10A-10C shows cleavage results from 2 different experiments on-target (AAVS1) and the three off-target (OT1, OT2, OT3) as well as the ratio of on- to off-target of dimerization mutants ELD, KKR and ELD-KKR with additional substitution mutation (every amino acid for wild-type) at R416 or K525. Also shown are results with ELD_S418D, ELD_N476D, ELD_I479T, ELD_Q481E, ELD_N527D, and ELD_Q531R mutants.

TABLE 10A

| | AAVS1 | OT1 | OT2 | OT3 | OT4 | ratio |
|---|---|---|---|---|---|---|
| parental | 57.77 | 9.73 | 1.31 | 1.67 | 1.20 | 4.15 |
| parental | 55.40 | 9.06 | 1.27 | 1.38 | 0.98 | 4.37 |
| parental | 60.63 | 11.83 | 1.81 | 1.87 | 1.39 | 3.59 |
| parental | 55.39 | 13.05 | 2.15 | 2.26 | 2.05 | 2.84 |
| half dose | 34.13 | 2.50 | 0.23 | 0.31 | 0.12 | 10.81 |
| half dose | 36.73 | 2.67 | 0.19 | 0.41 | 0.23 | 10.49 |
| half dose | 42.08 | 3.72 | 0.32 | 0.51 | 0.30 | 8.67 |
| half dose | 40.22 | 3.17 | 0.47 | 0.57 | 0.32 | 8.87 |
| ELD_R416A | 59.22 | 1.32 | 0.80 | 0.70 | 0.22 | 19.46 |
| ELD_R416C | 61.50 | 2.50 | 1.31 | 1.08 | 0.27 | 11.93 |
| ELD_R416D | 52.20 | 0.12 | 0.61 | 0.16 | 0.02 | 57.66 |
| ELD_R416E | 76.17 | 0.49 | 1.83 | 0.24 | 0.05 | 29.04 |
| ELD_R416F | 75.24 | 3.87 | 2.09 | 1.24 | 0.24 | 10.12 |
| ELD_R416G | 48.30 | 0.66 | 0.90 | 0.71 | 0.15 | 19.98 |
| ELD_R416H | 82.77 | 6.04 | 4.48 | 1.81 | 0.31 | 6.55 |
| ELD_R416I | 28.47 | 3.86 | 0.68 | 0.71 | 0.50 | 4.94 |
| ELD_R416K | 18.07 | 0.92 | 0.33 | 0.37 | 0.15 | 10.14 |
| ELD_R416L | 51.90 | 4.62 | 1.46 | 1.22 | 0.51 | 6.65 |
| ELD_R416M | 60.27 | 2.91 | 1.09 | 0.99 | 0.29 | 11.43 |
| ELD_R416N | 74.77 | 0.83 | 1.12 | 0.59 | 0.11 | 28.19 |
| ELD_R416P | 2.10 | 0.08 | 0.03 | 0.02 | 0.06 | 10.70 |
| ELD_R416Q | 76.84 | 3.23 | 3.09 | 1.30 | 0.25 | 9.76 |
| ELD_R416S | 58.67 | 0.61 | 0.85 | 0.72 | 0.06 | 26.28 |
| ELD_R416T | 49.52 | 1.82 | 0.93 | 0.81 | 0.15 | 13.37 |
| ELD_R416V | 47.52 | 7.94 | 1.70 | 1.36 | 0.94 | 3.98 |
| ELD_R416W | 54.95 | 2.33 | 1.09 | 1.02 | 0.36 | 11.44 |

TABLE 10A-continued

|  | AAVS1 | OT1 | OT2 | OT3 | OT4 | ratio |
|---|---|---|---|---|---|---|
| ELD_R416Y | 81.38 | 20.16 | 7.28 | 3.53 | 1.44 | 2.51 |
| ELD_K525A | 63.30 | 0.30 | 0.12 | 0.14 | 0.11 | 94.56 |
| ELD_K525C | 74.28 | 2.89 | 0.48 | 0.80 | 0.51 | 15.90 |
| ELD_K525D | 41.76 | 0.11 | 0.04 | 0.03 | 0.07 | 163.80 |
| ELD_K525E | 64.31 | 0.07 | 0.08 | 0.10 | 0.10 | 188.65 |
| ELD_K525F | 23.10 | 1.13 | 0.04 | 0.18 | 0.35 | 13.67 |
| ELD_K525G | 54.21 | 0.34 | 0.25 | 0.21 | 0.08 | 61.86 |
| ELD_K525H | 41.07 | 0.79 | 0.17 | 0.24 | 0.28 | 27.65 |
| ELD_K525I | 68.23 | 2.29 | 0.28 | 0.47 | 0.61 | 18.71 |
| ELD_K525L | 27.08 | 0.48 | 0.09 | 0.21 | 0.20 | 27.89 |
| ELD_K525M | 32.75 | 0.25 | 0.08 | 0.13 | 0.10 | 58.51 |
| ELD_K525N | 41.84 | 0.56 | 0.14 | 0.30 | 0.21 | 34.59 |
| ELD_K525P | 8.45 | 0.02 | 0.03 | 0.02 | 0.03 | 92.43 |
| ELD_K525Q | 47.10 | 0.48 | 0.31 | 0.34 | 0.11 | 38.14 |
| ELD_K525R | 51.08 | 10.86 | 1.17 | 1.35 | 1.93 | 3.34 |
| ELD_K525S | 65.83 | 0.53 | 0.22 | 0.23 | 0.15 | 58.28 |
| ELD_K525T | 74.60 | 2.75 | 0.48 | 0.94 | 0.44 | 16.19 |
| ELD_K525V | 72.57 | 2.82 | 0.36 | 0.58 | 0.40 | 17.40 |
| ELD_K525W | 18.26 | 0.88 | 0.06 | 0.11 | 0.34 | 13.16 |
| ELD_K525Y | 37.75 | 2.21 | 0.14 | 0.21 | 0.82 | 11.17 |
| ELD_S418D | 57.94 | 0.33 | 0.11 | 0.21 | 0.09 | 77.35 |
| ELD_N476D | 70.96 | 0.10 | 0.06 | 0.04 | 0.03 | 304.50 |
| ELD_I479T | 60.88 | 0.10 | 0.11 | 0.04 | 0.07 | 196.27 |
| ELD_Q481E | 68.89 | 0.16 | 0.07 | 0.12 | 0.08 | 162.31 |
| ELD_N527D | 48.34 | 0.64 | 0.13 | 0.29 | 0.07 | 42.42 |
| ELD_Q531R | 54.06 | 0.97 | 0.12 | 0.13 | 0.09 | 41.65 |
| GFP | 0.00 | 0.01 | 0.02 | 0.03 | 0.03 | NA |
| GFP | 0.00 | 0.04 | 0.01 | 0.03 | 0.02 | NA |
| parental | 1.01 | 0.89 | 0.80 | 0.93 | 0.85 | 1.11 |
| parental | 0.97 | 0.83 | 0.78 | 0.77 | 0.70 | 1.17 |
| parental | 1.06 | 1.08 | 1.11 | 1.04 | 0.99 | 0.96 |
| parental | 0.97 | 1.20 | 1.32 | 1.26 | 1.46 | 0.76 |
| half dose | 0.60 | 0.23 | 0.14 | 0.17 | 0.08 | 2.89 |
| half dose | 0.64 | 0.24 | 0.12 | 0.23 | 0.16 | 2.81 |
| half dose | 0.73 | 0.34 | 0.20 | 0.28 | 0.21 | 2.32 |
| half dose | 0.70 | 0.29 | 0.29 | 0.32 | 0.23 | 2.37 |
| ELD_R416A | 1.03 | 0.12 | 0.49 | 0.39 | 0.15 | 5.21 |
| ELD_R416C | 1.07 | 0.23 | 0.80 | 0.60 | 0.19 | 3.19 |
| ELD_R416D | 0.91 | 0.01 | 0.37 | 0.09 | 0.02 | 15.43 |
| ELD_R416E | 1.33 | 0.05 | 1.12 | 0.13 | 0.13 | 7.77 |
| ELD_R416F | 1.31 | 0.35 | 1.28 | 0.69 | 0.17 | 2.71 |
| ELD_R416G | 0.84 | 0.06 | 0.55 | 0.39 | 0.11 | 5.35 |
| ELD_R416H | 1.44 | 0.55 | 2.74 | 1.01 | 0.22 | 1.75 |
| ELD_R416I | 0.50 | 0.35 | 0.42 | 0.40 | 0.36 | 1.32 |
| ELD_R416K | 0.32 | 0.08 | 0.20 | 0.21 | 0.11 | 2.71 |
| ELD_R416L | 0.91 | 0.42 | 0.89 | 0.68 | 0.36 | 1.78 |
| ELD_R416M | 1.05 | 0.27 | 0.67 | 0.55 | 0.20 | 3.06 |
| ELD_R416N | 1.30 | 0.08 | 0.69 | 0.33 | 0.08 | 7.54 |
| ELD_R416P | 0.04 | 0.01 | 0.02 | 0.01 | 0.04 | 2.86 |
| ELD_R416Q | 1.34 | 0.30 | 1.89 | 0.73 | 0.18 | 2.61 |
| ELD_R416S | 1.02 | 0.06 | 0.52 | 0.40 | 0.04 | 7.03 |
| ELD_R416T | 0.86 | 0.17 | 0.57 | 0.45 | 0.11 | 3.58 |
| ELD_R416V | 0.83 | 0.73 | 1.04 | 0.76 | 0.67 | 1.06 |
| ELD_R416W | 0.96 | 0.21 | 0.67 | 0.57 | 0.25 | 3.06 |
| ELD_R416Y | 1.42 | 1.85 | 4.46 | 1.96 | 1.02 | 0.67 |
| ELD_K525A | 1.10 | 0.03 | 0.08 | 0.08 | 0.08 | 25.30 |
| ELD_K525C | 1.30 | 0.26 | 0.29 | 0.45 | 0.36 | 4.26 |
| ELD_K525D | 0.73 | 0.01 | 0.02 | 0.02 | 0.05 | 43.83 |
| ELD_K525E | 1.12 | 0.01 | 0.05 | 0.05 | 0.07 | 50.48 |
| ELD_K525F | 0.40 | 0.10 | 0.03 | 0.10 | 0.25 | 3.66 |
| ELD_K525G | 0.95 | 0.03 | 0.15 | 0.12 | 0.05 | 16.55 |
| ELD_K525H | 0.72 | 0.07 | 0.11 | 0.13 | 0.20 | 7.40 |
| ELD_K525I | 1.19 | 0.21 | 0.17 | 0.26 | 0.43 | 5.01 |
| ELD_K525L | 0.47 | 0.04 | 0.06 | 0.12 | 0.14 | 7.46 |
| ELD_K525M | 0.57 | 0.02 | 0.05 | 0.07 | 0.07 | 15.66 |
| ELD_K525N | 0.73 | 0.05 | 0.09 | 0.17 | 0.15 | 9.26 |
| ELD_K525P | 0.15 | 0.00 | 0.02 | 0.01 | 0.02 | 24.73 |
| ELD_K525Q | 0.82 | 0.04 | 0.19 | 0.19 | 0.08 | 10.20 |
| ELD_K525R | 0.89 | 0.99 | 0.72 | 0.75 | 1.37 | 0.89 |
| ELD_K525S | 1.15 | 0.05 | 0.13 | 0.13 | 0.11 | 15.60 |
| ELD_K525T | 1.30 | 0.25 | 0.29 | 0.53 | 0.31 | 4.33 |
| ELD_K525V | 1.27 | 0.26 | 0.22 | 0.33 | 0.29 | 4.66 |
| ELD_K525W | 0.32 | 0.08 | 0.04 | 0.06 | 0.24 | 3.52 |
| ELD_K525Y | 0.66 | 0.20 | 0.08 | 0.11 | 0.59 | 2.99 |
| ELD_S418D | 1.01 | 0.03 | 0.07 | 0.12 | 0.06 | 20.70 |
| ELD_N476D | 1.24 | 0.01 | 0.04 | 0.02 | 0.02 | 81.48 |
| ELD_I479T | 1.06 | 0.01 | 0.07 | 0.02 | 0.05 | 52.52 |
| ELD_Q481E | 1.20 | 0.01 | 0.04 | 0.06 | 0.06 | 43.43 |
| ELD_N527D | 0.84 | 0.06 | 0.08 | 0.16 | 0.05 | 11.35 |
| ELD_Q531R | 0.94 | 0.09 | 0.07 | 0.07 | 0.06 | 11.15 |
| GFP | 0.00 | 0.00 | 0.01 | 0.02 | 0.02 | ND |
| GFP | 0.00 | 0.00 | 0.00 | 0.02 | 0.02 | ND |

TABLE 10B

|  | AAVS1 | OT1 | OT2 | OT3 | OT4 | ratio |
|---|---|---|---|---|---|---|
| parental | 57.77 | 9.73 | 1.31 | 1.67 | 1.20 | 4.15 |
| parental | 55.40 | 9.06 | 1.27 | 1.38 | 0.98 | 4.37 |
| parental | 60.63 | 11.83 | 1.81 | 1.87 | 1.39 | 3.59 |
| parental | 55.39 | 13.05 | 2.15 | 2.26 | 2.05 | 2.84 |
| half dose | 34.13 | 2.50 | 0.23 | 0.31 | 0.12 | 10.81 |
| half dose | 36.73 | 2.67 | 0.19 | 0.41 | 0.23 | 10.49 |
| half dose | 42.08 | 3.72 | 0.32 | 0.51 | 0.30 | 8.67 |
| half dose | 40.22 | 3.17 | 0.47 | 0.57 | 0.32 | 8.87 |
| KKR_R416A | 54.27 | 3.73 | 0.13 | 0.25 | 0.57 | 11.60 |
| KKR_R416C | 54.00 | 5.09 | 0.35 | 0.41 | 0.94 | 7.95 |
| KKR_R416D | 44.62 | 0.27 | 0.05 | 0.04 | 0.12 | 90.35 |
| KKR_R416E | 68.27 | 1.58 | 0.03 | 0.16 | 0.62 | 28.47 |
| KKR_R416F | 63.29 | 3.94 | 0.33 | 0.38 | 1.09 | 11.04 |
| KKR_R416G | 48.98 | 2.04 | 0.12 | 0.24 | 0.55 | 16.60 |
| KKR_R416H | 73.76 | 9.86 | 0.52 | 0.91 | 2.96 | 5.18 |
| KKR_R416I | 23.42 | 2.91 | 0.38 | 0.61 | 0.44 | 5.39 |
| KKR_R416K | 25.56 | 1.96 | 0.31 | 0.64 | 0.30 | 7.98 |
| KKR_R416L | 46.72 | 6.32 | 0.47 | 0.78 | 0.87 | 5.53 |
| KKR_R416M | 53.48 | 5.09 | 0.45 | 0.64 | 0.93 | 7.52 |
| KKR_R416N | 69.54 | 2.49 | 0.07 | 0.24 | 0.75 | 19.57 |
| KKR_R416P | 1.75 | 0.05 | 0.02 | 0.02 | 0.06 | 11.88 |
| KKR_R416Q | 69.01 | 6.21 | 0.13 | 0.44 | 2.08 | 7.79 |
| KKR_R416S | 61.68 | 4.36 | 0.27 | 0.32 | 0.94 | 10.47 |
| KKR_R416T | 55.82 | 6.64 | 0.31 | 0.72 | 1.18 | 6.31 |
| KKR_R416V | 40.09 | 4.97 | 0.79 | 1.04 | 0.99 | 5.15 |
| KKR_R416W | 41.18 | 3.67 | 0.32 | 0.40 | 0.49 | 8.44 |
| KKR_R416Y | 72.44 | 20.12 | 1.70 | 2.41 | 3.83 | 2.58 |
| KKR_K525A | 61.16 | 0.92 | 0.09 | 0.13 | 0.21 | 45.07 |
| KKR_K525C | 62.86 | 3.74 | 0.13 | 0.31 | 0.37 | 13.80 |
| KKR_K525D | 36.17 | 0.14 | 0.00 | 0.03 | 0.04 | 168.94 |
| KKR_K525E | 52.52 | 0.24 | 0.02 | 0.06 | 0.07 | 133.17 |
| KKR_K525F | 25.30 | 0.74 | 0.58 | 0.34 | 0.16 | 13.86 |
| KKR_K525G | 52.93 | 1.09 | 0.04 | 0.13 | 0.34 | 33.16 |
| KKR_K525H | 41.28 | 2.61 | 0.29 | 0.34 | 0.24 | 11.88 |
| KKR_K525I | 57.29 | 2.40 | 0.16 | 0.28 | 0.24 | 18.57 |
| KKR_K525L | 30.26 | 0.79 | 0.06 | 0.15 | 0.07 | 28.15 |
| KKR_K525M | 46.57 | 1.29 | 0.15 | 0.17 | 0.19 | 26.01 |
| KKR_K525N | 44.68 | 1.61 | 0.15 | 0.25 | 0.27 | 19.51 |
| KKR_K525P | 2.44 | 0.04 | 0.02 | 0.01 | 0.03 | 25.01 |
| KKR_K525Q | 52.58 | 1.55 | 0.09 | 0.12 | 0.26 | 25.97 |
| KKR_K525R | 52.25 | 9.51 | 2.04 | 1.57 | 1.18 | 3.65 |
| KKR_K525S | 63.23 | 1.06 | 0.10 | 0.12 | 0.33 | 39.16 |
| KKR_K525T | 66.66 | 5.06 | 0.24 | 0.32 | 0.45 | 10.97 |
| KKR_K525V | 58.68 | 2.62 | 0.18 | 0.18 | 0.18 | 18.57 |
| KKR_K525W | 17.81 | 0.52 | 0.09 | 0.21 | 0.05 | 20.68 |
| KKR_K525Y | 35.10 | 1.42 | 0.70 | 0.41 | 0.15 | 13.09 |
| KKR_S418D | 73.70 | 1.47 | 0.19 | 0.23 | 0.34 | 32.91 |
| KKR_N476D | 36.23 | 0.05 | 0.03 | 0.06 | 0.02 | 230.91 |
| KKR_I479T | 67.02 | 0.76 | 0.14 | 0.64 | 0.12 | 40.47 |
| KKR_Q481E | 66.20 | 0.25 | 0.04 | 0.04 | 0.03 | 183.51 |
| KKR_N527D | 54.55 | 1.95 | 0.37 | 0.57 | 0.26 | 17.27 |
| KKR_Q531R | 54.73 | 2.17 | 0.78 | 0.80 | 0.24 | 13.73 |
| GFP | 0.00 | 0.01 | 0.02 | 0.03 | 0.03 | NA |
| GFP | 0.00 | 0.04 | 0.01 | 0.03 | 0.02 | NA |
| parental | 1.01 | 0.89 | 0.80 | 0.93 | 0.85 | 1.11 |
| parental | 0.97 | 0.83 | 0.78 | 0.77 | 0.70 | 1.17 |
| parental | 1.06 | 1.08 | 1.11 | 1.04 | 0.99 | 0.96 |
| parental | 0.97 | 1.20 | 1.32 | 1.26 | 1.46 | 0.76 |
| half dose | 0.60 | 0.23 | 0.14 | 0.17 | 0.08 | 2.89 |
| half dose | 0.64 | 0.24 | 0.12 | 0.23 | 0.16 | 2.81 |
| half dose | 0.73 | 0.34 | 0.20 | 0.28 | 0.21 | 2.32 |
| half dose | 0.70 | 0.29 | 0.29 | 0.32 | 0.23 | 2.37 |
| KKR_R416A | 0.95 | 0.34 | 0.08 | 0.14 | 0.40 | 3.10 |
| KKR_R416C | 0.94 | 0.47 | 0.21 | 0.23 | 0.67 | 2.13 |
| KKR_R416D | 0.78 | 0.03 | 0.03 | 0.02 | 0.09 | 24.18 |
| KKR_R416E | 1.19 | 0.14 | 0.02 | 0.09 | 0.44 | 7.62 |

TABLE 10B-continued

|  | AAVS1 | OT1 | OT2 | OT3 | OT4 | ratio |
|---|---|---|---|---|---|---|
| KKR_R416F | 1.10 | 0.36 | 0.20 | 0.21 | 0.78 | 2.95 |
| KKR_R416G | 0.85 | 0.19 | 0.07 | 0.14 | 0.39 | 4.44 |
| KKR_R416H | 1.29 | 0.90 | 0.32 | 0.51 | 2.11 | 1.38 |
| KKR_R416I | 0.41 | 0.27 | 0.23 | 0.34 | 0.31 | 1.44 |
| KKR_R416K | 0.45 | 0.18 | 0.19 | 0.36 | 0.21 | 2.13 |
| KKR_R416L | 0.82 | 0.58 | 0.29 | 0.44 | 0.62 | 1.48 |
| KKR_R416M | 0.93 | 0.47 | 0.28 | 0.36 | 0.66 | 2.01 |
| KKR_R416N | 1.21 | 0.23 | 0.04 | 0.14 | 0.54 | 5.24 |
| KKR_R416P | 0.03 | 0.00 | 0.01 | 0.01 | 0.04 | 3.18 |
| KKR_R416Q | 1.20 | 0.57 | 0.08 | 0.24 | 1.48 | 2.08 |
| KKR_R416S | 1.08 | 0.40 | 0.16 | 0.18 | 0.67 | 2.80 |
| KKR_R416T | 0.97 | 0.61 | 0.19 | 0.40 | 0.84 | 1.69 |
| KKR_R416V | 0.70 | 0.46 | 0.48 | 0.58 | 0.70 | 1.38 |
| KKR_R416W | 0.72 | 0.34 | 0.19 | 0.22 | 0.35 | 2.26 |
| KKR_R416Y | 1.26 | 1.84 | 1.04 | 1.34 | 2.73 | 0.69 |
| KKR_K525A | 1.07 | 0.08 | 0.06 | 0.07 | 0.15 | 12.06 |
| KKR_K525C | 1.10 | 0.34 | 0.08 | 0.17 | 0.26 | 3.69 |
| KKR_K525D | 0.63 | 0.01 | 0.00 | 0.02 | 0.03 | 45.21 |
| KKR_K525E | 0.92 | 0.02 | 0.01 | 0.03 | 0.05 | 35.63 |
| KKR_K525F | 0.44 | 0.07 | 0.36 | 0.19 | 0.11 | 3.71 |
| KKR_K525G | 0.92 | 0.10 | 0.03 | 0.07 | 0.24 | 8.87 |
| KKR_K525H | 0.72 | 0.24 | 0.18 | 0.19 | 0.17 | 3.18 |
| KKR_K525I | 1.00 | 0.22 | 0.10 | 0.16 | 0.17 | 4.97 |
| KKR_K525L | 0.53 | 0.07 | 0.04 | 0.08 | 0.05 | 7.53 |
| KKR_K525M | 0.81 | 0.12 | 0.09 | 0.10 | 0.13 | 6.96 |
| KKR_K525N | 0.78 | 0.15 | 0.09 | 0.14 | 0.20 | 5.22 |
| KKR_K525P | 0.04 | 0.00 | 0.01 | 0.01 | 0.02 | 6.69 |
| KKR_K525Q | 0.92 | 0.14 | 0.06 | 0.07 | 0.18 | 6.95 |
| KKR_K525R | 0.91 | 0.87 | 1.25 | 0.87 | 0.84 | 0.98 |
| KKR_K525S | 1.10 | 0.10 | 0.06 | 0.07 | 0.24 | 10.48 |
| KKR_K525T | 1.16 | 0.46 | 0.15 | 0.18 | 0.32 | 2.94 |
| KKR_K525V | 1.02 | 0.24 | 0.11 | 0.10 | 0.13 | 4.97 |
| KKR_K525W | 0.31 | 0.05 | 0.05 | 0.12 | 0.03 | 5.53 |
| KKR_K525Y | 0.61 | 0.13 | 0.43 | 0.23 | 0.11 | 3.50 |
| KKR_S418D | 1.29 | 0.13 | 0.12 | 0.13 | 0.25 | 8.81 |
| KKR_N476D | 0.63 | 0.00 | 0.02 | 0.03 | 0.01 | 61.79 |
| KKR_I479T | 1.17 | 0.07 | 0.09 | 0.36 | 0.08 | 10.83 |
| KKR_Q481E | 1.16 | 0.02 | 0.02 | 0.02 | 0.02 | 49.10 |
| KKR_N527D | 0.95 | 0.18 | 0.23 | 0.32 | 0.19 | 4.62 |
| KKR_Q531R | 0.96 | 0.20 | 0.48 | 0.44 | 0.17 | 3.68 |
| GFP | 0.00 | 0.00 | 0.01 | 0.02 | 0.02 | ND |
| GFP | 0.00 | 0.00 | 0.00 | 0.02 | 0.02 | ND |

TABLE 10C

|  | AAVS1 | OT1 | OT2 | OT3 | OT4 | ratio |
|---|---|---|---|---|---|---|
| parental | 57.77 | 9.73 | 1.31 | 1.67 | 1.20 | 4.15 |
| parental | 55.40 | 9.06 | 1.27 | 1.38 | 0.98 | 4.37 |
| parental | 60.63 | 11.83 | 1.81 | 1.87 | 1.39 | 3.59 |
| parental | 55.39 | 13.05 | 2.15 | 2.26 | 2.05 | 2.84 |
| half dose | 34.13 | 2.50 | 0.23 | 0.31 | 0.12 | 10.81 |
| half dose | 36.73 | 2.67 | 0.19 | 0.41 | 0.23 | 10.49 |
| half dose | 42.08 | 3.72 | 0.32 | 0.51 | 0.30 | 8.67 |
| half dose | 40.22 | 3.17 | 0.47 | 0.57 | 0.32 | 8.87 |
| ELD_KKR_R416A | 67.11 | 1.14 | 0.16 | 0.37 | 0.12 | 37.44 |
| ELD_KKR_R416C | 68.42 | 2.75 | 0.34 | 0.72 | 0.29 | 16.66 |
| ELD_KKR_R416D | 70.61 | 0.04 | 0.04 | 0.05 | 0.03 | 457.42 |
| ELD_KKR_R416E | 91.13 | 0.41 | 0.11 | 0.19 | 0.07 | 116.98 |
| ELD_KKR_R416F | 87.13 | 2.62 | 0.57 | 0.81 | 0.38 | 19.92 |
| ELD_KKR_R416G | 47.93 | 0.47 | 0.08 | 0.17 | 0.12 | 57.10 |
| ELD_KKR_R416H | 94.25 | 18.51 | 3.09 | 3.36 | 2.33 | 3.45 |
| ELD_KKR_R416I | 13.03 | 1.02 | 0.30 | 0.33 | 0.23 | 6.95 |
| ELD_KKR_R416K | 11.52 | 0.91 | 0.12 | 0.23 | 0.11 | 8.39 |
| ELD_KKR_R416L | 44.91 | 3.13 | 0.50 | 0.74 | 0.48 | 9.26 |
| ELD_KKR_R416M | 69.25 | 3.99 | 0.47 | 0.85 | 0.47 | 11.98 |
| ELD_KKR_R416N | 89.31 | 0.55 | 0.16 | 0.35 | 0.12 | 76.30 |
| ELD_KKR_R416P | 0.11 | 0.01 | 0.01 | 0.01 | 0.03 | 1.86 |
| ELD_KKR_R416Q | 88.16 | 7.54 | 1.10 | 1.66 | 0.73 | 7.99 |
| ELD_KKR_R416S | 71.87 | 0.61 | 0.22 | 0.28 | 0.13 | 58.20 |
| ELD_KKR_R416T | 62.11 | 3.51 | 0.50 | 0.99 | 0.43 | 11.45 |
| ELD_KKR_R416V | 34.90 | 4.49 | 1.08 | 1.14 | 0.86 | 4.62 |
| ELD_KKR_R416W | 39.15 | 1.20 | 0.21 | 0.36 | 0.16 | 20.34 |
| ELD_KKR_R416Y | 85.93 | 62.16 | 24.08 | 16.89 | 17.97 | 0.71 |
| ELD_KKR_K525A | 73.85 | 0.07 | 0.01 | 0.04 | 0.03 | 493.98 |

TABLE 10C-continued

|  | AAVS1 | OT1 | OT2 | OT3 | OT4 | ratio |
|---|---|---|---|---|---|---|
| ELD_KKR_K525C | 82.14 | 0.55 | 0.12 | 0.12 | 0.19 | 83.07 |
| ELD_KKR_K525D | 5.01 | 0.02 | 0.01 | 0.02 | 0.04 | 56.71 |
| ELD_KKR_K525E | 23.62 | 0.02 | 0.01 | 0.03 | 0.02 | 288.19 |
| ELD_KKR_K525F | 12.65 | 0.28 | 0.07 | 0.08 | 0.04 | 27.09 |
| ELD_KKR_K525G | 56.50 | 0.07 | 0.04 | 0.04 | 0.02 | 358.56 |
| ELD_kkR_K525H | 36.28 | 0.27 | 0.04 | 0.06 | 0.07 | 81.26 |
| ELD_KKR_K525I | 80.42 | 0.51 | 0.04 | 0.13 | 0.12 | 100.52 |
| ELD_KKR_K525L | 14.33 | 0.02 | 0.01 | 0.04 | 0.04 | 119.70 |
| ELD_KKR_K525M | 27.60 | 0.09 | 0.02 | 0.04 | 0.03 | 157.04 |
| ELD_KKR_K525N | 36.50 | 0.23 | 0.04 | 0.05 | 0.04 | 102.77 |
| ELD_KKR_K525P | 0.01 | 0.03 | 0.03 | 0.02 | 0.02 | 0.11 |
| ELD_KKR_K525Q | 41.98 | 0.10 | 0.03 | 0.07 | 0.03 | 169.31 |
| ELD_KKR_K525R | 53.62 | 14.69 | 2.18 | 1.97 | 2.52 | 2.51 |
| ELD_KKR_K525S | 77.66 | 0.11 | 0.02 | 0.06 | 0.05 | 316.50 |
| ELD_KKR_K525T | 84.74 | 0.68 | 0.07 | 0.21 | 0.21 | 72.27 |
| ELD_KKR_K525V | 83.33 | 0.48 | 0.04 | 0.06 | 0.09 | 122.99 |
| ELD_KKR_K525W | 8.64 | 0.10 | 0.02 | 0.03 | 0.05 | 44.17 |
| ELD_KKR_K525Y | 25.83 | 0.83 | 0.07 | 0.11 | 0.11 | 23.03 |
| ELD_KKR_S418D | 53.46 | 0.07 | 0.01 | 0.01 | 0.03 | 442.19 |
| ELD_KKR_N476D | 6.29 | 0.02 | 0.01 | 0.02 | 0.03 | 77.38 |
| ELD_KKR_I479T | 52.47 | 0.02 | 0.01 | 0.02 | 0.03 | 730.00 |
| ELD_KKR_Q481E | 69.91 | 0.03 | 0.02 | 0.02 | 0.02 | 784.97 |
| ELD_KKR_N527D | 36.03 | 0.07 | 0.02 | 0.04 | 0.02 | 235.36 |
| ELD_KKR_Q531R | 63.71 | 0.91 | 0.08 | 0.29 | 0.08 | 46.84 |
| GFP | 0.00 | 0.01 | 0.02 | 0.03 | 0.03 | NA |
| GFP | 0.00 | 0.04 | 0.01 | 0.03 | 0.02 | NA |
| parental | 1.01 | 0.89 | 0.80 | 0.93 | 0.85 | 1.11 |
| parental | 0.97 | 0.83 | 0.78 | 0.77 | 0.70 | 1.17 |
| parental | 1.06 | 1.08 | 1.11 | 1.04 | 0.99 | 0.96 |
| parental | 0.97 | 1.20 | 1.32 | 1.26 | 1.46 | 0.76 |
| half dose | 0.60 | 0.23 | 0.14 | 0.17 | 0.08 | 2.89 |
| half dose | 0.64 | 0.24 | 0.12 | 0.23 | 0.16 | 2.81 |
| half dose | 0.73 | 0.34 | 0.20 | 0.28 | 0.21 | 2.32 |
| half dose | 0.70 | 0.29 | 0.29 | 0.32 | 0.23 | 2.37 |
| ELD_KKR_R416A | 1.17 | 0.10 | 0.10 | 0.21 | 0.08 | 10.02 |
| ELD_KKR_R416C | 1.19 | 0.25 | 0.21 | 0.40 | 0.21 | 4.46 |
| ELD_KKR_R416D | 1.23 | 0.00 | 0.02 | 0.03 | 0.03 | 122.40 |
| ELD_KKR_R416E | 1.59 | 0.04 | 0.07 | 0.10 | 0.05 | 31.30 |
| ELD_KKR_R416F | 1.52 | 0.24 | 0.35 | 0.45 | 0.27 | 5.33 |
| ELD_KKR_R416G | 0.84 | 0.04 | 0.05 | 0.10 | 0.08 | 15.28 |
| ELD_KKR_R416H | 1.64 | 1.70 | 1.89 | 1.87 | 1.66 | 0.92 |
| ELD_KKR_R416I | 0.23 | 0.09 | 0.18 | 0.18 | 0.16 | 1.86 |
| ELD_KKR_R416K | 0.20 | 0.08 | 0.08 | 0.13 | 0.08 | 2.25 |
| ELD_KKR_R416L | 0.78 | 0.29 | 0.31 | 0.41 | 0.34 | 2.48 |
| ELD_KKR_R416M | 1.21 | 0.37 | 0.29 | 0.48 | 0.34 | 3.20 |
| ELD_KKR_R416N | 1.56 | 0.05 | 0.10 | 0.19 | 0.08 | 20.42 |
| ELD_KKR_R416P | 0.00 | 0.00 | 0.01 | 0.00 | 0.02 | 0.50 |
| ELD_KKR_R416Q | 1.54 | 0.69 | 0.67 | 0.93 | 0.52 | 2.14 |
| ELD_KKR_R416S | 1.25 | 0.06 | 0.14 | 0.16 | 0.09 | 15.57 |
| ELD_KKR_R416T | 1.08 | 0.32 | 0.31 | 0.55 | 0.30 | 3.06 |
| ELD_KKR_R416V | 0.61 | 0.41 | 0.66 | 0.63 | 0.61 | 1.24 |
| ELD_KKR_R416W | 0.68 | 0.11 | 0.13 | 0.20 | 0.11 | 5.44 |
| ELD_KKR_R416Y | 1.50 | 5.69 | 14.74 | 9.41 | 12.79 | 0.19 |
| ELD_KKR_K525A | 1.29 | 0.01 | 0.00 | 0.02 | 0.02 | 132.18 |
| ELD_KKR_K525C | 1.43 | 0.05 | 0.08 | 0.07 | 0.14 | 22.23 |
| ELD_KKR_K525D | 0.09 | 0.00 | 0.01 | 0.01 | 0.03 | 15.18 |
| ELD_KKR_K525E | 0.41 | 0.00 | 0.00 | 0.02 | 0.02 | 77.12 |
| ELD_KKR_K525F | 0.22 | 0.03 | 0.04 | 0.05 | 0.03 | 7.25 |
| ELD_KKR_K525G | 0.99 | 0.01 | 0.02 | 0.02 | 0.01 | 95.95 |
| ELD_kkR_K525H | 0.63 | 0.03 | 0.03 | 0.03 | 0.05 | 21.74 |
| ELD_KKR_K525I | 1.40 | 0.05 | 0.03 | 0.07 | 0.08 | 26.90 |
| ELD_KKR_K525L | 0.25 | 0.00 | 0.01 | 0.01 | 0.02 | 32.03 |
| ELD_KKR_K525M | 0.48 | 0.01 | 0.01 | 0.02 | 0.02 | 42.02 |
| ELD_KKR_K525N | 0.64 | 0.02 | 0.02 | 0.03 | 0.03 | 27.50 |
| ELD_KKR_K525P | 0.00 | 0.00 | 0.02 | 0.01 | 0.02 | 0.03 |
| ELD_KKR_K525Q | 0.73 | 0.01 | 0.02 | 0.04 | 0.03 | 45.31 |
| ELD_KKR_K525R | 0.94 | 1.35 | 1.33 | 1.10 | 1.80 | 0.67 |
| ELD_KKR_K525S | 1.36 | 0.01 | 0.01 | 0.03 | 0.04 | 84.69 |
| ELD_KKR_K525T | 1.48 | 0.06 | 0.04 | 0.12 | 0.15 | 19.34 |
| ELD_KKR_K525V | 1.45 | 0.04 | 0.03 | 0.04 | 0.07 | 32.91 |
| ELD_KKR_K525W | 0.15 | 0.01 | 0.01 | 0.04 | 0.03 | 11.82 |
| ELD_KKR_K525Y | 0.45 | 0.08 | 0.04 | 0.06 | 0.08 | 6.16 |
| ELD_KKR_S418D | 0.93 | 0.01 | 0.01 | 0.01 | 0.02 | 118.32 |
| ELD_KKR_N476D | 0.11 | 0.00 | 0.01 | 0.01 | 0.01 | 20.31 |
| ELD_KKR_I479T | 0.92 | 0.00 | 0.01 | 0.01 | 0.02 | 195.34 |
| ELD_KKR_Q481E | 1.22 | 0.00 | 0.01 | 0.01 | 0.02 | 210.05 |
| ELD_KKR_N527D | 0.63 | 0.01 | 0.01 | 0.02 | 0.01 | 62.98 |
| ELD_KKR_Q531R | 1.11 | 0.08 | 0.05 | 0.16 | 0.06 | 12.53 |

TABLE 10C-continued

|  | AAVS1 | OT1 | OT2 | OT3 | OT4 | ratio |
|---|---|---|---|---|---|---|
| GFP | 0.00 | 0.00 | 0.01 | 0.02 | 0.02 | ND |
| GFP | 0.00 | 0.00 | 0.00 | 0.02 | 0.02 | ND |

Tables 11A-11C shows cleavage results from 2 different experiments on-target (AAVS1) and three off-target (OT1, OT2, OT3) as well as the ratio of on- to off-target of the indicated mutants, including substitution mutants at 418, 422 and 525 in combination with dimerization mutants ELD and/or KKR.

TABLE 11A

|  | AAVS1 | OT1 | OT2 | OT3 | OT4 | ratio |
|---|---|---|---|---|---|---|
| Parental | 63.63 | 15.40 | 3.50 | 3.29 | 3.11 | 2.52 |
| Parental | 63.10 | 18.77 | 3.50 | 3.63 | 3.01 | 2.18 |
| Parental | 60.00 | 11.17 | 2.50 | 2.92 | 2.79 | 3.10 |
| Parental | 56.67 | 13.75 | 2.05 | 2.62 | 2.28 | 2.74 |
| half dose | 43.53 | 6.13 | 0.58 | 0.98 | 0.58 | 5.26 |
| half dose | 45.07 | 6.62 | 0.81 | 0.77 | 0.67 | 5.08 |
| half dose | 36.53 | 3.47 | 0.31 | 0.48 | 0.30 | 8.01 |
| half dose | 34.68 | 3.72 | 0.28 | 0.68 | 0.43 | 6.80 |
| ELD_S418A | 64.85 | 6.75 | 4.13 | 3.56 | 1.13 | 4.16 |
| ELD_S418C | 48.50 | 6.15 | 2.17 | 3.19 | 1.45 | 3.74 |
| ELD_S418D | 63.65 | 1.90 | 1.07 | 0.93 | 0.51 | 14.47 |
| ELD_S418E | 80.24 | 0.52 | 0.20 | 0.31 | 0.16 | 67.61 |
| ELD_S418F | 18.36 | 6.25 | 0.52 | 0.77 | 0.25 | 2.35 |
| ELD_S418G | 41.80 | 17.17 | 1.22 | 1.15 | 4.53 | 1.74 |
| ELD_S418H | 52.02 | 6.20 | 3.38 | 3.05 | 0.97 | 3.82 |
| ELD_S418I | 18.67 | 0.11 | 0.18 | 0.14 | 0.03 | 40.45 |
| ELD_S418K | 47.05 | 2.90 | 4.22 | 3.37 | 1.19 | 4.03 |
| ELD_S418L | 11.43 | 0.23 | 0.16 | 0.42 | 0.05 | 13.30 |
| ELD_S418M | 24.02 | 0.64 | 0.50 | 0.67 | 0.13 | 12.39 |
| ELD_S418N | 51.08 | 6.04 | 3.49 | 2.41 | 0.62 | 4.07 |
| ELD_S418P | 85.88 | 25.87 | 11.22 | 5.63 | 3.90 | 1.84 |
| ELD_S418Q | 49.25 | 1.33 | 1.93 | 1.38 | 0.21 | 10.18 |
| ELD_S418R | 43.75 | 3.65 | 6.46 | 3.11 | 0.68 | 3.15 |
| ELD_S418T | 41.87 | 0.63 | 0.58 | 0.56 | 0.08 | 22.56 |
| ELD_S418V | 32.95 | 0.21 | 0.34 | 0.27 | 0.04 | 38.58 |
| ELD_S418W | 19.69 | 1.28 | 1.00 | 0.88 | 0.15 | 5.95 |
| ELD_S418Y | 21.45 | 1.68 | 0.57 | 0.72 | 0.34 | 6.47 |
| ELD_R422A | 4.83 | 0.09 | 0.07 | 0.09 | 0.04 | 16.58 |
| ELD_R422C | 29.95 | 1.75 | 0.47 | 0.84 | 0.31 | 8.89 |
| ELD_R422D | 40.01 | 0.84 | 0.50 | 0.40 | 0.07 | 22.15 |
| ELD_R422E | 45.73 | 0.85 | 0.32 | 0.38 | 0.07 | 28.14 |
| ELD_R422F | 39.31 | 3.33 | 1.22 | 2.37 | 0.62 | 5.22 |
| ELD_R422G | 41.33 | 1.35 | 0.43 | 0.92 | 0.18 | 14.32 |
| ELD_R422H | 62.83 | 5.04 | 1.65 | 2.12 | 0.40 | 6.83 |
| ELD_R422I | 35.81 | 3.13 | 0.31 | 1.37 | 0.43 | 6.83 |
| ELD_R422K | 72.35 | 21.16 | 8.36 | 4.17 | 2.86 | 1.98 |
| ELD_R422L | 53.80 | 10.24 | 0.63 | 2.14 | 1.15 | 3.80 |
| ELD_R422M | 40.21 | 5.14 | 0.67 | 1.71 | 1.00 | 4.71 |
| ELD_R422N | 39.71 | 2.03 | 0.80 | 1.24 | 0.20 | 9.30 |
| ELD_R422P | 15.62 | 0.13 | 0.12 | 0.11 | 0.05 | 37.48 |
| ELD_R422Q | 56.20 | 8.88 | 0.84 | 2.12 | 0.73 | 4.47 |
| ELD_R422S | 43.70 | 2.29 | 0.87 | 1.55 | 0.30 | 8.72 |
| ELD_R422T | 50.86 | 4.10 | 0.76 | 1.53 | 0.31 | 7.59 |
| ELD_R422V | 44.61 | 4.71 | 0.43 | 1.50 | 0.55 | 6.21 |
| ELD_R422W | 31.71 | 1.43 | 1.03 | 1.61 | 0.25 | 7.34 |
| ELD_R422Y | 53.71 | 4.91 | 2.23 | 3.44 | 0.74 | 4.75 |
| ELD_S418D | 63.93 | 0.40 | 0.26 | 0.47 | 0.15 | 49.93 |
| ELD_N476D | 77.78 | 0.09 | 0.06 | 0.05 | 0.13 | 234.74 |
| ELD_I479T | 60.14 | 0.13 | 0.08 | 0.02 | 0.05 | 219.23 |
| ELD_Q481E | 74.06 | 0.15 | 0.08 | 0.22 | 0.05 | 149.62 |
| ELD_N527D | 50.14 | 1.36 | 0.12 | 0.65 | 0.11 | 22.37 |
| ELD_Q531R | 64.05 | 2.11 | 0.31 | 0.40 | 0.18 | 21.40 |
| ELD_R416D | 49.54 | 0.16 | 0.42 | 0.20 | 0.14 | 54.16 |
| ELD_R416E | 72.49 | 0.55 | 1.40 | 0.29 | 0.11 | 30.73 |
| ELD_R416N | 72.79 | 1.18 | 1.65 | 1.20 | 0.16 | 17.38 |
| ELD_R416S | 52.96 | 1.24 | 0.96 | 0.90 | 0.27 | 15.67 |
| ELD_K525A | 67.68 | 0.40 | 0.37 | 0.32 | 0.12 | 55.85 |
| ELD_K525E | 55.90 | 0.08 | 0.07 | 0.04 | 0.14 | 170.65 |
| ELD_K525G | 54.53 | 0.44 | 0.21 | 0.20 | 0.18 | 52.62 |
| ELD_K525S | 69.63 | 0.68 | 0.42 | 0.44 | 0.22 | 39.85 |
| ELD_Q481A | 71.88 | 0.19 | 0.09 | 0.13 | 0.13 | 132.21 |

TABLE 11A-continued

|  | AAVS1 | OT1 | OT2 | OT3 | OT4 | ratio |
|---|---|---|---|---|---|---|
| ELD_Q481C | 72.36 | 0.19 | 0.19 | 0.43 | 0.36 | 61.88 |
| ELD_Q481D | 89.61 | 2.43 | 0.21 | 3.17 | 0.76 | 13.64 |
| ELD_Q481S | 59.95 | 0.08 | 0.05 | 0.16 | 0.07 | 168.18 |
| gfp | 0.01 | 0.02 | 0.00 | 0.02 | 0.09 | NA |
| gfp | 0.01 | 0.01 | 0.01 | 0.00 | 0.12 | NA |
| parental | 1.05 | 1.04 | 1.21 | 1.06 | 1.11 | 0.96 |
| parental | 1.04 | 1.27 | 1.21 | 1.17 | 1.08 | 0.83 |
| parental | 0.99 | 0.76 | 0.87 | 0.94 | 1.00 | 1.18 |
| parental | 0.93 | 0.93 | 0.71 | 0.84 | 0.81 | 1.04 |
| half dose | 0.72 | 0.42 | 0.20 | 0.32 | 0.21 | 2.00 |
| half dose | 0.74 | 0.45 | 0.28 | 0.25 | 0.24 | 1.93 |
| half dose | 0.60 | 0.23 | 0.11 | 0.16 | 0.11 | 3.04 |
| half dose | 0.57 | 0.25 | 0.10 | 0.22 | 0.15 | 2.58 |
| ELD_S418A | 1.07 | 0.46 | 1.43 | 1.14 | 0.41 | 1.58 |
| ELD_S418C | 0.80 | 0.42 | 0.75 | 1.02 | 0.52 | 1.42 |
| ELD_S418D | 1.05 | 0.13 | 0.37 | 0.30 | 0.18 | 5.49 |
| ELD_S418E | 1.32 | 0.03 | 0.07 | 0.10 | 0.06 | 25.68 |
| ELD_S418F | 0.30 | 0.42 | 0.18 | 0.25 | 0.09 | 0.89 |
| ELD_S418G | 0.69 | 1.16 | 0.42 | 0.37 | 1.62 | 0.66 |
| ELD_S418H | 0.85 | 0.42 | 1.17 | 0.98 | 0.35 | 1.45 |
| ELD_S418I | 0.31 | 0.01 | 0.06 | 0.04 | 0.01 | 15.36 |
| ELD_S418K | 0.77 | 0.20 | 1.46 | 1.08 | 0.43 | 1.53 |
| ELD_S418L | 0.19 | 0.02 | 0.06 | 0.14 | 0.02 | 5.05 |
| ELD_S418M | 0.39 | 0.04 | 0.17 | 0.22 | 0.05 | 4.71 |
| ELD_S418N | 0.84 | 0.41 | 1.21 | 0.77 | 0.22 | 1.54 |
| ELD_S418P | 1.41 | 1.75 | 3.88 | 1.81 | 1.39 | 0.70 |
| ELD_S418Q | 0.81 | 0.09 | 0.67 | 0.44 | 0.07 | 3.87 |
| ELD_S418R | 0.72 | 0.25 | 2.24 | 1.00 | 0.24 | 1.19 |
| ELD_S418T | 0.69 | 0.04 | 0.20 | 0.18 | 0.03 | 8.57 |
| ELD_S418V | 0.54 | 0.01 | 0.12 | 0.09 | 0.01 | 14.65 |
| ELD_S418W | 0.32 | 0.09 | 0.35 | 0.28 | 0.05 | 2.26 |
| ELD_S418Y | 0.35 | 0.11 | 0.20 | 0.23 | 0.12 | 2.46 |
| ELD_R422A | 0.08 | 0.01 | 0.02 | 0.03 | 0.01 | 6.30 |
| ELD_R422C | 0.49 | 0.12 | 0.16 | 0.27 | 0.11 | 3.37 |
| ELD_R422D | 0.66 | 0.06 | 0.17 | 0.13 | 0.02 | 8.41 |
| ELD_R422E | 0.75 | 0.06 | 0.11 | 0.12 | 0.03 | 10.69 |
| ELD_R422F | 0.65 | 0.23 | 0.42 | 0.76 | 0.22 | 1.98 |
| ELD_R422G | 0.68 | 0.09 | 0.15 | 0.30 | 0.07 | 5.44 |
| ELD_R422H | 1.03 | 0.34 | 0.57 | 0.68 | 0.14 | 2.59 |
| ELD_R422I | 0.59 | 0.21 | 0.11 | 0.44 | 0.15 | 2.59 |
| ELD_R422K | 1.19 | 1.43 | 2.89 | 1.34 | 1.02 | 0.75 |
| ELD_R422L | 0.88 | 0.69 | 0.22 | 0.69 | 0.41 | 1.44 |
| ELD_R422M | 0.66 | 0.35 | 0.23 | 0.55 | 0.36 | 1.79 |
| ELD_R422N | 0.65 | 0.14 | 0.28 | 0.40 | 0.07 | 3.53 |
| ELD_R422P | 0.26 | 0.01 | 0.04 | 0.04 | 0.02 | 14.24 |
| ELD_R422Q | 0.92 | 0.60 | 0.29 | 0.68 | 0.26 | 1.70 |
| ELD_R422S | 0.72 | 0.16 | 0.30 | 0.50 | 0.11 | 3.31 |
| ELD_R422T | 0.84 | 0.28 | 0.26 | 0.49 | 0.11 | 2.88 |
| ELD_R422V | 0.73 | 0.32 | 0.15 | 0.48 | 0.20 | 2.36 |
| ELD_R422W | 0.52 | 0.10 | 0.36 | 0.52 | 0.09 | 2.79 |
| ELD_R422Y | 0.88 | 0.33 | 0.77 | 1.10 | 0.26 | 1.80 |
| ELD_S418D | 1.05 | 0.03 | 0.09 | 0.15 | 0.06 | 18.96 |
| ELD_N476D | 1.28 | 0.01 | 0.02 | 0.02 | 0.05 | 89.15 |
| ELD_I479T | 0.99 | 0.01 | 0.03 | 0.01 | 0.02 | 83.26 |
| ELD_Q481E | 1.22 | 0.01 | 0.03 | 0.07 | 0.02 | 56.82 |
| ELD_N527D | 0.82 | 0.09 | 0.04 | 0.21 | 0.04 | 8.50 |
| ELD_Q531R | 1.05 | 0.14 | 0.11 | 0.13 | 0.07 | 8.13 |
| ELD_R416D | 0.81 | 0.01 | 0.15 | 0.06 | 0.05 | 20.57 |
| ELD_R416E | 1.19 | 0.04 | 0.48 | 0.09 | 0.04 | 11.67 |
| ELD_R416N | 1.20 | 0.08 | 0.57 | 0.38 | 0.06 | 6.60 |
| ELD_R416S | 0.87 | 0.08 | 0.33 | 0.29 | 0.10 | 5.95 |
| ELD_K525A | 1.11 | 0.03 | 0.13 | 0.10 | 0.04 | 21.21 |
| ELD_K525E | 0.92 | 0.01 | 0.02 | 0.01 | 0.05 | 64.81 |
| ELD_K525G | 0.90 | 0.03 | 0.07 | 0.06 | 0.07 | 19.99 |
| ELD_K525S | 1.14 | 0.05 | 0.14 | 0.14 | 0.08 | 15.13 |
| ELD_Q481A | 1.18 | 0.01 | 0.03 | 0.04 | 0.05 | 50.21 |
| ELD_Q481C | 1.19 | 0.01 | 0.07 | 0.14 | 0.13 | 23.50 |
| ELD_Q481D | 1.47 | 0.16 | 0.07 | 1.02 | 0.27 | 5.18 |
| ELD_Q481S | 0.99 | 0.01 | 0.02 | 0.05 | 0.02 | 63.87 |
| gfp | 0.00 | 0.00 | 0.00 | 0.01 | 0.03 | ND |
| gfp | 0.00 | 0.00 | 0.00 | 0.00 | 0.04 | ND |

TABLE 11B

| | AAVS1 | OT1 | OT2 | OT3 | OT4 | ratio |
|---|---|---|---|---|---|---|
| parental | 63.63 | 15.40 | 3.50 | 3.29 | 3.11 | 2.52 |
| parental | 63.10 | 18.77 | 3.50 | 3.63 | 3.01 | 2.18 |
| parental | 60.00 | 11.17 | 2.50 | 2.92 | 2.79 | 3.10 |
| parental | 56.67 | 13.75 | 2.05 | 2.62 | 2.28 | 2.74 |
| half dose | 43.53 | 6.13 | 0.58 | 0.98 | 0.58 | 5.26 |
| half dose | 45.07 | 6.62 | 0.81 | 0.77 | 0.67 | 5.08 |
| half dose | 36.53 | 3.47 | 0.31 | 0.48 | 0.30 | 8.01 |
| half dose | 34.68 | 3.72 | 0.28 | 0.68 | 0.43 | 6.80 |
| KKR_S418A | 56.84 | 12.20 | 0.70 | 0.94 | 1.88 | 3.61 |
| KKR_S418C | 42.72 | 6.97 | 1.14 | 1.05 | 1.26 | 4.10 |
| KKR_S418D | 65.24 | 1.15 | 0.16 | 0.14 | 0.27 | 37.87 |
| KKR_S418E | 72.45 | 0.34 | 0.09 | 0.16 | 0.11 | 104.85 |
| KKR_S418F | 14.90 | 1.08 | 0.23 | 0.34 | 0.42 | 7.19 |
| KKR_S418G | 44.80 | 8.06 | 7.82 | 3.45 | 1.44 | 2.16 |
| KKR_S418H | 55.57 | 12.98 | 1.14 | 1.42 | 3.65 | 2.89 |
| KKR_S418I | 29.78 | 0.28 | 0.06 | 0.03 | 0.13 | 61.12 |
| KKR_S418K | 52.01 | 17.69 | 1.58 | 1.17 | 3.44 | 2.18 |
| KKR_S418L | 10.83 | 0.41 | 0.03 | 0.05 | 0.14 | 16.89 |
| KKR_S418M | 30.93 | 1.55 | 0.19 | 0.17 | 0.46 | 13.08 |
| KKR_S418N | 59.19 | 19.05 | 1.08 | 1.70 | 4.67 | 2.23 |
| KKR_S418P | 79.20 | 28.77 | 3.90 | 3.93 | 9.53 | 1.72 |
| KKR_S418Q | 55.07 | 7.54 | 0.22 | 0.56 | 1.94 | 5.37 |
| KKR_S418R | 45.79 | 19.09 | 2.31 | 1.60 | 5.19 | 1.62 |
| KKR_S418T | 57.23 | 6.33 | 0.27 | 0.54 | 1.25 | 6.83 |
| KKR_S418V | 44.43 | 0.40 | 0.04 | 0.10 | 0.23 | 57.69 |
| KKR_S418W | 18.26 | 1.60 | 0.15 | 0.37 | 0.61 | 6.71 |
| KKR_S418Y | 21.75 | 2.48 | 0.48 | 0.51 | 0.82 | 5.07 |
| KKR_R422A | 57.41 | 2.68 | 0.24 | 0.61 | 1.20 | 12.14 |
| KKR_R422C | 31.57 | 1.22 | 0.13 | 0.31 | 0.34 | 15.77 |
| KKR_R422D | 49.90 | 0.25 | 0.03 | 0.05 | 0.28 | 82.29 |
| KKR_R422E | 49.76 | 0.17 | 0.02 | 0.08 | 0.14 | 120.71 |
| KKR_R422F | 39.99 | 2.29 | 0.20 | 0.32 | 0.48 | 12.16 |
| KKR_R422G | 40.90 | 1.64 | 0.20 | 0.36 | 0.57 | 14.79 |
| KKR_R422H | 63.43 | 4.33 | 0.37 | 0.72 | 1.45 | 9.23 |
| KKR_R422I | 35.55 | 1.97 | 0.31 | 0.41 | 0.33 | 11.76 |
| KKR_R422K | 71.20 | 22.19 | 0.97 | 3.16 | 6.13 | 2.19 |
| KKR_R422L | 52.15 | 3.79 | 0.94 | 1.36 | 0.91 | 7.44 |
| KKR_R422M | 39.52 | 2.40 | 0.56 | 0.65 | 0.46 | 9.75 |
| KKR_R422N | 46.21 | 1.84 | 0.15 | 0.44 | 0.81 | 14.23 |
| KKR_R422P | 28.51 | 0.20 | 0.02 | 0.03 | 0.06 | 92.81 |
| KKR_R422Q | 60.24 | 4.53 | 0.56 | 1.63 | 1.31 | 7.50 |
| KKR_R422S | 52.09 | 1.55 | 0.17 | 0.63 | 0.90 | 16.02 |
| KKR_R422T | 54.57 | 2.99 | 0.24 | 0.81 | 0.91 | 11.03 |
| KKR_R422V | 41.66 | 1.61 | 0.24 | 0.52 | 0.30 | 15.58 |
| KKR_R422W | 33.25 | 3.71 | 0.14 | 0.47 | 0.67 | 6.66 |
| KKR_R422Y | 52.98 | 4.80 | 0.37 | 0.74 | 1.26 | 7.39 |
| KKR_S418D | 70.21 | 1.58 | 0.12 | 0.12 | 0.20 | 34.83 |
| KKR_N476D | 36.24 | 0.11 | 0.04 | 0.12 | 0.02 | 119.52 |
| KKR_I479T | 70.33 | 1.26 | 0.21 | 1.21 | 0.09 | 25.35 |
| KKR_Q481E | 70.45 | 0.55 | 0.13 | 0.05 | 0.17 | 78.95 |
| KKR_N527D | 57.06 | 3.84 | 0.54 | 1.35 | 0.71 | 8.86 |
| KKR_Q531R | 58.48 | 3.90 | 1.42 | 1.97 | 0.82 | 7.22 |
| KKR_R416D | 57.64 | 0.37 | 0.04 | 0.01 | 0.28 | 82.22 |
| KKR_R416E | 69.37 | 1.55 | 0.04 | 0.14 | 1.50 | 21.50 |
| KKR_R416N | 70.11 | 7.61 | 0.17 | 0.53 | 3.59 | 5.89 |
| KKR_R416S | 58.34 | 5.62 | 0.24 | 0.49 | 1.25 | 7.68 |
| KKR_K525A | 55.21 | 0.79 | 0.03 | 0.14 | 0.20 | 47.44 |
| KKR_K525E | 49.76 | 0.25 | 0.01 | 0.02 | 0.11 | 126.10 |
| KKR_K525G | 54.38 | 1.97 | 0.08 | 0.17 | 0.45 | 20.33 |
| KKR_K525S | 64.03 | 2.23 | 0.11 | 0.12 | 0.54 | 21.34 |
| KKR_Q481A | 61.41 | 0.31 | 0.02 | 0.03 | 0.13 | 123.36 |
| KKR_Q481C | 64.51 | 4.04 | 0.09 | 0.02 | 0.42 | 14.11 |
| KKR_Q481D | 75.10 | 6.05 | 0.09 | 0.13 | 0.80 | 10.64 |
| KKR_Q481S | 56.88 | 0.45 | 0.00 | 0.00 | 0.12 | 98.94 |
| gfp | 0.01 | 0.02 | 0.00 | 0.02 | 0.09 | NA |
| gfp | 0.01 | 0.01 | 0.01 | 0.00 | 0.12 | NA |
| parental | 1.05 | 1.04 | 1.21 | 1.06 | 1.11 | 0.96 |
| parental | 1.04 | 1.27 | 1.21 | 1.17 | 1.08 | 0.83 |
| parental | 0.99 | 0.76 | 0.87 | 0.94 | 1.00 | 1.18 |
| parental | 0.93 | 0.93 | 0.71 | 0.84 | 0.81 | 1.04 |
| half dose | 0.72 | 0.42 | 0.20 | 0.32 | 0.21 | 2.00 |
| half dose | 0.74 | 0.45 | 0.28 | 0.25 | 0.24 | 1.93 |
| half dose | 0.60 | 0.23 | 0.14 | 0.16 | 0.11 | 3.04 |
| half dose | 0.57 | 0.25 | 0.10 | 0.22 | 0.15 | 2.58 |
| KKR_S418A | 0.93 | 0.83 | 0.24 | 0.30 | 0.67 | 1.37 |
| KKR_S418C | 0.70 | 0.47 | 0.39 | 0.34 | 0.45 | 1.56 |
| KKR_S418D | 1.07 | 0.08 | 0.06 | 0.05 | 0.10 | 14.38 |
| KKR_S418E | 1.19 | 0.02 | 0.03 | 0.05 | 0.04 | 39.82 |
| KKR_S418F | 0.24 | 0.07 | 0.08 | 0.11 | 0.15 | 2.73 |
| KKR_S418G | 0.74 | 0.55 | 2.71 | 1.11 | 0.52 | 0.82 |
| KKR_S418H | 0.91 | 0.88 | 0.40 | 0.46 | 1.31 | 1.10 |
| KKR_S418I | 0.49 | 0.02 | 0.02 | 0.01 | 0.04 | 23.21 |
| KKR_S418K | 0.85 | 1.20 | 0.55 | 0.38 | 1.23 | 0.83 |
| KKR_S418L | 0.18 | 0.03 | 0.01 | 0.02 | 0.05 | 6.41 |
| KKR_S418M | 0.51 | 0.10 | 0.07 | 0.05 | 0.16 | 4.97 |
| KKR_S418N | 0.97 | 1.29 | 0.37 | 0.55 | 1.67 | 0.85 |
| KKR_S418P | 1.30 | 1.95 | 1.35 | 1.26 | 3.41 | 0.65 |
| KKR_S418Q | 0.90 | 0.51 | 0.08 | 0.18 | 0.69 | 2.04 |
| KKR_S418R | 0.75 | 1.29 | 0.80 | 0.51 | 1.86 | 0.62 |
| KKR_S418T | 0.94 | 0.43 | 0.09 | 0.17 | 0.45 | 2.60 |
| KKR_S418V | 0.73 | 0.03 | 0.01 | 0.03 | 0.08 | 21.91 |
| KKR_S418W | 0.30 | 0.11 | 0.05 | 0.12 | 0.22 | 2.55 |
| KKR_S418Y | 0.36 | 0.17 | 0.17 | 0.16 | 0.29 | 1.92 |
| KKR_R422A | 0.94 | 0.18 | 0.08 | 0.20 | 0.43 | 4.61 |
| KKR_R422C | 0.52 | 0.08 | 0.05 | 0.10 | 0.12 | 5.99 |
| KKR_R422D | 0.82 | 0.02 | 0.01 | 0.02 | 0.10 | 31.25 |
| KKR_R422E | 0.82 | 0.01 | 0.01 | 0.02 | 0.05 | 45.84 |
| KKR_R422F | 0.66 | 0.15 | 0.07 | 0.10 | 0.17 | 4.62 |
| KKR_R422G | 0.67 | 0.11 | 0.07 | 0.12 | 0.20 | 5.62 |
| KKR_R422H | 1.04 | 0.29 | 0.13 | 0.23 | 0.52 | 3.51 |
| KKR_R422I | 0.58 | 0.13 | 0.11 | 0.13 | 0.12 | 4.47 |
| KKR_R422K | 1.17 | 1.50 | 0.33 | 1.01 | 2.19 | 0.83 |
| KKR_R422L | 0.86 | 0.26 | 0.33 | 0.44 | 0.33 | 2.83 |
| KKR_R422M | 0.65 | 0.16 | 0.19 | 0.21 | 0.16 | 3.70 |
| KKR_R422N | 0.76 | 0.12 | 0.05 | 0.14 | 0.29 | 5.40 |
| KKR_R422P | 0.47 | 0.01 | 0.01 | 0.01 | 0.02 | 35.25 |
| KKR_R422Q | 0.99 | 0.31 | 0.19 | 0.52 | 0.47 | 2.85 |
| KKR_R422S | 0.86 | 0.10 | 0.06 | 0.20 | 0.32 | 6.09 |
| KKR_R422T | 0.90 | 0.20 | 0.08 | 0.26 | 0.32 | 4.19 |
| KKR_R422V | 0.68 | 0.11 | 0.08 | 0.17 | 0.11 | 5.92 |
| KKR_R422W | 0.55 | 0.25 | 0.05 | 0.15 | 0.24 | 2.53 |
| KKR_R422Y | 0.87 | 0.33 | 0.13 | 0.24 | 0.45 | 2.81 |
| KKR_S418D | 1.15 | 0.11 | 0.04 | 0.04 | 0.07 | 13.23 |
| KKR_N476D | 0.60 | 0.01 | 0.01 | 0.04 | 0.01 | 45.39 |
| KKR_I479T | 1.16 | 0.09 | 0.07 | 0.39 | 0.03 | 9.63 |
| KKR_Q481E | 1.16 | 0.04 | 0.04 | 0.02 | 0.06 | 29.98 |
| KKR_N527D | 0.94 | 0.26 | 0.19 | 0.43 | 0.26 | 3.36 |
| KKR_Q531R | 0.96 | 0.26 | 0.49 | 0.63 | 0.29 | 2.74 |
| KKR_R416D | 0.95 | 0.03 | 0.01 | 0.00 | 0.10 | 31.22 |
| KKR_R416E | 1.14 | 0.11 | 0.01 | 0.04 | 0.54 | 8.17 |
| KKR_R416N | 1.15 | 0.52 | 0.06 | 0.17 | 1.28 | 2.24 |
| KKR_R416S | 0.96 | 0.38 | 0.08 | 0.16 | 0.45 | 2.92 |
| KKR_K525A | 0.91 | 0.05 | 0.01 | 0.04 | 0.07 | 18.02 |
| KKR_K525E | 0.82 | 0.02 | 0.00 | 0.01 | 0.04 | 47.89 |
| KKR_K525G | 0.89 | 0.13 | 0.03 | 0.06 | 0.16 | 7.72 |
| KKR_K525S | 1.05 | 0.15 | 0.04 | 0.04 | 0.19 | 8.11 |
| KKR_Q481A | 1.01 | 0.02 | 0.01 | 0.01 | 0.05 | 46.85 |
| KKR_Q481C | 1.06 | 0.27 | 0.03 | 0.01 | 0.15 | 5.36 |
| KKR_Q481D | 1.23 | 0.41 | 0.03 | 0.04 | 0.28 | 4.04 |
| KKR_Q481S | 0.93 | 0.03 | 0.00 | 0.00 | 0.04 | 37.57 |
| gfp | 0.00 | 0.00 | 0.00 | 0.01 | 0.03 | ND |
| gfp | 0.00 | 0.00 | 0.00 | 0.00 | 0.04 | ND |

TABLE 11C

| | AAVS1 | OT1 | OT2 | OT3 | OT4 | ratio |
|---|---|---|---|---|---|---|
| Parental | 63.63 | 15.40 | 3.50 | 3.29 | 3.11 | 2.52 |
| Parental | 63.10 | 18.77 | 3.50 | 3.63 | 3.01 | 2.18 |
| Parental | 60.00 | 11.17 | 2.50 | 2.92 | 2.79 | 3.10 |
| Parental | 56.67 | 13.75 | 2.05 | 2.62 | 2.28 | 2.74 |
| half dose | 43.53 | 6.13 | 0.58 | 0.98 | 0.58 | 5.26 |
| half dose | 45.07 | 6.62 | 0.81 | 0.77 | 0.67 | 5.08 |
| half dose | 36.53 | 3.47 | 0.31 | 0.48 | 0.30 | 8.01 |
| half dose | 34.68 | 3.72 | 0.28 | 0.68 | 0.43 | 6.80 |
| ELD_KKR_S418A | 56.41 | 3.20 | 0.67 | 0.90 | 0.57 | 10.56 |
| ELD_KKR_S418C | 24.43 | 0.74 | 0.21 | 0.35 | 0.28 | 15.51 |
| ELD_KKR_S418D | 48.70 | 0.08 | 0.03 | 0.05 | 0.12 | 172.57 |
| ELD_KKR_S418E | 58.18 | 0.04 | 0.01 | 0.02 | 0.05 | 470.11 |
| ELD_KKR_S418F | 5.17 | 0.18 | 0.06 | 0.09 | 0.13 | 11.37 |
| ELD_KKR_S418G | 26.97 | 9.45 | 2.45 | 1.64 | 1.93 | 1.74 |
| ELD_KKR_S418H | 40.18 | 3.40 | 0.55 | 0.75 | 0.76 | 7.36 |
| ELD_KKR_S418I | 5.96 | 0.02 | 0.02 | 0.02 | 0.10 | 37.01 |

TABLE 11C-continued

|  | AAVS1 | OT1 | OT2 | OT3 | OT4 | ratio |
|---|---|---|---|---|---|---|
| ELD_KKR_S418K | 34.84 | 3.16 | 1.33 | 1.29 | 0.92 | 5.20 |
| ELD_KKR_S418L | 1.79 | 0.03 | 0.01 | 0.01 | 0.14 | 9.91 |
| ELD_KKR_S418M | 8.86 | 0.09 | 0.05 | 0.06 | 0.10 | 30.11 |
| ELD_KKR_S418N | 44.66 | 8.43 | 0.90 | 1.34 | 0.95 | 3.84 |
| ELD_KKR_S418P | 91.49 | 35.58 | 9.89 | 6.21 | 8.86 | 1.51 |
| ELD_KKR_S418Q | 39.47 | 0.85 | 0.10 | 0.31 | 0.25 | 26.33 |
| ELD_KKR_S418R | 29.54 | 5.45 | 3.22 | 1.52 | 2.05 | 2.41 |
| ELD_KKR_S418T | 34.61 | 0.24 | 0.07 | 0.14 | 0.09 | 64.01 |
| ELD_KKR_S418V | 18.75 | 0.03 | 0.03 | 0.05 | 0.11 | 87.69 |
| ELD_KKR_S418W | 6.01 | 0.12 | 0.10 | 0.08 | 0.13 | 13.82 |
| ELD_KKR_S418Y | 7.26 | 0.33 | 0.09 | 0.06 | 0.12 | 12.07 |
| ELD_KKR_R422A | 3.43 | 0.03 | 0.01 | 0.05 | 0.15 | 14.34 |
| ELD_KKR_R422C | 13.04 | 0.09 | 0.07 | 0.03 | 0.11 | 43.05 |
| ELD_KKR_R422D | 21.98 | 0.02 | 0.02 | 0.01 | 0.08 | 166.09 |
| ELD_KKR_R422E | 25.12 | 0.03 | 0.00 | 0.03 | 0.14 | 124.28 |
| ELD_KKR_R422F | 20.43 | 0.69 | 0.03 | 0.30 | 0.16 | 17.27 |
| ELD_KKR_R422G | 19.82 | 0.05 | 0.02 | 0.03 | 0.12 | 89.17 |
| ELD_KKR_R422H | 58.50 | 0.65 | 0.08 | 0.39 | 0.23 | 43.21 |
| ELD_KKR_R422I | 16.94 | 0.22 | 0.05 | 0.14 | 0.15 | 30.61 |
| ELD_KKR_R422K | 78.47 | 23.05 | 2.17 | 3.34 | 3.98 | 2.41 |
| ELD_KKR_R422L | 37.68 | 0.71 | 0.17 | 0.28 | 0.23 | 27.22 |
| ELD_KKR_R422M | 20.81 | 0.21 | 0.05 | 0.20 | 0.18 | 32.91 |
| ELD_KKR_R422N | 23.17 | 0.04 | 0.03 | 0.06 | 0.11 | 93.57 |
| ELD_KKR_R422P | 3.63 | 0.03 | 0.02 | 0.01 | 0.09 | 23.37 |
| ELD_KKR_R422Q | 43.13 | 0.53 | 0.10 | 0.23 | 0.14 | 43.28 |
| ELD_KKR_R422S | 32.72 | 0.15 | 0.04 | 0.20 | 0.20 | 54.65 |
| ELD_KKR_R422T | 37.16 | 0.29 | 0.04 | 0.09 | 0.17 | 62.72 |
| ELD_KKR_R422V | 23.36 | 0.18 | 0.02 | 0.06 | 0.14 | 57.49 |
| ELD_KKR_R422W | 13.07 | 0.32 | 0.03 | 0.10 | 0.10 | 23.58 |
| ELD_KKR_R422Y | 37.28 | 1.31 | 0.08 | 0.46 | 0.31 | 17.28 |
| ELD_KKR_S418D | 44.22 | 0.09 | 0.03 | 0.01 | 0.07 | 219.68 |
| ELD_KKR_N476D | 4.51 | 0.03 | 0.01 | 0.02 | 0.07 | 36.91 |
| ELD_KKR_I479T | 41.46 | 0.03 | 0.02 | 0.01 | 0.09 | 278.85 |
| ELD_KKR_Q481E | 66.40 | 0.03 | 0.04 | 0.01 | 0.08 | 413.30 |
| ELD_KKR_N527D | 32.76 | 0.15 | 0.05 | 0.11 | 0.11 | 78.86 |
| ELD_KKR_Q531R | 56.63 | 0.60 | 0.02 | 0.24 | 0.12 | 57.58 |
| ELD_KKR_R416D | 67.30 | 0.06 | 0.03 | 0.06 | 0.09 | 283.84 |
| ELD_KKR_R416E | 90.77 | 0.45 | 0.06 | 0.13 | 0.14 | 116.83 |
| ELD_KKR_R416N | 88.98 | 0.73 | 0.14 | 0.31 | 0.19 | 65.36 |
| ELD_KKR_R416S | 62.78 | 1.06 | 0.11 | 0.45 | 0.17 | 35.01 |
| ELD_KKR_K525A | 66.59 | 0.04 | 0.02 | 0.03 | 0.13 | 296.70 |
| ELD_KKR_K525E | 18.58 | 0.04 | 0.02 | 0.01 | 0.09 | 122.53 |
| ELD_KKR_K525G | 49.73 | 0.12 | 0.01 | 0.07 | 0.08 | 178.32 |
| ELD_KKR_K525S | 74.03 | 0.09 | 0.03 | 0.05 | 0.11 | 258.39 |
| ELD_KKR_Q481A | 92.58 | 0.03 | 0.04 | 0.00 | 0.09 | 570.76 |
| ELD_KKR_Q481C | 72.98 | 0.06 | 0.04 | 0.03 | 0.12 | 298.84 |
| ELD_KKR_Q481D | 91.87 | 0.43 | 0.02 | 0.04 | 0.22 | 128.41 |
| ELD_KKR_Q481S | 58.67 | 0.03 | 0.02 | 0.01 | 0.08 | 422.94 |
| gfp | 0.01 | 0.02 | 0.00 | 0.02 | 0.09 | NA |
| gfp | 0.01 | 0.01 | 0.01 | 0.00 | 0.12 | NA |
| parental | 1.05 | 1.04 | 1.21 | 1.06 | 1.11 | 0.96 |
| parental | 1.04 | 1.27 | 1.21 | 1.17 | 1.08 | 0.83 |
| parental | 0.99 | 0.76 | 0.87 | 0.94 | 1.00 | 1.18 |
| parental | 0.93 | 0.93 | 0.71 | 0.84 | 0.81 | 1.04 |
| half dose | 0.72 | 0.42 | 0.20 | 0.32 | 0.21 | 2.00 |
| half dose | 0.74 | 0.45 | 0.28 | 0.25 | 0.24 | 1.93 |
| half dose | 0.60 | 0.23 | 0.11 | 0.16 | 0.11 | 3.04 |
| half dose | 0.57 | 0.25 | 0.10 | 0.22 | 0.15 | 2.58 |
| ELD_KKR_S418A | 0.93 | 0.22 | 0.23 | 0.29 | 0.21 | 4.01 |
| ELD_KKR_S418C | 0.40 | 0.05 | 0.07 | 0.11 | 0.10 | 5.89 |
| ELD_KKR_S418D | 0.80 | 0.01 | 0.01 | 0.01 | 0.04 | 65.54 |
| ELD_KKR_S418E | 0.96 | 0.00 | 0.00 | 0.01 | 0.02 | 178.54 |
| ELD_KKR_S418F | 0.08 | 0.01 | 0.02 | 0.03 | 0.05 | 4.32 |
| ELD_KKR_S418G | 0.44 | 0.64 | 0.85 | 0.53 | 0.69 | 0.66 |
| ELD_KKR_S418H | 0.66 | 0.23 | 0.19 | 0.24 | 0.27 | 2.79 |
| ELD_KKR_S418I | 0.10 | 0.00 | 0.01 | 0.01 | 0.04 | 14.06 |
| ELD_KKR_S418K | 0.57 | 0.21 | 0.46 | 0.41 | 0.33 | 1.97 |
| ELD_KKR_S418L | 0.03 | 0.00 | 0.00 | 0.00 | 0.05 | 3.77 |
| ELD_KKR_S418M | 0.15 | 0.01 | 0.02 | 0.02 | 0.03 | 11.43 |
| ELD_KKR_S418N | 0.73 | 0.57 | 0.31 | 0.43 | 0.34 | 1.46 |
| ELD_KKR_S418P | 1.50 | 2.41 | 3.42 | 1.99 | 3.17 | 0.57 |
| ELD_KKR_S418Q | 0.65 | 0.06 | 0.03 | 0.10 | 0.09 | 10.00 |
| ELD_KKR_S418R | 0.49 | 0.37 | 1.12 | 0.49 | 0.73 | 0.92 |
| ELD_KKR_S418T | 0.57 | 0.02 | 0.02 | 0.05 | 0.03 | 24.31 |
| ELD_KKR_S418V | 0.31 | 0.00 | 0.01 | 0.02 | 0.04 | 33.30 |
| ELD_KKR_S418W | 0.10 | 0.01 | 0.03 | 0.03 | 0.05 | 5.25 |
| ELD_KKR_S418Y | 0.12 | 0.02 | 0.03 | 0.02 | 0.04 | 4.58 |
| ELD_KKR_R422A | 0.06 | 0.00 | 0.00 | 0.02 | 0.05 | 5.45 |
| ELD_KKR_R422C | 0.21 | 0.01 | 0.03 | 0.01 | 0.04 | 16.35 |
| ELD_KKR_R422D | 0.36 | 0.00 | 0.01 | 0.00 | 0.03 | 63.08 |
| ELD_KKR_R422E | 0.41 | 0.00 | 0.00 | 0.01 | 0.05 | 47.20 |
| ELD_KKR_R422F | 0.34 | 0.05 | 0.01 | 0.10 | 0.06 | 6.56 |
| ELD_KKR_R422G | 0.33 | 0.00 | 0.01 | 0.01 | 0.04 | 33.87 |
| ELD_KKR_R422H | 0.96 | 0.04 | 0.03 | 0.13 | 0.08 | 16.41 |
| ELD_KKR_R422I | 0.28 | 0.02 | 0.02 | 0.04 | 0.05 | 11.63 |
| ELD_KKR_R422K | 1.29 | 1.56 | 0.75 | 1.07 | 1.42 | 0.92 |
| ELD_KKR_R422L | 0.62 | 0.05 | 0.06 | 0.09 | 0.08 | 10.34 |
| ELD_KKR_R422M | 0.34 | 0.01 | 0.02 | 0.06 | 0.06 | 12.50 |
| ELD_KKR_R422N | 0.38 | 0.00 | 0.01 | 0.02 | 0.04 | 35.54 |
| ELD_KKR_R422P | 0.06 | 0.00 | 0.01 | 0.00 | 0.03 | 8.87 |
| ELD_KKR_R422Q | 0.71 | 0.04 | 0.03 | 0.07 | 0.05 | 16.44 |
| ELD_KKR_R422S | 0.54 | 0.01 | 0.02 | 0.06 | 0.07 | 20.75 |
| ELD_KKR_R422T | 0.61 | 0.02 | 0.01 | 0.03 | 0.06 | 23.82 |
| ELD_KKR_R422V | 0.38 | 0.01 | 0.01 | 0.02 | 0.05 | 21.83 |
| ELD_KKR_R422W | 0.21 | 0.02 | 0.01 | 0.03 | 0.04 | 8.95 |
| ELD_KKR_R422Y | 0.61 | 0.09 | 0.03 | 0.15 | 0.11 | 6.56 |
| ELD_KKR_S418D | 0.73 | 0.01 | 0.01 | 0.00 | 0.03 | 83.43 |
| ELD_KKR_N476D | 0.07 | 0.00 | 0.00 | 0.01 | 0.02 | 14.02 |
| ELD_KKR_I479T | 0.68 | 0.00 | 0.01 | 0.00 | 0.03 | 105.90 |
| ELD_KKR_Q481E | 1.09 | 0.00 | 0.01 | 0.00 | 0.03 | 156.97 |
| ELD_KKR_N527D | 0.54 | 0.01 | 0.02 | 0.04 | 0.04 | 29.95 |
| ELD_KKR_Q531R | 0.93 | 0.04 | 0.01 | 0.08 | 0.04 | 21.87 |
| ELD_KKR_R416D | 1.11 | 0.00 | 0.01 | 0.02 | 0.03 | 107.80 |
| ELD_KKR_R416E | 1.49 | 0.03 | 0.02 | 0.04 | 0.05 | 44.37 |
| ELD_KKR_R416N | 1.46 | 0.05 | 0.05 | 0.10 | 0.07 | 24.82 |
| ELD_KKR_R416S | 1.03 | 0.07 | 0.04 | 0.14 | 0.05 | 13.30 |
| ELD_KKR_K525A | 1.09 | 0.00 | 0.01 | 0.01 | 0.05 | 112.68 |
| ELD_KKR_K525E | 0.31 | 0.00 | 0.01 | 0.00 | 0.03 | 46.53 |
| ELD_KKR_K525G | 0.82 | 0.01 | 0.00 | 0.02 | 0.03 | 67.72 |
| ELD_KKR_K525S | 1.22 | 0.01 | 0.01 | 0.02 | 0.04 | 98.13 |
| ELD_KKR_Q481A | 1.52 | 0.00 | 0.02 | 0.00 | 0.03 | 216.77 |
| ELD_KKR_Q481C | 1.20 | 0.00 | 0.01 | 0.01 | 0.04 | 113.49 |
| ELD_KKR_Q481D | 1.51 | 0.03 | 0.01 | 0.01 | 0.08 | 48.77 |
| ELD_KKR_Q481S | 0.96 | 0.00 | 0.01 | 0.00 | 0.03 | 160.62 |
| gfp | 0.00 | 0.00 | 0.00 | 0.01 | 0.03 | ND |
| gfp | 0.00 | 0.00 | 0.00 | 0.00 | 0.04 | ND |

Tables 12A-12C shows cleavage results from 2 different experiments on-target (AAVS1) and three off-target (OT1, OT2, OT3) as well as the ratio of on- to off-target of the indicated mutants.

TABLE 12A

|  | AAVS1 | OT1 | OT2 | OT3 | OT4 | ratio |
|---|---|---|---|---|---|---|
| parental pair | 46.50 | 6.60 | 1.46 | 1.41 | 1.26 | 4.33 |
| parental pair | 40.06 | 3.57 | 0.90 | 1.05 | 0.70 | 6.44 |
| parental pair | 45.74 | 5.54 | 1.36 | 1.37 | 1.24 | 4.81 |
| parental pair | 41.20 | 3.92 | 1.04 | 0.94 | 0.86 | 6.09 |
| half dose | 29.20 | 1.82 | 0.31 | 0.26 | 0.31 | 10.78 |
| half dose | 29.32 | ND | 0.27 | 0.36 | 0.31 | ND |
| half dose | 24.58 | 1.06 | 0.20 | 0.19 | 0.17 | 15.16 |
| half dose | 24.63 | 1.16 | 0.34 | 0.30 | 0.17 | 12.53 |
| ELD_K448A | 59.76 | 7.05 | 0.93 | 2.04 | 1.40 | 5.23 |
| ELD_K448C | 63.80 | 9.43 | 3.22 | 2.51 | 2.11 | 3.69 |
| ELD_K448D | 3.14 | 0.04 | 0.05 | 0.05 | 0.07 | 15.10 |
| ELD_K448E | 75.48 | 19.58 | 6.59 | 3.86 | 2.19 | 2.34 |
| ELD_K448F | 5.08 | 0.06 | 0.20 | 0.09 | 0.05 | 12.65 |
| ELD_K448G | 42.70 | 2.67 | 0.33 | 1.26 | 0.68 | 8.65 |
| ELD_K448H | 6.19 | 0.19 | 0.27 | 0.15 | 0.09 | 8.89 |
| ELD_K448I | 3.65 | 0.07 | 0.10 | 0.13 | 0.08 | 9.54 |
| ELD_K448L | 5.82 | 0.13 | 0.15 | 0.24 | 0.11 | 9.22 |
| ELD_K448M | 69.53 | 9.69 | 5.97 | 3.41 | 1.87 | 3.32 |
| ELD_K448N | 14.00 | 0.77 | 0.44 | 0.78 | 0.43 | 5.79 |
| ELD_K448P | 0.10 | 0.02 | 0.03 | 0.03 | 0.03 | 0.95 |
| ELD_K448Q | 76.82 | 16.60 | 4.64 | 3.11 | 3.12 | 2.80 |
| ELD_K448R | 73.43 | 9.83 | 2.60 | 3.52 | 1.87 | 4.12 |
| ELD_K448S | 45.95 | 6.15 | 1.53 | 1.88 | 1.16 | 4.29 |
| ELD_K448T | 34.16 | 3.41 | 2.85 | 1.96 | 0.82 | 3.78 |
| ELD_K448V | 13.46 | 1.47 | 0.58 | 0.70 | 0.53 | 4.09 |
| ELD_K448W | 0.93 | 0.02 | 0.04 | 0.05 | 0.05 | 5.74 |
| ELD_K448Y | 7.36 | 0.21 | 0.52 | 0.28 | 0.15 | 6.37 |
| ELD_I479A | 41.45 | 0.03 | 0.04 | 0.04 | 0.06 | 248.65 |

TABLE 12A-continued

| | AAVS1 | OT1 | OT2 | OT3 | OT4 | ratio |
|---|---|---|---|---|---|---|
| ELD_I479C | 32.55 | 0.02 | 0.09 | 0.05 | 0.10 | 124.76 |
| ELD_I479D | 0.98 | 0.03 | 0.01 | 0.02 | 0.06 | 7.69 |
| ELD_I479E | 1.46 | 0.02 | 0.03 | 0.05 | 0.03 | 11.56 |
| ELD_I479F | 22.48 | 0.02 | 0.04 | 0.03 | 0.11 | 112.11 |
| ELD_I479G | 11.09 | 0.02 | 0.04 | 0.01 | 0.04 | 88.84 |
| ELD_I479H | 18.97 | 0.04 | 0.03 | 0.02 | 0.05 | 142.61 |
| ELD_I479K | 0.44 | 0.02 | 0.01 | 0.04 | 0.07 | 3.22 |
| ELD_I479L | 39.31 | 0.29 | 0.13 | 0.22 | 0.96 | 24.66 |
| ELD_I479M | 41.44 | 1.30 | 0.41 | 0.41 | 0.61 | 15.17 |
| ELD_I479N | 20.15 | 0.03 | 0.01 | 0.03 | 0.06 | 168.10 |
| ELD_I479P | 3.79 | 0.03 | 0.01 | 0.04 | 0.04 | 32.04 |
| ELD_I479Q | 64.22 | 0.03 | 0.05 | 0.03 | 0.10 | 294.99 |
| ELD_I479R | 3.21 | 0.03 | 0.01 | 0.03 | 0.10 | 18.05 |
| ELD_I479S | 36.20 | 0.02 | 0.03 | 0.06 | 0.09 | 184.80 |
| ELD_I479T | 45.91 | 0.05 | 0.07 | 0.04 | 0.09 | 185.53 |
| ELD_I479V | 49.92 | 0.20 | 0.24 | 0.11 | 0.11 | 75.50 |
| ELD_I479W | 3.90 | 0.00 | 0.04 | 0.04 | 0.04 | 31.51 |
| ELD_I479Y | 23.34 | 0.02 | 0.04 | 0.04 | 0.03 | 178.07 |
| ELD_S418D | 43.61 | 0.12 | 0.14 | 0.17 | 0.10 | 82.58 |
| ELD_N476D | 60.68 | 0.03 | 0.05 | 0.05 | 0.04 | 342.95 |
| ELD_I479T | 41.58 | 0.05 | 0.08 | 0.04 | 0.07 | 175.66 |
| ELD_Q481E | 54.21 | 0.05 | 0.08 | 0.15 | 0.07 | 159.57 |
| ELD_N527D | 35.49 | 0.36 | 0.11 | 0.32 | 0.07 | 41.19 |
| ELD_Q531R | 45.27 | 0.51 | 0.11 | 0.23 | 0.17 | 44.55 |
| ELD_R416N | 59.39 | 0.33 | 0.56 | 0.42 | 0.11 | 41.97 |
| ELD_R416D | 30.56 | 0.12 | 0.21 | 0.04 | 0.03 | 76.33 |
| ELD_R416E | 51.84 | 0.18 | 0.74 | 0.30 | 0.12 | 38.76 |
| ELD_R416S | 38.94 | 0.40 | 0.39 | 0.46 | 0.13 | 28.23 |
| ELD_K525A | 45.40 | 0.11 | 0.21 | 0.12 | 0.11 | 81.02 |
| ELD_K525E | 33.51 | 0.02 | 0.01 | 0.09 | 0.06 | 196.02 |
| ELD_K525G | 33.61 | 0.07 | 0.09 | 0.09 | 0.10 | 95.62 |
| ELD_K525S | 50.08 | 0.23 | 0.18 | 0.11 | 0.11 | 80.29 |
| ELD_Q481A | 46.06 | 0.02 | 0.06 | 0.09 | 0.04 | 227.61 |
| ELD_Q481D | 73.79 | 0.48 | 0.11 | 0.53 | 0.20 | 56.16 |
| ELD_Q481C | 47.38 | 0.06 | 0.10 | 0.23 | 0.17 | 86.03 |
| ELD_Q481S | 36.39 | 0.01 | 0.03 | 0.06 | 0.02 | 304.40 |
| ELD_S418E | 50.36 | 0.07 | 0.09 | 0.07 | 0.08 | 162.21 |
| ELD_R422H | 38.80 | 0.66 | 0.38 | 0.58 | 0.12 | 22.30 |
| GFP | 0.03 | 0.02 | 0.06 | 0.02 | 0.05 | NA |
| GFP | 0.04 | 0.01 | 0.04 | 0.06 | 0.03 | NA |
| parental pair | 1.07 | 1.35 | 1.23 | 1.18 | 1.25 | 0.80 |
| parental pair | 0.92 | 0.73 | 0.75 | 0.88 | 0.69 | 1.19 |
| parental pair | 1.05 | 1.13 | 1.14 | 1.15 | 1.22 | 0.89 |
| parental pair | 0.95 | 0.80 | 0.88 | 0.79 | 0.85 | 1.12 |
| half dose | 0.67 | 0.37 | 0.26 | 0.22 | 0.31 | 1.99 |
| half dose | 0.68 | ND | 0.23 | 0.30 | 0.30 | ND |
| half dose | 0.57 | 0.22 | 0.17 | 0.16 | 0.17 | 2.80 |
| half dose | 0.57 | 0.24 | 0.28 | 0.25 | 0.17 | 2.31 |
| ELD_K448A | 1.38 | 1.44 | 0.78 | 1.71 | 1.38 | 0.97 |
| ELD_K448C | 1.47 | 1.92 | 2.71 | 2.11 | 2.08 | 0.68 |
| ELD_K448D | 0.07 | 0.01 | 0.04 | 0.04 | 0.07 | 2.79 |
| ELD_K448E | 1.74 | 3.99 | 5.54 | 3.24 | 2.16 | 0.43 |
| ELD_K448F | 0.12 | 0.01 | 0.17 | 0.07 | 0.05 | 2.33 |
| ELD_K448G | 0.98 | 0.54 | 0.28 | 1.06 | 0.67 | 1.60 |
| ELD_K448H | 0.14 | 0.04 | 0.22 | 0.13 | 0.09 | 1.64 |
| ELD_K448I | 0.08 | 0.01 | 0.08 | 0.11 | 0.08 | 1.76 |
| ELD_K448L | 0.13 | 0.03 | 0.13 | 0.20 | 0.10 | 1.70 |
| ELD_K448M | 1.60 | 1.97 | 5.02 | 2.86 | 1.84 | 0.61 |
| ELD_K448N | 0.32 | 0.16 | 0.37 | 0.65 | 0.42 | 1.07 |
| ELD_K448P | 0.00 | 0.00 | 0.02 | 0.03 | 0.03 | 0.17 |
| ELD_K448Q | 1.77 | 3.38 | 3.90 | 2.61 | 3.07 | 0.52 |
| ELD_K448R | 1.69 | 2.00 | 2.19 | 2.96 | 1.84 | 0.76 |
| ELD_K448S | 1.06 | 1.25 | 1.29 | 1.58 | 1.14 | 0.79 |
| ELD_K448T | 0.79 | 0.69 | 2.40 | 1.64 | 0.80 | 0.70 |
| ELD_K448V | 0.31 | 0.30 | 0.49 | 0.59 | 0.53 | 0.76 |
| ELD_K448W | 0.02 | 0.01 | 0.04 | 0.04 | 0.05 | 1.06 |
| ELD_K448Y | 0.17 | 0.04 | 0.44 | 0.24 | 0.14 | 1.18 |
| ELD_I479A | 0.96 | 0.01 | 0.03 | 0.03 | 0.06 | 45.88 |
| ELD_I479C | 0.75 | 0.00 | 0.07 | 0.04 | 0.10 | 23.02 |
| ELD_I479D | 0.02 | 0.01 | 0.01 | 0.02 | 0.06 | 1.42 |
| ELD_I479E | 0.03 | 0.00 | 0.02 | 0.04 | 0.03 | 2.13 |
| ELD_I479F | 0.52 | 0.00 | 0.03 | 0.03 | 0.11 | 20.69 |
| ELD_I479G | 0.26 | 0.01 | 0.04 | 0.01 | 0.05 | 16.39 |
| ELD_I479H | 0.44 | 0.01 | 0.02 | 0.02 | 0.05 | 26.31 |
| ELD_I479K | 0.01 | 0.00 | 0.01 | 0.03 | 0.07 | 0.59 |
| ELD_I479L | 0.91 | 0.06 | 0.11 | 0.18 | 0.94 | 4.55 |
| ELD_I479M | 0.96 | 0.26 | 0.35 | 0.34 | 0.60 | 2.80 |
| ELD_I479N | 0.46 | 0.01 | 0.01 | 0.02 | 0.06 | 31.02 |
| ELD_I479P | 0.09 | 0.01 | 0.01 | 0.03 | 0.04 | 5.91 |
| ELD_I479Q | 1.48 | 0.01 | 0.04 | 0.03 | 0.10 | 54.43 |
| ELD_I479R | 0.07 | 0.01 | 0.01 | 0.03 | 0.10 | 3.33 |
| ELD_I479S | 0.83 | 0.00 | 0.03 | 0.05 | 0.09 | 34.10 |
| ELD_I479T | 1.06 | 0.01 | 0.06 | 0.03 | 0.09 | 34.23 |
| ELD_I479V | 1.15 | 0.04 | 0.20 | 0.09 | 0.10 | 13.93 |
| ELD_I479W | 0.09 | 0.00 | 0.04 | 0.03 | 0.04 | 5.81 |
| ELD_I479Y | 0.54 | 0.00 | 0.03 | 0.04 | 0.03 | 32.86 |
| ELD_S418D | 1.01 | 0.02 | 0.12 | 0.15 | 0.10 | 15.24 |
| ELD_N476D | 1.40 | 0.01 | 0.04 | 0.05 | 0.04 | 63.28 |
| ELD_I479T | 0.96 | 0.01 | 0.07 | 0.03 | 0.07 | 32.41 |
| ELD_Q481E | 1.25 | 0.01 | 0.07 | 0.12 | 0.06 | 29.44 |
| ELD_N527D | 0.82 | 0.07 | 0.09 | 0.27 | 0.07 | 7.60 |
| ELD_Q531R | 1.04 | 0.10 | 0.09 | 0.19 | 0.17 | 8.22 |
| ELD_R416N | 1.37 | 0.07 | 0.47 | 0.35 | 0.11 | 7.74 |
| ELD_R416D | 0.70 | 0.03 | 0.18 | 0.03 | 0.03 | 14.08 |
| ELD_R416E | 1.20 | 0.04 | 0.62 | 0.25 | 0.12 | 7.15 |
| ELD_R416S | 0.90 | 0.08 | 0.33 | 0.38 | 0.13 | 5.21 |
| ELD_K525A | 1.05 | 0.02 | 0.18 | 0.10 | 0.11 | 14.95 |
| ELD_K525E | 0.77 | 0.00 | 0.01 | 0.07 | 0.06 | 36.17 |
| ELD_K525G | 0.77 | 0.01 | 0.08 | 0.08 | 0.10 | 17.64 |
| ELD_K525S | 1.15 | 0.05 | 0.15 | 0.09 | 0.11 | 14.81 |
| ELD_Q481A | 1.06 | 0.00 | 0.05 | 0.07 | 0.04 | 42.00 |
| ELD_Q481D | 1.70 | 0.10 | 0.09 | 0.44 | 0.19 | 10.36 |
| ELD_Q481C | 1.09 | 0.01 | 0.08 | 0.19 | 0.16 | 15.87 |
| ELD_Q481S | 0.84 | 0.00 | 0.02 | 0.05 | 0.02 | 56.17 |
| ELD_S418E | 1.16 | 0.02 | 0.08 | 0.06 | 0.08 | 29.93 |
| ELD_R422H | 0.89 | 0.13 | 0.32 | 0.49 | 0.12 | 4.11 |
| GFP | 0.00 | 0.00 | 0.05 | 0.02 | 0.05 | ND |
| GFP | 0.00 | 0.00 | 0.04 | 0.05 | 0.03 | ND |
| parental pair | 46.50 | 6.60 | 1.46 | 1.41 | 1.26 | 4.33 |
| parental pair | 40.06 | 3.57 | 0.90 | 1.05 | 0.70 | 6.44 |
| parental pair | 45.74 | 5.54 | 1.36 | 1.37 | 1.24 | 4.81 |
| parental pair | 41.20 | 3.92 | 1.04 | 0.94 | 0.86 | 6.09 |
| half dose | 29.20 | 1.82 | 0.31 | 0.26 | 0.31 | 10.78 |
| half dose | 29.32 | ND | 0.27 | 0.36 | 0.31 | ND |
| half dose | 24.58 | 1.06 | 0.20 | 0.19 | 0.17 | 15.16 |
| half dose | 24.63 | 1.16 | 0.34 | 0.30 | 0.17 | 12.53 |
| ELD_K448A | 59.76 | 7.05 | 0.93 | 2.04 | 1.40 | 5.23 |
| ELD_K448C | 63.80 | 9.43 | 3.22 | 2.51 | 2.11 | 3.69 |
| ELD_K448D | 3.14 | 0.04 | 0.05 | 0.05 | 0.07 | 15.10 |
| ELD_K448E | 75.48 | 19.58 | 6.59 | 3.86 | 2.19 | 2.34 |
| ELD_K448F | 5.08 | 0.06 | 0.20 | 0.09 | 0.05 | 12.65 |
| ELD_K448G | 42.70 | 2.67 | 0.33 | 1.26 | 0.68 | 8.65 |
| ELD_K448H | 6.19 | 0.19 | 0.27 | 0.15 | 0.09 | 8.89 |
| ELD_K448I | 3.65 | 0.07 | 0.10 | 0.13 | 0.08 | 9.54 |
| ELD_K448L | 5.82 | 0.13 | 0.15 | 0.24 | 0.11 | 9.22 |
| ELD_K448M | 69.53 | 9.69 | 5.97 | 3.41 | 1.87 | 3.32 |
| ELD_K448N | 14.00 | 0.77 | 0.44 | 0.78 | 0.43 | 5.79 |
| ELD_K448P | 0.10 | 0.02 | 0.03 | 0.03 | 0.03 | 0.95 |
| ELD_K448Q | 76.82 | 16.60 | 4.64 | 3.11 | 3.12 | 2.80 |
| ELD_K448R | 73.43 | 9.83 | 2.60 | 3.52 | 1.87 | 4.12 |
| ELD_K448S | 45.95 | 6.15 | 1.53 | 1.88 | 1.16 | 4.29 |
| ELD_K448T | 34.16 | 3.41 | 2.85 | 1.96 | 0.82 | 3.78 |
| ELD_K448V | 13.46 | 1.47 | 0.58 | 0.70 | 0.53 | 4.09 |
| ELD_K448W | 0.93 | 0.02 | 0.04 | 0.05 | 0.05 | 5.74 |
| ELD_K448Y | 7.36 | 0.21 | 0.52 | 0.28 | 0.15 | 6.37 |
| GFP | 0.03 | 0.02 | 0.06 | 0.02 | 0.05 | NA |
| GFP | 0.04 | 0.01 | 0.04 | 0.06 | 0.03 | NA |
| parental pair | 46.50 | 6.60 | 1.46 | 1.41 | 1.26 | 4.33 |
| parental pair | 40.06 | 3.57 | 0.90 | 1.05 | 0.70 | 6.44 |
| parental pair | 45.74 | 5.54 | 1.36 | 1.37 | 1.24 | 4.81 |
| parental pair | 41.20 | 3.92 | 1.04 | 0.94 | 0.86 | 6.09 |
| half dose | 29.20 | 1.82 | 0.31 | 0.26 | 0.31 | 10.78 |
| half dose | 29.32 | ND | 0.27 | 0.36 | 0.31 | ND |
| half dose | 24.58 | 1.06 | 0.20 | 0.19 | 0.17 | 15.16 |
| half dose | 24.63 | 1.16 | 0.34 | 0.30 | 0.17 | 12.53 |
| ELD_I479A | 41.45 | 0.03 | 0.04 | 0.04 | 0.06 | 248.65 |
| ELD_I479C | 32.55 | 0.02 | 0.09 | 0.05 | 0.10 | 124.76 |
| ELD_I479D | 0.98 | 0.03 | 0.01 | 0.02 | 0.06 | 7.69 |
| ELD_I479E | 1.46 | 0.02 | 0.03 | 0.05 | 0.03 | 11.56 |
| ELD_I479F | 22.48 | 0.02 | 0.04 | 0.03 | 0.11 | 112.11 |
| ELD_I479G | 11.09 | 0.02 | 0.04 | 0.01 | 0.04 | 88.84 |
| ELD_I479H | 18.97 | 0.04 | 0.03 | 0.02 | 0.05 | 142.61 |
| ELD_I479K | 0.44 | 0.02 | 0.01 | 0.04 | 0.07 | 3.22 |
| ELD_I479L | 39.31 | 0.29 | 0.13 | 0.22 | 0.96 | 24.66 |
| ELD_I479M | 41.44 | 1.30 | 0.41 | 0.41 | 0.61 | 15.17 |
| ELD_I479N | 20.15 | 0.03 | 0.01 | 0.03 | 0.06 | 168.10 |

TABLE 12A-continued

|  | AAVS1 | OT1 | OT2 | OT3 | OT4 | ratio |
|---|---|---|---|---|---|---|
| ELD_I479P | 3.79 | 0.03 | 0.01 | 0.04 | 0.04 | 32.04 |
| ELD_I479Q | 64.22 | 0.03 | 0.05 | 0.03 | 0.10 | 294.99 |
| ELD_I479R | 3.21 | 0.03 | 0.01 | 0.03 | 0.10 | 18.05 |
| ELD_I479S | 36.20 | 0.02 | 0.03 | 0.06 | 0.09 | 184.80 |
| ELD_I479T | 45.91 | 0.05 | 0.07 | 0.04 | 0.09 | 185.53 |
| ELD_I479V | 49.92 | 0.20 | 0.24 | 0.11 | 0.11 | 75.50 |
| ELD_I479W | 3.90 | 0.00 | 0.04 | 0.04 | 0.04 | 31.51 |
| ELD_I479Y | 23.34 | 0.02 | 0.04 | 0.04 | 0.03 | 178.07 |
| GFP | 0.03 | 0.02 | 0.06 | 0.02 | 0.05 | NA |
| GFP | 0.04 | 0.01 | 0.04 | 0.06 | 0.03 | NA |

TABLE 12B

|  | AAVS1 | OT1 | OT2 | OT3 | OT4 | ratio |
|---|---|---|---|---|---|---|
| parental pair | 46.50 | 6.60 | 1.46 | 1.41 | 1.26 | 4.33 |
| parental pair | 40.06 | 3.57 | 0.90 | 1.05 | 0.70 | 6.44 |
| parental pair | 45.74 | 5.54 | 1.36 | 1.37 | 1.24 | 4.81 |
| parental pair | 41.20 | 3.92 | 1.04 | 0.94 | 0.86 | 6.09 |
| half dose | 29.20 | 1.82 | 0.31 | 0.26 | 0.31 | 10.78 |
| half dose | 29.32 | ND | 0.27 | 0.36 | 0.31 | ND |
| half dose | 24.58 | 1.06 | 0.20 | 0.19 | 0.17 | 15.16 |
| half dose | 24.63 | 1.16 | 0.34 | 0.30 | 0.17 | 12.53 |
| KKR_K448A | 58.79 | 4.46 | 0.58 | 1.06 | 0.89 | 8.42 |
| KKR_K448C | 57.00 | 7.57 | 1.34 | 1.41 | 2.28 | 4.52 |
| KKR_K448D | 2.66 | 0.04 | 0.04 | 0.04 | 0.02 | 18.94 |
| KKR_K448E | 64.43 | 6.96 | 0.21 | 0.73 | 1.86 | 6.60 |
| KKR_K448F | 5.15 | 0.07 | 0.05 | 0.02 | 0.13 | 18.91 |
| KKR_K448G | 13.56 | 0.05 | 0.05 | 0.03 | 0.06 | 74.17 |
| KKR_K448H | 7.39 | 0.09 | 0.02 | 0.07 | 0.17 | 21.44 |
| KKR_K448I | 4.04 | 0.16 | 0.05 | 0.06 | 0.08 | 11.63 |
| KKR_K448L | 5.85 | 0.08 | 0.08 | 0.04 | 0.08 | 21.19 |
| KKR_K448M | 62.00 | 6.17 | 0.51 | 0.84 | 2.83 | 5.99 |
| KKR_K448N | 15.19 | 0.75 | 0.21 | 0.20 | 0.22 | 10.96 |
| KKR_K448P | 0.04 | 0.02 | 0.03 | 0.03 | 0.04 | 0.31 |
| KKR_K448Q | 65.53 | 7.52 | 1.10 | 1.28 | 3.51 | 4.89 |
| KKR_K448R | 58.33 | 7.45 | 0.71 | 1.00 | 1.49 | 5.48 |
| KKR_K448S | 46.58 | 4.04 | 0.75 | 0.90 | 0.87 | 7.10 |
| KKR_K448T | 34.43 | 3.18 | 0.43 | 0.41 | 1.45 | 6.28 |
| KKR_K448V | 14.04 | 1.09 | 0.31 | 0.36 | 0.35 | 6.68 |
| KKR_K448W | 0.64 | 0.03 | 0.05 | 0.06 | 0.04 | 3.70 |
| KKR_K448Y | 8.97 | 0.11 | 0.18 | 0.09 | 0.10 | 18.95 |
| KKR_I479A | 39.97 | 0.06 | 0.05 | 0.10 | 0.07 | 144.06 |
| KKR_I479C | 41.45 | 0.51 | 0.17 | 0.27 | 0.05 | 41.20 |
| KKR_I479D | 6.45 | 0.01 | 0.03 | 0.04 | 0.04 | 54.74 |
| KKR_I479E | 13.23 | 0.02 | 0.04 | 0.02 | 0.07 | 83.65 |
| KKR_I479F | 25.15 | 0.08 | 0.11 | 0.12 | 0.02 | 76.19 |
| KKR_I479G | 18.48 | 0.03 | 0.04 | 0.02 | 0.11 | 95.39 |
| KKR_I479H | 19.66 | 0.04 | 0.03 | 0.04 | 0.07 | 113.04 |
| KKR_I479K | 0.78 | 0.01 | 0.04 | 0.01 | 0.06 | 6.35 |
| KKR_I479L | 40.10 | 1.91 | 2.96 | 0.90 | 0.20 | 6.71 |
| KKR_I479M | 43.43 | 2.12 | 1.33 | 1.35 | 0.19 | 8.68 |
| KKR_I479N | 25.03 | 0.04 | 0.05 | 0.11 | 0.08 | 91.41 |
| KKR_I479P | 1.28 | 0.03 | 0.04 | 0.06 | 0.07 | 6.30 |
| KKR_I479Q | 59.57 | 1.32 | 0.54 | 0.77 | 0.05 | 22.11 |
| KKR_I479R | 3.17 | 0.03 | 0.04 | 0.01 | 0.04 | 26.74 |
| KKR_I479S | 35.64 | 0.05 | 0.06 | 0.06 | 0.03 | 167.22 |
| KKR_I479T | 48.64 | 0.44 | 0.06 | 0.50 | 0.08 | 45.12 |
| KKR_I479V | 49.23 | 0.48 | 0.18 | 0.32 | 0.25 | 40.12 |
| KKR_I479W | 6.86 | 0.02 | 0.01 | 0.06 | 0.05 | 46.92 |
| KKR_I479Y | 21.50 | 0.04 | 0.04 | 0.04 | 0.05 | 120.50 |
| KKR_S418D | 47.81 | 0.26 | 0.07 | 0.10 | 0.10 | 90.39 |
| KKR_N476D | 19.63 | 0.06 | 0.03 | 0.04 | 0.04 | 119.60 |
| KKR_I479T | 46.95 | 0.30 | 0.11 | 0.28 | 0.06 | 62.71 |
| KKR_Q481E | 47.06 | 0.16 | 0.09 | 0.05 | 0.07 | 127.97 |
| KKR_N527D | 39.17 | 0.85 | 0.20 | 0.40 | 0.37 | 21.48 |
| KKR_Q531R | 36.99 | 1.08 | 0.30 | 0.63 | 0.28 | 16.15 |
| KKR_R416N | 54.55 | 0.92 | 0.05 | 0.18 | 0.49 | 33.30 |
| KKR_R416D | 36.70 | 0.11 | 0.03 | 0.04 | 0.14 | 120.60 |
| KKR_R416E | 51.32 | 0.35 | 0.03 | 0.06 | 0.33 | 66.66 |
| KKR_R416S | 39.97 | 1.41 | 0.18 | 0.22 | 0.62 | 16.48 |
| KKR_K525A | 39.26 | 0.46 | 0.05 | 0.07 | 0.18 | 50.61 |
| KKR_K525E | 32.52 | 0.07 | 0.01 | 0.11 | 0.07 | 128.95 |
| KKR_K525G | 34.47 | 0.43 | 0.10 | 0.08 | 0.24 | 40.02 |
| KKR_K525S | 40.86 | 0.39 | 0.02 | 0.12 | 0.19 | 56.36 |

TABLE 12B-continued

|  | AAVS1 | OT1 | OT2 | OT3 | OT4 | ratio |
|---|---|---|---|---|---|---|
| KKR_Q481A | 46.97 | 0.04 | 0.02 | 0.08 | 0.02 | 294.46 |
| KKR_Q481D | 55.80 | 1.06 | 0.05 | 0.05 | 0.17 | 42.03 |
| KKR_Q481C | 39.74 | 0.81 | 0.08 | 0.05 | 0.04 | 40.79 |
| KKR_Q481S | 36.46 | 0.12 | 0.05 | 0.07 | 0.05 | 128.50 |
| KKR_S418E | 50.83 | 0.20 | 0.06 | 0.06 | 0.05 | 137.52 |
| KKR_R422H | 40.44 | 0.77 | 0.10 | 0.15 | 0.40 | 28.46 |
| GFP | 0.03 | 0.02 | 0.06 | 0.02 | 0.05 | NA |
| GFP | 0.04 | 0.01 | 0.04 | 0.06 | 0.03 | NA |
| parental pair | 1.07 | 1.35 | 1.23 | 1.18 | 1.25 | 0.80 |
| parental pair | 0.92 | 0.73 | 0.75 | 0.88 | 0.69 | 1.19 |
| parental pair | 1.05 | 1.13 | 1.14 | 1.15 | 1.22 | 0.89 |
| parental pair | 0.95 | 0.80 | 0.88 | 0.79 | 0.85 | 1.12 |
| half dose | 0.67 | 0.37 | 0.26 | 0.22 | 0.31 | 1.99 |
| half dose | 0.68 | ND | 0.23 | 0.30 | 0.30 | ND |
| half dose | 0.57 | 0.22 | 0.17 | 0.16 | 0.17 | 2.80 |
| half dose | 0.57 | 0.24 | 0.28 | 0.25 | 0.17 | 2.31 |
| KKR_K448A | 1.36 | 0.91 | 0.49 | 0.89 | 0.87 | 1.55 |
| KKR_K448C | 1.31 | 1.54 | 1.13 | 1.18 | 2.25 | 0.83 |
| KKR_K448D | 0.06 | 0.01 | 0.04 | 0.03 | 0.02 | 3.50 |
| KKR_K448E | 1.49 | 1.42 | 0.18 | 0.61 | 1.84 | 1.22 |
| KKR_K448F | 0.12 | 0.01 | 0.04 | 0.02 | 0.13 | 3.49 |
| KKR_K448G | 0.31 | 0.01 | 0.04 | 0.02 | 0.06 | 13.69 |
| KKR_K448H | 0.17 | 0.02 | 0.02 | 0.06 | 0.16 | 3.96 |
| KKR_K448I | 0.09 | 0.03 | 0.04 | 0.05 | 0.08 | 2.15 |
| KKR_K448L | 0.13 | 0.02 | 0.07 | 0.04 | 0.08 | 3.91 |
| KKR_K448M | 1.43 | 1.26 | 0.43 | 0.71 | 2.79 | 1.10 |
| KKR_K448N | 0.35 | 0.15 | 0.18 | 0.17 | 0.22 | 2.02 |
| KKR_K448P | 0.00 | 0.00 | 0.03 | 0.02 | 0.04 | 0.06 |
| KKR_K448Q | 1.51 | 1.53 | 0.93 | 1.07 | 3.45 | 0.90 |
| KKR_K448R | 1.34 | 1.52 | 0.60 | 0.84 | 1.47 | 1.01 |
| KKR_K448S | 1.07 | 0.82 | 0.63 | 0.75 | 0.86 | 1.31 |
| KKR_K448T | 0.79 | 0.65 | 0.36 | 0.35 | 1.43 | 1.16 |
| KKR_K448V | 0.32 | 0.22 | 0.26 | 0.30 | 0.34 | 1.23 |
| KKR_K448W | 0.01 | 0.01 | 0.04 | 0.05 | 0.04 | 0.68 |
| KKR_K448Y | 0.21 | 0.02 | 0.15 | 0.07 | 0.10 | 3.50 |
| KKR_I479A | 0.92 | 0.01 | 0.04 | 0.08 | 0.07 | 26.58 |
| KKR_I479C | 0.96 | 0.10 | 0.14 | 0.23 | 0.05 | 7.60 |
| KKR_I479D | 0.15 | 0.00 | 0.02 | 0.04 | 0.04 | 10.10 |
| KKR_I479E | 0.31 | 0.00 | 0.03 | 0.02 | 0.07 | 15.44 |
| KKR_I479F | 0.58 | 0.02 | 0.09 | 0.10 | 0.02 | 14.06 |
| KKR_I479G | 0.43 | 0.01 | 0.03 | 0.02 | 0.11 | 17.60 |
| KKR_I479H | 0.45 | 0.01 | 0.03 | 0.03 | 0.07 | 20.86 |
| KKR_I479K | 0.02 | 0.00 | 0.03 | 0.01 | 0.06 | 1.17 |
| KKR_I479L | 0.92 | 0.39 | 2.49 | 0.76 | 0.20 | 1.24 |
| KKR_I479M | 1.00 | 0.43 | 1.12 | 1.13 | 0.19 | 1.60 |
| KKR_I479N | 0.58 | 0.01 | 0.04 | 0.09 | 0.08 | 16.87 |
| KKR_I479P | 0.03 | 0.01 | 0.03 | 0.05 | 0.07 | 1.16 |
| KKR_I479Q | 1.37 | 0.27 | 0.45 | 0.65 | 0.05 | 4.08 |
| KKR_I479R | 0.07 | 0.01 | 0.03 | 0.01 | 0.04 | 4.93 |
| KKR_I479S | 0.82 | 0.01 | 0.05 | 0.05 | 0.03 | 30.85 |
| KKR_I479T | 1.12 | 0.09 | 0.05 | 0.42 | 0.08 | 8.33 |
| KKR_I479V | 1.14 | 0.10 | 0.15 | 0.27 | 0.24 | 7.40 |
| KKR_I479W | 0.16 | 0.00 | 0.01 | 0.05 | 0.05 | 8.66 |
| KKR_I479Y | 0.50 | 0.01 | 0.03 | 0.04 | 0.05 | 22.23 |
| KKR_S418D | 1.10 | 0.05 | 0.06 | 0.09 | 0.10 | 16.68 |
| KKR_N476D | 0.45 | 0.01 | 0.02 | 0.03 | 0.04 | 22.07 |
| KKR_I479T | 1.08 | 0.06 | 0.09 | 0.24 | 0.06 | 11.57 |
| KKR_Q481E | 1.08 | 0.03 | 0.07 | 0.04 | 0.07 | 23.61 |
| KKR_N527D | 0.90 | 0.17 | 0.17 | 0.33 | 0.37 | 3.96 |
| KKR_Q531R | 0.85 | 0.22 | 0.25 | 0.53 | 0.28 | 2.98 |
| KKR_R416N | 1.26 | 0.19 | 0.04 | 0.15 | 0.48 | 6.14 |
| KKR_R416D | 0.85 | 0.02 | 0.02 | 0.03 | 0.13 | 22.25 |
| KKR_R416E | 1.18 | 0.07 | 0.02 | 0.05 | 0.32 | 12.30 |
| KKR_R416S | 0.92 | 0.29 | 0.15 | 0.18 | 0.61 | 3.04 |
| KKR_K525A | 0.91 | 0.09 | 0.05 | 0.06 | 0.18 | 9.34 |
| KKR_K525E | 0.75 | 0.01 | 0.01 | 0.09 | 0.07 | 23.79 |
| KKR_K525G | 0.79 | 0.09 | 0.09 | 0.07 | 0.24 | 7.38 |
| KKR_K525S | 0.94 | 0.08 | 0.02 | 0.10 | 0.19 | 10.40 |
| KKR_Q481A | 1.08 | 0.01 | 0.02 | 0.06 | 0.02 | 54.33 |
| KKR_Q481D | 1.29 | 0.22 | 0.04 | 0.04 | 0.17 | 7.75 |
| KKR_Q481C | 0.92 | 0.16 | 0.07 | 0.04 | 0.04 | 7.53 |
| KKR_Q481S | 0.84 | 0.02 | 0.04 | 0.06 | 0.05 | 23.71 |
| KKR_S418E | 1.17 | 0.04 | 0.05 | 0.05 | 0.05 | 25.37 |
| KKR_R422H | 0.93 | 0.16 | 0.08 | 0.13 | 0.39 | 5.25 |
| GFP | 0.00 | 0.00 | 0.05 | 0.02 | 0.05 | ND |
| GFP | 0.00 | 0.00 | 0.04 | 0.05 | 0.03 | ND |
| parental pair | 46.50 | 6.60 | 1.46 | 1.41 | 1.26 | 4.33 |
| parental pair | 40.06 | 3.57 | 0.90 | 1.05 | 0.70 | 6.44 |

TABLE 12B-continued

|  | AAVS1 | OT1 | OT2 | OT3 | OT4 | ratio |
|---|---|---|---|---|---|---|
| parental pair | 45.74 | 5.54 | 1.36 | 1.37 | 1.24 | 4.81 |
| parental pair | 41.20 | 3.92 | 1.04 | 0.94 | 0.86 | 6.09 |
| half dose | 29.20 | 1.82 | 0.31 | 0.26 | 0.31 | 10.78 |
| half dose | 29.32 | ND | 0.27 | 0.36 | 0.31 | ND |
| half dose | 24.58 | 1.06 | 0.20 | 0.19 | 0.17 | 15.16 |
| half dose | 24.63 | 1.16 | 0.34 | 0.30 | 0.17 | 12.53 |
| KKR_K448A | 58.79 | 4.46 | 0.58 | 1.06 | 0.89 | 8.42 |
| KKR_K448C | 57.00 | 7.57 | 1.34 | 1.41 | 2.28 | 4.52 |
| KKR_K448D | 2.66 | 0.04 | 0.04 | 0.04 | 0.02 | 18.94 |
| KKR_K448E | 64.43 | 6.96 | 0.21 | 0.73 | 1.86 | 6.60 |
| KKR_K448F | 5.15 | 0.07 | 0.05 | 0.02 | 0.13 | 18.91 |
| KKR_K448G | 13.56 | 0.05 | 0.05 | 0.03 | 0.06 | 74.17 |
| KKR_K448H | 7.39 | 0.09 | 0.02 | 0.07 | 0.17 | 21.44 |
| KKR_K448I | 4.04 | 0.16 | 0.05 | 0.06 | 0.08 | 11.63 |
| KKR_K448L | 5.85 | 0.08 | 0.08 | 0.04 | 0.08 | 21.19 |
| KKR_K448M | 62.00 | 6.17 | 0.51 | 0.84 | 2.83 | 5.99 |
| KKR_K448N | 15.19 | 0.75 | 0.21 | 0.20 | 0.22 | 10.96 |
| KKR_K448P | 0.04 | 0.02 | 0.03 | 0.03 | 0.04 | 0.31 |
| KKR_K448Q | 65.53 | 7.52 | 1.10 | 1.28 | 3.51 | 4.89 |
| KKR_K448R | 58.33 | 7.45 | 0.71 | 1.00 | 1.49 | 5.48 |
| KKR_K448S | 46.58 | 4.04 | 0.75 | 0.90 | 0.87 | 7.10 |
| KKR_K448T | 34.43 | 3.18 | 0.43 | 0.41 | 1.45 | 6.28 |
| KKR_K448V | 14.04 | 1.09 | 0.31 | 0.36 | 0.35 | 6.68 |
| KKR_K448W | 0.64 | 0.03 | 0.05 | 0.06 | 0.04 | 3.70 |
| KKR_K448Y | 8.97 | 0.11 | 0.18 | 0.09 | 0.10 | 18.95 |
| GFP | 0.03 | 0.02 | 0.06 | 0.02 | 0.05 | NA |
| GFP | 0.04 | 0.01 | 0.04 | 0.06 | 0.03 | NA |
| parental pair | 46.50 | 6.60 | 1.46 | 1.41 | 1.26 | 4.33 |
| parental pair | 40.06 | 3.57 | 0.90 | 1.05 | 0.70 | 6.44 |
| parental pair | 45.74 | 5.54 | 1.36 | 1.37 | 1.24 | 4.81 |
| parental pair | 41.20 | 3.92 | 1.04 | 0.94 | 0.86 | 6.09 |
| half dose | 29.20 | 1.82 | 0.31 | 0.26 | 0.31 | 10.78 |
| half dose | 29.32 | ND | 0.27 | 0.36 | 0.31 | ND |
| half dose | 24.58 | 1.06 | 0.20 | 0.19 | 0.17 | 15.16 |
| half dose | 24.63 | 1.16 | 0.34 | 0.30 | 0.17 | 12.53 |
| KKR_I479A | 39.97 | 0.06 | 0.05 | 0.10 | 0.07 | 144.06 |
| KKR_I479C | 41.45 | 0.51 | 0.17 | 0.27 | 0.05 | 41.20 |
| KKR_I479D | 6.45 | 0.01 | 0.03 | 0.04 | 0.04 | 54.74 |
| KKR_I479E | 13.23 | 0.02 | 0.04 | 0.02 | 0.07 | 83.65 |
| KKR_I479F | 25.15 | 0.05 | 0.08 | 0.11 | 0.12 | 76.19 |
| KKR_I479G | 18.48 | 0.03 | 0.04 | 0.02 | 0.11 | 95.39 |
| KKR_I479H | 19.66 | 0.04 | 0.03 | 0.04 | 0.07 | 113.04 |
| KKR_I479K | 0.78 | 0.01 | 0.04 | 0.01 | 0.06 | 6.35 |
| KKR_I479L | 40.10 | 1.91 | 2.96 | 0.90 | 0.20 | 6.71 |
| KKR_I479M | 43.43 | 2.12 | 1.33 | 1.35 | 0.19 | 8.68 |
| KKR_I479N | 25.03 | 0.04 | 0.05 | 0.11 | 0.08 | 91.41 |
| KKR_I479P | 1.28 | 0.03 | 0.04 | 0.06 | 0.07 | 6.30 |
| KKR_I479Q | 59.57 | 1.32 | 0.54 | 0.77 | 0.05 | 22.11 |
| KKR_I479R | 3.17 | 0.03 | 0.04 | 0.01 | 0.04 | 26.74 |
| KKR_I479S | 35.64 | 0.05 | 0.06 | 0.06 | 0.03 | 167.22 |
| KKR_I479T | 48.64 | 0.44 | 0.06 | 0.50 | 0.08 | 45.12 |
| KKR_I479V | 49.23 | 0.48 | 0.18 | 0.32 | 0.25 | 40.12 |
| KKR_I479W | 6.86 | 0.02 | 0.01 | 0.06 | 0.05 | 46.92 |
| KKR_I479Y | 21.50 | 0.04 | 0.04 | 0.04 | 0.05 | 120.50 |
| GFP | 0.03 | 0.02 | 0.06 | 0.02 | 0.05 | NA |
| GFP | 0.04 | 0.01 | 0.04 | 0.06 | 0.03 | NA |

TABLE 12C

|  | AAVS1 | OT1 | OT2 | OT3 | OT4 | ratio |
|---|---|---|---|---|---|---|
| parental pair | 46.50 | 6.60 | 1.46 | 1.41 | 1.26 | 4.33 |
| parental pair | 40.06 | 3.57 | 0.90 | 1.05 | 0.70 | 6.44 |
| parental pair | 45.74 | 5.54 | 1.36 | 1.37 | 1.24 | 4.81 |
| parental pair | 41.20 | 3.92 | 1.04 | 0.94 | 0.86 | 6.09 |
| half dose | 29.20 | 1.82 | 0.31 | 0.26 | 0.31 | 10.78 |
| half dose | 29.32 | ND | 0.27 | 0.36 | 0.31 | ND |
| half dose | 24.58 | 1.06 | 0.20 | 0.19 | 0.17 | 15.16 |
| half dose | 24.63 | 1.16 | 0.34 | 0.30 | 0.17 | 12.53 |
| ELD_KKR_K448A | 61.79 | 1.69 | 0.26 | 0.70 | 0.46 | 19.89 |
| ELD_KKR_K448C | 64.98 | 6.21 | 1.34 | 1.40 | 1.79 | 6.05 |
| ELD_KKR_K448D | 0.08 | 0.03 | 0.02 | 0.01 | 0.04 | 0.86 |
| ELD_KKR_K448E | 84.95 | 18.50 | 0.87 | 1.02 | 2.25 | 3.75 |
| ELD_KKR_K448F | 0.72 | 0.02 | 0.02 | 0.05 | 0.04 | 5.26 |
| ELD_KKR_K448G | 8.15 | 0.03 | 0.05 | 0.06 | 0.09 | 36.59 |

TABLE 12C-continued

|  | AAVS1 | OT1 | OT2 | OT3 | OT4 | ratio |
|---|---|---|---|---|---|---|
| ELD_KKR_K448H | 1.10 | 0.02 | 0.02 | 0.04 | 0.08 | 7.22 |
| ELD_KKR_K448I | 0.19 | 0.02 | 0.01 | 0.04 | 0.03 | 1.94 |
| ELD_KKR_K448L | 0.59 | 0.03 | 0.05 | 0.02 | 0.05 | 4.00 |
| ELD_KKR_K448M | 81.10 | 9.18 | 1.14 | 1.81 | 2.50 | 5.55 |
| ELD_KKR_K448N | 4.51 | 0.16 | 0.19 | 0.10 | 0.11 | 8.02 |
| ELD_KKR_K448P | 0.04 | 0.03 | 0.03 | 0.04 | 0.08 | 0.24 |
| ELD_KKR_K448Q | 90.81 | 20.83 | 4.03 | 3.99 | 8.91 | 2.41 |
| ELD_KKR_K448R | 82.04 | 6.56 | 0.76 | 1.63 | 0.95 | 8.29 |
| ELD_KKR_K448S | 40.23 | 2.31 | 0.42 | 0.67 | 0.41 | 10.57 |
| ELD_KKR_K448T | 19.29 | 1.14 | 0.43 | 0.37 | 0.37 | 8.40 |
| ELD_KKR_K448V | 3.93 | 0.34 | 0.15 | 0.28 | 0.19 | 4.07 |
| ELD_KKR_K448W | 0.04 | 0.04 | 0.04 | 0.02 | 0.10 | 0.20 |
| ELD_KKR_K448Y | 1.79 | 0.01 | 0.13 | 0.02 | 0.08 | 7.54 |
| ELD_KKR_I479A | 0.79 | 0.01 | 0.02 | 0.03 | 0.06 | 7.35 |
| ELD_KKR_I479C | 14.11 | 0.06 | 0.04 | 0.03 | 0.07 | 70.49 |
| ELD_KKR_I479D | 0.01 | 0.04 | 0.04 | 0.01 | 0.03 | 0.07 |
| ELD_KKR_I479E | 0.04 | 0.02 | 0.04 | 0.06 | 0.04 | 0.23 |
| ELD_KKR_I479F | 5.13 | 0.03 | 0.01 | 0.03 | 0.03 | 50.10 |
| ELD_KKR_I479G | 0.08 | 0.03 | 0.03 | 0.03 | 0.05 | 0.58 |
| ELD_KKR_I479H | 0.09 | 0.02 | 0.04 | 0.04 | 0.04 | 0.66 |
| ELD_KKR_I479K | 0.04 | 0.03 | 0.04 | 0.01 | 0.03 | 0.37 |
| ELD_KKR_I479L | 27.72 | 0.05 | 0.17 | 0.12 | 0.08 | 66.94 |
| ELD_KKR_I479M | 34.75 | 0.22 | 0.22 | 0.10 | 0.10 | 53.87 |
| ELD_KKR_I479N | 0.12 | 0.01 | 0.06 | 0.04 | 0.03 | 0.83 |
| ELD_KKR_I479P | 0.04 | 0.03 | 0.02 | 0.04 | 0.04 | 0.33 |
| ELD_KKR_I479Q | 53.80 | 0.03 | 0.04 | 0.07 | 0.04 | 303.42 |
| ELD_KKR_I479R | 0.05 | 0.02 | 0.07 | 0.06 | 0.01 | 0.27 |
| ELD_KKR_I479S | 0.46 | 0.01 | 0.05 | 0.03 | 0.06 | 3.16 |
| ELD_KKR_I479T | 28.74 | 0.03 | 0.04 | 0.03 | 0.09 | 154.73 |
| ELD_KKR_I479V | 36.57 | 0.05 | 0.04 | 0.06 | 0.05 | 184.04 |
| ELD_KKR_I479W | 0.04 | 0.04 | 0.01 | 0.03 | 0.04 | 0.28 |
| ELD_KKR_I479Y | 1.00 | 0.01 | 0.04 | 0.04 | 0.03 | 8.20 |
| ELD_KKR_S418D | 22.59 | 0.02 | 0.05 | 0.04 | 0.08 | 115.05 |
| ELD_KKR_N476D | 2.29 | 0.03 | 0.03 | 0.04 | 0.08 | 12.55 |
| ELD_KKR_I479T | 20.33 | 0.03 | 0.03 | 0.06 | 0.06 | 116.86 |
| ELD_KKR_Q481E | 43.53 | 0.01 | 0.03 | 0.04 | 0.11 | 234.62 |
| ELD_KKR_N527D | 15.86 | 0.03 | 0.03 | 0.06 | 0.02 | 112.24 |
| ELD_KKR_Q531R | 31.62 | 0.17 | 0.06 | 0.13 | 0.04 | 80.56 |
| ELD_KKR_R416N | 70.71 | 0.06 | 0.06 | 0.07 | 0.12 | 227.36 |
| ELD_KKR_R416D | 32.67 | 0.03 | 0.02 | 0.01 | 0.04 | 349.76 |
| ELD_KKR_R416E | 66.68 | 0.13 | 0.06 | 0.10 | 0.05 | 198.02 |
| ELD_KKR_R416S | 36.47 | 0.20 | 0.05 | 0.13 | 0.08 | 79.49 |
| ELD_KKR_K525A | 36.88 | 0.02 | 0.05 | 0.02 | 0.04 | 292.90 |
| ELD_KKR_K525E | 8.26 | 0.01 | 0.01 | 0.02 | 0.08 | 74.88 |
| ELD_KKR_K525G | 24.82 | 0.02 | 0.03 | 0.07 | 0.05 | 142.86 |
| ELD_KKR_K525S | 46.15 | 0.04 | 0.02 | 0.12 | 0.07 | 184.82 |
| ELD_KKR_Q481A | 82.60 | 0.04 | 0.02 | 0.04 | 0.04 | 559.53 |
| ELD_KKR_Q481D | 89.32 | 0.19 | 0.03 | 0.04 | 0.06 | 279.60 |
| ELD_KKR_Q481C | 50.98 | 0.06 | 0.01 | 0.02 | 0.04 | 410.14 |
| ELD_KKR_Q481S | 36.72 | 0.02 | 0.04 | 0.06 | 0.05 | 214.56 |
| ELD_KKR_S418E | 38.52 | 0.04 | 0.02 | 0.05 | 0.02 | 303.63 |
| ELD_KKR_R422H | 37.96 | 0.14 | 0.09 | 0.11 | 0.08 | 93.14 |
| GFP | 0.03 | 0.02 | 0.06 | 0.02 | 0.05 | NA |
| GFP | 0.04 | 0.01 | 0.04 | 0.06 | 0.03 | NA |
| parental pair | 1.07 | 1.35 | 1.23 | 1.18 | 1.25 | 0.80 |
| parental pair | 0.92 | 0.73 | 0.75 | 0.88 | 0.69 | 1.19 |
| parental pair | 1.05 | 1.13 | 1.14 | 1.15 | 1.22 | 0.89 |
| parental pair | 0.95 | 0.80 | 0.88 | 0.79 | 0.85 | 1.12 |
| half dose | 0.67 | 0.37 | 0.26 | 0.22 | 0.31 | 1.99 |
| half dose | 0.68 | ND | 0.23 | 0.30 | 0.30 | ND |
| half dose | 0.57 | 0.22 | 0.17 | 0.16 | 0.17 | 2.80 |
| half dose | 0.57 | 0.24 | 0.28 | 0.25 | 0.17 | 2.31 |
| ELD_KKR_K448A | 1.42 | 0.34 | 0.22 | 0.59 | 0.45 | 3.67 |
| ELD_KKR_K448C | 1.50 | 1.26 | 1.12 | 1.18 | 1.76 | 1.12 |
| ELD_KKR_K448D | 0.00 | 0.01 | 0.02 | 0.01 | 0.03 | 0.16 |
| ELD_KKR_K448E | 1.96 | 3.77 | 0.73 | 0.86 | 2.21 | 0.69 |
| ELD_KKR_K448F | 0.02 | 0.00 | 0.02 | 0.04 | 0.04 | 0.97 |
| ELD_KKR_K448G | 0.19 | 0.01 | 0.04 | 0.05 | 0.09 | 6.75 |
| ELD_KKR_K448H | 0.03 | 0.00 | 0.01 | 0.03 | 0.07 | 1.33 |
| ELD_KKR_K448I | 0.00 | 0.00 | 0.01 | 0.03 | 0.03 | 0.36 |
| ELD_KKR_K448L | 0.01 | 0.01 | 0.05 | 0.01 | 0.05 | 0.74 |
| ELD_KKR_K448M | 1.87 | 1.87 | 0.95 | 1.52 | 2.46 | 1.02 |
| ELD_KKR_K448N | 0.10 | 0.03 | 0.16 | 0.08 | 0.11 | 1.48 |
| ELD_KKR_K448P | 0.00 | 0.01 | 0.03 | 0.03 | 0.08 | 0.04 |
| ELD_KKR_K448Q | 2.09 | 4.24 | 3.39 | 3.35 | 8.77 | 0.44 |
| ELD_KKR_K448R | 1.89 | 1.34 | 0.64 | 1.37 | 0.93 | 1.53 |
| ELD_KKR_K448S | 0.93 | 0.47 | 0.35 | 0.57 | 0.40 | 1.95 |
| ELD_KKR_K448T | 0.44 | 0.23 | 0.36 | 0.31 | 0.36 | 1.55 |

TABLE 12C-continued

| | AAVS1 | OT1 | OT2 | OT3 | OT4 | ratio |
|---|---|---|---|---|---|---|
| ELD_KKR_K448V | 0.09 | 0.07 | 0.13 | 0.24 | 0.19 | 0.75 |
| ELD_KKR_K448W | 0.00 | 0.01 | 0.03 | 0.02 | 0.10 | 0.04 |
| ELD_KKR_K448Y | 0.04 | 0.00 | 0.11 | 0.02 | 0.08 | 1.39 |
| ELD_KKR_I479A | 0.02 | 0.00 | 0.02 | 0.02 | 0.06 | 1.36 |
| ELD_KKR_I479C | 0.33 | 0.01 | 0.03 | 0.03 | 0.07 | 13.01 |
| ELD_KKR_I479D | 0.00 | 0.01 | 0.03 | 0.01 | 0.03 | 0.01 |
| ELD_KKR_I479E | 0.00 | 0.01 | 0.03 | 0.05 | 0.04 | 0.04 |
| ELD_KKR_I479F | 0.12 | 0.01 | 0.01 | 0.03 | 0.03 | 9.24 |
| ELD_KKR_I479G | 0.00 | 0.01 | 0.03 | 0.02 | 0.04 | 0.11 |
| ELD_KKR_I479H | 0.00 | 0.00 | 0.04 | 0.04 | 0.04 | 0.12 |
| ELD_KKR_I479K | 0.00 | 0.01 | 0.03 | 0.01 | 0.03 | 0.07 |
| ELD_KKR_I479L | 0.64 | 0.01 | 0.14 | 0.10 | 0.08 | 12.35 |
| ELD_KKR-I479M | 0.80 | 0.05 | 0.19 | 0.08 | 0.10 | 9.94 |
| ELD_KKR_I479N | 0.00 | 0.00 | 0.05 | 0.03 | 0.03 | 0.15 |
| ELD_KKR_I479P | 0.00 | 0.01 | 0.02 | 0.04 | 0.03 | 0.06 |
| ELD_KKR_I479Q | 1.24 | 0.01 | 0.03 | 0.06 | 0.04 | 55.98 |
| ELD_KKR_I479R | 0.00 | 0.00 | 0.06 | 0.05 | 0.01 | 0.05 |
| ELD_KKR_I479S | 0.01 | 0.00 | 0.05 | 0.02 | 0.05 | 0.58 |
| ELD_KKR_I479T | 0.66 | 0.01 | 0.03 | 0.02 | 0.09 | 28.55 |
| ELD_KKR_I479V | 0.84 | 0.01 | 0.04 | 0.05 | 0.05 | 33.96 |
| ELD_KKR_I479W | 0.00 | 0.01 | 0.01 | 0.02 | 0.04 | 0.05 |
| ELD_KKR_I479Y | 0.02 | 0.00 | 0.03 | 0.04 | 0.03 | 1.51 |
| ELD_KKR_S418D | 0.52 | 0.00 | 0.04 | 0.03 | 0.08 | 21.23 |
| ELD_KKR_N476D | 0.05 | 0.01 | 0.03 | 0.03 | 0.08 | 2.32 |
| ELD_KKR_I479T | 0.47 | 0.01 | 0.02 | 0.05 | 0.05 | 21.56 |
| ELD_KKR_Q481E | 1.00 | 0.00 | 0.02 | 0.04 | 0.11 | 43.29 |
| ELD_KKR_N527D | 0.37 | 0.01 | 0.03 | 0.05 | 0.02 | 20.71 |
| ELD_KKR_Q531R | 0.73 | 0.03 | 0.05 | 0.11 | 0.04 | 14.86 |
| ELD_KKR_R416N | 1.63 | 0.01 | 0.05 | 0.06 | 0.11 | 41.95 |
| ELD_KKR_R416D | 0.75 | 0.01 | 0.02 | 0.01 | 0.04 | 64.54 |
| ELD_KKR_R416E | 1.54 | 0.03 | 0.05 | 0.08 | 0.05 | 36.54 |
| ELD_KKR_R416S | 0.84 | 0.04 | 0.05 | 0.11 | 0.08 | 14.67 |
| ELD_KKR_K525A | 0.85 | 0.00 | 0.04 | 0.01 | 0.04 | 54.04 |
| ELD_KKR_K525E | 0.19 | 0.00 | 0.01 | 0.01 | 0.07 | 13.82 |
| ELD_KKR_K525G | 0.57 | 0.00 | 0.03 | 0.06 | 0.05 | 26.36 |
| ELD_KKR_K525S | 1.06 | 0.01 | 0.02 | 0.10 | 0.07 | 34.10 |
| ELD_KKR_Q481A | 1.90 | 0.01 | 0.02 | 0.03 | 0.04 | 103.24 |
| ELD_KKR_Q481D | 2.06 | 0.04 | 0.03 | 0.04 | 0.05 | 51.59 |
| ELD_KKR_Q481C | 1.18 | 0.01 | 0.01 | 0.02 | 0.04 | 75.68 |
| ELD_KKR_Q481S | 0.85 | 0.00 | 0.04 | 0.05 | 0.05 | 39.59 |
| ELD_KKR_S418E | 0.89 | 0.01 | 0.02 | 0.04 | 0.02 | 56.02 |
| ELD_KKR_R422H | 0.88 | 0.03 | 0.07 | 0.09 | 0.08 | 17.19 |
| GFP | 0.00 | 0.00 | 0.05 | 0.02 | 0.05 | ND |
| GFP | 0.00 | 0.00 | 0.04 | 0.05 | 0.05 | ND |
| parental pair | 46.50 | 6.60 | 1.46 | 1.41 | 1.26 | 4.33 |
| parental pair | 40.06 | 3.57 | 0.90 | 1.05 | 0.70 | 6.44 |
| parental pair | 45.74 | 5.54 | 1.36 | 1.37 | 1.24 | 4.81 |
| parental pair | 41.20 | 3.92 | 1.04 | 0.94 | 0.86 | 6.09 |
| half dose | 29.20 | 1.82 | 0.31 | 0.26 | 0.31 | 10.78 |
| half dose | 29.32 | ND | 0.27 | 0.36 | 0.31 | ND |
| half dose | 24.58 | 1.06 | 0.20 | 0.19 | 0.17 | 15.16 |
| half dose | 24.63 | 1.16 | 0.34 | 0.30 | 0.17 | 12.53 |
| ELD_KKR_K448A | 61.79 | 1.69 | 0.26 | 0.70 | 0.46 | 19.89 |
| ELD_KKR_K448C | 64.98 | 6.21 | 1.34 | 1.40 | 1.79 | 6.05 |
| ELD_KKR_K448D | 0.08 | 0.03 | 0.02 | 0.01 | 0.04 | 0.86 |
| ELD_KKR_K448E | 84.95 | 18.50 | 0.87 | 1.02 | 2.25 | 3.75 |
| ELD_KKR_K448F | 0.72 | 0.02 | 0.02 | 0.05 | 0.04 | 5.26 |
| ELD_KKR_K448G | 8.15 | 0.03 | 0.05 | 0.06 | 0.09 | 36.59 |
| ELD_KKR_K448H | 1.10 | 0.02 | 0.02 | 0.04 | 0.08 | 7.22 |
| ELD_KKR_K448I | 0.19 | 0.02 | 0.01 | 0.04 | 0.03 | 1.94 |
| ELD_KKR_K448L | 0.59 | 0.03 | 0.05 | 0.02 | 0.05 | 4.00 |
| ELD_KKR_K448M | 81.10 | 9.18 | 1.14 | 1.81 | 2.50 | 5.55 |
| ELD_KKR_K448N | 4.51 | 0.16 | 0.19 | 0.10 | 0.11 | 8.02 |
| ELD_KKR_K448P | 0.04 | 0.03 | 0.03 | 0.04 | 0.08 | 0.24 |
| ELD_KKR_K448Q | 90.81 | 20.83 | 4.03 | 3.99 | 8.91 | 2.41 |
| ELD_KKR_K448R | 82.04 | 6.56 | 0.76 | 1.63 | 0.95 | 8.29 |
| ELD_KKR_K448S | 40.23 | 2.31 | 0.42 | 0.67 | 0.41 | 10.57 |
| ELD_KKR_K448T | 19.29 | 1.14 | 0.43 | 0.37 | 0.37 | 8.40 |
| ELD_KKR_K448V | 3.93 | 0.34 | 0.15 | 0.28 | 0.19 | 4.07 |
| ELD_KKR_K448W | 0.04 | 0.04 | 0.04 | 0.02 | 0.10 | 0.20 |
| ELD_KKR_K448Y | 1.79 | 0.01 | 0.13 | 0.02 | 0.08 | 7.54 |
| GFP | 0.03 | 0.02 | 0.06 | 0.02 | 0.05 | NA |
| GFP | 0.04 | 0.01 | 0.04 | 0.06 | 0.03 | NA |
| parental pair | 46.50 | 6.60 | 1.46 | 1.41 | 1.26 | 4.33 |
| parental pair | 40.06 | 3.57 | 0.90 | 1.05 | 0.70 | 6.44 |
| parental pair | 45.74 | 5.54 | 1.36 | 1.37 | 1.24 | 4.81 |
| parental pair | 41.20 | 3.92 | 1.04 | 0.94 | 0.86 | 6.09 |
| half dose | 29.20 | 1.82 | 0.31 | 0.26 | 0.31 | 10.78 |
| half dose | 29.32 | ND | 0.27 | 0.36 | 0.31 | ND |
| half dose | 24.58 | 1.06 | 0.20 | 0.19 | 0.17 | 15.16 |
| half dose | 24.63 | 1.16 | 0.34 | 0.30 | 0.17 | 12.53 |
| ELD_KKR_I479A | 0.79 | 0.01 | 0.02 | 0.03 | 0.06 | 7.35 |
| ELD_KKR_I479C | 14.11 | 0.06 | 0.04 | 0.03 | 0.07 | 70.49 |
| ELD_KKR_I479D | 0.01 | 0.04 | 0.04 | 0.01 | 0.03 | 0.07 |
| ELD_KKR_I479E | 0.04 | 0.02 | 0.04 | 0.06 | 0.04 | 0.23 |
| ELD_KKR_I479F | 5.13 | 0.03 | 0.01 | 0.03 | 0.03 | 50.10 |
| ELD_KKR_I479G | 0.08 | 0.03 | 0.03 | 0.03 | 0.05 | 0.58 |
| ELD_KKR_I479H | 0.09 | 0.02 | 0.04 | 0.04 | 0.04 | 0.66 |
| ELD_KKR_I479K | 0.04 | 0.03 | 0.04 | 0.01 | 0.03 | 0.37 |
| ELD_KKR_I479L | 27.72 | 0.05 | 0.17 | 0.12 | 0.08 | 66.94 |
| ELD_KKR_I479M | 34.75 | 0.22 | 0.22 | 0.10 | 0.10 | 53.87 |
| ELD_KKR_I479N | 0.12 | 0.02 | 0.06 | 0.04 | 0.03 | 0.83 |
| ELD_KKR_I479P | 0.04 | 0.03 | 0.02 | 0.04 | 0.04 | 0.33 |
| ELD_KKR_I479Q | 53.80 | 0.03 | 0.04 | 0.07 | 0.04 | 303.42 |
| ELD_KKR_I479R | 0.05 | 0.02 | 0.07 | 0.06 | 0.01 | 0.27 |
| ELD_KKR_I479S | 0.46 | 0.01 | 0.05 | 0.03 | 0.06 | 3.16 |
| ELD_KKR_I479T | 28.74 | 0.03 | 0.04 | 0.03 | 0.09 | 154.73 |
| ELD_KKR_I479V | 36.57 | 0.05 | 0.04 | 0.06 | 0.05 | 184.04 |
| ELD_KKR_I479W | 0.04 | 0.04 | 0.01 | 0.03 | 0.04 | 0.28 |
| ELD_KKR_I479Y | 1.00 | 0.01 | 0.04 | 0.04 | 0.03 | 8.20 |
| GFP | 0.03 | 0.02 | 0.06 | 0.02 | 0.05 | NA |
| GFP | 0.04 | 0.01 | 0.04 | 0.06 | 0.03 | NA |

Tables 13A through 13C show on- and off-target cleavage events using AAVS1 targeted ZFNs with the indicated mutations (ELD, KKR, ELD/KKR and further mutations indicated).

TABLE 13A

| | AAVS1 | OT1 | OT2 | OT3 | OT4 | ratio |
|---|---|---|---|---|---|---|
| parental | 47.96 | 4.32 | 2.12 | 1.05 | 0.84 | 5.76 |
| parental | 46.45 | 4.34 | 1.84 | 1.11 | 1.06 | 5.57 |
| parental | 45.83 | 3.15 | 1.28 | 0.77 | 0.92 | 7.49 |
| parental | 47.63 | 4.30 | 1.67 | 0.99 | 1.03 | 5.97 |
| half dose | 30.79 | 1.21 | 0.38 | 0.19 | 0.18 | 15.72 |
| half dose | 31.59 | 1.19 | 0.23 | 0.28 | 0.18 | 16.78 |
| half dose | 29.49 | 0.76 | 0.35 | 0.21 | 0.16 | 19.93 |
| half dose | 28.04 | 0.85 | 0.31 | 0.20 | 0.17 | 18.41 |
| ELD_N527A | 20.52 | 0.76 | 0.34 | 0.42 | 0.28 | 11.37 |
| ELD_N527C | 16.30 | 0.80 | 0.25 | 0.25 | 0.17 | 11.05 |
| ELD_N527D | 45.05 | 0.42 | 0.11 | 0.21 | 0.12 | 53.34 |
| ELD_N527E | 18.93 | 0.06 | 0.08 | 0.13 | 0.09 | 52.04 |
| ELD_N527F | 5.32 | 0.21 | 0.16 | 0.15 | 0.02 | 9.79 |
| ELD_N527G | 25.25 | 1.22 | 0.92 | 0.60 | 0.71 | 7.32 |
| ELD_N527H | 20.69 | 1.65 | 1.10 | 0.55 | 0.13 | 6.05 |
| ELD_N527I | 1.58 | 0.04 | 0.02 | 0.07 | 0.01 | 11.16 |
| ELD_N527K | 14.65 | 1.31 | 0.66 | 0.49 | 0.11 | 5.70 |
| ELD_N527L | 3.37 | 0.22 | 0.12 | 0.09 | 0.06 | 6.90 |
| ELD_N527M | 6.61 | 0.44 | 0.18 | 0.23 | 0.08 | 7.06 |
| ELD_N527P | 34.71 | 2.50 | 0.97 | 0.72 | 0.63 | 7.20 |
| ELD_N527Q | 25.72 | 2.62 | 1.76 | 1.13 | 0.99 | 3.96 |
| ELD_N527R | 17.38 | 1.70 | 1.07 | 0.37 | 0.28 | 5.08 |
| ELD_N527S | 22.51 | 0.93 | 0.67 | 0.37 | 0.32 | 9.83 |
| ELD_N527T | 25.14 | 0.25 | 0.14 | 0.12 | 0.04 | 45.36 |
| ELD_N527V | 4.22 | 0.14 | 0.09 | 0.10 | 0.05 | 10.88 |
| ELD_N527W | 3.33 | 0.17 | 0.05 | 0.11 | 0.04 | 9.07 |
| ELD_N527Y | 5.34 | 0.22 | 0.18 | 0.12 | 0.06 | 9.29 |
| ELD_Q481A | 56.06 | 0.06 | 0.10 | 0.14 | 0.05 | 160.54 |
| ELD_Q481C | 61.83 | 0.05 | 0.28 | 0.35 | 0.22 | 69.22 |
| ELD_Q481D | 78.20 | 0.54 | 0.21 | 0.87 | 0.29 | 40.90 |
| ELD_Q481E | 61.09 | 0.03 | 0.05 | 0.12 | 0.04 | 248.97 |
| ELD_Q481F | 0.50 | 0.02 | 0.05 | 0.02 | 0.05 | 3.54 |
| ELD_Q481G | 33.52 | 0.43 | 0.32 | 0.74 | 0.24 | 19.41 |
| ELD_Q481H | 71.31 | 7.24 | 5.48 | 1.76 | 0.15 | 4.87 |
| ELD_Q481I | 0.95 | 0.04 | 0.04 | 0.07 | 0.02 | 5.29 |
| ELD_Q481K | 19.90 | 0.05 | 0.06 | 0.05 | 0.04 | 102.54 |
| ELD_Q481L | 1.22 | 0.03 | 0.05 | 0.05 | 0.03 | 7.88 |
| ELD_Q481M | 5.62 | 0.02 | 0.05 | 0.04 | 0.04 | 35.82 |
| ELD_Q481N | 36.71 | 1.29 | 0.50 | 0.65 | 0.22 | 13.81 |
| ELD_Q481P | 1.99 | 0.02 | 0.01 | 0.07 | 0.04 | 14.21 |
| ELD_Q481R | 5.62 | 0.04 | 0.02 | 0.04 | 0.01 | 45.70 |
| ELD_Q481S | 50.84 | 0.05 | 0.07 | 0.14 | 0.04 | 171.76 |

TABLE 13A-continued

| | AAVS1 | OT1 | OT2 | OT3 | OT4 | ratio |
|---|---|---|---|---|---|---|
| ELD_Q481T | 36.86 | 0.05 | 0.07 | 0.11 | 0.01 | 150.05 |
| ELD_Q481V | 1.45 | 0.03 | 0.06 | 0.06 | 0.02 | 8.28 |
| ELD_Q481W | 0.24 | 0.03 | 0.02 | 0.04 | 0.03 | 1.95 |
| ELD_Q481Y | 1.75 | 0.04 | 0.04 | 0.05 | 0.02 | 11.96 |
| ELD_S418D | 49.76 | 0.13 | 0.14 | 0.15 | 0.07 | 100.32 |
| ELD_N476D | 63.24 | 0.10 | 0.03 | 0.09 | 0.06 | 222.11 |
| ELD_I479T | 49.59 | 0.05 | 0.20 | 0.03 | 0.09 | 134.46 |
| ELD_Q481E | 65.37 | 0.07 | 0.12 | 0.13 | 0.07 | 168.40 |
| ELD_N527D | 42.99 | 0.45 | 0.15 | 0.31 | 0.06 | 44.51 |
| ELD_Q531R | 53.22 | 0.73 | 0.21 | 0.23 | 0.16 | 40.16 |
| ELD_R416D | 40.79 | 0.07 | 0.39 | 0.05 | 0.05 | 73.16 |
| ELD_R416E | 57.69 | 0.13 | 1.39 | 0.09 | 0.11 | 33.54 |
| ELD_R416N | 62.32 | 0.32 | 1.90 | 0.45 | 0.13 | 22.24 |
| ELD_R416S | 47.72 | 0.37 | 1.19 | 0.82 | 0.19 | 18.57 |
| ELD_K525A | 55.65 | 0.07 | 0.23 | 0.10 | 0.15 | 101.13 |
| ELD_K525E | 49.34 | 0.05 | 0.08 | 0.09 | 0.08 | 164.69 |
| ELD_K525G | 47.83 | 0.12 | 0.25 | 0.06 | 0.12 | 86.58 |
| ELD_K525S | 60.06 | 0.28 | 0.37 | 0.16 | 0.16 | 62.41 |
| GFP | 0.01 | 0.02 | 0.03 | 0.02 | 0.05 | NA |
| GFP | 0.01 | 0.03 | 0.02 | 0.05 | 0.06 | NA |
| parental | 1.02 | 1.07 | 1.23 | 1.08 | 0.87 | 0.93 |
| parental | 0.99 | 1.08 | 1.06 | 1.13 | 1.10 | 0.90 |
| parental | 0.98 | 0.78 | 0.74 | 0.79 | 0.96 | 1.21 |
| parental | 1.01 | 1.07 | 0.97 | 1.01 | 1.07 | 0.96 |
| half dose | 0.66 | 0.30 | 0.22 | 0.19 | 0.19 | 2.54 |
| half dose | 0.67 | 0.30 | 0.13 | 0.29 | 0.19 | 2.71 |
| half dose | 0.63 | 0.19 | 0.20 | 0.21 | 0.17 | 3.22 |
| half dose | 0.60 | 0.21 | 0.18 | 0.20 | 0.17 | 2.97 |
| ELD_N527A | 0.44 | 0.19 | 0.20 | 0.43 | 0.29 | 1.84 |
| ELD_N527C | 0.35 | 0.20 | 0.15 | 0.25 | 0.18 | 1.78 |
| ELD_N527D | 0.96 | 0.10 | 0.06 | 0.21 | 0.12 | 8.61 |
| ELD_N527E | 0.40 | 0.02 | 0.05 | 0.13 | 0.09 | 8.40 |
| ELD_N527F | 0.11 | 0.05 | 0.09 | 0.15 | 0.02 | 1.58 |
| ELD_N527G | 0.54 | 0.30 | 0.54 | 0.61 | 0.74 | 1.18 |
| ELD_N527H | 0.44 | 0.41 | 0.63 | 0.56 | 0.13 | 0.98 |
| ELD_N527I | 0.03 | 0.01 | 0.01 | 0.07 | 0.01 | 1.80 |
| ELD_N527K | 0.31 | 0.32 | 0.38 | 0.50 | 0.11 | 0.92 |
| ELD_N527L | 0.07 | 0.05 | 0.07 | 0.09 | 0.06 | 1.11 |
| ELD_N527M | 0.14 | 0.11 | 0.11 | 0.24 | 0.08 | 1.14 |
| ELD_N527P | 0.74 | 0.62 | 0.56 | 0.73 | 0.66 | 1.16 |
| ELD_N527Q | 0.55 | 0.65 | 1.02 | 1.15 | 1.03 | 0.64 |
| ELD_N527R | 0.37 | 0.42 | 0.62 | 0.38 | 0.29 | 0.82 |
| ELD_N527S | 0.48 | 0.23 | 0.39 | 0.38 | 0.34 | 1.59 |
| ELD_N527T | 0.54 | 0.06 | 0.08 | 0.12 | 0.04 | 7.32 |
| ELD_N527V | 0.09 | 0.03 | 0.05 | 0.11 | 0.06 | 1.76 |
| ELD_N527W | 0.07 | 0.04 | 0.03 | 0.11 | 0.04 | 1.46 |
| ELD_N527Y | 0.11 | 0.05 | 0.11 | 0.12 | 0.06 | 1.50 |
| ELD_Q481A | 1.19 | 0.01 | 0.06 | 0.14 | 0.05 | 25.92 |
| ELD_Q481C | 1.32 | 0.01 | 0.16 | 0.36 | 0.23 | 11.17 |
| ELD_Q481D | 1.67 | 0.13 | 0.12 | 0.89 | 0.31 | 6.60 |
| ELD_Q481E | 1.30 | 0.01 | 0.03 | 0.12 | 0.05 | 40.19 |
| ELD_Q481F | 0.01 | 0.00 | 0.03 | 0.02 | 0.05 | 0.57 |
| ELD_Q481G | 0.71 | 0.11 | 0.19 | 0.75 | 0.25 | 3.13 |
| ELD_Q481H | 1.52 | 1.80 | 3.18 | 1.80 | 0.16 | 0.79 |
| ELD_Q481I | 0.02 | 0.01 | 0.02 | 0.07 | 0.02 | 0.85 |
| ELD_Q481K | 0.42 | 0.01 | 0.04 | 0.05 | 0.04 | 16.55 |
| ELD_Q481L | 0.03 | 0.01 | 0.03 | 0.04 | 0.03 | 1.27 |
| ELD_Q481M | 0.12 | 0.00 | 0.03 | 0.04 | 0.04 | 5.78 |
| ELD_Q481N | 0.78 | 0.32 | 0.29 | 0.66 | 0.23 | 2.23 |
| ELD_Q481P | 0.04 | 0.00 | 0.01 | 0.07 | 0.04 | 2.29 |
| ELD_Q481R | 0.12 | 0.01 | 0.04 | 0.04 | 0.01 | 7.38 |
| ELD_Q481S | 1.08 | 0.01 | 0.04 | 0.14 | 0.04 | 27.73 |
| ELD_Q481T | 0.78 | 0.01 | 0.04 | 0.11 | 0.01 | 24.22 |
| ELD_Q481V | 0.03 | 0.01 | 0.03 | 0.06 | 0.02 | 1.34 |
| ELD_Q481W | 0.01 | 0.01 | 0.01 | 0.04 | 0.03 | 0.32 |
| ELD_Q481Y | 0.04 | 0.01 | 0.02 | 0.05 | 0.02 | 1.93 |
| ELD_S418D | 1.06 | 0.03 | 0.08 | 0.16 | 0.08 | 16.19 |
| ELD_N476D | 1.35 | 0.03 | 0.02 | 0.10 | 0.06 | 35.85 |
| ELD_I479T | 1.06 | 0.01 | 0.11 | 0.03 | 0.09 | 21.71 |
| ELD_Q481E | 1.39 | 0.02 | 0.07 | 0.13 | 0.07 | 27.18 |
| ELD_N527D | 0.92 | 0.11 | 0.09 | 0.32 | 0.06 | 7.18 |
| ELD_Q531R | 1.13 | 0.18 | 0.12 | 0.24 | 0.16 | 6.48 |
| ELD_R416D | 0.87 | 0.02 | 0.23 | 0.05 | 0.05 | 11.81 |
| ELD_R416E | 1.23 | 0.03 | 0.80 | 0.10 | 0.12 | 5.41 |
| ELD_R416N | 1.33 | 0.08 | 1.10 | 0.46 | 0.14 | 3.59 |
| ELD_R416S | 1.02 | 0.09 | 0.69 | 0.84 | 0.20 | 3.00 |
| ELD_K525A | 1.18 | 0.02 | 0.13 | 0.11 | 0.15 | 16.33 |
| ELD_K525E | 1.05 | 0.01 | 0.05 | 0.09 | 0.09 | 26.58 |
| ELD_K525G | 1.02 | 0.03 | 0.14 | 0.06 | 0.13 | 13.98 |
| ELD_K525S | 1.28 | 0.07 | 0.21 | 0.17 | 0.16 | 10.07 |
| GFP | 0.00 | 0.01 | 0.02 | 0.02 | 0.06 | ND |
| GFP | 0.00 | 0.01 | 0.01 | 0.05 | 0.06 | ND |

TABLE 13B

| | AAVS1 | OT1 | OT2 | OT3 | OT4 | ratio |
|---|---|---|---|---|---|---|
| parental | 47.96 | 4.32 | 2.12 | 1.05 | 0.84 | 5.76 |
| parental | 46.45 | 4.34 | 1.84 | 1.11 | 1.06 | 5.57 |
| parental | 45.83 | 3.15 | 1.28 | 0.77 | 0.92 | 7.49 |
| parental | 47.63 | 4.30 | 1.67 | 0.99 | 1.03 | 5.97 |
| half dose | 30.79 | 1.21 | 0.38 | 0.19 | 0.18 | 15.72 |
| half dose | 31.59 | 1.19 | 0.23 | 0.28 | 0.18 | 16.78 |
| half dose | 29.49 | 0.76 | 0.35 | 0.21 | 0.16 | 19.93 |
| half dose | 28.04 | 0.85 | 0.31 | 0.20 | 0.17 | 18.41 |
| KKR_N527A | 18.75 | 0.77 | 0.48 | 0.29 | 0.43 | 9.48 |
| KKR_N527C | 9.00 | 0.30 | 0.39 | 0.17 | 0.21 | 8.43 |
| KKR_N527D | 46.36 | 0.77 | 0.48 | 0.61 | 0.21 | 22.42 |
| KKR_N527E | 24.41 | 0.65 | 0.66 | 0.25 | 0.26 | 13.36 |
| KKR_N527F | 3.53 | 0.14 | 0.21 | 0.06 | 0.06 | 7.42 |
| KKR_N527G | 26.10 | 1.25 | 0.46 | 0.54 | 0.45 | 9.69 |
| KKR_N527H | 16.67 | 0.89 | 0.99 | 0.40 | 0.31 | 6.42 |
| KKR_N527I | 0.98 | 0.03 | 0.07 | 0.03 | 0.02 | 6.78 |
| KKR_N527K | 18.96 | 0.77 | 0.77 | 0.40 | 0.34 | 8.32 |
| KKR_N527L | ND | ND | ND | ND | ND | ND |
| KKR_N527M | 5.67 | 0.22 | 0.43 | 0.20 | 0.18 | 5.48 |
| KKR_N527P | 15.11 | 0.10 | 0.10 | 0.13 | 0.05 | 39.87 |
| KKR_N527Q | 17.36 | 1.69 | 1.19 | 0.40 | 0.34 | 4.79 |
| KKR_N527R | ND | ND | ND | ND | ND | ND |
| KKR_N527S | 20.83 | 0.84 | 0.44 | 0.49 | 0.31 | 10.04 |
| KKR_N527T | ND | ND | ND | ND | ND | ND |
| KKR_N527V | 1.40 | 0.04 | 0.05 | 0.07 | 0.02 | 7.59 |
| KKR_N527W | ND | ND | ND | ND | ND | ND |
| KKR_N527Y | ND | ND | ND | ND | ND | ND |
| KKR_Q481A | 48.27 | 0.15 | 0.05 | 0.03 | 0.09 | 150.70 |
| KKR_Q481C | 53.52 | 1.44 | 0.15 | 0.04 | 0.28 | 27.84 |
| KKR_Q481D | 60.01 | 1.15 | 0.07 | 0.10 | 0.30 | 37.18 |
| KKR_Q481E | 56.82 | 0.18 | 0.04 | 0.03 | 0.08 | 167.29 |
| KKR_Q481F | 0.88 | 0.05 | 0.04 | 0.04 | 0.05 | 5.12 |
| KKR_Q481G | 23.60 | 2.40 | 0.55 | 0.25 | 0.31 | 6.72 |
| KKR_Q481H | 55.88 | 2.69 | 0.15 | 0.51 | 2.74 | 9.18 |
| KKR_Q481I | 2.97 | 0.03 | 0.05 | 0.04 | 0.02 | 21.98 |
| KKR_Q481K | 2.17 | 0.03 | 0.03 | 0.02 | 0.06 | 16.91 |
| KKR_Q481L | 6.95 | 0.03 | 0.01 | 0.03 | 0.03 | 66.91 |
| KKR_Q481M | 21.59 | 0.06 | 0.04 | 0.06 | 0.03 | 116.95 |
| KKR_Q481N | 38.65 | 0.50 | 0.09 | 0.12 | 0.22 | 41.46 |
| KKR_Q481P | 4.78 | 0.03 | 0.07 | 0.02 | 0.03 | 31.55 |
| KKR_Q481R | 7.85 | 0.05 | 0.04 | 0.05 | 0.02 | 47.90 |
| KKR_Q481S | 47.95 | 0.29 | 0.07 | 0.03 | 0.11 | 93.90 |
| KKR_Q481T | 35.61 | 0.06 | 0.06 | 0.04 | 0.05 | 170.00 |
| KKR_Q481V | 2.27 | 0.02 | 0.03 | 0.07 | 0.03 | 15.14 |
| KKR_Q481W | 0.11 | 0.03 | 0.02 | 0.04 | 0.01 | 1.10 |
| KKR_Q481Y | 12.71 | 0.22 | 0.03 | 0.09 | 0.11 | 28.31 |
| KKR_S418D | 49.74 | 0.26 | 0.10 | 0.08 | 0.13 | 89.43 |
| KKR_N476D | 27.43 | 0.03 | 0.02 | 0.07 | 0.03 | 166.00 |
| KKR_I479T | 51.62 | 0.29 | 0.13 | 0.25 | 0.12 | 65.91 |
| KKR_Q481E | 52.15 | 0.07 | 0.09 | 0.08 | 0.09 | 158.02 |
| KKR_N527D | 46.85 | 1.06 | 0.60 | 0.70 | 0.85 | 14.62 |
| KKR_Q531R | 43.62 | 0.65 | 0.79 | 0.41 | 0.27 | 20.59 |
| KKR_R416D | 47.19 | 0.14 | 0.03 | 0.11 | 0.20 | 97.96 |
| KKR_R416E | 56.98 | 0.55 | 0.04 | 0.04 | 0.78 | 40.63 |
| KKR_R416N | 60.68 | 1.19 | 0.18 | 0.28 | 1.20 | 21.34 |
| KKR_R416S | 44.42 | 1.37 | 0.21 | 0.18 | 0.51 | 19.53 |
| KKR_K525A | 49.24 | 0.19 | 0.03 | 0.07 | 0.14 | 112.49 |
| KKR_K525E | 42.36 | 0.06 | 0.06 | 0.06 | 0.07 | 163.51 |
| KKR_K525G | 44.05 | 0.47 | 0.09 | 0.07 | 0.27 | 48.61 |
| KKR_K525S | 50.87 | 0.44 | 0.08 | 0.16 | 0.29 | 52.53 |
| GFP | 0.01 | 0.02 | 0.03 | 0.02 | 0.05 | NA |
| GFP | 0.01 | 0.03 | 0.02 | 0.05 | 0.06 | NA |
| parental | 1.02 | 1.07 | 1.23 | 1.08 | 0.87 | 0.93 |
| parental | 0.99 | 1.08 | 1.06 | 1.13 | 1.10 | 0.90 |
| parental | 0.98 | 0.78 | 0.74 | 0.79 | 0.96 | 1.21 |
| parental | 1.01 | 1.07 | 0.97 | 1.01 | 1.07 | 0.96 |

TABLE 13B-continued

|  | AAVS1 | OT1 | OT2 | OT3 | OT4 | ratio |
|---|---|---|---|---|---|---|
| half dose | 0.66 | 0.30 | 0.22 | 0.19 | 0.19 | 2.54 |
| half dose | 0.67 | 0.30 | 0.13 | 0.29 | 0.19 | 2.71 |
| half dose | 0.63 | 0.19 | 0.20 | 0.21 | 0.17 | 3.22 |
| half dose | 0.60 | 0.21 | 0.18 | 0.20 | 0.17 | 2.97 |
| KKR_N527A | 0.40 | 0.19 | 0.28 | 0.30 | 0.45 | 1.53 |
| KKR_N527C | 0.19 | 0.07 | 0.23 | 0.17 | 0.21 | 1.36 |
| KKR_N527D | 0.99 | 0.19 | 0.28 | 0.62 | 0.22 | 3.62 |
| KKR_N527E | 0.52 | 0.16 | 0.38 | 0.26 | 0.27 | 2.16 |
| KKR_N527F | 0.08 | 0.04 | 0.12 | 0.06 | 0.07 | 1.20 |
| KKR_N527G | 0.56 | 0.31 | 0.27 | 0.55 | 0.47 | 1.56 |
| KKR_N527H | 0.35 | 0.22 | 0.58 | 0.40 | 0.33 | 1.04 |
| KKR_N527I | 0.02 | 0.01 | 0.04 | 0.03 | 0.02 | 1.09 |
| KKR_N527K | 0.40 | 0.19 | 0.45 | 0.41 | 0.36 | 1.34 |
| KKR_N527L | ND | ND | ND | ND | ND | ND |
| KKR_N527M | 0.12 | 0.06 | 0.25 | 0.20 | 0.19 | 0.88 |
| KKR_N527P | 0.32 | 0.03 | 0.06 | 0.13 | 0.05 | 6.44 |
| KKR_N527Q | 0.37 | 0.42 | 0.69 | 0.41 | 0.36 | 0.77 |
| KKR_N527R | ND | ND | ND | ND | ND | ND |
| KKR_N527S | 0.44 | 0.21 | 0.25 | 0.50 | 0.32 | 1.62 |
| KKR_N527T | ND | ND | ND | ND | ND | ND |
| KKR_N527V | 0.03 | 0.01 | 0.03 | 0.07 | 0.02 | 1.23 |
| KKR_N527W | ND | ND | ND | ND | ND | ND |
| KKR_N527Y | ND | ND | ND | ND | ND | ND |
| KKR_Q481A | 1.03 | 0.04 | 0.03 | 0.03 | 0.09 | 24.33 |
| KKR_Q481C | 1.14 | 0.36 | 0.09 | 0.04 | 0.30 | 4.49 |
| KKR_Q481D | 1.28 | 0.29 | 0.04 | 0.10 | 0.31 | 6.00 |
| KKR_Q481E | 1.21 | 0.05 | 0.02 | 0.03 | 0.08 | 27.00 |
| KKR_Q481F | 0.02 | 0.01 | 0.02 | 0.04 | 0.05 | 0.83 |
| KKR_Q481G | 0.50 | 0.60 | 0.32 | 0.26 | 0.33 | 1.08 |
| KKR_Q481H | 1.19 | 0.67 | 0.09 | 0.52 | 0.11 | 2.85 |
| KKR_Q481I | 0.06 | 0.01 | 0.03 | 0.04 | 0.02 | 3.55 |
| KKR_Q481K | 0.05 | 0.01 | 0.02 | 0.02 | 0.06 | 2.73 |
| KKR_Q481L | 0.15 | 0.01 | 0.01 | 0.03 | 0.03 | 10.80 |
| KKR_Q481M | 0.46 | 0.01 | 0.02 | 0.06 | 0.03 | 18.88 |
| KKR_Q481N | 0.82 | 0.12 | 0.05 | 0.12 | 0.23 | 6.69 |
| KKR_Q481P | 0.10 | 0.01 | 0.04 | 0.02 | 0.03 | 5.09 |
| KKR_Q481R | 0.17 | 0.01 | 0.02 | 0.05 | 0.03 | 7.73 |
| KKR_Q481S | 1.02 | 0.07 | 0.04 | 0.03 | 0.11 | 15.16 |
| KKR_Q481T | 0.76 | 0.01 | 0.04 | 0.04 | 0.05 | 27.44 |
| KKR_Q481V | 0.05 | 0.01 | 0.02 | 0.07 | 0.03 | 2.44 |
| KKR_Q481W | 0.00 | 0.01 | 0.01 | 0.04 | 0.01 | 0.18 |
| KKR_Q481Y | 0.27 | 0.05 | 0.02 | 0.09 | 0.11 | 4.57 |
| KKR_S418D | 1.06 | 0.06 | 0.06 | 0.08 | 0.13 | 14.44 |
| KKR_N476D | 0.58 | 0.01 | 0.04 | 0.08 | 0.04 | 26.80 |
| KKR_I479T | 1.10 | 0.07 | 0.08 | 0.25 | 0.12 | 10.64 |
| KKR_Q481E | 1.11 | 0.02 | 0.05 | 0.08 | 0.09 | 25.51 |
| KKR_N527D | 1.00 | 0.26 | 0.35 | 0.71 | 0.88 | 2.36 |
| KKR_Q531R | 0.93 | 0.16 | 0.46 | 0.42 | 0.28 | 3.32 |
| KKR_R416D | 1.00 | 0.03 | 0.02 | 0.11 | 0.21 | 15.81 |
| KKR_R416E | 1.21 | 0.14 | 0.02 | 0.04 | 0.81 | 6.56 |
| KKR_R416N | 1.29 | 0.29 | 0.10 | 0.28 | 1.25 | 3.44 |
| KKR_R416S | 0.95 | 0.34 | 0.12 | 0.19 | 0.53 | 3.15 |
| KKR_K525A | 1.05 | 0.05 | 0.02 | 0.07 | 0.15 | 18.16 |
| KKR_K525E | 0.90 | 0.02 | 0.03 | 0.06 | 0.08 | 26.39 |
| KKR_K525G | 0.94 | 0.12 | 0.05 | 0.08 | 0.28 | 7.85 |
| KKR_K525S | 1.08 | 0.11 | 0.05 | 0.16 | 0.30 | 8.48 |
| GFP | 0.00 | 0.01 | 0.02 | 0.02 | 0.06 | ND |
| GFP | 0.00 | 0.01 | 0.01 | 0.05 | 0.06 | ND |

TABLE 13C

|  | AAVS1 | OT1 | OT2 | OT3 | OT4 | ratio |
|---|---|---|---|---|---|---|
| parental | 47.96 | 4.32 | 2.12 | 1.05 | 0.84 | 5.76 |
| parental | 46.45 | 4.34 | 1.84 | 1.11 | 1.06 | 5.57 |
| parental | 45.83 | 3.15 | 1.28 | 0.77 | 0.92 | 7.49 |
| parental | 47.63 | 4.30 | 1.67 | 0.99 | 1.03 | 5.97 |
| half dose | 30.79 | 1.21 | 0.38 | 0.19 | 0.18 | 15.72 |
| half dose | 31.59 | 1.19 | 0.23 | 0.28 | 0.18 | 16.78 |
| half dose | 29.49 | 0.76 | 0.35 | 0.21 | 0.16 | 19.93 |
| half dose | 28.04 | 0.85 | 0.31 | 0.20 | 0.17 | 18.41 |
| ELD_KKR_N527A | 8.62 | 0.25 | 0.14 | 0.13 | 0.17 | 12.54 |
| ELD_KKR_N527C | 3.27 | 0.10 | 0.08 | 0.04 | 0.09 | 10.70 |
| ELD_KKR_N527D | 34.90 | 0.05 | 0.04 | 0.07 | 0.07 | 155.15 |
| ELD_KKR_N527E | 4.64 | 0.03 | 0.03 | 0.05 | 0.06 | 26.18 |

TABLE 13C-continued

|  | AAVS1 | OT1 | OT2 | OT3 | OT4 | ratio |
|---|---|---|---|---|---|---|
| ELD_KKR_N527F | 0.68 | 0.03 | 0.07 | 0.05 | 0.04 | 3.54 |
| ELD_KKR_N527G | 12.78 | 0.30 | 0.08 | 0.40 | 0.34 | 11.37 |
| ELD_KKR_N527H | 7.94 | 0.58 | 0.68 | 0.31 | 0.22 | 4.44 |
| ELD_KKR_N527I | 0.02 | 0.03 | 0.03 | 0.01 | 0.06 | 0.13 |
| ELD_KKR_N527K | 6.75 | 0.36 | 0.29 | 0.29 | 0.12 | 6.35 |
| ELD_KKR_N527L | 3.18 | 0.13 | 0.10 | 0.15 | 0.06 | 7.23 |
| ELD_KKR_N527M | 1.31 | 0.07 | 0.14 | 0.09 | 0.09 | 3.29 |
| ELD_KKR_N527P | 10.03 | 0.04 | 0.04 | 0.06 | 0.06 | 48.92 |
| ELD_KKR_N527Q | 9.15 | 0.90 | 0.82 | 0.33 | 0.20 | 4.07 |
| ELD_KKR_N527R | 16.97 | 1.78 | 1.21 | 0.54 | 0.35 | 4.37 |
| ELD_KKR_N527S | 9.71 | 0.12 | 0.14 | 0.15 | 0.16 | 16.85 |
| ELD_KKR_N527T | 26.89 | 0.14 | 0.08 | 0.16 | 0.11 | 55.91 |
| ELD_KKR_N527V | 1.39 | 0.30 | 0.03 | 0.09 | 0.10 | 2.67 |
| ELD_KKR_N527W | 1.86 | 0.06 | 0.05 | 0.05 | 0.07 | 8.21 |
| ELD_KKR_N527Y | 2.63 | 0.09 | 0.10 | 0.09 | 0.09 | 7.19 |
| ELD_KKR_Q481A | 86.30 | 0.02 | 0.04 | 0.04 | 0.09 | 462.88 |
| ELD_KKR_Q481C | 66.07 | 0.05 | 0.03 | 0.05 | 0.09 | 300.25 |
| ELD_KKR_Q481D | 90.46 | 0.12 | 0.05 | 0.10 | 0.16 | 214.39 |
| ELD_KKR_Q481E | 57.02 | 0.04 | 0.03 | 0.04 | 0.05 | 343.26 |
| ELD_KKR_Q481F | 0.02 | 0.04 | 0.02 | 0.08 | 0.05 | 0.09 |
| ELD_KKR_Q481G | 18.06 | 0.34 | 0.13 | 0.18 | 0.12 | 23.46 |
| ELD_KKR_Q481H | 84.29 | 22.17 | 0.65 | 4.71 | 1.07 | 2.95 |
| ELD_KKR_Q481I | 0.05 | 0.03 | 0.01 | 0.02 | 0.06 | 0.47 |
| ELD_KKR_Q481K | 3.36 | 0.03 | 0.05 | 0.02 | 0.10 | 17.13 |
| ELD_KKR_Q481L | 0.12 | 0.03 | 0.01 | 0.03 | 0.06 | 0.96 |
| ELD_KKR_Q481M | 1.92 | 0.03 | 0.03 | 0.09 | 0.08 | 8.29 |
| ELD_KKR_Q481N | 29.35 | 0.20 | 0.05 | 0.13 | 0.09 | 62.01 |
| ELD_KKR_Q481P | 0.45 | 0.03 | 0.05 | 0.03 | 0.10 | 1.82 |
| ELD_KKR_Q481R | 3.75 | 0.03 | 0.04 | 0.03 | 0.03 | 28.89 |
| ELD_KKR_Q481S | 54.96 | 0.02 | 0.04 | 0.07 | 0.05 | 308.59 |
| ELD_KKR_Q481T | 33.31 | 0.02 | 0.02 | 0.00 | 0.07 | 290.95 |
| ELD_KKR_Q481V | 0.11 | 0.03 | 0.01 | 0.03 | 0.09 | 0.67 |
| ELD_KKR_Q481W | 0.01 | 0.02 | 0.04 | 0.04 | 0.07 | 0.06 |
| ELD_KKR_Q481Y | 0.40 | 0.03 | 0.01 | 0.02 | 0.05 | 3.52 |
| ELD_KKR_S418D | 40.13 | 0.03 | 0.03 | 0.03 | 0.06 | 278.01 |
| ELD_KKR_N476D | 5.72 | 0.03 | 0.04 | 0.02 | 0.02 | 53.02 |
| ELD_KKR_I479T | 45.10 | 0.04 | 0.04 | 0.06 | 0.07 | 214.05 |
| ELD_KKR_Q481E | 68.22 | 0.02 | 0.04 | 0.09 | 0.07 | 308.56 |
| ELD_KKR_N527D | 29.60 | 0.05 | 0.04 | 0.14 | 0.08 | 98.76 |
| ELD_KKR_Q531R | 46.16 | 0.20 | 0.10 | 0.09 | 0.09 | 95.03 |
| ELD_KKR_R416D | 54.14 | 0.03 | 0.01 | 0.04 | 0.10 | 298.38 |
| ELD_KKR_R416E | 79.47 | 0.13 | 0.16 | 0.12 | 0.09 | 157.31 |
| ELD_KKR_R416N | 80.25 | 0.32 | 0.23 | 0.43 | 0.26 | 64.21 |
| ELD_KKR_R416S | 51.99 | 0.25 | 0.16 | 0.20 | 0.12 | 72.26 |
| ELD_KKR_K525A | 56.83 | 0.03 | 0.01 | 0.04 | 0.03 | 508.42 |
| ELD_KKR_K525E | 19.36 | 0.03 | 0.02 | 0.05 | 0.07 | 114.28 |
| ELD_KKR_K525G | 46.19 | 0.03 | 0.04 | 0.09 | 0.08 | 186.72 |
| ELD_KKR_K525S | 68.60 | 0.03 | 0.07 | 0.05 | 0.08 | 301.52 |
| GFP | 0.01 | 0.02 | 0.03 | 0.02 | 0.05 | NA |
| GFP | 0.01 | 0.03 | 0.02 | 0.05 | 0.06 | NA |
| parental | 1.02 | 1.07 | 1.23 | 1.08 | 0.87 | 0.93 |
| parental | 0.99 | 1.08 | 1.06 | 1.13 | 1.10 | 0.90 |
| parental | 0.98 | 0.78 | 0.74 | 0.79 | 0.96 | 1.21 |
| parental | 1.01 | 1.07 | 0.97 | 1.01 | 1.07 | 0.96 |
| half dose | 0.66 | 0.30 | 0.22 | 0.19 | 0.19 | 2.54 |
| half dose | 0.67 | 0.30 | 0.13 | 0.29 | 0.19 | 2.71 |
| half dose | 0.63 | 0.19 | 0.20 | 0.21 | 0.17 | 3.22 |
| half dose | 0.60 | 0.21 | 0.18 | 0.20 | 0.17 | 2.97 |
| ELD_KKR_N527A | 0.18 | 0.06 | 0.08 | 0.14 | 0.17 | 2.02 |
| ELD_KKR_N527C | 0.07 | 0.02 | 0.04 | 0.04 | 0.10 | 1.73 |
| ELD_KKR_N527D | 0.74 | 0.01 | 0.02 | 0.07 | 0.07 | 25.05 |
| ELD_KKR_N527E | 0.10 | 0.01 | 0.02 | 0.05 | 0.06 | 4.23 |
| ELD_KKR_N527F | 0.01 | 0.01 | 0.04 | 0.05 | 0.04 | 0.57 |
| ELD_KKR_N527G | 0.27 | 0.08 | 0.05 | 0.40 | 0.35 | 1.84 |
| ELD_KKR_N527H | 0.17 | 0.14 | 0.40 | 0.31 | 0.23 | 0.72 |
| ELD_KKR_N527I | 0.00 | 0.01 | 0.02 | 0.01 | 0.07 | 0.02 |
| ELD_KKR_N527K | 0.14 | 0.09 | 0.17 | 0.29 | 0.13 | 1.03 |
| ELD_KKR_N527L | 0.07 | 0.03 | 0.06 | 0.15 | 0.06 | 1.17 |
| ELD_KKR_N527M | 0.03 | 0.02 | 0.08 | 0.10 | 0.10 | 0.53 |
| ELD_KKR_N527P | 0.21 | 0.01 | 0.03 | 0.07 | 0.06 | 7.90 |
| ELD_KKR_N527Q | 0.19 | 0.22 | 0.48 | 0.34 | 0.21 | 0.66 |
| ELD_KKR_N527R | 0.36 | 0.44 | 0.70 | 0.55 | 0.36 | 0.71 |
| ELD_KKR_N527S | 0.21 | 0.03 | 0.08 | 0.15 | 0.17 | 2.72 |
| ELD_KKR_N527T | 0.57 | 0.03 | 0.04 | 0.17 | 0.11 | 9.02 |
| ELD_KKR_N527V | 0.03 | 0.07 | 0.02 | 0.09 | 0.10 | 0.43 |
| ELD_KKR_N527W | 0.04 | 0.02 | 0.03 | 0.05 | 0.07 | 1.33 |
| ELD_KKR_N527Y | 0.06 | 0.02 | 0.06 | 0.09 | 0.10 | 1.16 |
| ELD_KKR_Q481A | 1.84 | 0.00 | 0.02 | 0.04 | 0.09 | 74.72 |

TABLE 13C-continued

| | AAVS1 | OT1 | OT2 | OT3 | OT4 | ratio |
|---|---|---|---|---|---|---|
| ELD_KKR_Q481C | 1.41 | 0.01 | 0.02 | 0.05 | 0.10 | 48.47 |
| ELD_KKR_Q481D | 1.93 | 0.03 | 0.03 | 0.10 | 0.16 | 34.61 |
| ELD_KKR_Q481E | 1.21 | 0.01 | 0.02 | 0.04 | 0.05 | 55.41 |
| ELD_KKR_Q481F | 0.00 | 0.01 | 0.01 | 0.08 | 0.05 | 0.01 |
| ELD_KKR_Q481G | 0.38 | 0.08 | 0.07 | 0.18 | 0.13 | 3.79 |
| ELD_KKR_Q481H | 1.79 | 5.51 | 0.38 | 4.81 | 1.12 | 0.48 |
| ELD_KKR_Q481I | 0.00 | 0.01 | 0.00 | 0.02 | 0.06 | 0.08 |
| ELD_KKR_Q481K | 0.07 | 0.01 | 0.03 | 0.02 | 0.10 | 2.77 |
| ELD_KKR_Q481L | 0.00 | 0.01 | 0.01 | 0.03 | 0.06 | 0.16 |
| ELD_KKR_Q481M | 0.04 | 0.01 | 0.02 | 0.09 | 0.09 | 1.34 |
| ELD_KKR_Q481N | 0.62 | 0.05 | 0.03 | 0.13 | 0.09 | 10.01 |
| ELD_KKR_Q481P | 0.01 | 0.01 | 0.02 | 0.08 | 0.11 | 0.29 |
| ELD_KKR_Q481R | 0.08 | 0.01 | 0.02 | 0.03 | 0.03 | 4.66 |
| ELD_KKR_Q481S | 1.17 | 0.00 | 0.02 | 0.07 | 0.05 | 49.81 |
| ELD_KKR_Q481T | 0.71 | 0.01 | 0.01 | 0.00 | 0.07 | 46.97 |
| ELD_KKR_Q481V | 0.00 | 0.01 | 0.01 | 0.03 | 0.09 | 0.11 |
| ELD_KKR_Q481W | 0.00 | 0.00 | 0.02 | 0.04 | 0.08 | 0.01 |
| ELD_KKR_Q481Y | 0.01 | 0.01 | 0.01 | 0.02 | 0.05 | 0.57 |
| ELD_KKR_S418D | 0.85 | 0.01 | 0.02 | 0.03 | 0.06 | 44.88 |
| ELD_KKR_N476D | 0.12 | 0.01 | 0.02 | 0.02 | 0.02 | 8.56 |
| ELD_KKR_I479T | 0.96 | 0.01 | 0.02 | 0.06 | 0.07 | 34.55 |
| ELD_KKR_Q481E | 1.45 | 0.00 | 0.02 | 0.09 | 0.08 | 49.81 |
| ELD_KKR_N527D | 0.63 | 0.01 | 0.02 | 0.14 | 0.08 | 15.94 |
| ELD_KKR_Q531R | 0.98 | 0.05 | 0.06 | 0.09 | 0.09 | 15.34 |
| ELD_KKR_R416D | 1.15 | 0.01 | 0.01 | 0.04 | 0.10 | 48.17 |
| ELD_KKR_R416E | 1.69 | 0.03 | 0.09 | 0.12 | 0.09 | 25.39 |
| ELD_KKR_R416N | 1.71 | 0.08 | 0.13 | 0.44 | 0.28 | 10.37 |
| ELD_KKR_R416S | 1.11 | 0.06 | 0.09 | 0.20 | 0.12 | 11.66 |
| ELD_KKR_K525A | 1.21 | 0.01 | 0.01 | 0.04 | 0.03 | 82.07 |
| ELD_KKR_K525E | 0.41 | 0.01 | 0.01 | 0.05 | 0.08 | 18.45 |
| ELD_KKR_K525G | 0.98 | 0.01 | 0.03 | 0.09 | 0.08 | 30.14 |
| ELD_KKR_K525S | 1.46 | 0.01 | 0.04 | 0.05 | 0.08 | 48.67 |
| GFP | 0.00 | 0.01 | 0.02 | 0.02 | 0.06 | ND |
| GFP | 0.00 | 0.01 | 0.01 | 0.05 | 0.06 | ND |

Tables 14A-14C shows results with the indicated mutants.

TABLE 14A

| | AAVS1 | OT1 | OT2 | OT3 | OT4 | ratio |
|---|---|---|---|---|---|---|
| parental | 42.55 | 7.68 | 3.88 | 2.05 | 2.94 | 2.57 |
| parental | 41.57 | 6.44 | 3.50 | 1.64 | 2.72 | 2.91 |
| parental | 41.51 | 6.14 | 2.93 | 1.36 | 2.25 | 3.27 |
| parental | 38.53 | 6.24 | 3.14 | 1.32 | 2.35 | 2.95 |
| half dose | 32.45 | 2.46 | 1.00 | 0.46 | 0.63 | 7.14 |
| half dose | 31.98 | 2.41 | 1.02 | 0.53 | 0.51 | 7.16 |
| half dose | 27.34 | 1.29 | 0.45 | 0.19 | 0.34 | 12.05 |
| half dose | 30.04 | 2.06 | 0.91 | 0.36 | 0.61 | 7.63 |
| ELD_N476A | 43.61 | 3.28 | 1.86 | 1.50 | 1.15 | 5.60 |
| ELD_N476C | 46.78 | 3.74 | 1.92 | 1.35 | 0.97 | 5.86 |
| ELD_N476D | 67.25 | 0.20 | 0.09 | 0.18 | 0.16 | 106.44 |
| ELD_N476E | 65.43 | 0.07 | 0.06 | 0.08 | 0.07 | 228.99 |
| ELD_N476F | 18.10 | 1.22 | 1.12 | 0.77 | 0.39 | 5.16 |
| ELD_N476G | 62.70 | 3.13 | 0.60 | 0.56 | 0.41 | 13.33 |
| ELD_N476H | 41.57 | 4.94 | 3.07 | 1.81 | 2.48 | 3.38 |
| ELD_N476I | 30.48 | 0.21 | 0.55 | 0.29 | 0.25 | 23.42 |
| ELD_N476K | 32.00 | 3.78 | 1.00 | 1.62 | 0.46 | 4.67 |
| ELD_N476L | 12.47 | 0.13 | 0.15 | 0.14 | 0.10 | 23.76 |
| ELD_N476M | 27.91 | 2.27 | 1.14 | 0.73 | 0.81 | 5.64 |
| ELD_N476P | 40.20 | 6.83 | 3.21 | 1.40 | 2.79 | 2.82 |
| ELD_N476Q | 38.61 | 2.08 | 0.77 | 0.80 | 0.51 | 9.28 |
| ELD_N476R | 40.17 | 6.10 | 4.87 | 2.55 | 1.41 | 2.69 |
| ELD_N476S | 54.42 | 9.71 | 4.38 | 2.67 | 2.74 | 2.79 |
| ELD_N476T | 53.11 | 5.19 | 2.35 | 1.77 | 1.75 | 4.80 |
| ELD_N476V | 34.78 | 0.49 | 0.53 | 0.36 | 0.22 | 21.82 |
| ELD_N476W | 14.91 | 0.49 | 1.13 | 0.39 | 0.22 | 6.66 |
| ELD_N476Y | 26.63 | 2.53 | 1.63 | 0.73 | 1.41 | 4.24 |
| ELD_Q531A | 25.87 | 1.96 | 0.48 | 0.37 | 0.70 | 7.39 |
| ELD_Q531C | 12.57 | 0.16 | 0.11 | 0.21 | 0.09 | 21.86 |
| ELD_Q531D | 4.48 | 0.05 | 0.01 | 0.03 | 0.05 | 30.17 |
| ELD_Q531E | 29.54 | 0.06 | 0.02 | 0.06 | 0.05 | 150.94 |
| ELD_Q531F | 4.09 | 0.02 | 0.02 | 0.04 | 0.09 | 23.42 |
| ELD_Q531G | 7.39 | 0.56 | 0.20 | 0.27 | 0.45 | 5.00 |
| ELD_Q531H | 47.18 | 10.36 | 3.04 | 2.12 | 6.48 | 2.14 |
| ELD_Q531I | 25.66 | 0.05 | 0.02 | 0.04 | 0.06 | 141.34 |

TABLE 14A-continued

| | AAVS1 | OT1 | OT2 | OT3 | OT4 | ratio |
|---|---|---|---|---|---|---|
| ELD_Q531K | 42.12 | 7.43 | 4.18 | 1.80 | 6.55 | 2.11 |
| ELD_Q531L | 12.77 | 0.03 | 0.04 | 0.05 | 0.04 | 76.78 |
| ELD_Q531M | 30.65 | 0.35 | 0.40 | 0.31 | 0.19 | 24.46 |
| ELD_Q531N | 12.98 | 0.69 | 0.24 | 0.28 | 0.46 | 7.78 |
| ELD_Q531P | 5.30 | 0.05 | 0.03 | 0.08 | 0.05 | 26.25 |
| ELD_Q531R | 48.64 | 1.11 | 0.43 | 0.26 | 0.46 | 21.54 |
| ELD_Q531S | 14.86 | 0.39 | 0.17 | 0.20 | 0.33 | 13.64 |
| ELD_Q531T | 37.95 | 0.40 | 0.37 | 0.30 | 0.33 | 27.16 |
| ELD_Q531V | 33.24 | 0.11 | 0.12 | 0.12 | 0.02 | 87.92 |
| ELD_Q531W | 2.82 | 0.05 | 0.02 | 0.05 | 0.11 | 12.47 |
| ELD_Q531Y | 18.15 | 0.04 | 0.02 | 0.04 | 0.03 | 133.53 |
| ELD_S418D | 42.20 | 0.10 | 0.24 | 0.31 | 0.14 | 53.28 |
| ELD_N476D | 57.06 | 0.07 | 0.09 | 0.09 | 0.06 | 184.93 |
| ELD_I479T | 42.10 | 0.04 | 0.15 | 0.02 | 0.09 | 137.07 |
| ELD_Q481E | 52.80 | 0.04 | 0.04 | 0.19 | 0.09 | 145.99 |
| ELD_N527D | 35.32 | 0.60 | 0.18 | 0.24 | 0.08 | 32.04 |
| ELD_Q531R | 43.15 | 0.74 | 0.25 | 0.20 | 0.29 | 29.03 |
| ELD_R416N | 58.18 | 0.48 | 2.31 | 0.46 | 0.14 | 17.21 |
| ELD_R416D | 36.27 | 0.11 | 0.59 | 0.08 | 0.04 | 44.30 |
| ELD_R416E | 55.41 | 0.17 | 2.40 | 0.23 | 0.09 | 19.15 |
| ELD_R416S | 39.03 | 0.37 | 1.26 | 0.47 | 0.27 | 16.49 |
| ELD_K525A | 46.87 | 0.27 | 0.24 | 0.17 | 0.06 | 63.48 |
| ELD_K525E | 40.21 | 0.05 | 0.05 | 0.10 | 0.04 | 167.71 |
| ELD_K525G | 35.64 | 0.21 | 0.15 | 0.08 | 0.06 | 70.09 |
| ELD_K525S | 49.97 | 0.23 | 0.28 | 0.31 | 0.20 | 48.28 |
| ELD_Q481A | 55.82 | 0.04 | 0.05 | 0.16 | 0.05 | 191.70 |
| ELD_Q481D | 71.61 | 0.83 | 0.13 | 1.15 | 0.38 | 28.73 |
| ELD_Q481C | 50.24 | 0.17 | 0.16 | 0.23 | 0.20 | 66.34 |
| ELD_Q481S | 40.58 | 0.09 | 0.08 | 0.07 | 0.10 | 118.21 |
| ELD_S418E | 53.03 | 0.09 | 0.15 | 0.06 | 0.16 | 113.62 |
| ELD_R422H | 36.38 | 0.77 | 1.01 | 0.48 | 0.22 | 14.68 |
| ELD_I479Q | 58.23 | 0.03 | 0.03 | 0.05 | 0.06 | 337.38 |
| GFP | 0.09 | 0.03 | 0.01 | ND | 0.04 | NA |
| GFP | 0.08 | 0.02 | 0.03 | 0.01 | 0.02 | NA |

TABLE 14B

| | AAVS1 | OT1 | OT2 | OT3 | OT4 | ratio |
|---|---|---|---|---|---|---|
| parental | 42.55 | 7.68 | 3.88 | 2.05 | 2.94 | 2.57 |
| parental | 41.57 | 6.44 | 3.50 | 1.64 | 2.72 | 2.91 |
| parental | 41.51 | 6.14 | 2.93 | 1.36 | 2.25 | 3.27 |
| parental | 38.53 | 6.24 | 3.14 | 1.32 | 2.35 | 2.95 |
| half dose | 32.45 | 2.46 | 1.00 | 0.46 | 0.63 | 7.14 |
| half dose | 31.98 | 2.41 | 1.02 | 0.53 | 0.51 | 7.16 |
| half dose | 27.34 | 1.29 | 0.45 | 0.19 | 0.34 | 12.05 |
| half dose | 30.04 | 2.06 | 0.91 | 0.36 | 0.61 | 7.63 |
| KKR_N476A | 41.76 | 3.81 | 1.60 | 1.20 | 1.97 | 4.87 |
| KKR_N476C | 44.42 | 3.25 | 1.35 | 0.98 | 1.44 | 6.32 |
| KKR_N476D | 31.25 | 0.10 | 0.16 | 0.06 | 0.04 | 88.08 |
| KKR_N476E | 37.65 | 0.07 | 0.04 | 0.04 | 0.03 | 220.42 |
| KKR_N476F | 15.09 | 1.21 | 0.60 | 0.29 | 0.38 | 6.09 |
| KKR_N476G | 45.33 | 2.34 | 0.59 | 1.16 | 0.85 | 9.19 |
| KKR_N476H | 41.14 | 7.08 | 2.71 | 1.20 | 2.06 | 3.15 |
| KKR_N476I | 33.90 | 0.59 | 0.30 | 0.16 | 0.30 | 25.33 |
| KKR_N476K | 41.23 | 2.04 | 0.87 | 1.11 | 0.88 | 8.40 |
| KKR_N476L | 11.80 | 0.23 | 0.13 | 0.09 | 0.12 | 20.83 |
| KKR_N476M | 30.41 | 2.34 | 2.79 | 0.75 | 0.77 | 6.53 |
| KKR_N476P | 33.04 | 3.11 | 1.21 | 1.38 | 2.72 | 3.92 |
| KKR_N476Q | 38.61 | 1.03 | 0.42 | 0.50 | 0.58 | 15.21 |
| KKR_N476R | 44.34 | 6.29 | 3.71 | 1.38 | 3.07 | 3.07 |
| KKR_N476S | 49.87 | 9.00 | 3.00 | 2.07 | 4.76 | 2.65 |
| KKR_N476T | 48.39 | 4.98 | 2.03 | 1.55 | 2.71 | 4.29 |
| KKR_N476V | 39.89 | 0.55 | 0.23 | 0.22 | 0.46 | 27.20 |
| KKR_N476W | 13.62 | 1.05 | 1.64 | 0.36 | 0.38 | 3.97 |
| KKR_N476Y | 26.14 | 2.86 | 1.46 | 1.06 | 0.50 | 4.45 |
| KKR_Q531A | 33.77 | 3.29 | 2.47 | 0.89 | 0.94 | 4.45 |
| KKR_Q531C | 13.20 | 0.33 | 0.21 | 0.28 | 0.12 | 14.06 |
| KKR_Q531D | 6.11 | 0.05 | 0.02 | 0.04 | 0.08 | 31.32 |
| KKR_Q531E | 18.16 | 0.32 | 0.30 | 0.57 | 0.13 | 13.71 |
| KKR_Q531F | 4.27 | 0.04 | 0.04 | 0.04 | 0.06 | 24.16 |
| KKR_Q531G | 7.06 | 0.63 | 1.39 | 0.35 | 0.25 | 2.70 |
| KKR_Q531H | 38.76 | 6.91 | 1.57 | 0.91 | 2.35 | 3.30 |
| KKR_Q531I | 32.37 | 0.15 | 0.03 | 0.08 | 0.07 | 97.56 |
| KKR_Q531K | 38.59 | 9.56 | 6.05 | 1.62 | 1.05 | 2.11 |

TABLE 14B-continued

|  | AAVS1 | OT1 | OT2 | OT3 | OT4 | ratio |
|---|---|---|---|---|---|---|
| KKR_Q531L | 30.94 | 0.06 | 0.02 | 0.05 | 0.04 | 181.72 |
| KKR_Q531M | 39.71 | 1.07 | 0.57 | 0.46 | 0.37 | 16.08 |
| KKR_Q531N | 33.22 | 5.31 | 1.85 | 0.84 | 1.27 | 3.59 |
| KKR_Q531P | 3.89 | 0.08 | 0.09 | 0.06 | 0.05 | 13.73 |
| KKR_Q531R | 41.38 | 1.89 | 1.96 | 1.07 | 0.70 | 7.37 |
| KKR_Q531S | 20.41 | 1.59 | 0.79 | 0.52 | 0.35 | 6.18 |
| KKR_Q531T | 38.72 | 2.20 | 0.31 | 0.37 | 0.43 | 11.69 |
| KKR_Q531V | 33.72 | 0.81 | 0.05 | 0.07 | 0.18 | 30.51 |
| KKR_Q531W | 3.69 | 0.13 | 0.06 | 0.05 | 0.06 | 12.37 |
| KKR_Q531Y | 6.03 | 0.23 | 0.06 | 0.08 | 0.06 | 14.16 |
| KKR_S418D | 45.54 | 0.37 | 0.11 | 0.11 | 0.22 | 56.33 |
| KKR_N476D | 25.28 | 0.07 | 0.05 | 0.04 | 0.06 | 118.80 |
| KKR_I479T | 45.08 | 0.54 | 0.17 | 0.34 | 0.05 | 41.10 |
| KKR_Q481E | 46.92 | 0.28 | 0.03 | 0.06 | 0.10 | 97.21 |
| KKR_N527D | 34.74 | 1.03 | 0.51 | 0.56 | 0.40 | 13.88 |
| KKR_Q531R | 37.42 | 1.37 | 1.65 | 0.72 | 0.50 | 8.84 |
| KKR_R416N | 52.89 | 2.05 | 0.08 | 0.16 | 1.09 | 15.63 |
| KKR_R416D | 45.13 | 0.28 | 0.04 | 0.07 | 0.20 | 75.06 |
| KKR_R416E | 51.18 | 0.51 | 0.03 | 0.08 | 0.78 | 36.52 |
| KKR_R416S | 42.07 | 2.94 | 0.35 | 0.20 | 0.98 | 9.42 |
| KKR_K525A | 43.73 | 0.59 | 0.08 | 0.09 | 0.16 | 47.64 |
| KKR_K525E | 40.94 | 0.11 | 0.03 | 0.03 | 0.10 | 150.39 |
| KKR_K525G | 37.87 | 0.70 | 0.06 | 0.11 | 0.29 | 32.75 |
| KKR_K525S | 40.53 | 0.64 | 0.05 | 0.05 | 0.26 | 40.01 |
| KKR_Q481A | 48.58 | 0.07 | 0.03 | 0.04 | 0.08 | 212.03 |
| KKR_Q481D | 51.77 | 2.24 | 0.04 | 0.09 | 0.40 | 18.71 |
| KKR_Q481C | 40.58 | 1.50 | 0.10 | 0.07 | 0.31 | 20.44 |
| KKR_Q481S | 41.92 | 0.40 | 0.04 | 0.08 | 0.07 | 71.54 |
| KKR_S418E | 51.17 | 0.19 | 0.06 | 0.07 | 0.07 | 129.17 |
| KKR_R422H | 41.25 | 1.53 | 0.24 | 0.29 | 0.75 | 14.62 |
| KKR_I479Q | 47.54 | 1.66 | 0.95 | 0.53 | 0.09 | 14.68 |
| GFP | 0.09 | 0.03 | 0.01 | ND | 0.04 | NA |
| GFP | 0.08 | 0.02 | 0.03 | 0.01 | 0.02 | NA |

TABLE 14C

|  | AAVS1 | OT1 | OT2 | OT3 | OT4 | ratio |
|---|---|---|---|---|---|---|
| parental | 42.55 | 7.68 | 3.88 | 2.05 | 2.94 | 2.57 |
| parental | 41.57 | 6.44 | 3.50 | 1.64 | 2.72 | 2.91 |
| parental | 41.51 | 6.14 | 2.93 | 1.36 | 2.25 | 3.27 |
| parental | 38.53 | 6.24 | 3.14 | 1.32 | 2.35 | 2.95 |
| half dose | 32.45 | 2.46 | 1.00 | 0.46 | 0.63 | 7.14 |
| half dose | 31.98 | 2.41 | 1.02 | 0.53 | 0.51 | 7.16 |
| half dose | 27.34 | 1.29 | 0.45 | 0.19 | 0.34 | 12.05 |
| half dose | 30.04 | 2.06 | 0.91 | 0.36 | 0.61 | 7.63 |
| ELD_KKR_N476A | 38.74 | 0.88 | 0.22 | 0.75 | 0.33 | 17.82 |
| ELD_KKR_N476C | 46.45 | 0.54 | 0.56 | 0.43 | 0.24 | 26.33 |
| ELD_KKR_N476D | 8.21 | 0.02 | 0.02 | 0.04 | 0.07 | 56.96 |
| ELD_KKR_N476E | 1.99 | 0.04 | 0.01 | 0.03 | 0.05 | 15.67 |
| ELD_KKR_N476F | 6.61 | 0.21 | 0.16 | 0.05 | 0.11 | 12.56 |
| ELD_KKR_N476G | 58.20 | 0.10 | 0.07 | 0.08 | 0.07 | 185.26 |
| ELD_KKR_N476H | 36.62 | 2.95 | 1.48 | 1.06 | 1.09 | 5.57 |
| ELD_KKR_N476I | 13.54 | 0.03 | 0.03 | 0.02 | 0.02 | 141.62 |
| ELD_KKR_N476K | 25.76 | 0.31 | 0.10 | 0.60 | 0.10 | 23.29 |
| ELD_kkR_N476L | 1.67 | 0.04 | 0.01 | 0.06 | 0.04 | 11.86 |
| ELD_kkR_N476M | 16.01 | 0.29 | 0.12 | 0.17 | 0.12 | 23.13 |
| ELD_KKR_N476P | 28.84 | 1.82 | 0.61 | 0.74 | 1.21 | 6.59 |
| ELD_KKR_N476Q | 29.68 | 0.06 | 0.06 | 0.09 | 0.12 | 90.88 |
| ELD_KKR_N476R | 36.35 | 3.33 | 3.04 | 1.67 | 0.76 | 4.13 |
| ELD_KKR_N476S | 55.29 | 8.64 | 2.32 | 2.13 | 3.28 | 3.38 |
| ELD_KKR_N476T | 55.05 | 1.63 | 0.98 | 0.97 | 1.04 | 11.91 |
| ELD_KKR_N476V | 24.38 | 0.06 | 0.05 | 0.06 | 0.07 | 101.77 |
| ELD_KKR_N476W | 4.04 | 0.09 | 0.00 | 0.08 | 0.03 | 19.35 |
| ELD_KKR_N476Y | 13.95 | 0.80 | 0.30 | 0.38 | 0.17 | 8.47 |
| ELD_KKR_Q531A | 17.74 | 0.53 | 0.20 | 0.18 | 0.22 | 15.68 |
| ELD_KKR_Q531C | 3.11 | 0.03 | 0.02 | 0.02 | 0.08 | 20.54 |
| ELD_KKR_Q531D | 0.05 | 0.02 | 0.01 | 0.02 | 0.03 | 0.62 |
| ELD_KKR_Q531E | 5.44 | 0.04 | 0.03 | 0.03 | 0.04 | 38.30 |
| ELD_KKR_Q531F | 0.19 | 0.03 | 0.00 | 0.04 | 0.05 | 1.77 |
| ELD_KKR_Q531G | 1.37 | 0.16 | 0.11 | 0.06 | 0.07 | 3.36 |
| ELD_KKR_Q531H | 42.66 | 7.88 | 1.12 | 1.19 | 3.73 | 3.07 |
| ELD_KKR_Q531I | 2.61 | 0.03 | 0.01 | 0.04 | 0.05 | 20.98 |
| ELD_KKR_Q531K | 38.46 | 8.02 | 5.20 | 1.54 | 2.03 | 2.29 |
| ELD_KKR_Q531L | 0.34 | 0.03 | 0.01 | 0.03 | 0.09 | 2.13 |

TABLE 14C-continued

|  | AAVS1 | OT1 | OT2 | OT3 | OT4 | ratio |
|---|---|---|---|---|---|---|
| ELD_KKR_Q531M | 17.43 | 0.04 | 0.04 | 0.01 | 0.08 | 100.86 |
| ELD_KKR_Q531N | 6.41 | 0.40 | 0.22 | 0.08 | 0.09 | 8.17 |
| ELD_KKR_Q531P | 0.15 | 0.03 | 0.02 | 0.03 | 0.04 | 1.18 |
| ELD_KKR_Q531R | 43.88 | 0.46 | 0.15 | 0.18 | 0.10 | 48.73 |
| ELD_KKR_Q531S | 6.70 | 0.07 | 0.06 | 0.10 | 0.06 | 22.49 |
| ELD_KKR_Q531T | 29.41 | 0.06 | 0.03 | 0.07 | 0.05 | 144.03 |
| ELD_KKR_Q531V | 19.78 | 0.05 | 0.01 | 0.01 | 0.09 | 125.77 |
| ELD_KKR_Q531W | 0.19 | 0.05 | 0.02 | 0.02 | 0.02 | 1.27 |
| ELD_KKR_Q531Y | 1.50 | 0.06 | 0.02 | 0.02 | 0.06 | 9.52 |
| ELD_KKR_S418D | 31.26 | 0.05 | 0.02 | 0.04 | 0.03 | 226.26 |
| ELD_KKR_N476D | 4.18 | 0.03 | 0.01 | 0.02 | 0.03 | 44.63 |
| ELD_KKR_I479T | 27.06 | 0.05 | 0.03 | 0.06 | 0.05 | 139.49 |
| ELD_KKR_Q481E | 43.46 | 0.04 | 0.02 | 0.04 | 0.03 | 324.28 |
| ELD_KKR_N527D | 21.32 | 0.03 | 0.02 | 0.08 | 0.02 | 142.33 |
| ELD_KKR_Q531R | 35.54 | 0.16 | 0.07 | 0.08 | 0.06 | 94.23 |
| ELD_KKR_R416N | 68.24 | 0.22 | 0.11 | 0.16 | 0.14 | 106.90 |
| ELD_KKR_R416D | 38.22 | 0.05 | 0.04 | 0.03 | 0.03 | 259.98 |
| ELD_KKR_R416E | 69.86 | 0.05 | 0.09 | 0.08 | 0.12 | 207.67 |
| ELD_KKR_R416S | 37.02 | 0.33 | 0.11 | 0.12 | 0.11 | 54.52 |
| ELD_KKR_K525A | 44.65 | 0.04 | 0.02 | 0.02 | 0.10 | 262.08 |
| ELD_KKR_K525E | 15.13 | 0.02 | 0.03 | 0.03 | 0.05 | 108.50 |
| ELD_KKR_K525G | 31.56 | 0.04 | 0.03 | 0.02 | 0.07 | 199.27 |
| ELD_KKR_K525S | 46.57 | 0.02 | 0.02 | 0.04 | 0.04 | 405.87 |
| ELD_KKR_Q481A | 80.87 | 0.04 | 0.00 | 0.06 | 0.04 | 567.11 |
| ELD_KKR_Q481D | 85.06 | 0.25 | 0.03 | 0.10 | 0.14 | 162.56 |
| ELD_KKR_Q481C | 50.45 | 0.02 | 0.04 | 0.06 | 0.03 | 333.81 |
| ELD_KKR_Q481S | 39.61 | 0.04 | 0.00 | 0.03 | 0.05 | 342.28 |
| ELD_KKR_S418E | 46.25 | 0.04 | 0.03 | 0.01 | 0.09 | 273.38 |
| ELD_KKR_R422H | 37.06 | 0.27 | 0.06 | 0.07 | 0.12 | 72.00 |
| ELD_KKR_I479Q | 55.27 | 0.04 | 0.00 | 0.04 | 0.08 | 343.98 |
| GFP | 0.09 | 0.03 | 0.01 | ND | 0.04 | NA |
| GFP | 0.08 | 0.02 | 0.03 | 0.01 | 0.02 | NA |

Tables 15A through 15C show results of duplicate experiments with the indicated mutants.

TABLE 15A

|  | AAVS1 | OT1 | OT2 | OT3 | OT4 | ratio |
|---|---|---|---|---|---|---|
| parental | 66.27 | 11.83 | 3.46 | 4.41 | 2.67 | 2.96 |
| parental | 66.73 | 11.97 | 3.83 | 4.11 | 3.12 | 2.90 |
| parental | 62.81 | 10.97 | 3.22 | 3.14 | 2.45 | 3.18 |
| half dose | 48.04 | 3.58 | 0.80 | 0.88 | 0.39 | 8.51 |
| half dose | 43.89 | 3.26 | 0.75 | 0.78 | 0.66 | 8.05 |
| half dose | 45.19 | 2.87 | 0.64 | 0.97 | ND | 10.07 |
| ELD_T419D | 78.79 | 11.23 | 3.69 | 4.89 | 3.59 | 3.37 |
| ELD_Q420E | 32.41 | 3.86 | 1.44 | 1.99 | 1.16 | 3.84 |
| ELD_Q420R | 29.10 | 2.19 | 1.14 | 1.88 | 0.59 | 5.01 |
| ELD_E425D | 0.23 | 0.04 | 0.04 | 0.03 | 0.02 | 1.85 |
| ELD_S446A | 73.08 | 21.06 | 7.32 | 5.85 | 3.84 | 1.92 |
| ELD_S446D | 75.31 | 0.66 | 0.39 | 0.23 | 0.05 | 56.91 |
| ELD_S446R | 72.76 | 2.75 | 8.84 | 5.34 | 0.22 | 4.24 |
| ELD_S446T | 33.26 | 2.23 | 1.63 | 1.07 | 0.36 | 6.29 |
| ELD_R447A | 19.26 | 0.20 | 0.12 | 0.18 | 0.06 | 34.22 |
| ELD_R447E | 9.96 | 0.06 | 0.03 | 0.02 | 0.03 | 69.17 |
| ELD_R447Q | 21.02 | 0.38 | 0.51 | 0.37 | 0.06 | 15.96 |
| ELD_A470D | 0.06 | 0.09 | 0.01 | 0.04 | 0.03 | 0.34 |
| ELD_A470G | 14.66 | 0.21 | 0.14 | 0.42 | 0.06 | 17.59 |
| ELD_Y471E | 0.34 | 0.02 | 0.01 | 0.03 | 0.03 | 3.65 |
| ELD_Y471F | 47.88 | 0.10 | 0.17 | 0.45 | 0.03 | 63.86 |
| ELD_S472A | 74.79 | 14.00 | 7.01 | 6.05 | 3.59 | 2.44 |
| ELD_S472D | 71.65 | 0.26 | 1.22 | 0.62 | 0.12 | 32.28 |
| ELD_S472G | 51.69 | 5.45 | 4.09 | 3.94 | 1.83 | 3.38 |
| ELD_Y475E | 0.15 | 0.05 | 0.03 | 0.03 | 0.04 | 1.04 |
| ELD_Y475F | 39.94 | 7.76 | 1.80 | 2.48 | 2.23 | 2.80 |
| ELD_P478D | 86.44 | 0.39 | 0.02 | 0.12 | 0.13 | 133.89 |
| ELD_G480A | 83.61 | 23.32 | 6.80 | 6.63 | 12.01 | 1.71 |
| ELD_G480D | 86.31 | 2.13 | 0.10 | 1.26 | 1.48 | 17.34 |
| ELD_G480K | 83.45 | 21.94 | 6.63 | 4.99 | 14.57 | 1.73 |
| ELD_G480N | 72.90 | 20.19 | 1.90 | 5.23 | 4.81 | 2.27 |
| ELD_G480R | 70.85 | 21.55 | 6.56 | 3.58 | 10.49 | 1.68 |
| ELD_N492D | 0.67 | 0.06 | 0.03 | 0.04 | 0.06 | 3.66 |
| ELD_Q493E | 15.78 | 2.79 | 1.01 | 1.47 | 0.97 | 2.53 |
| ELD_N500D | 2.15 | 0.06 | 0.04 | 0.02 | 0.02 | 15.13 |
| ELD_N502D | 6.77 | 0.87 | 0.19 | 0.63 | 0.27 | 3.46 |

TABLE 15A-continued

| | AAVS1 | OT1 | OT2 | OT3 | OT4 | ratio |
|---|---|---|---|---|---|---|
| ELD_S521A | 78.63 | 13.46 | 4.39 | 6.26 | 3.30 | 2.87 |
| ELD_S521D | 0.52 | 0.12 | 0.03 | 0.03 | 0.05 | 2.34 |
| ELD_H523E | 82.23 | 4.72 | 6.32 | 4.82 | 1.28 | 4.80 |
| ELD_H523K | 69.86 | 9.95 | 3.49 | 4.30 | 1.94 | 3.55 |
| ELD_H523S | 80.18 | 17.34 | 8.96 | 6.98 | 4.84 | 2.10 |
| ELD_H523V | 41.49 | 3.56 | 2.12 | 2.32 | 1.08 | 4.58 |
| ELD_H523Y | 71.52 | 24.22 | 6.87 | 4.50 | 7.88 | 1.65 |
| ELD_G526D | 9.28 | 0.05 | 0.05 | 0.09 | 0.04 | 40.47 |
| ELD_G526N | 10.88 | 0.20 | 0.08 | 0.22 | 0.09 | 18.55 |
| ELD_G526S | 10.79 | 0.22 | 0.11 | 0.30 | 0.17 | 13.35 |
| ELD_A530D | 57.08 | 5.87 | 1.80 | 2.75 | 1.01 | 4.99 |
| ELD_Q531E | 48.43 | 0.08 | 0.07 | 0.03 | 0.06 | 207.58 |
| ELD_N536D | 4.93 | 0.39 | 0.07 | 0.22 | 0.13 | 6.10 |
| ELD_N540D | 17.44 | 2.97 | 1.59 | 1.72 | 1.17 | 2.34 |
| ELD_N542D | 82.04 | 26.01 | 8.78 | 6.82 | 5.77 | 1.73 |
| ELD_N573D | 36.59 | 6.49 | 2.30 | 2.30 | 1.81 | 2.84 |
| ELD_N574D | 7.62 | 0.98 | 0.23 | 0.53 | 0.33 | 3.66 |
| ELD_N578D | 23.28 | 2.69 | 1.33 | 1.78 | 0.96 | 3.45 |
| ELD_S418E | 77.93 | 0.13 | 0.16 | 0.20 | 0.11 | 130.43 |
| ELD_S418D | 69.74 | 0.48 | 0.17 | 0.63 | 0.22 | 46.38 |
| ELD_N476D | 74.70 | 0.01 | 0.04 | 0.07 | 0.09 | 352.05 |
| ELD_I479T | 60.80 | 0.12 | 0.12 | 0.01 | 0.06 | 201.14 |
| ELD_Q481E | 71.27 | 0.04 | 0.10 | 0.15 | 0.07 | 202.50 |
| ELD_N527D | 50.11 | 0.59 | 0.17 | 0.34 | 0.06 | 42.99 |
| ELD_Q531R | 63.19 | 0.91 | 0.14 | 0.28 | 0.20 | 41.47 |
| ELD_Q481A | 75.33 | 0.05 | 0.11 | 0.08 | 0.06 | 254.98 |
| ELD_R416E | 76.92 | 0.28 | 4.23 | 0.57 | 0.10 | 14.86 |
| ELD_K525A | 72.24 | 0.41 | 0.42 | 0.56 | 0.19 | 45.87 |
| ELD_K525S | 73.75 | 0.91 | 0.64 | 0.69 | 0.29 | 29.11 |
| ELD_I479Q | 77.13 | 0.06 | 0.04 | 0.05 | 0.06 | 373.93 |
| GFP | 0.09 | 0.04 | 0.04 | 0.02 | 0.05 | NA |
| GFP | 0.01 | 0.03 | 0.02 | 0.01 | 0.03 | NA |

TABLE 15B

| | AAVS1 | OT1 | OT2 | OT3 | OT4 | ratio |
|---|---|---|---|---|---|---|
| parental | 66.27 | 11.83 | 3.46 | 4.41 | 2.67 | 2.96 |
| parental | 66.73 | 11.97 | 3.83 | 4.11 | 3.12 | 2.90 |
| parental | 62.81 | 10.97 | 3.22 | 3.14 | 2.45 | 3.18 |
| half dose | 48.04 | 3.58 | 0.80 | 0.88 | 0.39 | 8.51 |
| half dose | 43.89 | 3.26 | 0.75 | 0.78 | 0.66 | 8.05 |
| half dose | 45.19 | 2.87 | 0.64 | 0.97 | ND | 10.07 |
| KKR_T419D | 75.79 | 14.88 | 7.12 | 6.14 | 4.34 | 2.33 |
| KKR_Q420E | 37.28 | 4.82 | 1.99 | 2.17 | 1.48 | 3.56 |
| KKR_Q420R | 27.41 | 4.09 | 1.16 | 1.21 | 1.28 | 3.54 |
| KKR_E425D | 0.23 | 0.04 | 0.04 | 0.04 | 0.02 | 1.59 |
| KKR_S446A | 69.60 | 17.74 | 5.75 | 5.60 | 9.07 | 1.82 |
| KKR_S446D | 71.48 | 0.11 | 0.03 | 0.04 | 0.05 | 311.16 |
| KKR_S446R | 69.10 | 3.80 | 0.35 | 0.33 | 2.39 | 10.05 |
| KKR_S446T | 68.15 | 6.99 | 3.88 | 2.40 | 4.04 | 3.94 |
| KKR_R447A | 32.43 | 0.01 | 0.02 | 0.03 | 0.06 | 249.14 |
| KKR_R447E | 10.88 | 0.03 | 0.01 | 0.03 | 0.03 | 112.41 |
| KKR_R447Q | 41.86 | 0.02 | 0.02 | 0.02 | 0.09 | 269.85 |
| KKR_A470D | 2.09 | 0.06 | 0.01 | 0.04 | 0.05 | 12.73 |
| KKR_A470G | 14.81 | 0.43 | 0.11 | 0.24 | 0.22 | 14.80 |
| KKR_Y471E | 0.29 | 0.01 | 0.00 | 0.01 | 0.01 | 10.77 |
| KKR_Y471F | 59.99 | 1.03 | 0.08 | 0.09 | 0.44 | 36.50 |
| KKR_S472A | 72.04 | 18.47 | 4.06 | 4.86 | 5.36 | 2.20 |
| KKR_S472D | 73.49 | 0.51 | 0.08 | 0.09 | 0.59 | 57.76 |
| KKR_S472G | 58.36 | 9.39 | 2.26 | 2.74 | 3.37 | 3.29 |
| KKR_Y475E | 0.08 | 0.01 | 0.02 | 0.02 | 0.01 | 1.43 |
| KKR_Y475F | 40.95 | 7.01 | 4.44 | 3.44 | 1.91 | 2.44 |
| KKR_P478D | 68.06 | 0.22 | 0.18 | 0.13 | 0.11 | 107.13 |
| KKR_G480A | 74.73 | 11.68 | 13.46 | 6.92 | 4.14 | 2.06 |
| KKR_G480D | ND | ND | ND | ND | ND | ND |
| KKR_G480K | 74.95 | 14.58 | 4.77 | 5.59 | 9.04 | 2.21 |
| KKR_G480N | 72.63 | 13.59 | 11.47 | 6.96 | 1.87 | 2.14 |
| KKR_G480R | 72.60 | 13.28 | 9.20 | 5.33 | 6.12 | 2.14 |
| KKR_N492D | 0.49 | 0.03 | 0.01 | 0.03 | 0.04 | 4.61 |
| KKR_Q493E | 19.03 | 2.00 | 1.24 | 1.14 | 0.85 | 3.64 |
| KKR_N500D | 2.44 | 0.02 | 0.01 | 0.03 | 0.03 | 25.48 |
| KKR_N502D | 10.57 | 0.43 | 0.18 | 0.51 | 0.24 | 7.77 |
| KKR_S521A | 73.75 | 14.27 | 4.57 | 4.50 | 3.63 | 2.73 |
| KKR_S521D | 0.02 | 0.04 | 0.03 | 0.03 | 0.03 | 0.14 |

TABLE 15B-continued

| | AAVS1 | OT1 | OT2 | OT3 | OT4 | ratio |
|---|---|---|---|---|---|---|
| KKR_H523E | 77.04 | 12.72 | 1.14 | 1.86 | 4.57 | 3.80 |
| KKR_H523K | 68.39 | 9.40 | 2.92 | 3.75 | 2.51 | 3.68 |
| KKR_H523S | 73.90 | 18.71 | 3.05 | 5.29 | 6.00 | 2.24 |
| KKR_H523V | 51.85 | 7.60 | 2.23 | 2.16 | 2.33 | 3.62 |
| KKR_H523Y | 65.36 | 9.66 | 7.27 | 5.25 | 3.16 | 2.58 |
| KKR_G526D | 9.91 | 0.10 | 0.03 | 0.11 | 0.05 | 34.03 |
| KKR_G526N | 9.13 | 0.48 | 0.08 | 0.20 | 0.36 | 8.18 |
| KKR_G526S | 9.33 | 0.23 | 0.04 | 0.26 | 0.12 | 14.26 |
| KKR_A530D | 67.48 | 13.32 | 5.25 | 6.01 | 4.12 | 2.35 |
| KKR_Q531E | 26.70 | 0.49 | 0.20 | 1.08 | 0.05 | 14.69 |
| KKR_N536D | 4.55 | 0.26 | 0.11 | 0.25 | 0.05 | 6.80 |
| KKR_N540D | 38.98 | 4.18 | 1.89 | 2.31 | 1.31 | 4.03 |
| KKR_N542D | 70.17 | 15.67 | 5.58 | 4.86 | 4.57 | 2.29 |
| KKR_N573D | 43.19 | 7.22 | 2.96 | 2.81 | 1.90 | 2.90 |
| KKR_N574D | 9.05 | 1.05 | 0.58 | 0.55 | 0.45 | 3.43 |
| KKR_N578D | 8.46 | 0.81 | 0.27 | 0.47 | 0.28 | 4.63 |
| KKR_S418E | 69.91 | 0.22 | 0.06 | 0.08 | 0.04 | 176.22 |
| KKR_S418D | 63.18 | 0.73 | 0.12 | 0.08 | 0.23 | 54.44 |
| KKR_N476D | 31.97 | 0.09 | 0.07 | 0.09 | 0.11 | 89.68 |
| KKR_I479T | 67.39 | 0.56 | 0.11 | 0.96 | 0.08 | 39.39 |
| KKR_Q481E | 67.03 | 0.16 | 0.03 | 0.04 | 0.08 | 213.25 |
| KKR_N527D | 49.72 | 1.12 | 0.19 | 0.75 | ND | 24.10 |
| KKR_Q531R | 53.34 | 1.41 | 0.71 | 1.19 | 0.38 | 14.45 |
| KKR_Q481A | 66.84 | 0.14 | 0.04 | 0.05 | 0.08 | 217.35 |
| KKR_R416E | 74.69 | 1.79 | 0.06 | 0.21 | 2.17 | 18.11 |
| KKR_K525A | 65.23 | 0.90 | 0.07 | 0.13 | 0.37 | 44.44 |
| KKR_K525S | 67.51 | 2.22 | 0.20 | 0.15 | 0.64 | 20.95 |
| KKR_I479Q | 73.07 | 1.99 | 1.11 | 1.34 | 0.11 | 16.06 |
| GFP | 0.09 | 0.04 | 0.04 | 0.02 | 0.05 | NA |
| GFP | 0.01 | 0.03 | 0.02 | 0.01 | 0.03 | NA |

TABLE 15C

| | AAVS1 | OT1 | OT2 | OT3 | OT4 | ratio |
|---|---|---|---|---|---|---|
| parental | 66.27 | 11.83 | 3.46 | 4.41 | 2.67 | 2.96 |
| parental | 66.73 | 11.97 | 3.83 | 4.11 | 3.12 | 2.90 |
| parental | 62.81 | 10.97 | 3.22 | 3.14 | 2.45 | 3.18 |
| half dose | 48.04 | 3.58 | 0.80 | 0.88 | 0.39 | 8.51 |
| half dose | 43.89 | 3.26 | 0.75 | 0.78 | 0.66 | 8.05 |
| half dose | 45.19 | 2.87 | 0.64 | 0.97 | ND | 10.07 |
| ELD_KKR_T419D | 85.90 | 11.12 | 5.15 | 6.07 | 4.42 | 3.21 |
| ELD_KKR_Q420E | 13.44 | 0.53 | 0.29 | 0.56 | 0.27 | 8.13 |
| ELD_KKR_Q420R | 11.95 | 0.85 | 0.21 | 0.41 | 0.22 | 7.07 |
| ELD_KKR_E425D | 0.08 | 0.02 | 0.02 | 0.04 | 0.01 | 0.57 |
| ELD_KKR_S446A | 74.69 | 23.06 | 7.98 | 6.61 | 8.35 | 1.62 |
| ELD_KKR_S446D | ND | ND | ND | ND | ND | ND |
| ELD_KKR_S446R | 65.40 | 3.05 | 1.55 | 1.67 | 0.40 | 9.79 |
| ELD_KKR_S446T | 60.85 | 2.91 | 6.14 | 1.43 | 1.80 | 4.96 |
| ELD_KKR_R447A | 3.05 | 0.01 | 0.01 | 0.02 | 0.01 | 54.51 |
| ELD_KKR_R447E | 0.11 | 0.01 | 0.01 | 0.03 | 0.04 | 1.15 |
| ELD_KKR_R447Q | 5.65 | 0.02 | 0.00 | 0.02 | 0.03 | 80.80 |
| ELD_KKR_A470D | 0.06 | 0.03 | 0.02 | 0.02 | 0.04 | 0.49 |
| ELD_KKR_A470G | 3.42 | 0.05 | 0.03 | 0.03 | 0.02 | 26.36 |
| ELD_KKR_Y471E | 0.08 | 0.00 | 0.01 | 0.01 | 0.02 | 2.19 |
| ELD_KKR_Y471F | 40.26 | 0.02 | 0.00 | 0.04 | 0.02 | 476.01 |
| ELD_KKR_S472A | 80.75 | 19.68 | 5.51 | 6.09 | 4.95 | 2.23 |
| ELD_KKR_S472D | 75.69 | 0.11 | 0.02 | 0.06 | 0.09 | 275.20 |
| ELD_KKR_S472G | 42.97 | 3.47 | 1.96 | 2.50 | 1.45 | 4.58 |
| ELD_KKR_Y475E | 0.04 | 0.00 | 0.01 | 0.02 | 0.04 | 0.59 |
| ELD_KKR_Y475F | 22.50 | 3.79 | 1.65 | 1.86 | 1.18 | 2.66 |
| ELD_KKR_P478D | 59.04 | 0.05 | 0.01 | 0.01 | 0.04 | 550.14 |
| ELD_KKR_G480A | 87.20 | 17.66 | 13.65 | 7.82 | 9.44 | 1.80 |
| ELD_KKR_G480D | 91.15 | 0.06 | 0.06 | 0.05 | 0.08 | 349.99 |
| ELD_KKR_G480K | 88.46 | 5.67 | 0.26 | 1.23 | 11.32 | 4.79 |
| ELD_KKR_G480N | 71.97 | 16.43 | 3.72 | 6.72 | 2.05 | 2.49 |
| ELD_KKR_G480R | 38.18 | 9.36 | 6.54 | 1.15 | 6.83 | 1.60 |
| ELD_KKR_N492D | 0.03 | 0.02 | 0.01 | 0.01 | 0.04 | 0.41 |
| ELD_KKR_Q493E | 5.52 | 0.58 | 0.23 | 0.37 | 0.23 | 3.92 |
| ELD_KKR_N500D | 0.07 | 0.02 | 0.03 | 0.03 | 0.04 | 0.58 |
| ELD_KKR_N502D | 1.10 | 0.07 | 0.03 | 0.10 | 0.04 | 4.30 |
| ELD_KKR_S521A | 81.32 | 12.31 | 3.39 | 6.02 | 2.84 | 3.31 |
| ELD_KKR_S521D | ND | 0.06 | 0.01 | 0.03 | 0.03 | ND |
| ELD_KKR_H523E | 83.69 | 3.33 | 1.05 | 1.37 | 1.10 | 12.21 |
| ELD_KKR_H523K | 71.56 | 5.67 | 1.65 | 3.19 | 1.01 | 6.21 |

TABLE 15C-continued

| | AAVS1 | OT1 | OT2 | OT3 | OT4 | ratio |
|---|---|---|---|---|---|---|
| ELD_KKR_H523S | 86.20 | 23.40 | 6.54 | 7.59 | 7.24 | 1.93 |
| ELD_KKR_H523V | 32.38 | 2.32 | 1.17 | 1.35 | 0.48 | 6.09 |
| ELD_KKR_H523Y | 68.44 | 20.77 | 8.90 | 4.64 | 6.21 | 1.69 |
| ELD_KKR_G526D | 0.45 | 0.05 | 0.01 | 0.05 | 0.02 | 3.23 |
| ELD_KKR_G526N | 1.43 | 0.02 | 0.03 | 0.03 | 0.01 | 14.61 |
| ELD_KKR_G526S | 1.56 | 0.05 | 0.02 | 0.05 | 0.03 | 10.66 |
| ELD_KKR_A530D | 57.66 | 4.57 | 1.75 | 4.02 | 1.33 | 4.94 |
| ELD_KKR_Q531E | 7.79 | 0.01 | 0.03 | 0.01 | 0.03 | 102.39 |
| ELD_KKR_N536D | 0.36 | 0.01 | 0.01 | 0.04 | 0.04 | 3.52 |
| ELD_KKR_N540D | 8.44 | 0.84 | 0.27 | 0.43 | 0.24 | 4.72 |
| ELD_KKR_N542D | 85.42 | 31.76 | 12.86 | 9.09 | 9.36 | 1.35 |
| ELD_KKR_N573D | 9.25 | 0.60 | 0.35 | 0.48 | 0.32 | 5.30 |
| ELD_KKR_N574D | 1.71 | 0.20 | 0.20 | 0.12 | 0.13 | 2.62 |
| ELD_KKR_N578D | 3.26 | 0.19 | 0.08 | 0.13 | 0.08 | 6.83 |
| ELD_KKR_S418E | 57.15 | 0.03 | 0.01 | 0.03 | 0.05 | 436.46 |
| ELD_KKR_S418D | 45.40 | 0.01 | 0.00 | 0.02 | 0.03 | 701.15 |
| ELD_KKR_N476D | 4.88 | 0.01 | 0.01 | 0.00 | 0.03 | 96.87 |
| ELD_KKR_I479T | 40.26 | 0.04 | 0.03 | 0.04 | 0.04 | 269.66 |
| ELD_KKR_Q481E | 64.61 | 0.04 | 0.00 | 0.04 | 0.06 | 478.02 |
| ELD_KKR_N527D | 35.62 | 0.06 | 0.03 | 0.11 | 0.03 | 155.89 |
| ELD_KKR_Q531R | 54.64 | 0.27 | 0.09 | 0.13 | 0.14 | 86.92 |
| ELD_KKR_Q481A | 93.96 | 0.04 | 0.03 | 0.03 | 0.03 | 715.38 |
| ELD_KKR_R416E | 89.58 | 0.21 | 0.10 | 0.18 | 0.07 | 162.49 |
| ELD_KKR_K525A | 68.22 | 0.01 | 0.03 | 0.05 | 0.04 | 547.87 |
| ELD_KKR_K525S | 72.67 | 0.04 | 0.02 | 0.05 | 0.06 | 436.42 |
| ELD_KKR_I479Q | 73.26 | 0.00 | 0.03 | 0.05 | 0.03 | 698.84 |
| GFP | 0.09 | 0.04 | 0.04 | 0.02 | 0.05 | NA |
| GFP | 0.01 | 0.03 | 0.02 | 0.01 | 0.03 | NA |

Tables 16A and 16B show results of target (AAVS1) and off-target cleavage using the indicated mutants.

TABLE 16A

| | On-target | | | | | | | |
|---|---|---|---|---|---|---|---|---|
| sample_id | AAVS1 % indels | OT1 % indels | OT2 % indels | OT3 % indels | OT4 % indels | OT5 % indels | All 5 Off-T total | On/Off ratio |
| 30035_30054_1 | 46.65 | 6.60 | 1.86 | 1.60 | 1.55 | 0.89 | 12.51 | 3.73 |
| 30035_30054_2 | 47.66 | 6.28 | 1.49 | 1.67 | 1.73 | 0.76 | 11.93 | 4.00 |
| ELD_K387S | 50.98 | 4.65 | 3.16 | 1.78 | 0.89 | 0.68 | 11.17 | 4.57 |
| ELD_K393S | 5.67 | 0.36 | 0.36 | 0.40 | 0.45 | 0.20 | 1.77 | 3.20 |
| ELD_K394S | 5.05 | 0.73 | 0.36 | 0.40 | 0.44 | 0.20 | 2.13 | 2.38 |
| ELD_R398S | 13.11 | 1.26 | 0.42 | 0.67 | 0.72 | 0.21 | 3.28 | 4.00 |
| ELD_K400S | 31.30 | 4.13 | 1.15 | 1.00 | 1.18 | 0.54 | 8.00 | 3.91 |
| ELD_K402S | 12.78 | 1.93 | 0.74 | 0.70 | 0.84 | 0.40 | 4.61 | 2.77 |
| ELD_R416S | 53.24 | 1.52 | 2.03 | 1.28 | 0.58 | 0.50 | 5.91 | 9.00 |
| ELD_R422S | 33.43 | 1.10 | 0.60 | 0.84 | 0.58 | 0.29 | 3.41 | 9.80 |
| ELD_K427S | 7.56 | 1.21 | 0.62 | 0.48 | 0.75 | 0.22 | 3.29 | 2.30 |
| ELD_K434S | 25.22 | 4.59 | 1.63 | 1.08 | 1.25 | 0.57 | 9.12 | 2.77 |
| ELD_R439S | 27.16 | 5.62 | 1.57 | 1.23 | 1.66 | 0.86 | 10.94 | 2.48 |
| ELD_K441S | 31.83 | 7.68 | 1.49 | 1.64 | 1.76 | 0.87 | 13.44 | 2.37 |
| ELD_R447S | 10.82 | 0.42 | 0.20 | 0.21 | 0.37 | 0.22 | 1.42 | 7.62 |
| ELD_K448S | 42.71 | 4.50 | 1.29 | 1.49 | 1.45 | 0.55 | 9.29 | 4.60 |
| ELD_K469S | 0.10 | 0.28 | 0.25 | 0.14 | 0.42 | 0.13 | 1.21 | 0.08 |
| ELD_R487S | 0.19 | 0.23 | 0.23 | 0.12 | 0.41 | 0.18 | 1.17 | 0.16 |
| ELD_R495S | 1.37 | 0.21 | 0.21 | 0.12 | 0.58 | 0.18 | 1.30 | 1.06 |
| ELD_K497S | 22.50 | 2.89 | 0.65 | 0.95 | 0.81 | 0.47 | 5.77 | 3.90 |
| ELD_K506S | 20.06 | 2.87 | 0.88 | 0.77 | 1.15 | 0.41 | 6.07 | 3.30 |
| ELD_K516S | 2.67 | 0.30 | 0.25 | 0.31 | 0.53 | 0.18 | 1.56 | 1.71 |
| ELD_K525S | 53.18 | 0.42 | 0.31 | 0.26 | 0.42 | 0.26 | 1.67 | 31.81 |
| ELD_K529S | 16.10 | 1.48 | 0.53 | 0.51 | 0.69 | 0.42 | 3.64 | 4.43 |
| ELD_R534S | 12.81 | 0.28 | 0.26 | 0.30 | 0.43 | 0.17 | 1.44 | 8.91 |
| ELD_K559S | 17.55 | 2.05 | 0.54 | 0.65 | 0.73 | 0.44 | 4.42 | 3.97 |
| ELD_R569S | 51.39 | 8.56 | 2.26 | 2.03 | 2.08 | 0.99 | 15.92 | 3.23 |
| ELD_R570S | 15.32 | 2.10 | 0.68 | 0.59 | 0.86 | 0.35 | 4.57 | 3.35 |
| ELD_K571S | 17.23 | 2.78 | 0.98 | 0.82 | 1.20 | 0.50 | 6.28 | 2.74 |
| KKR_K387S | 53.39 | 8.19 | 1.69 | 1.36 | 2.75 | 1.07 | 15.05 | 3.55 |
| KKR_K393S | 8.26 | 0.43 | 0.30 | 0.35 | 0.60 | 0.31 | 2.00 | 4.14 |
| KKR_K394S | 9.13 | 0.60 | 0.50 | 0.44 | 0.60 | 0.28 | 2.42 | 3.77 |
| KKR_R398S | 17.87 | 1.43 | 0.53 | 0.59 | 0.64 | 0.28 | 3.47 | 5.16 |
| KKR_K400S | 15.10 | 1.69 | 0.42 | 0.64 | 0.69 | 0.44 | 3.88 | 3.89 |
| KKR_K402S | 15.77 | 1.46 | 0.70 | 0.74 | 0.89 | 0.41 | 4.20 | 3.75 |
| KKR_R416S | 52.03 | 2.77 | 0.33 | 0.52 | 1.32 | 0.51 | 5.45 | 9.56 |
| KKR_R422S | 45.06 | 0.86 | 0.33 | 0.32 | 0.93 | 0.51 | 2.95 | 15.28 |
| KKR_K427S | 8.58 | 0.68 | 0.42 | 0.44 | 0.51 | 0.29 | 2.33 | 3.68 |
| KKR_K434S | 29.41 | 3.49 | 1.17 | 1.29 | 1.23 | 0.57 | 7.75 | 3.79 |
| KKR_R439S | 27.32 | 3.05 | 0.86 | 0.82 | 1.04 | 0.51 | 6.27 | 4.35 |
| KKR_K441S | 11.00 | 0.90 | 0.48 | 0.28 | 0.50 | 0.27 | 2.43 | 4.53 |
| KKR_R447S | 24.50 | 0.15 | 0.20 | 0.19 | 0.35 | 0.23 | 1.11 | 22.06 |
| KKR_K448S | 45.19 | 3.53 | 0.77 | 0.80 | 1.24 | 0.79 | 7.13 | 6.34 |
| KKR_K469S | 0.15 | 0.18 | 0.24 | 0.17 | 0.46 | 0.26 | 1.30 | 0.11 |
| KKR_R487S | 0.16 | 0.24 | 0.18 | 0.13 | 0.37 | 0.10 | 1.02 | 0.15 |
| KKR_R495S | 1.78 | 0.21 | 0.14 | 0.16 | 0.46 | 0.21 | 1.19 | 1.50 |
| KKR_K497S | 31.87 | 4.05 | 1.24 | 1.26 | 1.35 | 0.83 | 8.72 | 3.65 |
| KKR_K506S | 30.39 | 4.27 | 1.44 | 1.15 | 1.39 | 0.72 | 8.97 | 3.39 |
| KKR_K516S | 5.60 | 0.62 | 0.39 | 0.42 | 0.57 | 0.24 | 2.25 | 2.49 |
| KKR_K525S | 51.12 | 1.18 | 0.37 | 0.18 | 0.70 | 0.21 | 2.64 | 19.36 |
| KKR_K529S | 17.49 | 1.78 | 0.49 | 0.73 | 0.77 | 0.42 | 4.19 | 4.18 |

TABLE 16A-continued

| | On-target | | | | | | All 5 | |
|---|---|---|---|---|---|---|---|---|
| sample_id | AAVS1 % indels | OT1 % indels | OT2 % indels | OT3 % indels | OT4 % indels | OT5 % indels | Off-T total | On/Off ratio |
| KKR_R534S | 18.27 | 1.29 | 0.81 | 0.66 | 0.77 | 0.33 | 3.85 | 4.74 |
| KKR_K559S | 23.28 | 2.32 | 0.71 | 0.62 | 0.81 | 0.46 | 4.92 | 4.73 |
| KKR_R569S | 5.40 | 0.20 | 0.35 | 0.31 | 0.44 | 0.21 | 1.51 | 3.57 |
| KKR_R570S | 23.22 | 3.52 | 1.13 | 0.90 | 1.07 | 0.75 | 7.36 | 3.15 |
| KKR_K571S | 8.62 | 1.03 | 0.53 | 0.52 | 0.61 | 0.34 | 3.04 | 2.83 |
| EGFP | 0.12 | 0.16 | 0.23 | 0.14 | 0.40 | 0.15 | 0.21 | 0.57 |

TABLE 16B

| sample | AAVS1 | OT1 | OT2 | OT3 | OT4 | total | ratio |
|---|---|---|---|---|---|---|---|
| parents | 47.56 | 9.72 | 2.63 | 2.84 | 2.46 | 17.65 | 2.70 |
| parents | 49.08 | 11.10 | 3.09 | 3.71 | 3.06 | 20.97 | 2.34 |
| ELD_I414L | 37.57 | 4.36 | 2.12 | 2.24 | 1.18 | 9.91 | 3.79 |
| ELD_N417D | 67.23 | 17.94 | 5.20 | 5.03 | 3.71 | 31.89 | 2.11 |
| ELD_N417S | 29.91 | 7.81 | 1.11 | 1.56 | 2.17 | 12.65 | 2.37 |
| ELD_S418D | 46.39 | 0.29 | 0.14 | 0.34 | 0.16 | 0.93 | 49.69 |
| ELD_S418G | 32.76 | 11.10 | 0.81 | 1.11 | 4.23 | 17.25 | 1.90 |
| ELD_S418P | 67.64 | 19.29 | 11.36 | 5.53 | 3.85 | 40.03 | 1.69 |
| ELD_T419K | 54.75 | 12.34 | 3.49 | 3.64 | 2.83 | 22.29 | 2.46 |
| ELD_T419S | 56.92 | 11.83 | 3.66 | 3.51 | 2.26 | 21.27 | 2.68 |
| ELD_T419Y | 39.15 | 6.93 | 1.83 | 2.27 | 1.74 | 12.76 | 3.07 |
| ELD_Q420A | 37.22 | 9.61 | 1.07 | 1.81 | 2.61 | 15.10 | 2.46 |
| ELD_D421N | 39.03 | 13.33 | 1.77 | 2.41 | 5.30 | 22.80 | 1.71 |
| ELD_D421S | 50.44 | 16.11 | 1.73 | 2.46 | 6.35 | 26.65 | 1.89 |
| ELD_I423D | 14.05 | 1.84 | 0.39 | 0.75 | 0.57 | 3.55 | 3.96 |
| ELD_I423L | 57.80 | 15.54 | 2.48 | 3.29 | 3.51 | 24.82 | 2.33 |
| ELD_L424F | 67.38 | 20.09 | 10.08 | 6.00 | 4.01 | 40.18 | 1.68 |
| ELD_E425Q | 8.67 | 0.07 | 0.10 | 0.05 | 0.07 | 0.29 | 30.34 |
| ELD_M426I | 61.70 | 16.65 | 2.74 | 4.59 | 3.84 | 27.82 | 2.22 |
| ELD_K441E | 32.05 | 9.23 | 2.59 | 2.29 | 2.31 | 16.41 | 1.95 |
| ELD_K441D | 5.87 | 0.94 | 0.35 | 0.38 | 0.24 | 1.91 | 3.06 |
| ELD_K441L | 13.37 | 2.77 | 0.74 | 0.80 | 0.95 | 5.26 | 2.54 |
| ELD_H442R | 18.30 | 0.45 | 0.63 | 0.47 | 0.14 | 1.70 | 10.79 |
| ELD_G445E | 2.63 | 0.15 | 0.21 | 0.20 | 0.06 | 0.62 | 4.21 |
| ELD_S446G | 35.42 | 3.07 | 1.52 | 1.75 | 1.09 | 7.42 | 4.77 |
| ELD_T468N | 0.19 | 0.06 | 0.05 | 0.14 | 0.07 | 0.31 | 0.59 |
| ELD_S472K | 44.07 | 2.77 | 1.36 | 1.45 | 0.54 | 6.13 | 7.19 |
| ELD_G473D | 29.64 | 6.26 | 1.15 | 1.52 | 2.12 | 11.04 | 2.68 |
| ELD_G473K | 25.08 | 5.70 | 0.92 | 1.42 | 0.70 | 8.74 | 2.87 |
| ELD_N476S | 55.45 | 10.94 | 2.55 | 3.65 | 2.18 | 19.31 | 2.87 |
| ELD_N476D | 59.33 | 0.13 | 0.06 | 0.17 | 0.10 | 0.46 | 128.70 |
| ELD_P478S | 63.62 | 14.02 | 0.62 | 2.98 | 4.36 | 21.98 | 2.89 |
| ELD_I479T | 41.42 | 0.09 | 0.15 | 0.06 | 0.11 | 0.42 | 99.43 |
| ELD_G480S | 61.29 | 14.12 | 2.99 | 4.03 | 6.03 | 27.17 | 2.26 |
| ELD_Q481H | 67.73 | 14.54 | 6.96 | 4.37 | 0.32 | 26.19 | 2.59 |
| ELD_Q481E | 53.31 | 0.11 | 0.11 | 0.21 | 0.05 | 0.48 | 110.94 |
| ELD_Q481N | 35.13 | 3.37 | 0.59 | 1.56 | 0.35 | 5.88 | 5.97 |
| ELD_E484Q | 37.48 | 11.64 | 1.93 | 1.39 | 4.08 | 19.04 | 1.97 |
| ELD_P501S | 20.02 | 4.32 | 1.60 | 1.47 | 1.17 | 8.56 | 2.34 |
| ELD_G522S | 60.02 | 12.86 | 2.23 | 3.29 | 3.27 | 21.65 | 2.77 |
| ELD_H523F | 42.63 | 14.68 | 2.12 | 2.27 | 4.62 | 23.68 | 1.80 |
| ELD_N527D | 41.63 | 1.13 | 0.22 | 0.68 | 0.11 | 2.13 | 19.59 |
| ELD_N527G | 23.28 | 2.93 | 0.84 | 1.27 | 1.50 | 6.55 | 3.56 |
| ELD_N527K | 13.62 | 2.56 | 0.78 | 0.89 | 0.23 | 4.46 | 3.06 |
| ELD_Y528F | 52.40 | 12.72 | 3.52 | 3.03 | 2.79 | 22.05 | 2.38 |
| ELD_K529E | 22.98 | 2.77 | 0.58 | 1.51 | 0.54 | 5.40 | 4.25 |
| ELD_A530E | 41.94 | 3.37 | 0.57 | 1.18 | 0.85 | 5.97 | 7.03 |
| ELD_A530K | 46.55 | 6.55 | 1.31 | 1.71 | 1.50 | 11.07 | 4.21 |
| ELD_Q531N | 16.28 | 1.30 | 0.26 | 0.53 | 0.37 | 2.46 | 6.62 |
| ELD_Q531R | 50.98 | 1.64 | 0.30 | 0.48 | 0.39 | 2.81 | 18.14 |
| KKR_I414L | 51.17 | 9.11 | 1.42 | 2.80 | 2.95 | 16.28 | 3.14 |
| KKR_N417D | 73.10 | 16.32 | 2.74 | 3.50 | 5.59 | 28.14 | 2.60 |
| KKR_N417S | 33.80 | 4.26 | 2.65 | 2.30 | 1.26 | 10.47 | 3.23 |
| KKR_S418D | 58.61 | 0.57 | 0.20 | 0.15 | 0.16 | 1.08 | 54.37 |
| KKR_S418G | 41.59 | 4.18 | 5.48 | 2.79 | 1.37 | 13.82 | 3.01 |
| KKR_S418P | 74.02 | 17.76 | 3.16 | 3.61 | 8.51 | 33.05 | 2.24 |
| KKR_T419K | 63.65 | 16.14 | 3.82 | 4.06 | 4.22 | 28.25 | 2.25 |
| KKR_T419S | 66.12 | 13.56 | 2.63 | 3.54 | 3.41 | 23.14 | 2.86 |
| KKR_T419Y | 42.35 | 4.81 | 1.45 | 1.68 | 1.20 | 9.14 | 4.63 |
| KKR_Q420A | 44.62 | 4.92 | 2.87 | 2.81 | 1.17 | 11.78 | 3.79 |
| KKR_D421N | 39.41 | 8.14 | 6.27 | 2.59 | 1.84 | 18.84 | 2.09 |
| KKR_D421S | 51.41 | 10.28 | 7.67 | 3.19 | 2.50 | 23.64 | 2.17 |
| KKR_I423D | 29.67 | 2.84 | 0.93 | 1.08 | 0.66 | 5.50 | 5.39 |
| KKR_I423L | 66.91 | 13.71 | 4.37 | 4.47 | 3.16 | 25.72 | 2.60 |
| KKR_L424F | 73.65 | 23.87 | 5.78 | 6.31 | 12.31 | 48.26 | 1.53 |
| KKR_E425Q | 33.35 | 0.09 | 0.05 | 0.08 | 0.08 | 0.30 | 109.99 |
| KKR_M426I | 63.92 | 9.92 | 2.71 | 3.45 | 2.36 | 18.44 | 3.47 |
| KKR_K441E | 45.72 | 8.60 | 5.21 | 3.29 | 2.64 | 19.74 | 2.32 |
| KKR_K441D | 10.66 | 0.80 | 0.84 | 0.58 | 0.40 | 2.63 | 4.05 |
| KKR_K441L | 23.57 | 2.99 | 1.55 | 1.40 | 0.91 | 6.84 | 3.44 |
| KKR_H442R | 32.85 | 2.18 | 0.14 | 0.51 | 0.62 | 3.45 | 9.51 |
| KKR_G445E | 5.57 | 0.31 | 0.16 | 0.25 | 0.24 | 0.96 | 5.80 |
| KKR_S446G | 48.86 | 4.31 | 1.13 | 1.13 | 1.59 | 8.16 | 5.99 |
| KKR_T468N | 0.94 | 0.06 | 0.02 | 0.05 | 0.07 | 0.20 | 4.79 |
| KKR_S472K | 54.49 | 6.10 | 0.99 | 1.93 | 1.66 | 10.68 | 5.10 |
| KKR_G473D | 41.00 | 7.64 | 3.40 | 2.26 | 1.52 | 14.83 | 2.76 |
| KKR_G473K | 32.02 | 2.67 | 2.10 | 2.03 | 1.01 | 7.80 | 4.11 |
| KKR_N476S | 59.29 | 8.93 | 1.51 | 2.82 | 2.96 | 16.22 | 3.66 |
| KKR_N476D | 28.98 | 0.12 | 0.04 | 0.08 | 0.05 | 0.30 | 97.89 |
| KKR_P478S | 64.26 | 5.11 | 1.52 | 2.45 | 1.40 | 10.49 | 6.13 |
| KKR_I479T | 59.75 | 0.55 | 0.22 | 0.87 | 0.10 | 1.73 | 34.49 |
| KKR_G480S | 65.65 | 10.79 | 4.90 | 3.14 | 2.04 | 20.87 | 3.15 |
| KKR_Q481H | 69.52 | 6.10 | 0.12 | 1.41 | 6.52 | 14.16 | 4.91 |
| KKR_Q481E | 65.72 | 0.28 | 0.07 | 0.06 | 0.11 | 0.52 | 125.97 |
| KKR_Q481N | 35.21 | 2.64 | 0.10 | 0.83 | 1.15 | 4.72 | 7.46 |
| KKR_E484Q | 51.22 | 10.35 | 8.22 | 2.39 | 2.70 | 23.66 | 2.17 |
| KKR_P501S | 30.29 | 3.83 | 0.79 | 1.57 | 1.02 | 7.21 | 4.20 |
| KKR_G522S | 63.97 | 12.37 | 3.37 | 3.47 | 2.21 | 21.42 | 2.99 |
| KKR_H523F | 53.03 | 9.32 | 5.28 | 3.38 | 2.74 | 20.72 | 2.56 |
| KKR_N527D | 52.34 | 1.75 | 0.56 | 1.24 | 0.59 | 4.13 | 12.66 |
| KKR_N527G | 28.13 | 2.49 | 0.55 | 1.59 | 0.78 | 5.41 | 5.20 |
| KKR_N527K | 20.69 | 1.81 | 0.72 | 1.02 | 0.63 | 4.19 | 4.94 |
| KKR_Y528F | 57.87 | 8.88 | 2.17 | 2.83 | 2.86 | 16.73 | 3.46 |
| KKR_K529E | 30.72 | 3.64 | 1.05 | 1.62 | 1.22 | 7.53 | 4.08 |
| KKR_A530E | 58.94 | 9.65 | 3.18 | 4.82 | 2.87 | 20.52 | 2.87 |
| KKR_A530K | 60.15 | 3.86 | 1.26 | 1.87 | 0.86 | 7.84 | 7.67 |
| KKR_Q531N | 17.46 | 2.00 | 1.25 | 1.49 | 0.46 | 5.20 | 3.36 |
| KKR_Q531R | 56.70 | 1.99 | 1.28 | 2.44 | 0.62 | 6.33 | 8.96 |

Tables 17A through 17C show results with the indicated exemplary mutants, including exemplary double mutants.

TABLE 17A

| | AAVS1 | OT1 | OT2 | OT3 | OT4 | ratio |
|---|---|---|---|---|---|---|
| parental | 29.64 | 3.29 | 1.51 | 0.82 | 0.98 | 4.49 |
| parental | 30.09 | 3.79 | 1.91 | 0.97 | 1.09 | 3.88 |
| parental | 29.29 | 3.92 | 1.53 | 0.73 | 0.75 | 4.23 |
| half dose | 20.23 | 1.53 | 0.49 | 0.24 | 0.28 | 7.96 |
| half dose | 19.34 | 1.28 | 0.41 | 0.21 | 0.19 | 9.25 |
| half dose | 21.01 | 1.37 | 0.32 | 0.16 | 0.34 | 9.62 |
| ELD_R416E_S418E | 20.74 | 0.03 | 0.09 | 0.04 | 0.06 | 94.13 |
| ELD_R416E_N476D | 40.36 | 0.06 | 0.04 | 0.03 | 0.07 | 213.54 |
| ELD_R416E_I479T | 21.55 | 0.06 | 0.25 | 0.01 | 0.03 | 61.74 |
| ELD_R416E_Q481A | 2.83 | 0.05 | 0.02 | 0.01 | 0.07 | 19.59 |
| ELD_R416E_Q481E | 41.39 | 0.07 | 0.03 | 0.04 | 0.04 | 225.41 |
| ELD_R416E_K525S | 34.38 | 0.03 | 0.07 | 0.03 | 0.08 | 166.24 |
| ELD_S418E_N476D | 31.37 | 0.04 | 0.03 | 0.01 | 0.06 | 221.16 |

TABLE 17A-continued

|  | AAVS1 | OT1 | OT2 | OT3 | OT4 | ratio |
|---|---|---|---|---|---|---|
| ELD_S418E_I479T | 11.14 | 0.08 | 0.02 | 0.03 | 0.04 | 62.37 |
| ELD_S418E_Q481A | 3.20 | 0.03 | 0.02 | 0.03 | 0.11 | 16.08 |
| ELD_S418E_Q481E | 38.73 | 0.01 | 0.03 | 0.01 | 0.05 | 400.31 |
| ELD_S418E_K525S | 24.79 | 0.07 | 0.02 | 0.01 | 0.06 | 160.35 |
| ELD_N476D_I479T | 20.03 | 0.02 | 0.04 | 0.01 | 0.03 | 180.94 |
| ELD_N476D_Q481A | 12.76 | 0.03 | 0.04 | 0.02 | 0.05 | 88.57 |
| ELD_N476D_Q481E | 50.65 | 0.07 | 0.03 | 0.03 | 0.08 | 242.53 |
| ELD_N476D_K525S | 42.41 | 0.05 | 0.04 | 0.01 | 0.06 | 270.45 |
| ELD_I479T_Q481A | 8.92 | 0.07 | 0.02 | 0.01 | 0.02 | 72.43 |
| ELD_I479T_Q481E | 35.78 | 0.05 | 0.06 | 0.01 | 0.06 | 196.02 |
| ELD_I479T_K525S | 25.90 | 0.06 | 0.04 | 0.02 | 0.07 | 139.72 |
| ELD_R416S_K525S | 32.61 | 0.06 | 0.07 | 0.05 | 0.07 | 127.78 |
| ELD_R422S_K525S | 26.37 | 0.10 | 0.05 | 0.01 | 0.08 | 108.57 |
| ELD_K448S_K525S | 38.31 | 0.32 | 0.31 | 0.29 | 0.16 | 35.35 |
| ELD_Q481A_K525S | 15.18 | 0.09 | 0.05 | 0.01 | 0.07 | 67.80 |
| ELD_Q481E_K525S | 48.15 | 0.06 | 0.07 | 0.01 | 0.04 | 274.23 |
| ELD_K525S_Q531R | 46.91 | 0.07 | 0.06 | 0.06 | 0.10 | 168.33 |
| ELD_R416D_K448A | 33.83 | 0.09 | 0.41 | 0.07 | 0.05 | 54.89 |
| ELD_R416D_I479Q | 4.00 | 0.11 | 0.01 | 0.01 | 0.03 | 24.24 |
| ELD_R416D_Q481A | 0.98 | 0.07 | 0.02 | 0.04 | 0.03 | 6.23 |
| ELD_R416D_K525A | 5.58 | 0.07 | 0.07 | 0.02 | 0.04 | 26.88 |
| ELD_R416E_R422H | 36.93 | 0.10 | 0.41 | 0.10 | 0.04 | 56.30 |
| ELD_R416E_K448A | 46.84 | 0.24 | 1.54 | 0.27 | 0.08 | 22.04 |
| ELD_R416E_I479Q | 16.28 | 0.05 | 0.01 | 0.02 | 0.05 | 129.05 |
| ELD_R416E_K525A | 25.31 | 0.04 | 0.04 | 0.02 | 0.05 | 171.87 |
| ELD_R416E_N527D | 29.19 | 0.06 | 0.15 | 0.03 | 0.05 | 103.79 |
| ELD_S418E_K448A | 45.64 | 0.11 | 0.08 | 0.05 | 0.13 | 125.00 |
| ELD_S418E_I479Q | 11.10 | 0.05 | 0.03 | 0.03 | 0.07 | 60.83 |
| ELD_S418E_K525A | 18.22 | 0.05 | 0.03 | 0.00 | 0.06 | 132.51 |
| ELD_R422H_I479Q | 31.90 | 0.04 | 0.03 | 0.02 | 0.04 | 232.64 |
| ELD_R422H_Q481A | 15.51 | 0.07 | 0.07 | 0.01 | 0.04 | 84.46 |
| ELD_R422H_K525A | 31.01 | 0.07 | 0.05 | 0.03 | 0.05 | 152.49 |
| ELD_K448A_I479Q | 51.54 | 0.04 | 0.01 | 0.06 | 0.01 | 421.61 |
| ELD_K448A_Q481A | 35.37 | 0.08 | 0.01 | 0.06 | 0.05 | 173.76 |
| ELD_K448A_K525A | 43.95 | 0.17 | 0.15 | 0.22 | 0.13 | 65.65 |
| ELD_K448A_N527D | 32.41 | 0.58 | 0.13 | 0.21 | 0.08 | 32.34 |
| ELD_I479Q_Q481A | 4.15 | 0.04 | 0.02 | 0.01 | 0.08 | 28.92 |
| ELD_I479Q_K525A | 27.87 | 0.05 | 0.02 | 0.00 | 0.05 | 252.87 |
| ELD_Q481A_K525A | 8.65 | 0.04 | 0.03 | 0.01 | 0.05 | 65.76 |
| ELD_Q481A_N527D | 15.47 | 0.07 | 0.06 | 0.01 | 0.07 | 72.82 |
| ELD_K525A_N527D | 23.46 | 0.07 | 0.04 | 0.02 | 0.07 | 116.95 |
| ELD_S446D | 40.19 | 0.53 | 0.44 | 0.11 | 0.10 | 34.11 |
| ELD_G480D | 54.97 | 1.33 | 0.11 | 0.38 | 0.69 | 21.84 |
| ELD_S418E | 32.88 | 0.10 | 0.18 | 0.12 | 0.16 | 58.14 |
| ELD_N476D | 44.56 | 0.10 | 0.05 | 0.07 | 0.10 | 137.79 |
| ELD_I479T | 30.54 | 0.13 | 0.16 | 0.02 | 0.04 | 88.36 |
| ELD_Q481E | 40.57 | 0.06 | 0.05 | 0.15 | 0.04 | 139.98 |
| ELD_N527D | 26.68 | 0.41 | 0.13 | 0.14 | 0.07 | 35.71 |
| ELD_Q531R | 32.95 | 0.63 | 0.17 | 0.12 | 0.19 | 29.60 |
| ELD_I479Q | 50.31 | 0.06 | 0.03 | 0.01 | 0.05 | 313.15 |
| ELD_R416E | 46.99 | 0.37 | 2.36 | 0.24 | 0.17 | 15.03 |
| ELD_K525A | 41.41 | 0.31 | 0.38 | 0.14 | 0.13 | 42.92 |
| ELD_K525S | 39.15 | 0.18 | 0.42 | 0.15 | 0.12 | 44.95 |
| ELD_Q481A | 41.21 | 0.05 | 0.13 | 0.04 | 0.09 | 133.38 |
| GFP | 0.04 | 0.05 | 0.04 | 0.00 | 0.08 | NA |
| GFP | 0.05 | 0.06 | 0.02 | 0.02 | 0.05 | NA |
| GFP | 0.02 | 0.05 | 0.03 | 0.01 | 0.05 | NA |

TABLE 17B

|  | AAVS1 | OT1 | OT2 | OT3 | OT4 | Ratio |
|---|---|---|---|---|---|---|
| parental | 29.64 | 3.29 | 1.51 | 0.82 | 0.98 | 4.49 |
| parental | 30.09 | 3.79 | 1.91 | 0.97 | 1.09 | 3.88 |
| parental | 29.29 | 3.92 | 1.53 | 0.73 | 0.75 | 4.23 |
| half dose | 20.23 | 1.53 | 0.49 | 0.24 | 0.27 | 7.96 |
| half dose | 19.34 | 1.28 | 0.41 | 0.21 | 0.19 | 9.25 |
| half dose | 21.01 | 1.37 | 0.32 | 0.16 | 0.34 | 9.62 |
| KKR_R416E_S418E | 20.09 | 0.02 | 0.01 | 0.02 | 0.08 | 151.13 |
| KKR_R416E_N476D | 20.88 | 0.03 | 0.02 | 0.02 | 0.10 | 121.14 |
| KKR_R416E_I479T | 42.32 | 0.11 | 0.03 | 0.03 | 0.03 | 220.35 |
| KKR_R416E_Q481A | 0.05 | 0.08 | 0.03 | 0.03 | 0.05 | 0.28 |
| KKR_R416E_Q481E | 31.75 | 0.08 | 0.02 | 0.01 | 0.03 | 163.74 |
| KKR_R416E_K525S | 30.56 | 0.08 | 0.03 | 0.04 | 0.06 | 146.79 |
| KKR_S418E_N476D | 2.68 | 0.06 | 0.03 | 0.02 | 0.07 | 15.27 |
| KKR_S418E_I479T | 35.49 | 0.04 | 0.02 | 0.02 | 0.08 | 234.26 |
| KKR_S418E_Q481A | 1.55 | 0.08 | 0.01 | 0.02 | 0.05 | 9.60 |
| KKR_S418E_Q481E | 17.90 | 0.05 | 0.04 | 0.01 | 0.03 | 135.16 |
| KKR_S418E_K525S | 10.28 | 0.08 | 0.02 | 0.03 | 0.05 | 55.61 |
| KKR_N476D_I479T | 5.09 | 0.05 | 0.02 | 0.01 | 0.10 | 26.81 |
| KKR_N476D_Q481A | 4.44 | 0.08 | 0.05 | 0.01 | 0.06 | 22.35 |
| KKR_N476D_Q481E | 3.08 | 0.09 | 0.04 | 0.02 | 0.03 | 17.28 |
| KKR_N476D_K525S | 8.06 | 0.02 | 0.02 | 0.00 | 0.11 | 52.10 |
| KKR_I479T_Q481A | 25.89 | 0.05 | 0.01 | 0.01 | 0.05 | 204.61 |
| KKR_I479T_Q481E | 35.07 | 0.05 | 0.00 | 0.02 | 0.08 | 218.88 |
| KKR_I479T_K525S | 37.19 | 0.09 | 0.08 | 0.02 | 0.05 | 151.36 |
| KKR_R416S_K525S | 30.89 | 0.12 | 0.02 | 0.04 | 0.07 | 125.26 |
| KKR_R422S_K525S | 28.13 | 0.07 | 0.04 | 0.01 | 0.06 | 160.39 |
| KKR_K448S_K525S | 30.31 | 0.42 | 0.06 | 0.04 | 0.08 | 52.74 |
| KKR_Q481A_K525S | 4.99 | 0.03 | 0.02 | 0.04 | 0.05 | 36.01 |
| KKR_Q481E_K525S | 24.26 | 0.03 | 0.01 | 0.01 | 0.12 | 142.63 |
| KKR_K525S_Q531R | 31.33 | 0.20 | 0.05 | 0.01 | 0.12 | 83.63 |
| KKR_R416D_K448A | 34.82 | 0.06 | 0.07 | 0.05 | 0.04 | 160.49 |
| KKR_R416D_I479Q | 37.53 | 0.07 | 0.01 | 0.01 | 0.07 | 229.85 |
| KKR_R416D_Q481A | 1.51 | 0.05 | 0.01 | 0.03 | 0.05 | 10.67 |
| KKR_R416D_K525A | 8.83 | 0.09 | 0.02 | 0.01 | 0.11 | 40.27 |
| KKR_R416E_R422H | 39.63 | 0.19 | 0.02 | 0.03 | 0.08 | 122.95 |
| KKR_R416E_K448A | 43.43 | 0.13 | 0.05 | 0.04 | 0.03 | 106.38 |
| KKR_R416E_I479Q | 40.55 | 0.12 | 0.04 | 0.07 | 0.05 | 140.11 |
| KKR_R416E_K525A | 23.98 | 0.04 | 0.05 | 0.03 | 0.09 | 112.67 |
| KKR_R416E_N527D | 40.12 | 0.10 | 0.01 | 0.04 | 0.13 | 141.70 |
| KKR_S418E_K448A | 36.67 | 0.10 | 0.08 | 0.02 | 0.03 | 158.02 |
| KKR_S418E_I479Q | 36.46 | 0.07 | 0.09 | 0.03 | 0.02 | 173.06 |
| KKR_S418E_K525A | 6.28 | 0.08 | 0.01 | 0.04 | 0.04 | 36.37 |
| KKR_R422H_I479Q | 35.05 | 0.29 | 0.14 | 0.06 | 0.03 | 66.28 |
| KKR_R422H_Q481A | 12.81 | 0.06 | 0.03 | 0.01 | 0.10 | 64.84 |
| KKR_R422H_K525A | 31.03 | 0.11 | 0.04 | 0.05 | 0.05 | 126.26 |
| KKR_K448A_I479Q | 35.23 | 0.17 | 0.19 | 0.05 | 0.06 | 74.29 |
| KKR_K448A_Q481A | 19.81 | 0.11 | 0.01 | 0.03 | 0.03 | 116.04 |
| KKR_K448A_K525A | 36.25 | 0.08 | 0.04 | 0.01 | 0.07 | 183.47 |
| KKR_K448A_N527D | 29.74 | 0.30 | 0.12 | 0.04 | 0.10 | 55.29 |
| KKR_I479Q_Q481A | 31.65 | 0.09 | 0.07 | 0.01 | 0.06 | 128.89 |
| KKR_I479Q_K525A | 37.06 | 0.06 | 0.02 | 0.03 | 0.08 | 196.46 |
| KKR_Q481A_K525A | 3.09 | 0.06 | 0.01 | 0.03 | 0.05 | 21.23 |
| KKR_Q481A_N527D | ND | ND | ND | ND | ND | ND |
| KKR_K525A_N527D | ND | ND | ND | ND | ND | ND |
| KKR_S446D | 38.46 | 0.08 | 0.03 | 0.03 | 0.08 | 175.19 |
| KKR_G480D | 40.11 | 0.60 | 0.98 | 0.14 | 0.14 | 21.66 |
| KKR_S418D | 35.59 | 0.35 | 0.13 | 0.06 | 0.08 | 56.27 |
| KKR_N476D | 20.04 | 0.12 | 0.05 | 0.03 | 0.05 | 78.85 |
| KKR_I479T | 36.62 | 0.40 | 0.09 | 0.24 | 0.07 | 45.83 |
| KKR_Q481E | 37.26 | 0.15 | 0.03 | 0.01 | 0.08 | 137.34 |
| KKR_N527D | 29.30 | 0.98 | 0.37 | 0.24 | 0.30 | 15.48 |
| KKR_Q531R | 27.77 | 0.61 | 0.69 | 0.38 | 0.19 | 14.82 |
| KKR_I479Q | 40.88 | 1.28 | 0.74 | 0.35 | 0.09 | 16.60 |
| KKR_R416E | 41.76 | 0.49 | 0.06 | 0.05 | 0.55 | 35.99 |
| KKR_K525A | 33.81 | 0.46 | 0.04 | 0.07 | 0.19 | 44.54 |
| KKR_K525S | 35.00 | 1.05 | 0.15 | 0.14 | 0.24 | 22.10 |
| KKR_Q481A | 36.52 | 0.12 | 0.09 | 0.01 | 0.10 | 113.98 |
| GFP | 0.04 | 0.05 | 0.04 | 0.00 | 0.08 | NA |
| GFP | 0.05 | 0.06 | 0.02 | 0.02 | 0.05 | NA |
| GFP | 0.02 | 0.05 | 0.03 | 0.01 | 0.05 | NA |

TABLE 17C

|  | AAVS1 | OT1 | OT2 | OT3 | OT4 | ratio |
|---|---|---|---|---|---|---|
| parental | 29.64 | 3.29 | 1.51 | 0.82 | 0.98 | 4.49 |
| parental | 30.09 | 3.79 | 1.91 | 0.97 | 1.09 | 3.88 |
| parental | 29.29 | 3.92 | 1.53 | 0.73 | 0.75 | 4.23 |

TABLE 17C-continued

|  | AAVS1 | OT1 | OT2 | OT3 | OT4 | ratio |
|---|---|---|---|---|---|---|
| half dose | 20.23 | 1.53 | 0.49 | 0.24 | 0.27 | 7.96 |
| half dose | 19.34 | 1.28 | 0.41 | 0.21 | 0.19 | 9.25 |
| half dose | 21.01 | 1.37 | 0.32 | 0.16 | 0.34 | 9.62 |
| ELD_KKR_R416E_S418E | 1.12 | 0.06 | 0.01 | 0.04 | 0.08 | 5.75 |
| ELD_KKR_R416E_N476D | 0.08 | 0.02 | 0.01 | 0.02 | 0.05 | 0.90 |
| ELD_KKR_R416E_I479T | 9.58 | 0.01 | 0.01 | 0.01 | 0.07 | 93.64 |
| ELD_KKR_R416E_Q481A | 0.04 | 0.03 | 0.03 | 0.02 | 0.06 | 0.34 |
| ELD_KKR_R416E_Q481E | 15.79 | 0.01 | 0.01 | 0.02 | 0.07 | 146.87 |
| ELD_KKR_R416E_K525S | 18.64 | 0.07 | 0.03 | 0.01 | 0.06 | 110.61 |
| ELD_KKR_S418E_N476D | 0.03 | 0.05 | 0.03 | 0.01 | 0.06 | 0.19 |
| ELD_KKR_S418E_I479T | 0.07 | 0.06 | 0.05 | 0.02 | 0.05 | 0.39 |
| ELD_KKR_S418E_Q481A | 0.06 | 0.06 | 0.02 | 0.01 | 0.07 | 0.39 |
| ELD_KKR_S418E_Q481E | 0.25 | 0.06 | 0.02 | 0.01 | 0.06 | 1.60 |
| ELD_KKR_S418E_K525S | 0.04 | 0.07 | 0.01 | 0.01 | 0.06 | 0.28 |
| ELD_KKR_N476D_I479T | 0.01 | 0.08 | 0.03 | 0.01 | 0.07 | 0.06 |
| ELD_KKR_N476D_Q481A | 0.04 | 0.02 | 0.01 | 0.02 | 0.02 | 0.60 |
| ELD_KKR_N476D_Q481E | 0.04 | 0.07 | 0.04 | 0.01 | 0.05 | 0.22 |
| ELD_KKR_N476D_K525S | 0.03 | 0.05 | 0.05 | 0.00 | 0.04 | 0.19 |
| ELD_KKR_I479T_Q481A | 1.92 | 0.02 | 0.03 | 0.01 | 0.07 | 14.25 |
| ELD_KKR_I479T_Q481E | 1.71 | 0.06 | 0.04 | 0.02 | 0.04 | 11.29 |
| ELD_KKR_I479T_K525S | 0.87 | 0.03 | 0.02 | 0.02 | 0.07 | 6.00 |
| ELD_KKR_R416S_K525S | 16.65 | 0.08 | 0.02 | 0.04 | 0.08 | 77.13 |
| ELD_KKR_R422S_K525S | 8.09 | 0.10 | 0.02 | 0.01 | 0.07 | 39.66 |
| ELD_KKR_K448S_K525S | 34.04 | 0.06 | 0.03 | 0.02 | 0.06 | 203.03 |
| ELD_KKR_Q481A_K525S | 2.27 | 0.05 | 0.04 | 0.01 | 0.08 | 12.73 |
| ELD_KKR_Q481E_K525S | 1.58 | 0.04 | 0.04 | 0.02 | 0.05 | 10.24 |
| ELD_KKR_K525S_Q531R | 31.89 | 0.06 | 0.02 | 0.02 | 0.05 | 213.09 |
| ELD_KKR_R416D_K448A | 34.69 | 0.02 | 0.05 | 0.04 | 0.09 | 171.10 |
| ELD_KKR_R416D_I479Q | 0.64 | 0.09 | 0.04 | 0.01 | 0.08 | 2.97 |
| ELD_KKR_R416D_Q481A | 0.72 | 0.07 | 0.03 | 0.00 | 0.09 | 3.74 |
| ELD_KKR_R416D_K525A | 0.44 | 0.03 | 0.01 | 0.03 | 0.03 | 4.38 |
| ELD_KKR_R416E_R422H | 51.26 | 0.06 | 0.04 | 0.04 | 0.08 | 241.20 |
| ELD_KKR_R416E_K448A | 65.65 | 0.04 | 0.05 | 0.03 | 0.11 | 296.99 |
| ELD_KKR_R416E_I479Q | 9.45 | 0.03 | 0.01 | 0.03 | 0.06 | 69.73 |
| ELD_KKR_R416E_K525A | 8.87 | 0.06 | 0.02 | 0.03 | 0.07 | 50.16 |
| ELD_KKR_R416E_N527D | 8.77 | 0.06 | 0.02 | 0.00 | 0.05 | 65.60 |
| ELD_KKR_S418E_K448A | 12.39 | 0.07 | 0.01 | 0.02 | 0.02 | 105.55 |
| ELD_KKR_S418E_I479Q | 0.17 | 0.08 | 0.04 | 0.06 | 0.07 | 0.68 |
| ELD_KKR_S418E_K525A | 0.07 | 0.05 | 0.02 | 0.00 | 0.04 | 0.57 |
| ELD_KKR_R422H_I479Q | 6.81 | 0.04 | 0.01 | 0.01 | 0.10 | 39.89 |
| ELD_KKR_R422H_Q481A | 17.21 | 0.05 | 0.04 | 0.04 | 0.05 | 97.54 |
| ELD_KKR_R422H_K525A | 9.57 | 0.02 | 0.04 | 0.04 | 0.04 | 68.82 |
| ELD_KKR_K448A_I479Q | 33.17 | 0.06 | 0.01 | 0.01 | 0.07 | 209.50 |
| ELD_KKR_K448A_Q481A | 52.80 | 0.05 | 0.03 | 0.02 | 0.05 | 351.52 |
| ELD_KKR_K448A_K525A | 31.94 | 0.06 | 0.03 | 0.02 | 0.08 | 164.22 |
| ELD_KKR_K448A_N527D | 12.12 | 0.08 | 0.03 | 0.01 | 0.04 | 70.27 |
| ELD_KKR_I479Q_Q481A | 1.71 | 0.01 | 0.00 | 0.06 | 0.10 | 10.33 |
| ELD_KKR_I479Q_K525A | 1.27 | 0.09 | 0.05 | 0.02 | 0.06 | 5.70 |
| ELD_KKR_Q481A_K525A | 0.52 | 0.01 | 0.02 | 0.01 | 0.05 | 5.01 |
| ELD_KKR_Q481A_N527D | ND | ND | ND | ND | ND | ND |
| ELD_KKR_K525A_N527D | ND | ND | ND | ND | ND | ND |
| ELD_KKR_S446D | 15.36 | 0.04 | 0.02 | 0.04 | 0.08 | 83.81 |
| ELD_KKR_G480D | 64.90 | 0.09 | 0.02 | 0.06 | 0.15 | 200.43 |
| ELD_KKR_S418D | 26.63 | 0.05 | 0.03 | 0.00 | 0.08 | 167.71 |
| ELD_KKR_N476D | 4.22 | 0.02 | 0.05 | 0.02 | 0.03 | 36.30 |
| ELD_KKR_I479T | 26.01 | 0.05 | 0.05 | 0.04 | 0.03 | 153.83 |
| ELD_KKR_Q481E | 38.76 | 0.08 | 0.02 | 0.05 | 0.03 | 221.20 |
| ELD_KKR_N527D | 21.40 | 0.10 | 0.03 | 0.03 | 0.07 | 92.64 |
| ELD_KKR_Q531R | 30.69 | 0.17 | 0.05 | 0.10 | 0.03 | 89.70 |
| ELD_KKR_I479Q | 52.76 | 0.03 | 0.03 | 0.02 | 0.07 | 350.46 |
| ELD_KKR_R416E | 61.25 | 0.16 | 0.10 | 0.09 | 0.10 | 138.11 |
| ELD_KKR_K525A | 38.71 | 0.15 | 0.01 | 0.03 | 0.07 | 152.55 |
| ELD_KKR_K525S | 42.82 | 0.02 | 0.03 | 0.02 | 0.07 | 299.99 |
| ELD_KKR_Q481A | 70.60 | 0.07 | 0.02 | 0.04 | 0.06 | 383.30 |
| GFP | 0.04 | 0.05 | 0.04 | 0.00 | 0.08 | NA |
| GFP | 0.05 | 0.06 | 0.02 | 0.02 | 0.05 | NA |
| GFP | 0.02 | 0.05 | 0.03 | 0.01 | 0.05 | NA |

Tables 18A through 18C show results of using the indicated cleavage domain mutants.

TABLE 18A

|  | AAVS1 | OT1 | ratio |
|---|---|---|---|
| parental | 60.28 | 12.69 | 4.75 |
| parental | 57.85 | 9.71 | 5.96 |
| parental | 54.74 | 9.42 | 5.81 |
| half_dose | 51.05 | 5.51 | 9.26 |
| half_dose | 42.72 | 3.69 | 11.58 |
| half_dose | 50.26 | 7.75 | 6.49 |
| ELD_G480A | 71.44 | 10.67 | 6.70 |
| ELD_G480C | 62.08 | 8.04 | 7.72 |
| ELD_G480D | 64.70 | 0.79 | 82.32 |
| ELD_G480E | 76.47 | 0.57 | 134.21 |
| ELD_G480F | 40.12 | 1.20 | 33.37 |
| ELD_G480H | ND | 15.72 | ND |
| ELD_G480I | 41.29 | 4.05 | 10.19 |
| ELD_G480K | 68.06 | 14.64 | 4.65 |
| ELD_G480L | 41.04 | 2.35 | 17.49 |
| ELD_G480M | 39.95 | 3.93 | 10.16 |
| ELD_G480N | 57.82 | 11.58 | 4.99 |
| ELD_G480P | 45.73 | 1.29 | 35.32 |
| ELD_G480Q | 25.33 | 0.30 | 85.73 |
| ELD_G480R | 56.94 | 13.22 | 4.31 |
| ELD_G480S | 68.85 | 11.40 | 6.04 |
| ELD_G480T | 68.02 | 14.68 | 4.63 |
| ELD_G480V | 43.43 | 2.22 | 19.53 |
| ELD_G480W | 64.39 | 0.83 | 77.94 |
| ELD_G480Y | 45.27 | 2.45 | 18.51 |
| ELD_R416E | 66.43 | 0.40 | 164.15 |
| ELD_I479Q | 70.95 | 0.21 | 345.03 |
| ELD_G480D | 72.46 | 0.65 | 110.75 |
| ELD_Q481A | 58.01 | 0.34 | 173.11 |
| ELD_K525A | 66.31 | 0.60 | 111.25 |
| ELD_R416E_R422H | 48.29 | 0.07 | 679.24 |
| ELD_R416E_K448A | 70.50 | 0.50 | 142.30 |
| ELD_K448A_I479Q | 68.99 | 0.11 | 637.89 |
| ELD_K448A_Q481A | 41.36 | 0.12 | 333.89 |
| ELD_K448A_K525A | 70.69 | 0.24 | 300.02 |
| GFP | 0.11 | 0.03 | ND |
| GFP | 0.20 | 0.00 | ND |

TABLE 18B

|  | AAVS1 | OT1 | ratio |
|---|---|---|---|
| parental | 60.28 | 12.69 | 4.75 |
| parental | 57.85 | 9.71 | 5.96 |
| parental | 54.74 | 9.42 | 5.81 |
| half_dose | 51.05 | 5.51 | 9.26 |
| half_dose | 42.72 | 3.69 | 11.58 |
| half_dose | 50.26 | 7.75 | 6.49 |
| KKR_G480A | 65.59 | 6.54 | 10.03 |
| KKR_G480C | 56.27 | 5.14 | 10.94 |
| KKR_G480D | 56.11 | 1.00 | 56.19 |
| KKR_G480E | 56.49 | 0.73 | 77.63 |
| KKR_G480F | 34.91 | 0.78 | 44.55 |
| KKR_G480H | 60.07 | 8.52 | 7.05 |
| KKR_G480I | 38.68 | 1.60 | 24.22 |
| KKR_G480K | 65.79 | 11.26 | 5.84 |
| KKR_G480L | 41.92 | 1.13 | 36.98 |
| KKR_G480M | 55.69 | 5.66 | 9.84 |
| KKR_G480N | 61.56 | 9.62 | 6.40 |
| KKR_G480P | 54.84 | 1.32 | 41.45 |
| KKR_G480Q | 62.68 | 7.05 | 8.89 |
| KKR_G480R | 60.84 | 10.34 | 5.88 |
| KKR_G480S | 66.61 | 12.23 | 5.45 |
| KKR_G480T | 71.73 | 14.73 | 4.87 |
| KKR_G480V | 41.05 | 1.63 | 25.24 |
| KKR_G480W | 57.21 | 0.56 | 102.21 |
| KKR_G480Y | 46.86 | 3.28 | 14.27 |
| KKR_R416E | 70.79 | 1.45 | 48.82 |
| KKR_I479Q | 65.46 | 2.18 | 29.99 |
| KKR_G480D | 56.96 | 1.09 | 52.26 |
| KKR_Q481A | 62.91 | 0.17 | 366.11 |
| KKR_K525A | 66.35 | 1.35 | 49.21 |
| KKR_R416E_R422H | 69.06 | 0.08 | 847.00 |
| KKR_R416E_K448A | ND | 0.25 | ND |
| KKR_K448A_I479Q | 64.17 | 0.37 | 175.75 |
| KKR_K448A_Q481A | 35.73 | 0.17 | 214.80 |
| KKR_K448A_K525A | 64.77 | 0.34 | 192.29 |
| GFP | 0.11 | 0.03 | ND |
| GFP | 0.20 | 0.00 | ND |

TABLE 18C

|  | AAVS1 | OT1 | ratio |
|---|---|---|---|
| parental | 60.28 | 12.69 | 4.75 |
| parental | 57.85 | 9.71 | 5.96 |
| parental | 54.74 | 9.42 | 5.81 |
| half_dose | 51.05 | 5.51 | 9.26 |
| half_dose | 42.72 | 3.69 | 11.58 |
| half_dose | 50.26 | 7.75 | 6.49 |
| ELD_KKR_G480A | 83.25 | 15.29 | 5.44 |
| ELD_KKR_G480C | 62.30 | 6.18 | 10.09 |
| ELD_KKR_G480D | 68.39 | 0.17 | 400.26 |
| ELD_KKR_G480E | 64.32 | 0.16 | 390.88 |
| ELD_KKR_G480F | 50.56 | 2.10 | 24.03 |
| ELD_KKR_G480H | 70.45 | 19.84 | 3.55 |
| ELD_KKR_G480I | 30.54 | 1.41 | 21.66 |
| ELD_KKR_G480K | 75.70 | 4.49 | 16.88 |
| ELD_KKR_G480L | 29.27 | 0.35 | 83.87 |
| ELD_KKR_G480M | 38.29 | 2.25 | 17.05 |
| ELD_KKR_G480N | 62.58 | 10.50 | 5.96 |
| ELD_KKR_G480P | 46.49 | 0.10 | 446.75 |
| ELD_KKR_G480Q | 21.45 | 0.45 | 48.14 |
| ELD_KKR_G480R | 34.10 | 4.91 | 6.94 |
| ELD_KKR_G480S | 70.28 | 15.69 | 4.48 |
| ELD_KKR_G480T | 74.83 | 16.53 | 4.53 |
| ELD_KKR_G480V | 30.55 | 0.92 | 33.16 |
| ELD_KKR_G480W | 40.77 | 0.11 | 378.20 |
| ELD_KKR_G480Y | 38.97 | 1.69 | 23.09 |
| ELD_KKR_R416E | 75.31 | 0.36 | 207.10 |
| ELD_KKR_I479Q | 63.75 | 0.08 | 804.35 |
| ELD_KKR_G480D | 77.51 | 0.13 | 612.83 |
| ELD_KKR_Q481A | 86.20 | 0.12 | 731.56 |
| ELD_KKR_K525A | 56.37 | 0.06 | 969.83 |
| ELD_KKR_R416E_R422H | 58.35 | 0.06 | 996.94 |
| ELD_KKR_R416E_K448A | 84.57 | 0.07 | 1241.44 |
| ELD_KKR_K448A_I479Q | 43.78 | 0.03 | 1296.88 |
| ELD_KKR_K448A_Q481A | 63.32 | 0.08 | 816.13 |
| ELD_KKR_K448A_K525A | 48.43 | 0.13 | 384.71 |
| GFP | 0.11 | 0.03 | ND |
| GFP | 0.20 | 0.00 | ND |

Figure 16B:
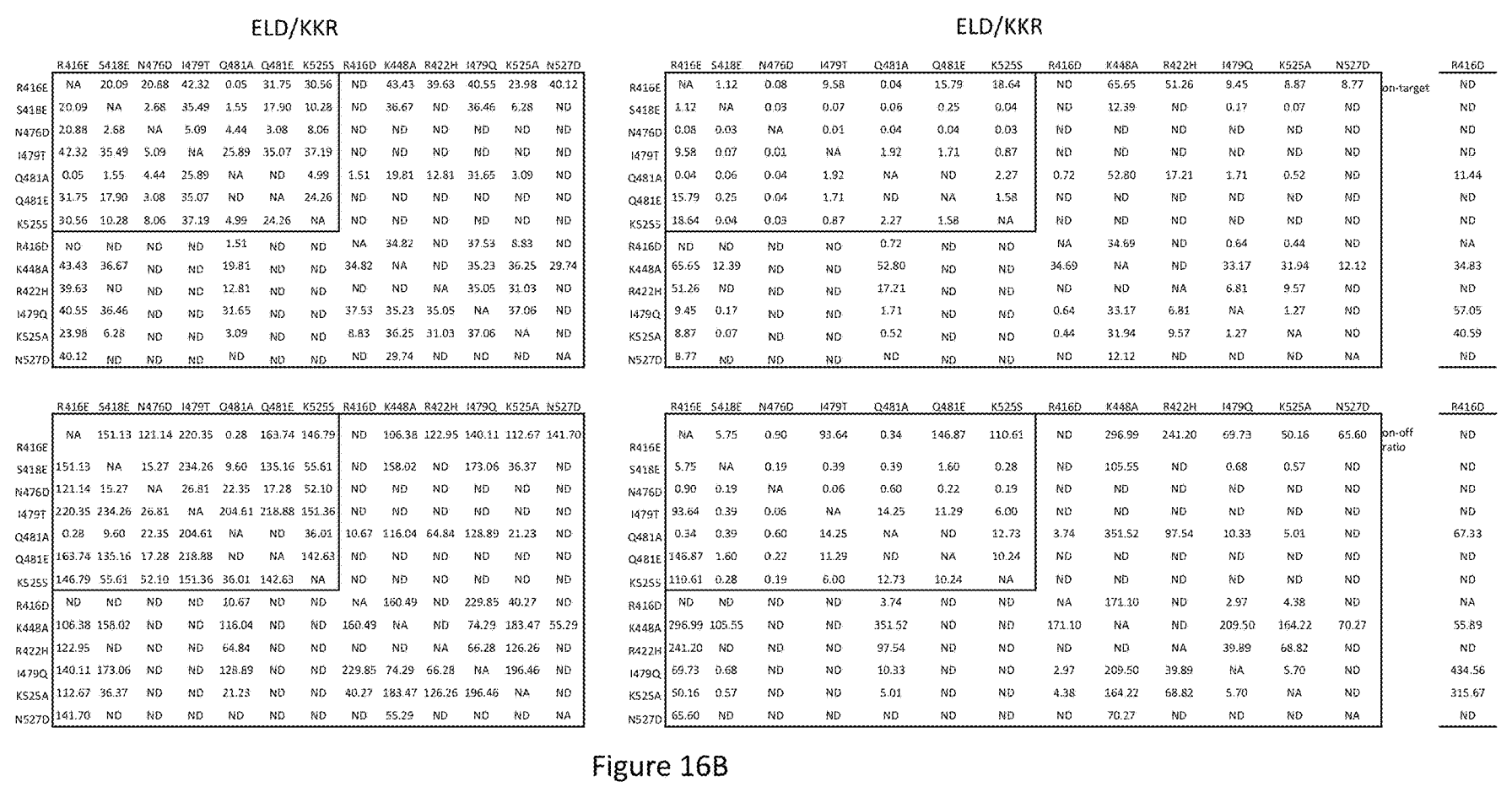

FIGS. 15 and 16 also show summaries of selected results with the indicated mutants.

The results demonstrate highly specific cleavage with the mutants described herein.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An engineered *Flavobacterium okeanokoites* (FokI) cleavage half-domain, wherein the engineered cleavage half-domain comprises one or more substitution mutations of a wild-type residue of the full length FokI cleavage domain as shown in SEQ ID NO:1, wherein the one or more substitution mutations are as follows:
   (i) the wild type Gln (Q) residue at position 481 is replaced with an Ala (A), Cys (C), Asp (D), Ser (S), or Glu (E) residue (Q481A, Q481C, Q481D, Q481S, or Q481E);
   (ii) the wild-type Ser (S) residue at position 418 is replaced with a Glu (E) or Asp (D) residue (S418E or S418D);
   (iii) the wild-type Ile (I) residue at position 479 is replaced with a Gln (Q) or Thr (T) residue (I479Q or I479T);
   (iv) the wild-type Pro (P) residue at position 478 is replaced an Asp (D) residue (P478D);
   (v) the wild-type Lys (K) residue at position 525 is replaced with an Ala (A), Cys (C), Glu (E), Ile (I), Ser (S), Thr (T) or Val (V) residue (K525A, K525C, K525E, K252I, K525S, K525T, or K525V);
   (vi) the wild-type Arg (R) residue as position 416 is replaced with an Asp (D), Glu (E), His (H) or Asn (N) residue (R416D, R416E, R416H, or R416N);
   (vii) the wild-type Gly (G) residue at position 480 is replaced with an Asp (D) residue (G480D);
   (viii) the wild-type Ser (S) residue a position 472 is replaced with an Asp (D) residue (S472D);
   (ix) the wild-type Asn (N) residue at position 476 is replaced with a Glu (E) residue or a Gly (G) residue (N476E or N476G);
   (x) the wild-type Gln (Q) residue at position 531 is replaced with an Arg (R) or Thr (T) residue (Q531R or Q531T);
   (xi) the wild-type Arg (R) residue at position 422 is replaced with a His (H) residue (R422H);
   (xii) the wild-type Ser (S) residue at position 446 is replaced with an Asp (D) residue (S446D);
   (xiii) the wild-type residue at position 448 is replaced with an Ala (A) residue (K448A);
   (xiv) the wild-type His (H) residue at position 523 is replaced with a Glu (E) residue (H523E);
   (xv) the wild-type Leu (L) residue at position 424 is replaced with a Phe (F) residue (L424F); and/or
   (xvi) the wild-type Asn (N) residue at position 542 is replaced with an Asp (D) residue (N542D).

2. The engineered cleavage half-domain of claim 1, comprising mutations as follows: the R416D, R416E, R416H, or R416N mutation and the R422H mutation; the R416D, R416E, R416H, or R416N mutation and the K448A mutation; the K448A and I479Q mutations; the K448A and Q481A mutations; and/or K448A mutation and the K525A, K525C, K525E, K252I, K525S, K525T, or K525V mutation.

3. The engineered cleavage half-domain of claim 1, further comprising an additional mutation at one or more of positions 432, 441, 483, 486, 487, 490, 496, 499, 527, 537, 538 and 559.

4. A heterodimer comprising a first engineered cleavage half-domain of claim 1 and a second cleavage half-domain.

5. A heterodimer comprising a first and second engineered cleavage half-domains according to claim 1.

6. An artificial nuclease comprising an engineered cleavage half-domain of claim 1, and an engineered DNA-binding domain.

7. An artificial nuclease comprising an engineered cleavage half-domain of claim 3, and an engineered DNA-binding domain.

8. The artificial nuclease of claim 6, wherein the engineered DNA-binding domain comprises a zinc finger protein, a TALE-effector domain or a single guide RNA (sgRNA).

9. The artificial nuclease of claim 8, wherein the zinc finger protein comprises at least three zinc finger DNA-binding domains, wherein each zinc finger DNA-binding domain comprises two beta sheets, an alpha helix, a recognition helix region that binds to a nucleotide sequence, and further wherein one or more of the zinc finger DNA-binding domains comprise mutations in amino acid residues (-5), (-9) and/or (-14), numbered relative to the start of the alpha helix region.

10. The artificial nuclease of claim 7, wherein the DNA-binding domain comprises a zinc finger protein, a TALE-effector domain or a single guide RNA (sgRNA).

11. The artificial nuclease of claim 10, wherein the zinc finger protein comprises at least three zinc finger DNA-binding domains, wherein each zinc finger DNA-binding domain comprises two beta sheets, an alpha helix, a recognition helix region that binds to a nucleotide sequence, and further wherein one or more of the zinc finger DNA-binding domains comprise mutations in amino acid residues (-5), (-9) and/or (-14), numbered relative to the start of the alpha helix region.

12. An isolated cell comprising the engineered cleavage half-domain of claim 1.

13. An isolated cell comprising the engineered cleavage half-domain of claim 3.

14. A method for cleaving genomic cellular chromatin in a region of interest, the method comprising:
    expressing an artificial nuclease according to claim 6 in a cell,
    wherein the nuclease site-specifically cleaves a nucleotide sequence in the region of interest of the genomic cellular chromatin.

15. The method of claim 14, further comprising contacting the cell with a donor polynucleotide; wherein cleavage of the cellular chromatin facilitates homologous recombination between the donor polypeptide and the cellular chromatin.

16. A method of cleaving at least two target sites in genomic cellular chromatin, the method comprising:
    cleaving at least first and second target sites in genomic cellular chromatin, wherein each target site is cleaved using a composition comprising an artificial nuclease according to claim 6.

* * * * *